(12) United States Patent
Taylor et al.

(10) Patent No.: US 9,968,685 B2
(45) Date of Patent: *May 15, 2018

(54) METHODS TO TREAT CANCER WITH CUPREDOXINS

(76) Inventors: Brad N. Taylor, Providence, RI (US); Rajeshwari Mehta, Orland Park, IL (US); Tohru Yamada, Lombard, IL (US); Craig Beattie, Chicago, IL (US); Tapas Das Gupta, River Forest, IL (US)

(*) Notice: Subject to any disclaimer, the term of this patent is extended or adjusted under 35 U.S.C. 154(b) by 335 days.

This patent is subject to a terminal disclaimer.

(21) Appl. No.: 12/338,480

(22) Filed: Dec. 18, 2008

(65) Prior Publication Data

US 2009/0202441 A1 Aug. 13, 2009

Related U.S. Application Data

(63) Continuation-in-part of application No. 12/314,703, filed on Dec. 15, 2008, now abandoned, and a continuation-in-part of application No. 12/028,683, filed on Feb. 8, 2008, now Pat. No. 8,232,244, and a continuation-in-part of application No. 11/488,693, filed on Jul. 19, 2006, now Pat. No. 7,556,810, and a continuation-in-part of application No. 11/244,105, filed on Oct. 6, 2005, now Pat. No. 7,691,383.

(60) Provisional application No. 61/013,709, filed on Dec. 14, 2007, provisional application No. 60/900,098, filed on Feb. 8, 2007, provisional application No. 60/700,297, filed on Jul. 19, 2005, provisional application No. 60/616,782, filed on Oct. 7, 2004, provisional application No. 60/680,500, filed on May 13, 2005.

(51) Int. Cl.

| | | |
|---|---|---|
| A61K 38/03 | (2006.01) |
| C07K 14/195 | (2006.01) |
| C07K 14/21 | (2006.01) |
| C07K 14/35 | (2006.01) |
| A61K 47/48 | (2006.01) |
| A61K 49/00 | (2006.01) |
| C07K 14/415 | (2006.01) |
| C12N 9/02 | (2006.01) |
| G01N 33/50 | (2006.01) |
| G01N 33/569 | (2006.01) |
| A61K 38/00 | (2006.01) |

(52) U.S. Cl.
CPC ........ *A61K 47/48246* (2013.01); *A61K 38/03* (2013.01); *A61K 49/0002* (2013.01); *A61K 49/0032* (2013.01); *A61K 49/0056* (2013.01); *C07K 14/195* (2013.01); *C07K 14/21* (2013.01); *C07K 14/35* (2013.01); *C07K 14/415* (2013.01); *C12N 9/0004* (2013.01); *G01N 33/5011* (2013.01); *G01N 33/569* (2013.01); *A61K 38/00* (2013.01); *G01N 2510/00* (2013.01)

(58) Field of Classification Search
None
See application file for complete search history.

(56) References Cited

U.S. PATENT DOCUMENTS

| 6,551,795 B1 * | 4/2003 | Rubenfield et al. ......... 435/69.1 |
| 2002/0110872 A1 * | 8/2002 | Chakrabarty et al. ....... 435/71.1 |
| 2002/0164703 A1 | 11/2002 | Pawlowski et al. |
| 2006/0149037 A1 | 7/2006 | Chakrabarty et al. |
| 2008/0226560 A1 | 9/2008 | Das Gupta et al. |

FOREIGN PATENT DOCUMENTS

| WO | 0044888 | 8/2000 |
| WO | 03097085 A1 | 11/2003 |
| WO | 2005018662 A1 | 3/2005 |
| WO | 2006088508 A2 | 8/2006 |
| WO | 2008033820 A2 | 3/2008 |
| WO | 2008033987 A2 | 3/2008 |
| WO | 2008098216 A2 | 8/2008 |
| WO | 2009078977 A2 | 6/2009 |

OTHER PUBLICATIONS

Yamada et al., PNAS, 2002, 99(22):14098-14103.*
Punj et al., Oncogene, 2004, 23:2367-2378.*
Senior, Proc Natl Acad Sci USA, 2002, 99:14098-14103.*
Ni et al., Cancer Letters 261:1-11 (2008).
Chaudhari et al., Biochemistry, American Chemical Society 46:7 1799-1810 (2007).
Punj, V. et al., Oncogene 23:13 2367-2378 (2004).
Yamada, T. et al., Proc. Natl. Acad. Sci. 99:22 14098-14103 (2002).
Yamada et al., Cell Cycle 3:6 pp. 752-755 (2004).
Yamada T. et al.: "Internalization of bacterial redox protein azurin in mammalian cells: entry domain and specificity," Cellular Microbiology, vol. 7, No. 10, pp. 1418-1431 (Jul. 5, 2005).

* cited by examiner

*Primary Examiner* — Nicole Kinsey White
(74) *Attorney, Agent, or Firm* — Benesch, Friedlander, Coplan & Aronoff LLP

(57) ABSTRACT

The present invention discloses methods and materials for killing and/or inhibiting the growth of a cancer cell via preferential entry of a cytotoxic compound. Preferential entry of the cytotoxic compound is accomplished by the use of protein transduction domains derived from cupredoxins, including the p18 and p28 truncations of azurin.

8 Claims, 83 Drawing Sheets

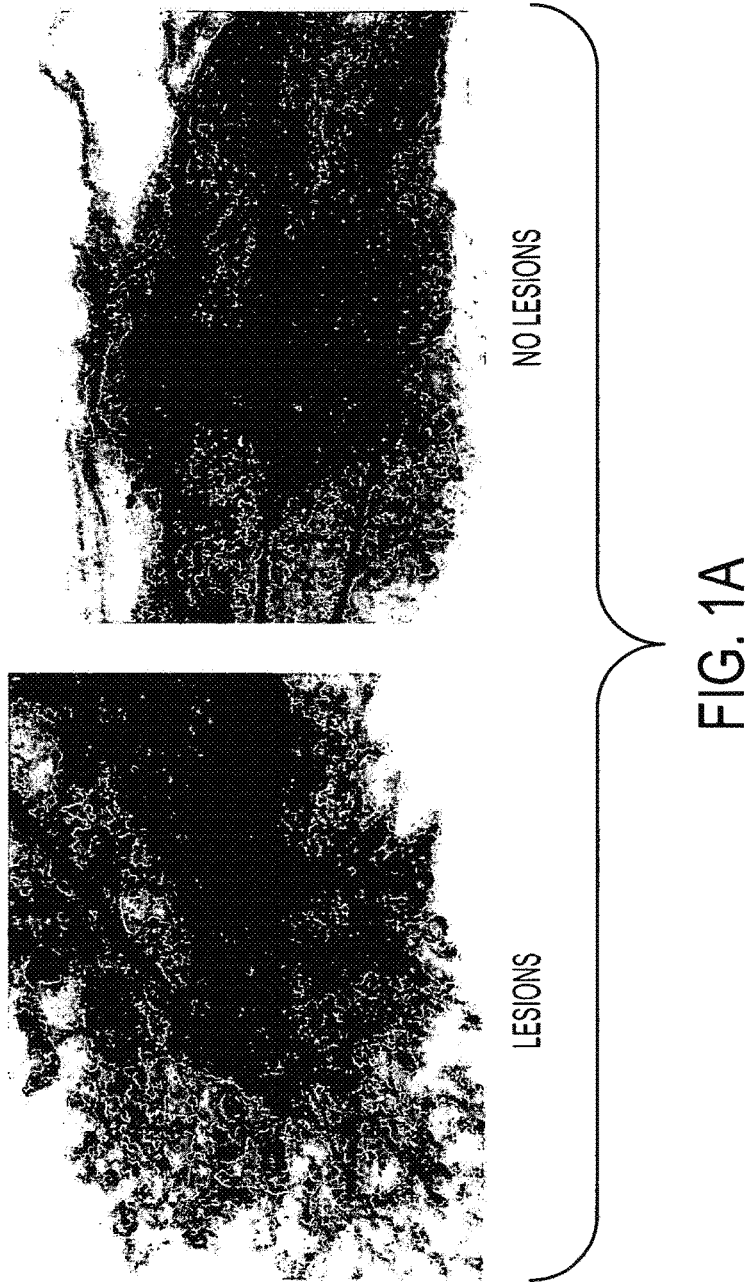

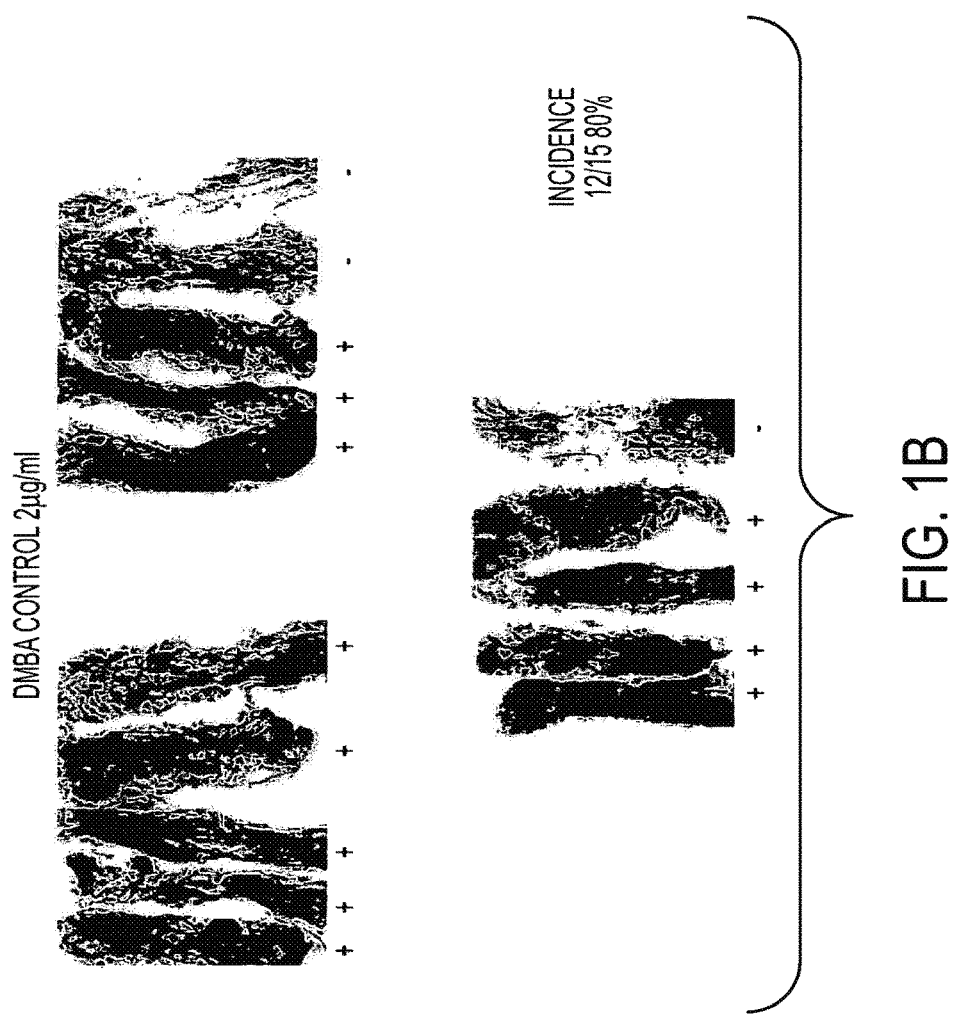

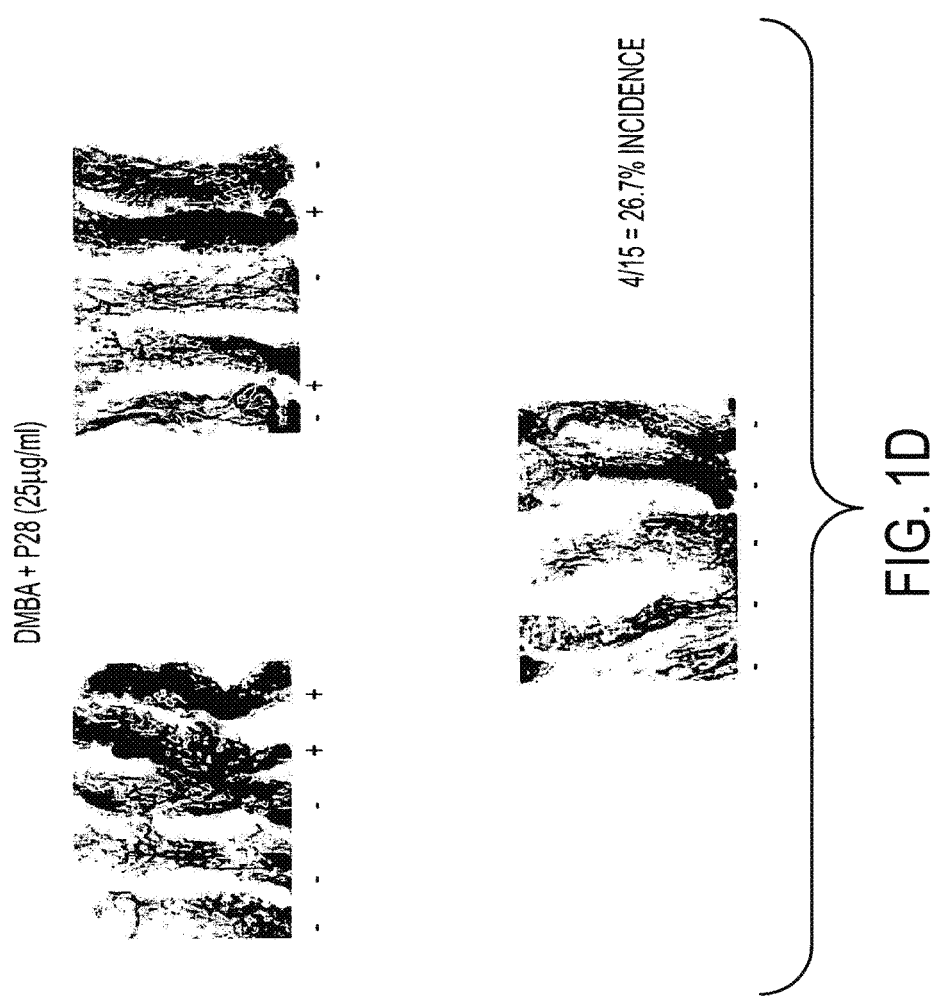

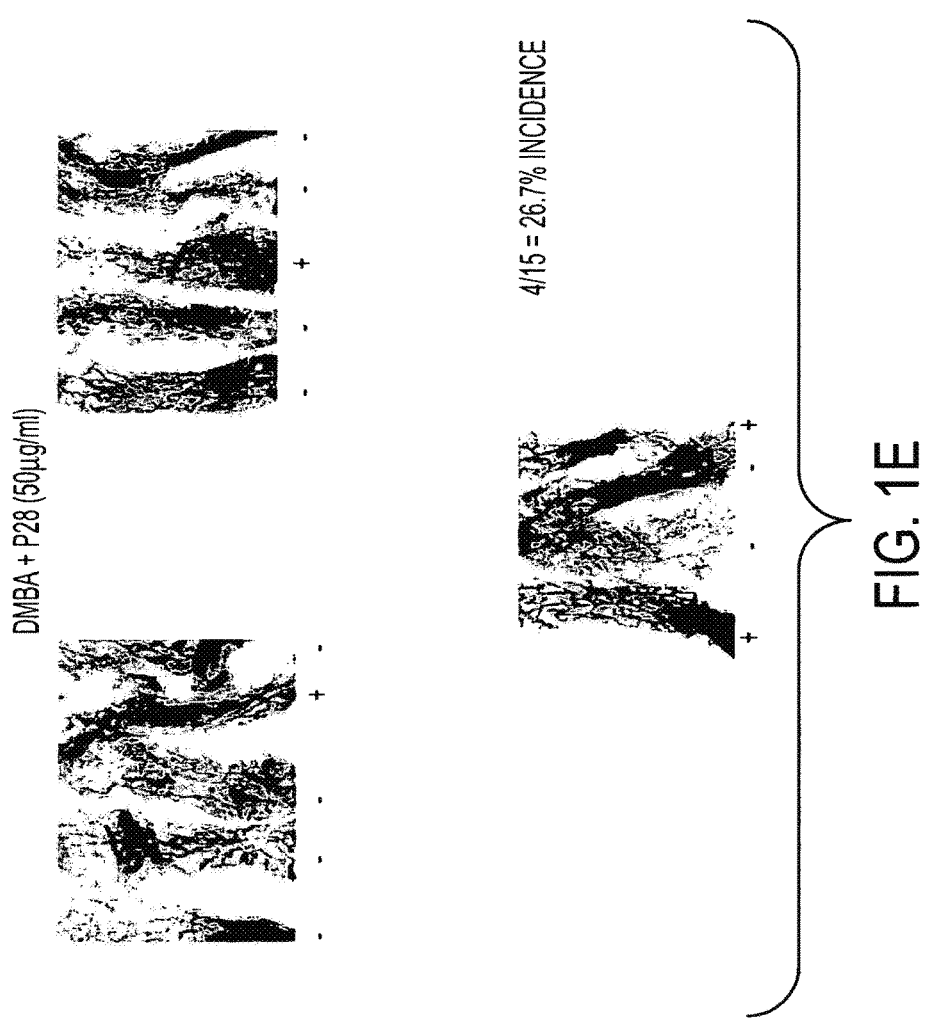

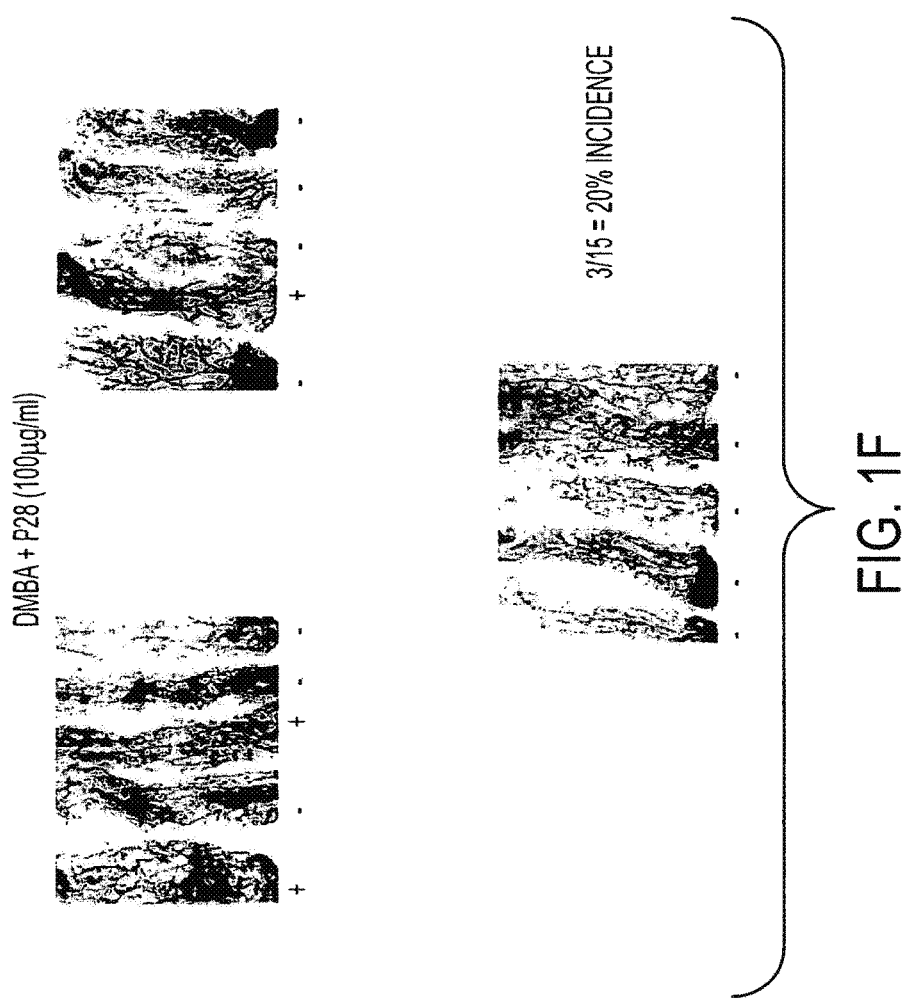

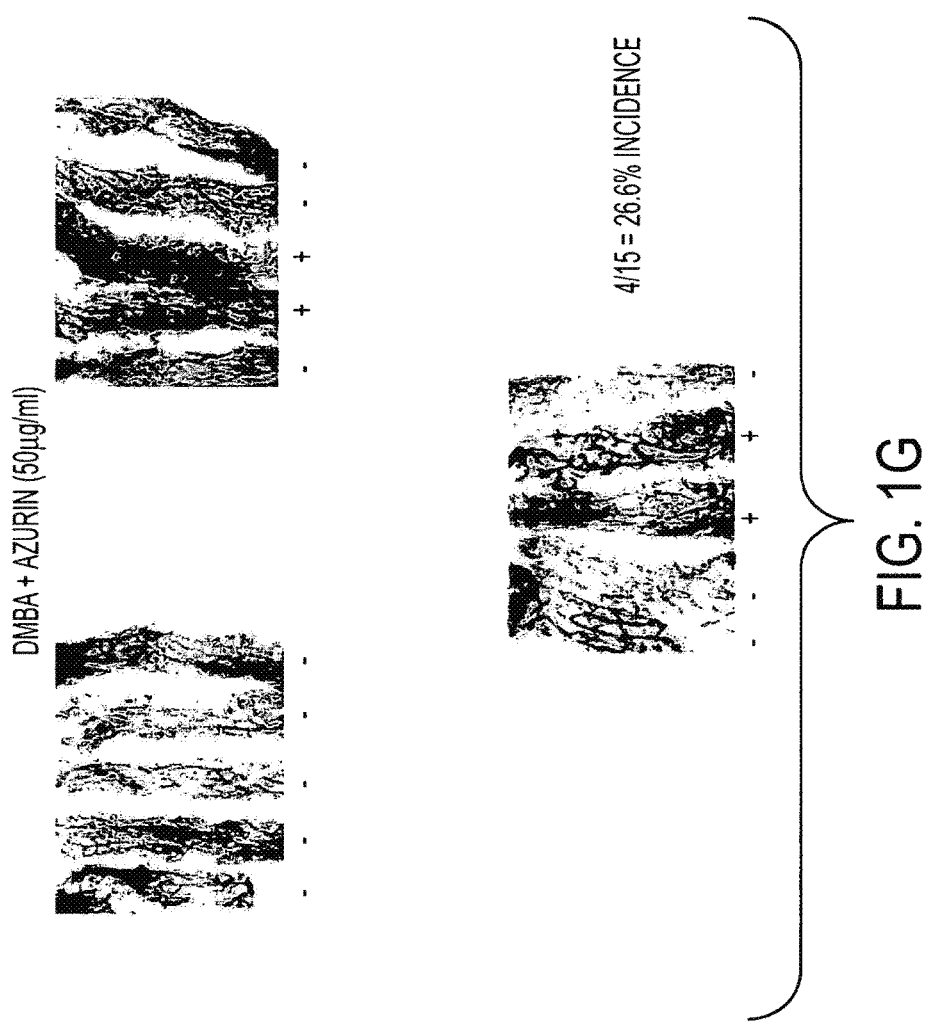

EXAMPLES OF DMBA-INDUCED MAMMARY DUCTAL LESIONS
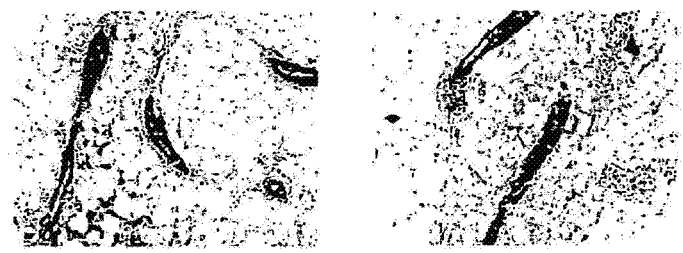
CONTROL DMBA ALONE
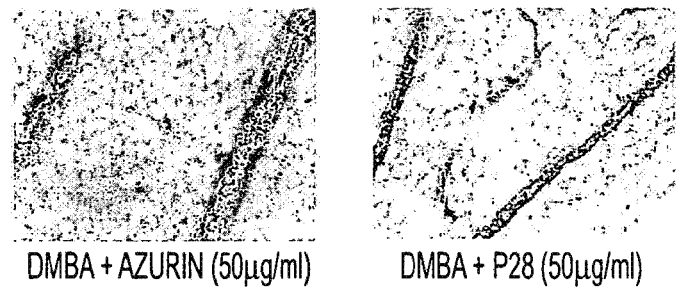
DMBA + AZURIN (50µg/ml)   DMBA + P28 (50µg/ml)
FIG. 3

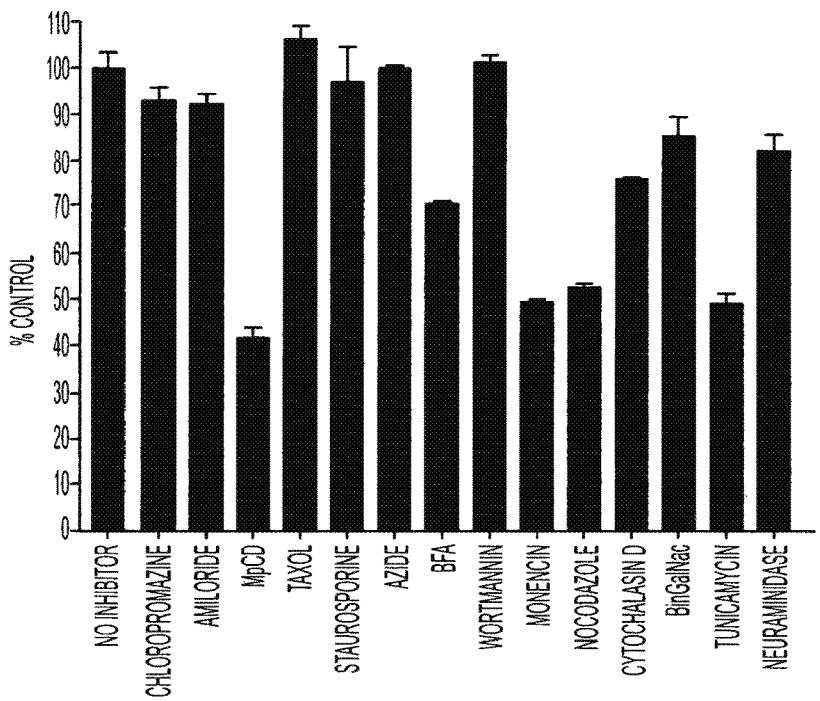
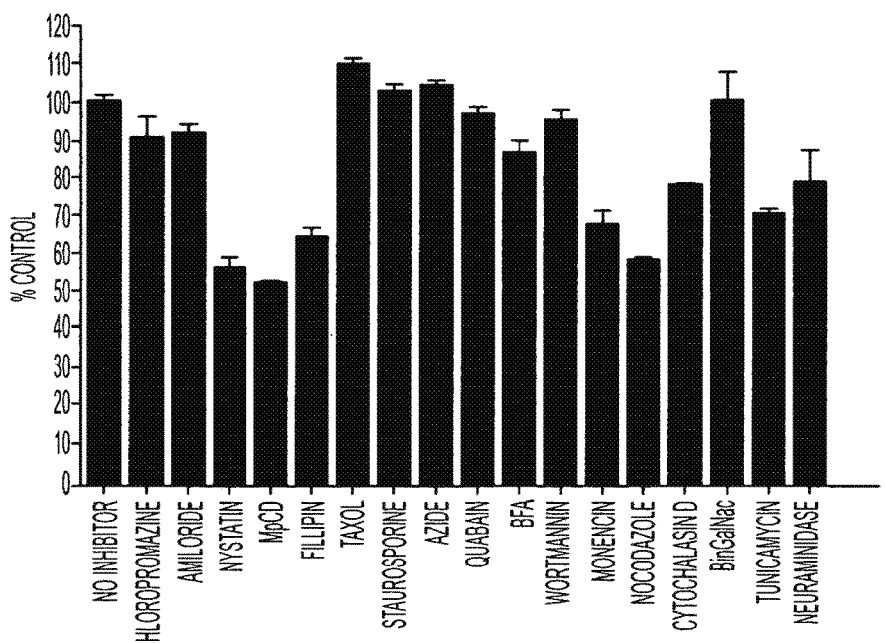
FIG. 14B

MEL-23 TUMOR ARG-8 200uM CONC. INJECTED 3-27-2008.
20 HOURS  48 HOURS 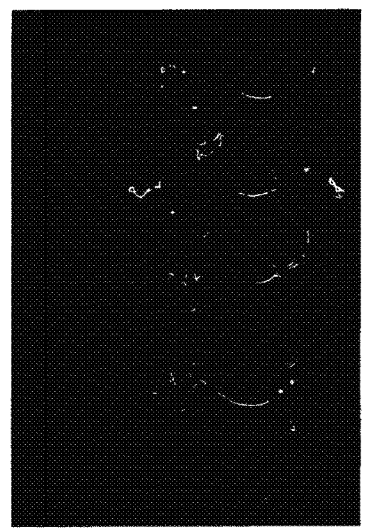
20mg/kg p28
20mg/kg p28
CONTROL PBS
CONTROL PBS
BLANK
FIG. 18C

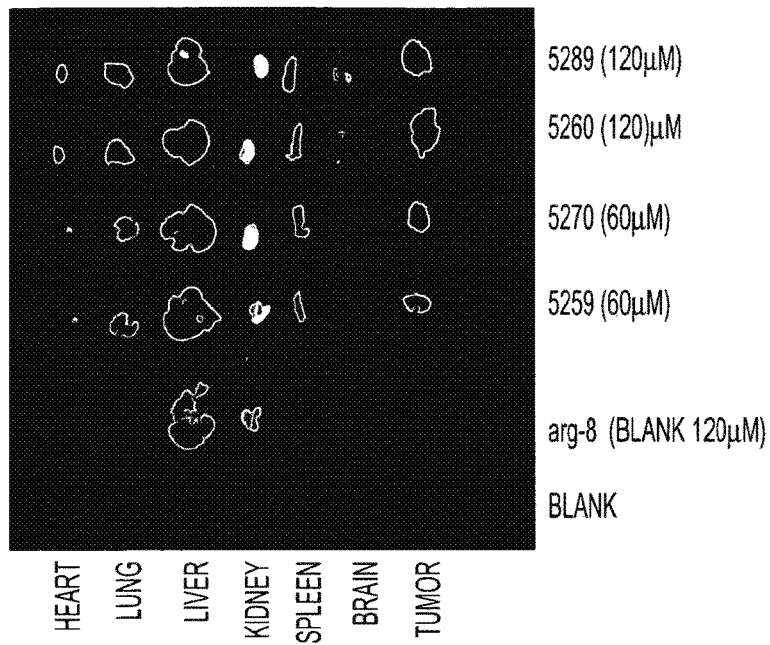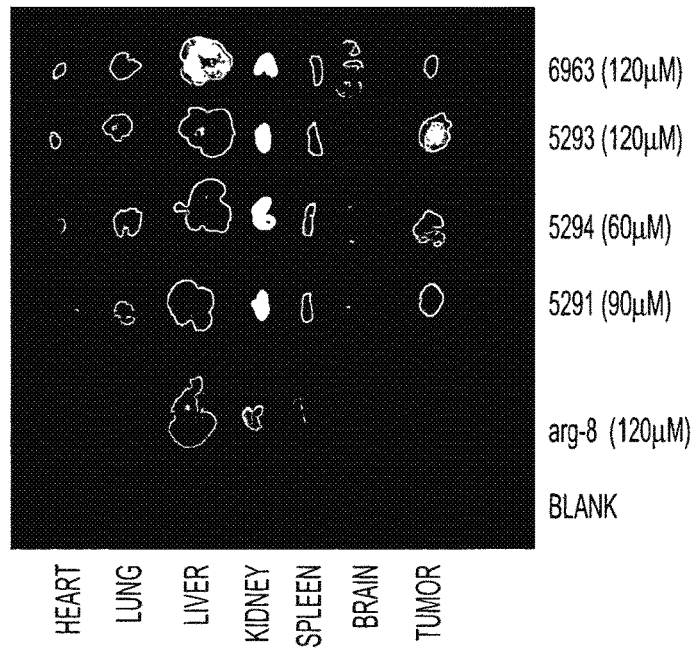
FIG. 35A

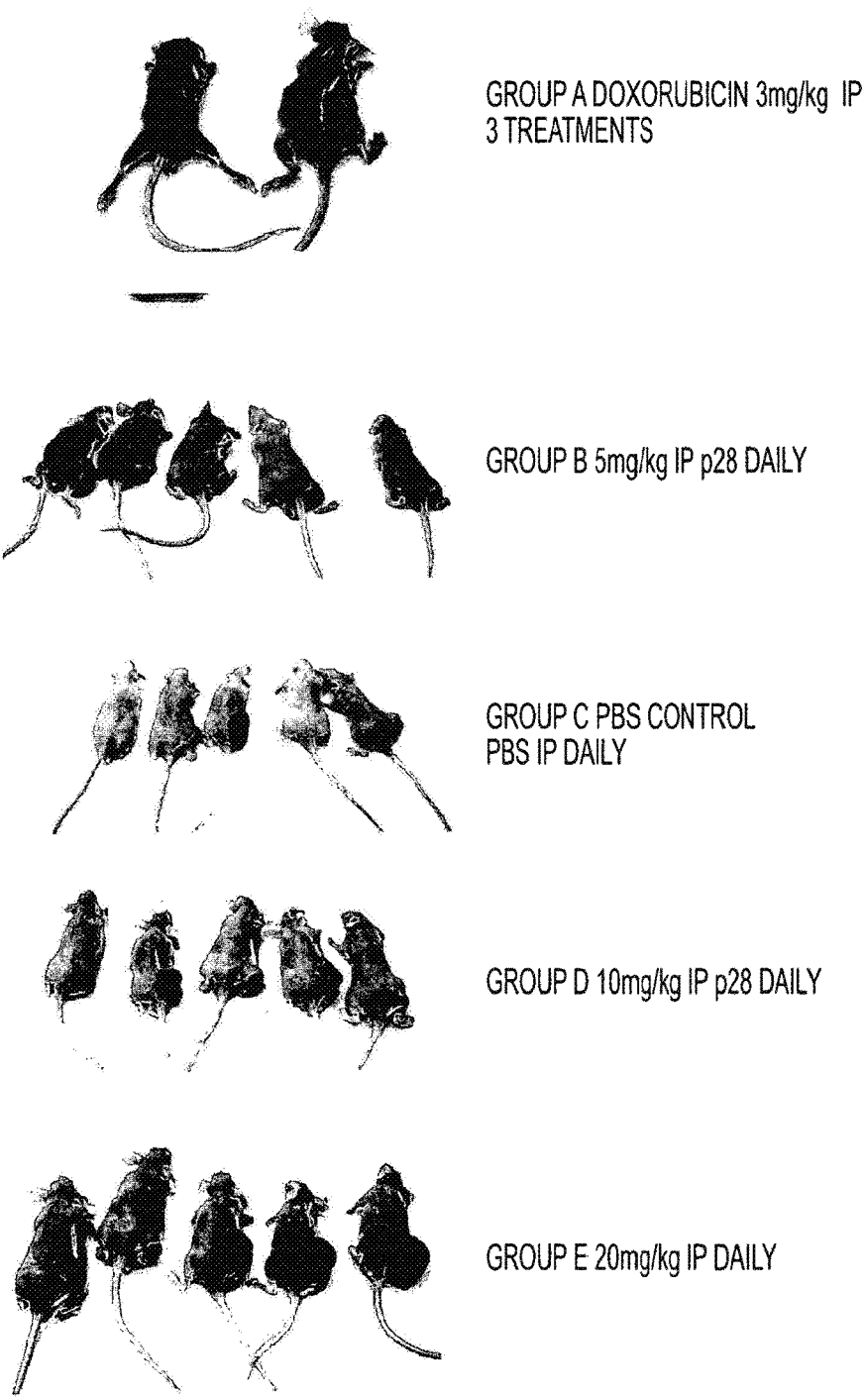
FIG. 39A-E

16 HOURS (4-1-2008)

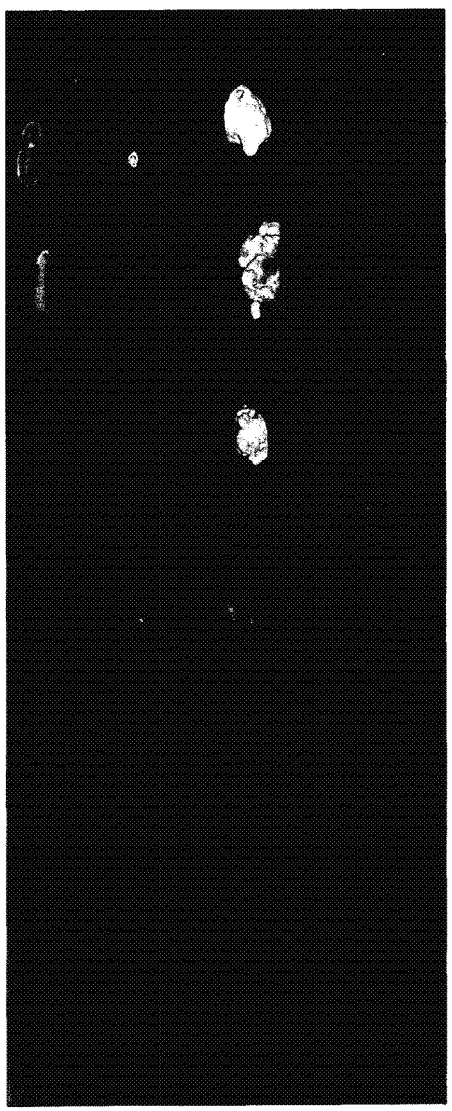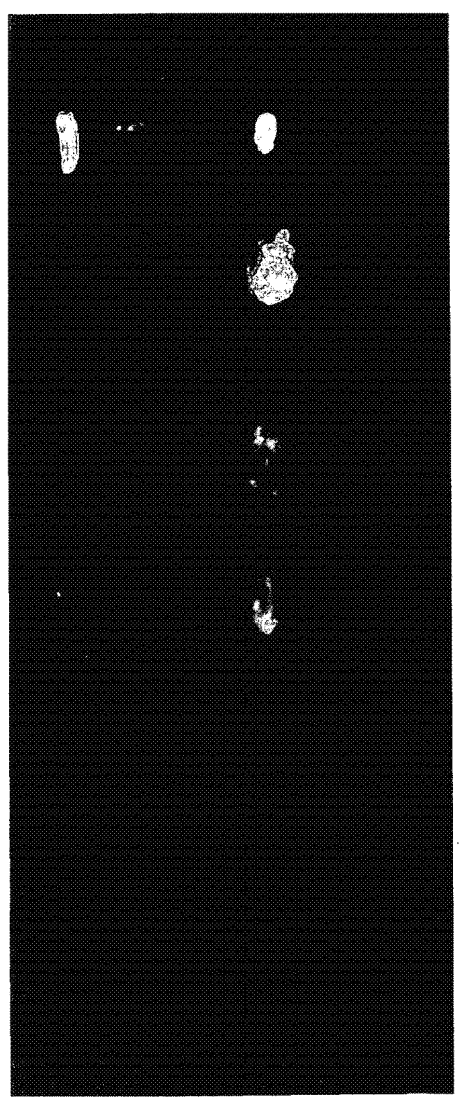
FIG. 45B

22 HOURS POST PEPTIDE INJECTION (TWO ANIMALS DEAD APPROX 3 HOURS) DISCOVERED AND SCANNED

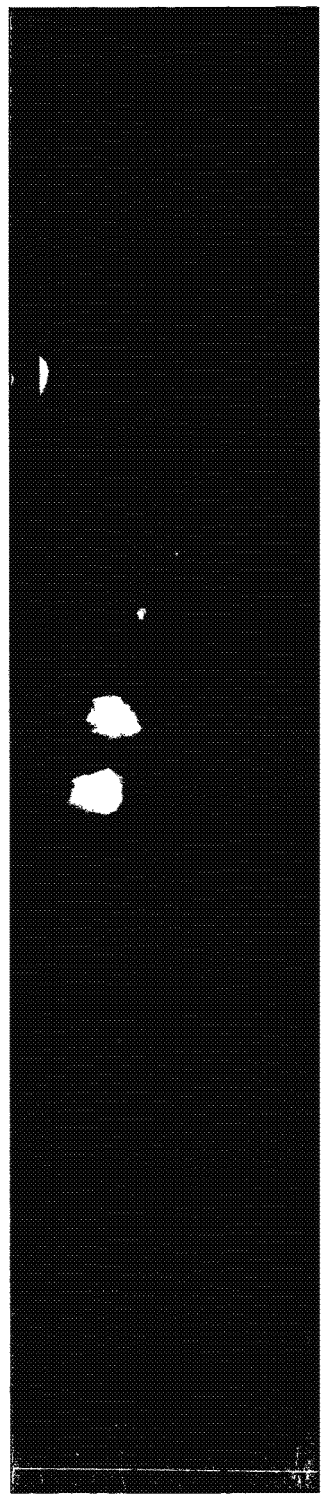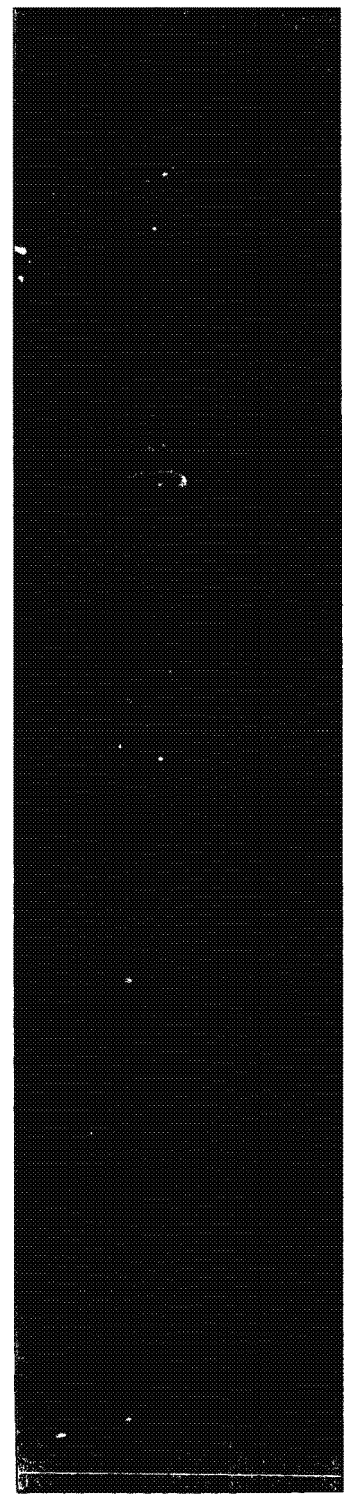
FIG. 48A

AZURIN TRUNCATION WITH ALPHA-HELICAL STRUCTURE

RESULT OF 70 ns SIMULATION

MEASUREMENT OF THIOETHER BRIDGE POSITIONS BASED ON DISTANCES BETWEEN Cα ATOMS IN A STIMULATED STRUCTURE

METHODS TO TREAT CANCER WITH CUPREDOXINS

RELATED APPLICATIONS

This application claims priority under 35 U.S.C. §§ 119 and 120 to and is a continuation in part of U.S. patent application Ser. No. 12/314,703, filed on Dec. 15, 2008 now abandoned, which claims priority to U.S. Patent Application Ser. No. 61/013,709, filed on Dec. 14, 2007; and is a continuation in part of Ser. No. 12/028,683, filed Feb. 8, 2008 now U.S. Pat. No. 8,232,244, which claims priority to U.S. Patent Application Ser. No. 60/900,098, filed Feb. 8, 2007; and is a continuation in part of application Ser. No. 11/488,693, filed Jul. 19, 2006 now U.S. Pat. No. 7,556,810, which claims priority to U.S. Patent Application Ser. No. 60/700,297, filed Jul. 19, 2005; and is a continuation in part of U.S. patent application Ser. No. 11/244,105, filed Oct. 6, 2005 now U.S. Pat. No. 7,691,383, which claims priority to U.S. Provisional Patent Application Ser. No. 60/616,782, filed Oct. 7, 2004, and U.S. Provisional Patent Application Ser. No. 60/680,500, filed May 13, 2005.

This application contains one (1) disc containing a sequence listing. The materials recorded in the compact disc are incorporated herein by reference in their entirety. The compact disc contains a single file named "14PR1418.txt" (49 KB, created on Feb. 5, 2009). The compact disc was created on Feb. 5, 2009.

FIELD OF THE INVENTION

The present invention relates to compositions comprising cupredoxins, and variants, derivatives and structural equivalents of cupredoxins that inhibit the development of premalignant lesions in mammalian cells, tissues and animals. The invention also relates to the use of cupredoxins, and variants, derivatives and structurally equivalents of cupredoxins, as chemopreventive agents in mammals to inhibit the development of premalignant lesions, and ultimately cancer.

BACKGROUND

Cancer chemoprevention is the use of natural, synthetic or biologic chemical agents to reverse, suppress, or prevent carcinogenic progression to invasive cancer. Recent clinical trials in preventing cancer in high-risk populations suggest that chemopreventive therapy is a realistic treatment for high-risk patients. Chemopreventive therapy is based on the concepts of multifocal field carcinogenesis and multistep carcinogenesis. In field carcinogenesis, generalized carcinogen exposure throughout the tissue field results in diffuse epithelial injury in tissue and clonal proliferation of the mutated cells. These genetic mutations throughout the field increase the likelihood that one or more premalignant or malignant lesions may develop in the field. Multistep carcinogenesis in the stepwise accumulation of these genetic and phenotypic alterations. Arresting one or more steps in the multistep carcinogenesis may impede or prevent the development of cancer. See generally Tsao et al., CA Cancer J Clin 54:150-180 (2004).

The mouse mammary gland organ culture (MMOC) assay may be used to evaluate the inhibitory effects of potential chemopreventive agents on both hormone-induced structural differentiation of mammary glands and on the development of DMBA-induced prencoplastic hyperplastic alveolar module-like lesions in the gland. Mammary glands from young, virgin animals, when incubated for 6 days in the presence of insulin (I)+prolactin (P)+aldosterone (A), can differentiate into fully-grown glands. These glands morphologically resemble the glands obtained from pregnant mice. Aldosterone can be replaced by estrogen (E)+progesterone (Pg) Inclusion of hydrocortisone (H) to the medium stimulates the functional differentiation of the mammary glands. Mehta and Banerjee, Acta Endocrinol. 80:501 (1975); Mehta and Moon, *Breast Cancer: Treatment and Prognosis* 300, 300 (Basil A Stoll ed., Blackwell Press 1986). Thus, the hormone-induced structural and functional differentiation, observed in this culture system, mimics the responses to hormones observed during various physiological stages of the animal.

Mice exhibit a distinct preneoplastic stage prior to cancer formation in MMOC. Such preneoplastic lesions in C3H mice are induced by murine mammary tumor virus or in BALB/c mice by DMBA. Exposure of the glands to 2 μg/ml DMBA between days 3 and 4 of growth phases followed by regression of the glands for 2-3 weeks in the medium containing only insulin, results in the formation of mammary alveolar lesions (MAL). Hawthorne et al., Pharmaceutical Biology 40:70-74 (2002); Mehta et al., Methods in Cell Science 19:19-24 (1997). Furthermore, transplantation of epithelial cells, prepared from glands containing the DMBA-induced mammary lesions, into syngeneic host resulted in the development of mammary adenocarcinoma. Telang et al., PNAS 76:5886-5890 (1979). Pathologically, these tumors were similar to those observed in vivo when mice of the same strain are administered DMBA. Id.

DMBA-induced mammary lesion formation in MMOC can be inhibited by a variety of classes of chemopreventive agents such as retinoids. These agents include chemopreventive agents derived from the natural products such as brassinin and resveretrol, thiols, antioxidants, inhibitors of ornithine decarboxylase such as OFMO and deguelin, inhibitors of prostaglandin synthesis, Ca regulators, etc. Jang et al., Science 275:218-220 (1997); Mehta, Eur. J. Cancer 36:1275-1282 (2000); Metha et al., J. Natl. Cancer Inst. 89:212-219 (1997). These studies clearly demonstrate that this organ culture system offers a unique model to determine the effectiveness of compounds against mammary carcinogenesis. The results can be expected to closely correlate to the inhibition obtained by in vivo administration of such compounds.

The MMOC may also be induced to form mammary ductal lesions (MDL). The MDL can be induced if estrogen and progesterone instead of aldosterone and hydrocortisone are included in the medium. The alveolar structures in the presence of ovarian steroids are very small but the intraductal lesions are observed in histopathological sections. Mehta et al., J. Natl. Cancer Inst. 93:1103-1106 (2001). The antiestrogens, which selectively work on ovarian hormone dependent ER+breast cancers such as tamoxifen, inhibited MDL formation and not MAL. Thus, this modified culture model in addition to conventional MAL induction protocol now can be used to evaluate effects of chemopreventive agents on both MAL and MOL.

The entry of a protein into a mammalian cell is often dictated by a small segment of the protein, which is commonly referred to as a "protein transduction domain" or PTD. This segment can be used as a signal attached to a foreign protein to facilitate transport of such a protein into a mammalian cell. For example, amphipathic peptides are used to facilitate uptake of DNA-cleaving metalloporphyrins as potential antitumor drugs in human fibroblasts HS68 or murine lymphocytic leukemia $L_{1210}$ cells (Chaloin, L. et al Bioconjugate Chem. 12:691-700, (2001)).

Peptides called cell-penetrating peptides (CPPs) or cell-delivery vectors (CDVs), such as penetratin, transportan, Tat (amino acids 47-57 or 48-60), and the model amphipathic peptide MAP, are short, amphipathic and cationic peptides and peptide derivatives, usually containing multiple lysine and arginine residues. Fischer, P. M., Med Res Rev, 27: 755-795 (2007). They form a class of small molecules receiving significant attention as potential transport agents or delivery vehicles for a variety of cargoes, including cytotoxic drugs, anti-sense oligo-nucleotides, proteins, and peptides, in gene therapy, and as decoy peptides. Hallbrink, M. et al. Biochim. Biophys. Acta 1515: 101-109 (2001); Lindgren, M., et al. Trends Pharmacol. Sci. 21: 99-103 (2000); Gusarova, et al, J Clin Invest, 117: 99-111 (2007); Melnick, A., Biochem Soc Trans, 35: 802-806 (2007); Astriab-Fisher et al., Pharm Res, 19: 744-754 (2002); El-Andaloussi et al., J Gene Med, 8: 1262-1273 (2006); Cashman et al., Mol Ther, 6: 813-823 (2002).

SUMMARY OF THE EMBODIMENTS

The present invention relates to compositions and methods comprising peptides that may be cupredoxins or variants, derivatives and structural equivalents of cupredoxins that preferentially enter cells and also inhibit the development of premalignant lesions in mammalian cells, tissues and animals.

The present invention further relates to methods comprising killing a cancer cell by contacting the cancer cell with a cytotoxic cupredoxin, wherein the cytotoxic cupredoxin preferentially enters the cancer cell via one or more endocytic pathways, and wherein the cytotoxic cupredoxin is a truncation of azurin, and wherein the truncation of azurin comprises one or more of the amino acids from the C-terminus of SEQ ID NO: 2. In some embodiments, the truncation of azurin is from *Pseudomonas aeruginosa*. In other embodiments, the truncation of azurin comprises SEQ ID NO: 2. In yet other embodiments, the truncation of azurin consists of SEQ ID NO: 2.

In another embodiment, the cytotoxic cupredoxin preferentially enters the cancer cell via caveolae-mediated endocytosis. In another embodiment, the entry of the cytotoxic cupredoxin into the cancer cell is mediated by the Golgi apparatus.

In a further embodiment, the cytotoxic cupredoxin comprises amino acids capable of contacting the cell membrane of the cancer cell irrespective of the cancer cell's status. In some embodiments, the cytotoxic cupredoxin contacts amino acids, cell surface peptides, and/or receptors on the cell membrane. In some embodiments, the cytotoxic cupredoxin may comprise each of the amino acids located at positions 69, 70, 75, 76, and 85 of SEQ ID NO: 1. In another embodiment, the cytotoxic cupredoxin comprises one or more of the amino acids located at positions 69, 70, 75, 76, and 85 of SEQ ID NO: 1. In any of these embodiments, these amino acids may be located at positions within the cytotoxic cupredoxin similar or homologous to those of SEQ ID NO: 1.

In another embodiment, the cytotoxic cupredoxin comprises an amino acid sequence selected from the group consisting of SEQ ID NO: 35, SEQ ID NO: 36, and SEQ ID NO: 37. In another embodiment, the cytotoxic cupredoxin consists of an amino acid sequence selected from the group consisting of SEQ ID NO: 35, SEQ ID NO: 36, and SEQ ID NO: 37.

The present invention further relates to isolated peptides capable of contacting the cell membrane of a cancer cell, entering the cancer cell via caveolae-mediated endocytosis, and killing the cancer cell, wherein the isolated peptides comprise the C-terminal amino acids of SEQ ID NO: 2. In some embodiments, the isolated peptide contacts amino acids, cell surface peptides, and/or receptors on the cell membrane. In some embodiments, the entry of the isolated peptide into the cancer cell is mediated by the Golgi apparatus. In other embodiments, the isolated peptide is from *Psuedomonas aeruginosa*. In further embodiments, the isolated peptide comprises SEQ ID NO: 2. In other embodiments, the isolated peptide consists of SEQ ID NO: 2. In yet other embodiments, the isolated peptide consists of the C-terminal amino acids of SEQ ID NO: 2. For example, the isolated peptide may comprise an amino acid sequence selected from the group consisting of SEQ ID NO: 35, SEQ ID NO: 36, and SEQ ID NO: 37 SEQ ID NO: 36. In another embodiment, the isolated peptide consists of an amino acid sequence selected from the group consisting of SEQ ID NO: 35, SEQ ID NO: 36, and SEQ ID NO: 37 SEQ ID NO: 36.

The present invention also relates to isolated peptides capable of contacting the cell membrane of a cancer cell, entering the cancer cell via caveolae-mediated endocytosis, and killing the cancer cell, wherein the isolated peptides comprise one or more of the amino acids found at positions 69, 70, 75, 76, and 85 of SEQ ID NO: 1. In further embodiments, an isolated peptide comprises each of the amino acids located at positions 69, 70, 75, 76, and 85 of SEQ ID NO: 1. In these embodiments, these amino acids may be located at positions within the isolated peptide similar or homologous to those of SEQ ID NO: 1. In some embodiments, the isolated peptide contacts amino acids, cell surface peptides, and/or receptors on the cell membrane.

The invention further relates to a pharmaceutical composition comprising one or more of the isolated peptides described above. In some embodiments, the pharmaceutical composition further comprises a pharmaceutically acceptable carrier. In other embodiments, in the pharmaceutically acceptable carrier is suitable for intravenous administration.

The invention further relates to a method comprising treating a mammalian patient by administering to the patient a therapeutically effective amount of one or more of the pharmaceutical compositions of the invention. In some embodiments, the patient is human. In other embodiments, the patient is at a higher risk to develop cancer than the general population. In further embodiments, the cancer is selected from melanoma, breast, pancreas, glioblastoma, astrocytoma, lung, colorectal, neck and head, bladder, prostate, skin, and cervical cancer. In other embodiments, the patient has at least one high risk feature. In another embodiment, the patient has premalignant lesions. In another embodiment, the patient has been cured of cancer or premalignant lesions. In some embodiments, the pharmaceutical composition is administered by a mode selected from the group consisting of intravenous injection, intramuscular injection, subcutaneous injection, inhalation, topical administration, transdermal patch, suppository, vitreous injection and oral. In a specific embodiment, the mode of administration is by intravenous injection.

The invention further relates to a kit comprising one or more of the pharmaceutical compositions of the invention in a vial. In some embodiments, the kit further comprises an apparatus to administer the active composition to a patient.

The invention further relates to a pharmaceutical composition comprising one or more of the isolated peptides of the invention and a cargo compound. In some embodiments, the isolated peptide is linked to the cargo compound. In one specific embodiment, the cargo compound is Tamoxifen. In other embodiments, the cargo compound is selected from the group consisting of a protein, lipoprotein, polypeptide, peptide, polysaccharide, nucleic acid, dye, microparticle, nanoparticle, toxin, and drug. In another embodiment, the cargo compound is a detectable substance. For example, the cargo compound may be an X-ray contrast agent detectable by X-ray CT, a magnetic resonance imaging contrast agent detectable by MRI, or an ultrasound contrast agent and is detectable by ultrasound. In some embodiments, the pharmaceutical composition further comprises a pharmaceutically acceptable carrier.

The invention also relates to a method comprising delivering a cargo compound into a cell by contacting the cell with a pharmaceutical composition comprising one or more of the isolated peptides described above and a cargo compound, as described above.

These and other aspects, advantages, and features of the invention will become apparent from the following figures and detailed description of the specific embodiments.

BRIEF DESCRIPTION OF THE SEQUENCES

SEQ ID NO: 1. Amino acid sequence of azurin from *Pseudomonas aeruginosa*
(Ala Glu Cys Ser Val Asp Ile Gln Gly Asn Asp Gln
Met Gln Phe Asn Thr Asn Ala Ile Thr Val Asp Lys
Ser Cys Lys Gln Phe Thr Val Asn Leu Ser His Pro
Gly Asn Leu Pro Lys Asn Val Met Gly His Asn Trp
Val Leu Ser Thr Ala Ala Asp Met Gln Gly Val Val
Thr Asp Gly Met Ala Ser Gly Leu Asp Lys Asp Tyr
Leu Lys Pro Asp Asp Ser Arg Val Ile Ala His Thr
Lys Leu Ile Gly Ser Gly Glu Lys Asp Ser Val Thr
Phe Asp Val Ser Lys Leu Lys Glu Gly Glu Gln Tyr
Met Phe Phe Cys Thr Phe Pro Gly His Ser Ala Leu
Met Lys Gly Thr Leu Thr Leu Lys).

SEQ ID NO: 2. Amino acid sequence of p28, *Pseudomonas aeruginosa* azurin residues 50-77
(Leu Ser Thr Ala Ala Asp Met Gln Gly Val Val Thr
Asp Gly Met Ala Ser Gly Leu Asp Lys Asp Tyr Leu
Lys Pro Asp Asp).

SEQ ID NO: 3. Amino acid sequence of plastocyanin from *Phormidium laminosum*
(Glu Thr Phe Thr Val Lys Met Gly Ala Asp Ser Gly
Leu Leu Gln Phe Glu Pro Ala Asn Val Thr Val His
Pro Gly Asp Thr Val Lys Trp Val Asn Asn Lys Leu
Pro Pro His Asn Ile Leu Phe Asp Asp Lys Gln Val
Pro Gly Ala Ser Lys Glu Leu Ala Asp Lys Leu Ser
His Ser Gln Leu Met Phe Ser Pro Gly Glu Ser Tyr
Glu Ile Thr Phe Ser Ser Asp Phe Pro Ala Gly Thr
Tyr Thr Tyr Tyr Cys Ala Pro His Arg Gly Ala Gly
Met Val Gly Lys Ile Thr Val Glu Gly).

SEQ ID NO: 4. Amino acid sequence of rusticyanin from *Thiobacillus ferrooxidans*
(Gly Thr Leu Asp Thr Thr Trp Lys Glu Ala Thr Leu
Pro Gln Val Lys Ala Met Leu Glu Lys Asp Thr Gly
Lys Val Ser Gly Asp Thr Val Thr Tyr Ser Gly Lys
Thr Val His Val Val Ala Ala Ala Val Leu Pro Gly
Phe Pro Phe Pro Ser Phe Glu Val His Asp Lys Lys
Asn Pro Thr Leu Glu Ile Pro Ala Gly Ala Thr Val
Asp Val Thr Phe Ile Asn Thr Asn Lys Gly Phe Gly
His Ser Phe Asp Ile Thr Lys Lys Gly Pro Pro Tyr
Ala Val Met Pro Val Ile Asp Pro Ile Val Ala Gly
Thr Gly Phe Ser Pro Val Pro Lys Asp Gly Lys Phe
Gly Tyr Thr Asp Phe Thr Trp His Pro Thr Ala Gly
Thr Tyr Tyr Tyr Val Cys Gln Ile Pro Gly His Ala
Ala Thr Gly Met Phe Gly Lys Ile Val Val Lys).

SEQ ID NO: 5. Amino acid sequence of pseudoazurin from *Achromobacter cycloclastes*
(Ala Asp Phe Glu Val His Met Leu Asn Lys Gly Lys
Asp Gly Ala Met Val Phe Glu Pro Ala Ser Leu Lys
Val Ala Pro Gly Asp Thr Val Thr Phe Ile Pro Thr
Asp Lys Gly His Asn Val Glu Thr Ile Lys Gly Met
Ile Pro Asp Gly Ala Gln Ala Phe Lys Ser Lys Ile
Asn Glu Asn Tyr Lys Val Thr Phe Thr Ala Pro Gly
Val Tyr Gly Val Lys Cys Thr Pro His Tyr Gly Met
Gly Met Val Gly Val Val Gln Val Gly Asp Ala Pro
Ala Asn Leu Glu Ala Val Lys Gly Ala Lys Asn Pro
Lys Lys Ala Gln Glu Arg Leu Asp Ala Ala Leu Ala
Ala Leu Gly Asn).

SEQ ID NO: 6. Amino acid sequence of azurin from *Alcaligenes faecalis*
(Ala Cys Asp Val Ser Ile Glu Gly Asn Asp Ser Met
Gln Phe Asn Thr Lys Ser Ile Val Val Asp Lys Thr
Cys Lys Glu Phe Thr Ile Asn Leu Lys His Thr Gly
Lys Leu Pro Lys Ala Ala Met Gly His Asn Val Val
Val Ser Lys Lys Ser Asp Glu Ser Ala Val Ala Thr
Asp Gly Met Lys Ala Gly Leu Asn Asn Asp Tyr Val
Lys Ala Gly Asp Glu Arg Val Ile Ala His Thr Ser
Val Ile Gly Gly Gly Glu Thr Asp Ser Val Thr Phe
Asp Val Ser Lys Leu Lys Glu Gly Glu Asp Tyr Ala
Phe Phe Cys Ser Phe Pro Gly His Trp Ser Ile Met
Lys Gly Thr Ile Glu Leu Gly Ser).

SEQ ID NO: 7. Amino acid sequence of azurin from *Achromobacter xylosoxidans* ssp. *denitrificans* I
(Ala Gln Cys Glu Ala Thr Ile Glu Ser Asn Asp Ala Met Gln Tyr Asn Leu Lys Glu Met Val Val Asp Lys Ser Cys Lys Gln Phe Thr Val His Leu Lys His Val Gly Lys Met Ala Lys Val Ala Met Gly His Asn Trp Val Leu Thr Lys Glu Ala Asp Lys Gln Gly Val Ala Thr Asp Gly Met Asn Ala Gly Leu Ala Gln Asp Tyr Val Lys Ala Gly Asp Thr Arg Val Ile Ala His Thr Lys Val Ile Gly Gly Gly Glu Ser Asp Ser Val Thr Phe Asp Val Ser Lys Leu Thr Pro Gly Glu Ala Tyr Ala Tyr Phe Cys Ser Phe Pro Gly His Trp Ala Met Met Lys Gly Thr Leu Lys Leu Ser Asn).

SEQ ID NO: 8. Amino acid sequence of azurin from *Bordetella bronchiseptica*
(Ala Glu Cys Ser Val Asp Ile Ala Gly Thr Asp Gln Met Gln Phe Asp Lys Lys Ala Ile Glu Val Ser Lys Ser Cys Lys Gln Phe Thr Val Asn Leu Lys His Thr Gly Lys Leu Pro Arg Asn Val Met Gly His Asn Trp Val Leu Thr Lys Thr Ala Asp Met Gln Ala Val Glu Lys Asp Gly Ile Ala Ala Gly Leu Asp Asn Gln Tyr Leu Lys Ala Gly Asp Thr Arg Val Leu Ala His Thr Lys Val Leu Gly Gly Gly Glu Ser Asp Ser Val Thr Phe Asp Val Ala Lys Leu Ala Ala Gly Asp Asp Tyr Thr Phe Phe Cys Ser Phe Pro Gly His Gly Ala Leu Met Lys Gly Thr Leu Lys Leu Val Asp).

SEQ ID NO: 9. Amino acid sequence of azurin from *Methylomonas* sp. J
(Ala Ser Cys Glu Thr Thr Val Thr Ser Gly Asp Thr Met Thr Tyr Ser Thr Arg Ser Ile Ser Val Pro Ala Ser Cys Ala Glu Phe Thr Val Asn Phe Glu His Lys Gly His Met Pro Lys Thr Gly Met Gly His Asn Trp Val Leu Ala Lys Ser Ala Asp Val Gly Asp Val Ala Lys Glu Gly Ala His Ala Gly Ala Asp Asn Asn Phe Val Thr Pro Gly Asp Lys Arg Val Ile Ala Phe Thr Pro Ile Ile Gly Gly Gly Glu Lys Thr Ser Val Lys Phe Lys Val Ser Ala Leu Ser Lys Asp Glu Ala Tyr Thr Tyr Phe Cys Ser Tyr Pro Gly His Phe Ser Met Met Arg Gly Thr Leu Lys Leu Glu Glu).

SEQ ID NO: 10. Amino acid sequence of azurin from *Neisseria meningitidis* Z2491
(Cys Ser Gln Glu Pro Ala Ala Pro Ala Ala Glu Ala Thr Pro Ala Ala Glu Ala Pro Ala Ser Glu Ala Pro Ala Ala Glu Ala Ala Pro Ala Asp Ala Ala Glu Ala Pro Ala Ala Gly Asn Cys Ala Ala Thr Val Glu Ser Asn Asp Asn Met Gln Phe Asn Thr Lys Asp Ile Gln Val Ser Lys Ala Cys Lys Glu Phe Thr Ile Thr Leu Lys His Thr Gly Thr Gln Pro Lys Thr Ser Met Gly His Asn Ile Val Ile Gly Lys Thr Glu Asp Met Asp Gly Ile Phe Lys Asp Gly Val Gly Ala Ala Asp Thr Asp Tyr Val Lys Pro Asp Asp Ala Arg Val Val Ala His Thr Lys Leu Ile Gly Gly Gly Glu Glu Ser Ser Leu Thr Leu Asp Pro Ala Lys Leu Ala Asp Gly Glu Tyr Lys Phe Ala Cys Thr Phe Pro Gly His Gly Ala Leu Met Asn Gly Lys Val Thr Leu Val Asp).

SEQ ID NO: 11. Amino acid sequence of azurin from *Pseudomonas fluorescen*
(Ala Glu Cys Lys Thr Thr Ile Asp Ser Thr Asp Gln Met Ser Phe Asn Thr Lys Ala Ile Glu Ile Asp Lys Ala Cys Lys Thr Phe Thr Val Glu Leu Thr His Ser Gly Ser Leu Pro Lys Asn Val Met Gly His Asn Leu Val Ile Ser Lys Gln Ala Asp Met Gln Pro Ile Ala Thr Asp Gly Leu Ser Ala Gly Ile Asp Lys Asn Tyr Leu Lys Glu Gly Asp Thr Arg Val Ile Ala His Thr Lys Val Ile Gly Ala Gly Glu Lys Asp Ser Leu Thr Ile Asp Val Ser Lys Leu Asn Ala Ala Glu Lys Tyr Gly Phe Phe Cys Ser Phe Pro Gly His Ile Ser Met Met Lys Gly Thr Val Thr Leu Lys).

SEQ ID NO: 12. Amino acid sequence of azurin from *Pseudomonas chlororaphis*
(Ala Glu Cys Lys Val Asp Val Asp Ser Thr Asp Gln Met Ser Phe Asn Thr Lys Glu Ile Thr Ile Asp Lys Ser Cys Lys Thr Phe Thr Val Asn Leu Thr His Ser Gly Ser Leu Pro Lys Asn Val Met Gly His Asn Trp Val Leu Ser Lys Ser Ala Asp Met Ala Gly Ile Ala Thr Asp Gly Met Ala Ala Gly Ile Asp Lys Asp Tyr Leu Lys Pro Gly Asp Ser Arg Val Ile Ala His Thr Lys Ile Ile Gly Ser Gly Glu Lys Asp Ser Val Thr Phe Asp Val Ser Lys Leu Thr Ala Gly Glu Ser Tyr Glu Phe Phe Cys Ser Phe Pro Gly His Asn Ser Met Met Lys Gly Ala Val Val Leu Lys).

SEQ ID NO: 13. Amino acid sequence of azurin from *Xylella fastidiosa* 9a5c
(Lys Thr Cys Ala Val Thr Ile Ser Ala Asn Asp Gln Met Lys Phe Asp Gln Asn Thr Ile Lys Ile Ala Ala Glu Cys Thr His Val Asn Leu Thr Leu Thr His Thr Gly Lys Lys Ser Ala Arg Val Met Gly His Asn Trp Val Leu Thr Lys Thr Thr Asp Met Gln Ala Val Ala -continued Leu Ala Gly Leu His Ala Thr Leu Ala Asp Asn Tyr Val Pro Lys Ala Asp Pro Arg Val Ile Ala His Thr Ala Ile Ile Gly Gly Gly Glu Arg Thr Ser Ile Thr Phe Pro Thr Asn Thr Leu Ser Lys Asn Val Ser Tyr Thr Phe Phe Cys Ser Phe Pro Gly His Trp Ala Leu Met Lys Gly Thr Leu Asn Phe Gly Gly).

SEQ ID NO: 14. Amino acid sequence of stellacyanin from *Cucumis sativus*
(Met Gln Ser Thr Val His Ile Val Gly Asp Asn Thr Gly Trp Ser Val Pro Ser Ser Pro Asn Phe Tyr Ser Gln Trp Ala Ala Gly Lys Thr Phe Arg Val Gly Asp Ser Leu Gln Phe Asn Phe Pro Ala Asn Ala His Asn Val His Glu Met Glu Thr Lys Gln Ser Phe Asp Ala Cys Asn Phe Val Asn Ser Asp Asn Asp Val Glu Arg Thr Ser Pro Val Ile Glu Arg Leu Asp Glu Leu Gly Met His Tyr Phe Val Cys Thr Val Gly Thr His Cys Ser Asn Gly Gln Lys Leu Ser Ile Asn Val Val Ala Ala Asn Ala Thr Val Ser Met Pro Pro Pro Ser Ser Ser Pro Pro Ser Ser Val Met Pro Pro Pro Val Met Pro Pro Pro Ser Pro Ser).

SEQ ID NO: 15. Amino acid sequence of auracyanin A from *Chloroflexus aurantiacus*
(Met Lys Ile Thr Leu Arg Met Met Val Leu Ala Val Leu Thr Ala Met Ala Met Val Leu Ala Ala Cys Gly Gly Gly Gly Ser Ser Gly Gly Ser Thr Gly Gly Gly Ser Gly Ser Gly Pro Val Thr Ile Glu Ile Gly Ser Lys Gly Glu Glu Leu Ala Phe Asp Lys Thr Glu Leu Thr Val Ser Ala Gly Gln Thr Val Thr Ile Arg Phe Lys Asn Asn Ser Ala Val Gln Gln His Asn Trp Ile Leu Val Lys Gly Gly Glu Ala Glu Ala Ala Asn Ile Ala Asn Ala Gly Leu Ser Ala Gly Pro Ala Ala Asn Tyr Leu Pro Ala Asp Lys Ser Asn Ile Ile Ala Glu Ser Pro Leu Ala Asn Gly Asn Glu Thr Val Glu Val Thr Phe Thr Ala Pro Ala Ala Gly Thr Tyr Leu Tyr Ile Cys Thr Val Pro Gly His Tyr Pro Leu Met Gln Gly Lys Leu Val Val Asn).

SEQ ID NO: 16. Amino acid sequence of auracyanin B from *Chloroflexus aurantiacus*
(Ala Ala Asn Ala Pro Gly Gly Ser Asn Val Val Asn Glu Thr Pro Ala Gln Thr Val Glu Val Arg Ala Ala Pro Asp Ala Leu Ala Phe Ala Gln Thr Ser Leu Ser Leu Pro Ala Asn Thr Val Val Arg Leu Asp Phe Val Asn Gln Asn Asn Leu Gly Val Gln His Asn Trp Val Leu Val Asn Gly Gly Asp Asp Val Ala Ala Ala Val -continued Asn Thr Ala Ala Gln Asn Asn Ala Asp Ala Leu Phe Val Pro Pro Asp Thr Pro Asn Ala Leu Ala Trp Thr Ala Met Leu Asn Ala Gly Glu Ser Gly Ser Val Thr Phe Arg Thr Pro Ala Pro Gly Thr Tyr Leu Tyr Ile Cys Thr Phe Pro Gly His Tyr Leu Ala Gly Met Lys Gly Thr Leu Thr Val Thr Pro).

SEQ ID NO: 17. Amino acid sequence of cucumber basic protein from *Cucumis sativus*
(Ala Val Tyr Val Val Gly Gly Ser Gly Gly Trp Thr Phe Asn Thr Glu Ser Trp Pro Lys Gly Lys Arg Phe Arg Ala Gly Asp Ile Leu Leu Phe Asn Tyr Asn Pro Ser Met His Asn Val Val Val Val Asn Gln Gly Gly Phe Ser Thr Cys Asn Thr Pro Ala Gly Ala Lys Val Tyr Thr Ser Gly Arg Asp Gln Ile Lys Leu Pro Lys Gly Gln Ser Tyr Phe Ile Cys Asn Phe Pro Gly His Cys Gln Ser Gly Met Lys Ile Ala Val Asn Ala Leu).

SEQ ID NO: 18. Amino acid sequence of Laz from *Neisseria gonorrhoeae* F62
(Cys Ser Gln Glu Pro Ala Ala Pro Ala Ala Glu Ala Thr Pro Ala Gly Glu Ala Pro Ala Ser Glu Ala Pro Ala Ala Glu Ala Ala Pro Ala Asp Ala Ala Glu Ala Pro Ala Gly Asn Cys Ala Ala Thr Val Glu Ser Asn Asp Asn Met Gln Phe Asn Thr Lys Asp Ile Gln Val Ser Lys Ala Cys Lys Glu Phe Thr Ile Thr Leu Lys His Thr Gly Thr Gln Pro Lys Ala Ser Met Gly His Asn Leu Val Ile Ala Lys Ala Glu Asp Met Asp Gly Val Phe Lys Asp Gly Val Gly Ala Ala Asp Thr Asp Tyr Val Lys Pro Asp Asp Ala Arg Val Val Ala His Thr Lys Leu Ile Gly Gly Gly Glu Glu Ser Ser Leu Thr Leu Asp Pro Ala Lys Leu Ala Asp Gly Asp Tyr Lys Phe Ala Cys Thr Phe Pro Gly His Gly Ala Leu Met Asn Gly Lys Val Thr Leu Val Asp).

SEQ ID NO: 19. Amino acid sequence of the azurin from *Vibrio parahaemolyticus*
(Met Ser Leu Arg Ile Leu Ala Ala Thr Leu Ala Leu Ala Gly Leu Ser Phe Gly Ala Gln Ala Ser Ala Glu Cys Glu Val Ser Ile Asp Ala Asn Asp Met Met Gln Phe Ser Thr Lys Thr Leu Ser Val Pro Ala Thr Cys Lys Glu Val Thr Leu Thr Leu Asn His Thr Gly Lys Met Pro Ala Gln Ser Met Gly His Asn Val Val Ile Ala Asp Thr Ala Asn Ile Gln Ala Val Gly Thr Asp Gly Met Ser Ala Gly Ala Asp Asn Ser Tyr Val Lys Pro Asp Asp Glu Arg Val Tyr Ala His Thr Lys Val -continued Val Gly Gly Gly Glu Ser Thr Ser Ile Thr Phe Ser Thr Glu Lys Met Thr Ala Gly Gly Asp Tyr Ser Phe Phe Cys Ser Phe Pro Gly His Trp Ala Ile Met Gln Gly Lys Phe Glu Phe Lys), SEQ ID NO: 20. Amino acid sequence of amino acids 57 to 89 of auracyanin B of *Chloroflexus aurantiacus*
(His Asn Trp Val Leu Val Asn Gly Gly Asp Asp Val Ala Ala Ala Val Asn Thr Ala Ala Gln Asn Asn Ala Asp Ala Leu Phe Val Pro Pro Pro Asp).

SEQ ID NO: 21. Amino acid sequence of amino acids 51-77 of *Pseudomonas syringae* azurin
(Ser Lys Lys Ala Asp Ala Ser Ala Ile Thr Thr Asp Gly Met Ser Val Gly Ile Asp Lys Asp Tyr Val Lys Pro Asp Asp).

SEQ ID NO: 22. Amino acid sequence of amino acids 89-115 of *Neisseria meningitidis* Laz
(Ile Gly Lys Thr Gln Asp Met Asp Gly Ile Phe Lys Asp Gly Val Gly Ala Ala Asp Thr Asp Tyr Val Lys Pro Asp Asp).

SEQ ID NO: 23. Amino acid sequence of amino acids 52-78 of *Vibrio parahaemolyticus* azurin
(Ala Asp Thr Ala Asn Ile Gln Ala Val Gly Thr Asp Gly Met Ser Ala Gly Ala Asp Asn Ser Tyr Val Lys Pro Asp Asp).

SEQ ID NO: 24. Amino acid sequence of amino acids 51-77 of *Bordetella bronchiseptica* azurin
(Thr Lys Thr Ala Asp Met Gln Ala Val Glu Lys Asp Gly Ile Ala Ala Gly Leu Asp Asn Gln Tyr Leu Lys Ala Gly Asp).

SEQ ID NO: 25. Amino acid sequence of p18, *Pseudomonas aeruginosa* azurin residues 50-67
(Leu Ser Thr Ala Ala Asp Met Gln Gly Val Val Thr Asp Gly Met Ala Ser Gly).

SEQ ID NO: 26. Amino acid sequence of amino acids 36-88 of *Pseudomonas aeruginosa* azurin
(Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly).

SEQ ID NO: 27. Amino acid sequence of amino acids 36 to 77 of *Pseudomonas aeruginosa* azurin
(Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp).

-continued

SEQ ID NO: 28. Amino acid sequence of amino acids 36 to 89 of *Pseudomonas aeruginosa* azurin
(Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly Ser).

SEQ ID NO: 29. Amino acid sequence of amino acids 36 to 128 of *Pseudomonas aeruginosa* azurin
(Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly Ser Gly Glu Lys Asp Ser Val Thr Phe Asp Val Ser Lys Leu Lys Glu Gly Glu Gln Tyr Met Phe Phe Cys Thr Phe Pro Gly His Ser Ala Leu Met Lys Gly Thr Leu Thr Leu Lys).

SEQ ID NO: 30. Amino acid sequence of amino acids 53 to 70 of *Pseudomonas aeruginosa* azurin
(Ala Ala Asp Met Gln Gly Val Val Thr Asp Gly Met Ala Ser Gly Leu Asp Lys).

SEQ ID NO: 31. Amino acid sequence of amino acids 53 to 64 of *Pseudomonas aeruginosa* azurin
(Ala Ala Asp Met Gln Gly Val Val Thr Asp Gly Met).

SEQ ID NO: 32. Amino acid sequence DGXXXXXDXXYXKXXD.

SEQ ID NO: 33. Amino acid sequence DGXXXXDXXYXKXXD.

SEQ ID NO: 34. Amino acid sequence of p18b, *Pseudomonas aeruginosa* azurin residues 60-77
(Val Thr Asp Gly Met Ala Ser Gly Leu Asp Lys Asp Tyr Leu Lys Pro Asp Asp).

SEQ ID NO: 35. Sequence of C-terminal 12 amino acids of p28, *Pseudomonas aeruginosa* azurin residues 66-77 (p12)
(Ser Gly Leu Asp Lys Asp Tyr Leu Lys Pro Asp Asp).

SEQ ID NO: 36. Sequence of C-terminal 10 amino acids of p28, *Pseudomonas aeruginosa* azurin residues 68-77
(Leu Asp Lys Asp Tyr Leu Lys Pro Asp Asp).

SEQ ID NO: 37. Sequence of C-terminal 11 amino acids of p28, *Pseudomonas aeruginosa* azurin residues 67-77
(Gly Leu Asp Lys Asp Tyr Leu Lys Pro Asp Asp).

SEQ ID NO: 38 is the amino acid sequence of a variant of the azurin truncation p28
(Leu Ser Thr Ala Ala Asp Met Gln Ala Val Val Thr Asp Thr Met Ala Ser Gly Leu Asp Lys Asp Tyr Leu Lys Pro Asp Asp).

SEQ ID NO: 39 is the amino acid sequence of a variant of the azurin truncation p28
(Leu Ser Thr Ala Ala Asp Leu Gln Gly Val Val Thr Asp Gly Leu Ala Ser Gly Leu Asp Lys Asp Tyr Leu Lys Pro Asp Asp).

SEQ ID NO: 40 is the amino acid sequence of a variant of the azurin truncation p28
(Leu Ser Thr Ala Ala Asp Val Gln Gly Val Val Thr Asp Gly Val Ala Ser Gly Leu Asp Lys Asp Tyr Leu Lys Pro Asp Asp).

SEQ ID NO: 41 is the amino acid sequence of a modified cupredoxin derived peptide
(Asp Asp Pro Lys Leu Tyr Asp Lys Asp Leu Gly Ser Ala Met Gly Asp Thr Val Val Gly Gln Met Asp Ala Ala Thr Ser Leu).

SEQ ID NO: 42 is the amino acid sequence of a modified cupredoxin derived peptide
(Acetylation-Leu Ser Thr Ala Ala Asp Met Gln Gly Val Val Thr Asp Gly Met Ala Ser Gly Leu Asp Lys Asp Tyr Leu Lys Pro Asp Asp-amidation).

SEQ ID NO: 43 is the amino acid sequence of a hexapeptide
(Val Ser Pro Pro Ala Arg).

SEQ ID NO: 44 is the amino acid sequence of a hexapeptide
(Tyr Thr Pro Pro Ala Leu).

SEQ ID NO: 45 is the amino acid sequence of a hexapeptide
(Phe Ser Phe Phe Ala Phe).

SEQ ID NO: 46 is the amino acid sequence of a modified cupredoxin-derived peptide
(Leu Ser Thr Ala Ala Asp Met Gln Gly Val Val Thr Asp Gly Met Ala Ser Gly Leu Asp Lys Asp Tyr Leu Thr Pro Gly Cys).

SEQ ID NO: 47 is the amino acid sequence of a modified cupredoxin-derived peptide
(Leu Ser Thr Ala Ala Asp Cys Gln Gly Val Val Thr Asp Gly Met Ala Ser Gly Leu Asp Lys Asp Tyr Leu Lys Pro Asp Asp).

SEQ ID NO: 48 is the amino acid sequence of a modified cupredoxin-derived peptide
(Leu Ser Thr Ala Ala Cys Met Gln Gly Val Val Thr Asp Gly Met Ala Ser Gly Leu Asp Lys Asp Tyr Leu Lys Pro Asp Asp).

SEQ ID NO: 49 is the amino acid sequence of a modified cupredoxin-derived peptide
(Leu Ser Thr Ala Cys Asp Met Gln Gly Val Val Thr Asp Gly Met Ala Ser Gly Leu Asp Lys Asp Tyr Leu Lys Pro Asp Asp).

SEQ ID NO: 50 is the amino acid sequence of a modified cupredoxin-derived peptide
(Leu Ser Thr Ala Ala Thr Met Gln Cys Val Val Thr Asp Gly Met Ala Ser Gly Leu Asp Lys Asp Tyr Leu Lys Pro Asp Asp).

SEQ ID NO: 51 is the amino acid sequence of a modified cupredoxin-derived peptide
(Leu Ser Thr Ala Ala Thr Met Gln Gly Cys Val Thr Asp Gly Met Ala Ser Gly Leu Asp Lys Asp Tyr Leu Lys Pro Asp Asp).

SEQ ID NO: 52 is the amino acid sequence of a modified cupredoxin-derived peptide
(Leu Ser Thr Ala Ala Asn Thr Gln Gly Cys Val Thr Asp Gly Met Ala Ser Gly Leu Asp Lys Asp Tyr Leu Lys Pro Asp Asp).

SEQ ID NO: 53 is the amino acid sequence of a modified cupredoxin-derived peptide
(Leu Ser Thr Ala Ala Asn Thr Gln Gly Val Cys Thr Asp Gly Met Ala Ser Gly Leu Asp Lys Asp Tyr Leu Lys Pro Asp Asp).

SEQ ID NO: 54 is the amino acid sequence of a modified cupredoxin-derived peptide
(Leu Ser Thr Ala Ala Asp Met Thr Ala Val Cys Thr Asp Gly Met Ala Ser Gly Leu Asp Lys Asp Tyr Leu Lys Pro Asp Asp).

SEQ ID NO: 55 is the amino acid sequence of a modified cupredoxin-derived peptide
(Leu Ser Thr Ala Ala Asp Met Thr Ala Val Val Cys Asp Gly Met Ala Ser Gly Leu Asp Lys Asp Tyr Leu Lys Pro Asp Asp).

SEQ ID NO: 56 is the amino acid sequence of a modified cupredoxin-derived peptide
(Leu Ser Thr Ala Ala Asp Met Gln Thr Val Val Cys Asp Gly Met Ala Ser Gly Leu Asp Lys Asp Tyr Leu Lys Pro Asp Asp).

SEQ ID NO: 57 is the amino acid sequence of a modified cupredoxin-derived peptide
(Leu Ser Thr Ala Ala Asp Met Gln Thr Val Val Thr Cys Gly Met Ala Ser Gly Leu Asp Lys Asp Tyr Leu Lys Pro Asp Asp).

SEQ ID NO: 58 is the amino acid sequence of a modified cupredoxin-derived peptide
(Leu Ser Thr Ala Ala Asp Met Gln Ala Thr Val Thr Cys Gly Met Ala Ser Gly Leu Asp Lys Asp Tyr Leu Lys Pro Asp Asp).

SEQ ID NO: 59 is the amino acid sequence of a modified cupredoxin-derived peptide
(Leu Ser Thr Ala Ala Asp Met Gln Ala Thr Val Thr Asp Cys Met Ala Ser Gly Leu Asp Lys Asp Tyr Leu Lys Pro Asp Asp).

SEQ ID NO: 60 is the amino acid sequence of a modified cupredoxin-derived peptide
(Leu Ser Thr Ala Ala Asp Met Gln Gly Val Thr Ala Asp Cys Met Ala Ser Gly Leu Asp Lys Asp Tyr Leu Lys Pro Asp Asp).

SEQ ID NO: 61 is the amino acid sequence of a modified cupredoxin-derived peptide
(Leu Ser Thr Ala Ala Asp Met Gln Gly Val Thr Ala Asp Gly Cys Ala Ser Gly Leu Asp Lys Asp Tyr Leu Lys Pro Asp Asp).

SEQ ID NO: 62 is the amino acid sequence of a modified cupredoxin-derived peptide
(Leu Ser Thr Ala Ala Asp Met Gln Gly Val Val Thr Asn Gly Cys Ala Ser Gly Leu Asp Lys Asp Tyr Leu Lys Pro Asp Asp).

SEQ ID NO: 63 is the amino acid sequence of a modified cupredoxin-derived peptide
(Leu Ser Thr Ala Ala Asp Met Gln Gly Val Val Thr Ala Thr Met Gly Ser Gly Leu Cys Lys Asp Tyr Leu Lys Pro Asp Asp).

SEQ ID NO: 64 is the amino acid sequence of a modified cupredoxin-derived peptide
(Leu Ser Thr Ala Ala Asp Met Gln Gly Val Val Thr Asp Leu Thr Ala Ser Gly Leu Cys Lys Asp Tyr Leu Lys Pro Asp Asp).

SEQ ID NO: 65 is the amino acid sequence of a modified cupredoxin-derived peptide
(Leu Ser Trp Ala Ala Asp Met Gln Gly Val Val Thr Asp Gly Met Ala Ser Gly Leu Asp Lys Asp Tyr Leu Lys Pro Asp Asp).

SEQ ID NO: 66 is the amino acid sequence of a modified cupredoxin-derived peptide
(Leu Ser Thr Ala Ala Asp Met Trp Gly Val Val Thr Asp Gly Met Ala Ser Gly Leu Asp Lys Asp Tyr Leu Lys Pro Asp Asp).

SEQ ID NO: 67 is the amino acid sequence of a modified cupredoxin-derived peptide
(Leu Ser Thr Ala Ala Asp Met Gln Gly Val Val Trp Asp Gly Met Ala Ser Gly Leu Asp Lys Asp Tyr Leu Lys Pro Asp Asp).

SEQ ID NO: 68 is the amino acid sequence of a modified cupredoxin-derived peptide
(Leu Ser Thr Ala Ala Asp Met Gln Gly Val Val Thr Asp Trp Met Ala Ser Gly Leu Asp Lys Asp Tyr Leu Lys Pro Asp Asp).

SEQ ID NO: 69 is the amino acid sequence of a modified cupredoxin-derived peptide
(Leu Ser Trp Ala Ala Asp Met Trp Gly Val Val Thr Asp Gly Met Ala Ser Gly Leu Asp Lys Asp Tyr Leu Lys Pro Asp Asp).

SEQ ID NO: 70 is the amino acid sequence of a modified cupredoxin-derived peptide
(Leu Ser Trp Ala Ala Asp Met Gln Gly Val Val Trp Asp Gly Met Ala Ser Gly Leu Asp Lys Asp Tyr Leu Lys Pro Asp Asp).

SEQ ID NO: 71 is the amino acid sequence of a modified cupredoxin-derived peptide
(Leu Ser Trp Ala Ala Asp Met Gln Gly Val Val Thr Asp Trp Met Ala Ser Gly Leu Asp Lys Asp Tyr Leu Lys Pro Asp Asp).

SEQ ID NO: 72 is the amino acid sequence of a modified cupredoxin-derived peptide
(Leu Ser Thr Ala Ala Asp Met Trp Gly Val Val Trp Asp Gly Met Ala Ser Gly Leu Asp Lys Asp Tyr Leu Lys Pro Asp Asp).

SEQ ID NO: 73 is the amino acid sequence of a modified cupredoxin-derived peptide
(Leu Ser Thr Ala Ala Asp Met Trp Gly Val Val Thr Asp Trp Met Ala Ser Gly Leu Asp Lys Asp Tyr Leu Lys Pro Asp Asp).

SEQ ID NO: 74 is the amino acid sequence of a modified cupredoxin-derived peptide
(Leu Ser Thr Ala Ala Asp Met Gln Gly Val Val Trp Asp Trp Met Ala Ser Gly Leu Asp Lys Asp Tyr Leu Lys Pro Asp Asp).

SEQ ID NO: 75 is the amino acid sequence of a modified cupredoxin-derived peptide
(Leu Ser Trp Ala Ala Asp Met Trp Gly Val Val Trp Asp Trp Met Ala Ser Gly Leu Asp Lys Asp Tyr Leu Lys Pro Asp Asp).

SEQ ID NO: 76 is the amino acid sequence of a modified cupredoxin-derived peptide
($X_1$ Ser $X_2$ Ala Ala Asp $X_3 X_4 X_5$ Val Val $X_6$ Asp $X_7 X_8$ Ala Ser Gly Leu Asp Lys Asp Tyr Leu Lys Pro Asp $X_9$).

SEQ ID NO: 77 is the amino acid sequence of a modified cupredoxin-derived peptide
($X_1$ Asp Pro Lys Leu Tyr Asp Lys Asp Leu Gly Ser Ala $X_2 X_3$ Asp $X_4$ Val Val $X_5 X_6 X_7$ Asp Ala Ala $X_8$ Ser $X_9$).

SEQ ID NO: 78 is a primer for pUC19-azu
(5'-CGGGATCCCC GGCAACCTGC CGAAGAACGT CATGGGC-3')

SEQ ID NO: 79 is a primer for pUC19-azu
(5'-CGGAATTCGC ATCACTTCAGG GTCAGGG-3')

SEQ ID NO: 80 is a primer for pGST-azu 36-50
(5'-GGCCACAACT GGGTACTGTG AACCGCCGCC GACATGCAG-3')

SEQ ID NO: 81 is a primer for pGST-azu 36-50
(5'-CTGCATGTCG GCGGCGGTTC ACAGTACCCA GTTGTGGCC-3').

SEQ ID NO: 82 is a primer for pGST-azu 36-77
(5'-CCTGAAGCCC GACGACTGAC GTGTCATCGC CCACACC-3')

SEQ ID NO: 83 is a primer for pGST-azu 36-77
(5'-GGTGTGGGCG ATGACACGTC AGTCGTCGGG CTTCAGG-3').

SEQ ID NO: 84 is a primer for pGST-azu 36-89
(5'-CCAAGCTGAT CGGCTCGTGA GAGAAGGACT CGGTGACC-3').

SEQ ID NO: 85 is a primer for pGST-azu 36-89
(5'-GGTCACCGAG TCCTTCTCTC ACGAGCCGAT CAGCTTGG-3').

-continued

SEQ ID NO: 86 is a primer for azu 50-77
(5'-CGGGATCCTG AGCACCGCCG CCGACATGCA GGG-3').

SEQ ID NO: 87 is a primer for an 67-77
(5'-CGGGATCCCC GGCCTGGAC AGGATTACCT GAAGCCCG-3')

SEQ ID NO: 88 is a reverse primer
(5'-CGGAATTCGC ATCACTTCAG GGTCAGGG-3').

SEQ ID NO: 89 is a primer for pGST-azu-50-66
(5'-GACGGCATGG CTTCCTGACT GGACAAGGAT TACC-3')

SEQ ID NO: 90 is a primer for pGST-azu-50-66
(5'-GGTAATCCTT GTCCAGTCAG GAAGCCATGC CGTC-3').

SEQ ID NO: 91 is a forward primer
(5'-CGGGATCCCC ATGGTGAGCA AGGGCG-3')

SEQ ID NO: 92 is a reverse primer
(5'-CGGAATTCCT TGTACAGCTC GTCCATGCCG-3')

SEQ ID NO: 93 is a primer for pGST-azu 50-77
(5'-CCGCTCGAGC CTGAGCACCG CCGCCATGCA GGG-3')

SEQ ID NO: 94 is a primer for pGST-azu 50-77
(5'-TTTTCCTTTT GCGGCCGCTC AGTCGTCGGG CTTCAGGTAA TC
C-3').

SEQ ID NO: 95 is the amino acid sequence of
polyarginine, or Arg8 (Arg Arg Arg Arg Arg Arg Arg
Arg)

SEQ ID NO: 96 is the amino acid sequence of a sec-
tion
of p18 (Ser Gly Leu Asp Lys Asp).

BRIEF DESCRIPTION OF THE FIGURES

FIG. 1 depicts photographs of all of the glands evaluated for the efficacy of p28 and azurin. FIG. 1A shows a representative photograph of alveolar lesions in a DMBA-treated gland and its comparison with a gland that was treated with DMBA along with a chemopreventive agent. FIGS. 1B-1G show representative photographs of the effects of p28 on the development of alveolar lesions.

FIG. 3 depicts photographs of representative sections of ductal lesions and effect of p28.

FIG. 39, (A) through (E). Depicts photographs of HT-1080 mice with lung metastases treated via their tail veins with (A) 3 mg/kg Doxorubicin IP, 3 treatments; (B) 5 mg/kg IP p28 daily; (C) PBS control, PBS IP daily; (D) 10 mg/kg IP p28 daily; (E) 20 mg/kg IP daily.

DETAILED DESCRIPTION OF THE INVENTION

Definitions

Figure 1C:

As used herein, the term "cell" includes either the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

As used herein, the term "pharmacologic activity" means the effect of a drug or other chemical on a biological system. The effect of chemical may be beneficial (therapeutic) or harmful (toxic). The pure chemicals or mixtures may be of natural origin (plant, animal, or mineral) or may be synthetic compounds.

As used herein, the term "premalignant" means precancerous, or before abnormal cells divide without control.

As used herein, the term "lesion" means an area of abnormal tissue.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "suffering from" includes presently exhibiting the symptoms of a pathological condition, having a pathological condition even without observable symptoms, in recovery from a pathological condition, or recovered from a pathological condition.

As used herein, the term "chemoprevention" is the use of drugs, vitamins, or other natural or synthetic agents, which may be biologic or chemical, to try to reduce the risk of, prevent, suppress, reverse, or delay the development, or recurrence of, cancer.

As used herein, the term "cytotoxic" refers to the quality of being toxic to cells. For example, a "cytotoxic cupredoxin" is a cupredoxin or variant, derivative, truncation, or structural equivalent thereof that is toxic to cells, including cancer cells.

A used herein, the term "treatment" includes preventing, lowering, stopping, or reversing the progression or severity of the condition or symptoms associated with a condition being treated. As such, the term "treatment" includes medical, therapeutic, and/or prophylactic administration, as appropriate. Treatment may also include preventing or lessening the development of a condition, such as cancer.

As used herein, the term "inhibit cell growth" means the slowing or ceasing of cell division and/or cell expansion. This term also includes the inhibition of cell development or increases in cell death.

A "therapeutically effective amount" is an amount effective to prevent, lower, stop or reverse the development of, or to partially or totally alleviate the existing symptoms of a particular condition for which the subject being treated. Determination of a therapeutically effective amount is well within the capability of those skilled in the art.

The term "substantially pure," as used herein, when used to modify a protein or other cellular product of the invention, refers to, for example, a protein isolated from the growth medium or cellular contents, in a form substantially free of, or unadulterated by, other proteins and/or other compounds. The term "substantially pure" refers to a factor in an amount of at least about 75%, by dry weight, of isolated fraction, or at least "75% substantially pure." More specifically, the term "substantially pure" refers to a compound of at least about 85%, by dry weight, of isolated fraction, or at least "85% substantially pure." Most specifically, the term "substantially pure" refers to a compound of at least about 95%, by dry weight, of isolated fraction, or at least "95% substantially pure." The term "substantially pure" may also be used to modify a synthetically-made protein or compound of the invention, where, for example, the synthetic protein is isolated from the reagents and by-products of the synthesis reaction(s).

The term "pharmaceutical grade," as used herein, when referring to a peptide or compound of the invention, is a peptide or compound that is isolated substantially or essentially from components which normally accompany the material as it is found in its natural state, including synthesis reagents and by-products, and substantially or essentially isolated from components that would impair its use as a pharmaceutical. For example, a "pharmaceutical grade" peptide may be isolated from any carcinogen. In some instances, "pharmaceutical grade" may be modified by the intended method of administration, such as "intravenous pharmaceutical grade," in order to specify a peptide or compound that is substantially or essentially isolated from any substance that would render the composition unsuitable for intravenous administration to a patient. For example, an "intravenous pharmaceutical grade" peptide may be isolated from detergents, such as SDS, and anti-bacterial agents, such as azide.

The terms "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region of a polypeptide refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to, nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. A "deletion" is the removal of one or more amino acids from within the polypeptide, while a "truncation" is the removal of one or more amino acids from one or both ends of the polypeptide. Thus, a variant peptide may be made by manipulation of genes encoding the polypeptide. A variant may be made by altering the basic composition or characteristics of the polypeptide, but not at least some of its pharmacologic activities. For example, a "variant" of azurin can be a mutated azurin that retains its ability to inhibit the development of premalignant mammalian cells. In some cases, a variant peptide is synthesized with non-natural amino acids, such as $\epsilon$-(3,5-dinitrobenzoyl)-Lys residues. Ghadiri & Fernholz, J. Am. Chem. Soc., 112:9633-9635 (1990). In some embodiments, the variant has not more than 20 amino acids replaced, deleted or inserted compared to wild-type peptide or part thereof. In some embodiments, the variant has not more than 15 amino acids replaced, deleted or inserted compared to wild-type peptide or part thereof. In some embodiments, the variant has not more than 10 amino acids replaced, deleted or inserted compared to wild-type peptide or part thereof. In some embodiments, the variant has not more than 6 amino acids replaced, deleted or inserted compared to wild-type peptide or part thereof. In some embodiments, the variant has not more than 5 amino acids replaced, deleted or inserted compared to wild-type peptide or part thereof. In some embodiments, the variant has not more than 3 amino acids replaced, deleted or inserted compared to wild-type peptide or part thereof. In other embodiments, the variant is created using the methods and techniques disclosed herein.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two three or more carbon atoms, typically one ($\alpha$) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can, for example, be a chemically modified azarin that retains its ability to inhibit angiogenesis in mammalian cells. Chemical modifications of interest include, but are not limited to, amidation, acetylation, sulfation, polyethylene glycol (PEG) modification, phosphorylation or glycosylation of the peptide, or other methods and techniques disclosed herein. In addition, a derivative peptide may be a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\text{\% amino acid sequence identity} = X/Y*100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

General

In some embodiments, the present invention provides compositions comprising cupredoxin, and variants, derivatives, truncations, and structural equivalents of cupredoxins, and methods to prevent the development of cancer in mammals. In other embodiments, the present invention provides compositions comprising cupredoxin, and variants, derivatives, truncations, and structural equivalents of cupredoxins that preferentially enter mammalian cells, including cancer cells. Other embodiments provide variants, derivatives and structural equivalents of cupredoxin that retain the ability to prevent the development of cancer or the re-occurrence of cancer in mammals. Particular embodiments provide compositions comprising *Pseudomonas aeruginosa* azurin, variants, derivatives and structural equivalents of azurin, and their use to treat patients, and particularly patients at a higher risk of developing cancer than the general population.

Other embodiments of the invention include methods to directly and/or preferentially penetrate cancer cells. Further embodiments of the invention include methods to directly and/or preferentially penetrate cancer and normal cells and have chemopreventive effects therein. Other embodiments provide methods to preferentially deliver therapeutic compounds to cancer cells. Finally, the invention provides methods to study the development of cancer in mammalian cells, tissues and animals by contacting the cells with a cupredoxin, or variant, derivative or structural equivalent thereof, before or after inducing premalignant lesions, and observing the development of premalignant and/or malignant cells. Yet other embodiments will be evident from the disclosure herein.

Preferential Entry Into Cells

Previously, it was known that a redox protein elaborated by *Pseudomonas aerugisnosa*, the cupredoxin azurin, selectively enters J774 lung cancer cells but not normal cells, and induces apoptosis. Zaborina et al., Microbiology 146:2521-2530 (2000). Azurin can also selectively enter and kill human melanoma UISO-Mel-2 or human breast cancer MCF-7 cells. Yamada et al., PNAS 99:14098-14103 (2002); Punj et al., Oncogene 23:2367-2378 (2004). Azurin from *P. aeruginosa* preferentially enters J774 murine reticulum cell sarcoma cells, forms a complex with and stabilizes the tumor suppressor protein p53, enhances the intracellular concentration of p53, and induces apoptosis. Yamada et al., Infection and Immunity 70:7054-7062 (2002). Detailed studies of various domains of the azurin molecule showed that amino acids 50-77 (p28) (SEQ ID NO: 2) represented a protein transduction domain PTD) critical for internalization and subsequent apoptotic activity. Yamada et al., Cell. Microbial. 7:1418-1431 (2005).

It is now known that azurin, and peptides derived from azurin, such as p28 and p18, have chemopreventive properties. It is now known that azurin and its derivative, p28, prevent formation of premalignant preneoplastic lesions in mouse mammary gland organ culture. In a mouse mammary gland organ culture model, azurin at 50 µg/ml was found to inhibit the formation of alveolar lesions by 67%. Likewise, p28 at 25 µg/ml was found to inhibit the formation of alveolar lesions by 67%. See Example 1. Further, azurin at 50 µg/ml was found to inhibit the formation of ductal lesions by 79%, and p28 at 25 µg/ml inhibited the formation of ductal lesions by 71%. See Example 1. Confocal microscopy and FAC showed that azurin and p28 entered normal murine mammary epithelial cells (MM3MG) and mammary cancer cells (4T1). p28 also entered human umbilical vein endothelial cells (HUVEC) in a temperature, time and concentration dependent manner and inhibited capillary tube formation of HUVEC plated on Matrigel® in a dose dependent manner. Confocal microscopy and FAC also showed that p18 selectively entered human melanoma (Mel-2,7,29), breast (MCF-7), ovarian (SK-OV3), pancreatic (CAPAN-2), glioblastoma (LN-229), astrocytoma (CCF-STTG1), prostate (LN-CAP), and kidney (ACHN-CRL1611) cell lines. In addition, imaging of p18 labeled with an infrared dye ($\lambda_{em}$ 800 nm) in athymic mice bearing xenografted melanoma tumors clearly demonstrated selective uptake in primary s.c. tumors and distant organ metastases without accumulating in normal organs and tissues. It is therefore now known that azurin and variants of azurin may be used to inhibit the formation of premalignant preneoplastic lesions, and thus the development of cancer, and specifically breast cancer, in mammalian patients.

Standard cancer treatment methods, including radiotherapy and chemotherapy, involve damaging the DNA of the cancer cell. The cellular response to normal DNA damage includes activation of DNA repair, cell cycle arrest and lethality (Hall, *Radiobiology for the Radiologist*, Harper and Row, 1988). For example, the induction of DNA double-strand breaks results in lethal chromosomal aberrations that include deletions, dicentrics, rings, and anaphase bridges (Hall, *Radiobiology for the Radiologist*, Harper and Row, 1994). Because of the selective uptake of the peptides of the present invention by tumors and various cancer cells, these peptides, including, in one embodiment, p18, may have use as a non-viral vector for introducing materials into tumors and cancer cells. For example, the peptides of the present invention may be used to introduce DNA or RNA fragments into a cancer cell thereby providing a therapeutic DNA or RNA fragment treatment to a tumor or cancer cell.

Protein transduction domains (PTDs) cluster into two groups based on their structural characteristics, cationic residues or amphipathic α-helix, although several fall into both classes. In general, cationic peptides initially interact with the cell membranes of prokaryotic and eukaryotic species by binding to negatively charged surface glycoproteins, facilitating efficient entry into a broad range of normal and malignant cell lines. Kondejewski, L. H., et al., J Biol Chem 277: 67-74 (2002); Fuchs, S. M. and Raines, R. T., Biochemistry, 43: 2438-2444 (2004). The binding of cationic peptides to HS is consistent with their high affinity for HS (Kd –109 nM), a value well in excess of that reported in the Examples below for azurin, p18 and p28. Tran, D. et al, Proc Natl Acad Sci USA 84: 7957-7961 (1987).

Azurin and peptides derived from it (e.g., p28 and p18) possess the unique property of preferentially entering cancer cells and inhibiting their proliferation through cytostatic and cytotoxic mechanisms. Redox proteins are not normally classified as cell-penetrating peptides (CPPs), or anti-proliferative agents. The entry of azurin, p28, and p18 is thought to be distinct from that of cationic CPPs. The amphipathic, azurin fragments p18 and p28 contain the 54-67 amino acid α-helical structure of azurin as well as a partial β-sheet structure. Aberrant N-glycosylation on several cell surface receptors, including integrins and cadherins, is associated with changes in progression and metastasis of cancers of diverse histogenesis, suggesting a role for as yet unknown N-glycoslyated cell surface protein(s) in the initial steps of azurin, p18 and p28 penetration. Partridge, E. A., et al, Science 306:120-124 (2004); Seales, E. C., et al., Cancer Res 65:4645-4652 (2005).

The temperature dependent entry of cationic CPPs, which supports an endocytotic component to cell penetration, is reflected in the entry of azurin and amino acid fragment 50-77 of azurin (p28). Yamada, T., et al., Cell Microbiol 7: 1418-1431 (2005). The entry of amino acids 50-67 of azurin (p18) into normal and malignant cells appears accelerated relative to p28. The lower $K_m$ and higher $V_{max}$ of p18 suggest that amino acids 50-67 of azurin define an amphipathic structure when associated with phospholipid membranes that more closely represents the actual PTD of azurin. However, an energy dependent endocytotic or pore related process does not appear to be the only entry mechanism available to these peptides. For example, the metabolic and membrane potential inhibitors sodium azide and ouabain ($Na^+K^+$ ATPase inhibitor), which inhibit the entry of cationic peptides, did not impair the entry of either p18 or p28 into UISO-Mel-2 cells or fibroblasts (FIG. 14 B,C), demonstrating that either peptide may penetrate the cell membrane directly.

Azurin derived peptides generally use different routes of penetration compared to the proposed routes of cellular penetration of other cationic CPPs, i.e., macropinocytosis, distribution to late endosomes or lysosomes along actin filaments or microtubules, and penetration at specific cell cycle stages, as inhibitors of each of these routes were singularly ineffective (FIG. 14 B,C). p18, p28 and azurin penetrate the plasma membrane and reach late endosmes, lysosomes and the golgi associated with caveolae in what has been described as a dynamin-independent clathrinin dependent carrier mediated manner. Kirkham, M. and Parton, R. G., Biochem Biophys Acta 1746:349-363 (2005). The striking inhibition of penetration by nocodazole and relative lack of inhibition by cytochalasin-D, which disrupts actin filaments, shows caveolae mediated entry. Id. This route of entry has been described for integral cell surface components and seemingly disparate molecules, i.e., dextran, and a broad range of pathogens or their products that also utilize caveolae to bypass classic endocytic pathways. Depletion of cholesterol from the plasma membrane with β-methylcylodextran, filipin or nystatin to disrupt lipid rafts, plasma membrane domains that provide fluid platforms to segregate membrane components and compartmentalize membranes, significantly inhibited the penetration of p18 (50%) and p28 (~60%) into UISO-Mel-2 cells and fibroblasts (35% and 42%, respectively) demonstrating that a significant percentage (~60%) of p18 and p28 penetrates the plasma membrane via caveolae. Caveolae are a 50- to 100-nm omega-shaped subset of lipid raft invaginations of the plasma membrane defined by the presence of caveolin specific proteins (caveolin-1, -2, or -3) that function as regulators of signal transduction.

Brefeldin A disrupts the Golgi apparatus and inhibited p18 accumulation. Thus, this pathway, and the Golgi apparatus, is also utilized in p18 and p28 entry and intracellular transport. Cell penetration of p18 and p28 via caveolae comports with the evidence that inhibitors of N-glycosylation reduce cell entry by 60% in UISO-Mel-2 cells and 25% and 35% respectively in fibroblasts. The percentile differences between p18 and p28 entry relate to the numbers of N-glycosylation membrane structures in cancer vs normal cells and the relative route of entry of p28 and p18 via this mechanism. FIG. 14 B, C.

Azurin, p28, and p18 all bind to cancer cells with high affinity and high capacity relative to many other potential anti-cancer peptides. After binding, this protein/receptor complex localizes in caveolae and is internalized, eventually moving (via caveosomes) to the golgi, ER, and nucleus. In addition to caveolar-mediated entry, kinetic analysis also demonstrates that p28 and p18 penetrate the plasma membrane via a non-clathrin caveolae mediated process. A clathrin- and caveolin-independent pathway exists as a constitutive internalization mechanism, such as for the interleukin 2 receptor and for certain glycosyl-phosphatidylinositol (GPI)-anchored proteins. Lamaze, C., et al., Mol Cell 7: 661-671 (2001); Sabharanjak, S., et al., Dev Cell, 2: 411-423 (2002). Clathrin- and caveolin-independent endocytosis is also used by pathogens to invade cells, either exclusively, as for the murine polyoma virus, or in combination with a conventional pathway, as is the case for the influenza virus. Ewers, H., et al, Proc Natl Acad Sci USA 102: 15110-15115 (2005); Sieczkarski, S. B. and Whittaker, G. R., J Virol, 76: 10455-10464 (2002). An increase in caveolin-1 expression in cancer cells over normal cells is not likely to be the sole basis for the preferential entry of azurin, p28 and p18 into cancer cells. Fibroblasts and a number of other normal cells also have significant numbers of caveolae on their surface.

Examples 18-24 show that p18 (amino acids 50-67 of azurin) and p28 (amino acids 50-77 of azurin) preferentially penetrate cancer cells via endocytotic, caveosome directed and caveosome independent pathways. The cellular penetration of p18 and p28 is unique relative to all current CPPs in its preference for cancer cells. Surprisingly, the C-terminal 10-12 amino acids of p28 (SEQ ID NOS: 35, 36, and 37) comprise a domain primarily responsible for cell cycle inhibition and apoptotic activity/cytotoxicity. Furthermore, this same domain is most likely to contact specific residues on a cell membrane regardless of the cell's status and thus facilitate entry; amino acids 69, 70, 75, 76, and 85 of azurin in particular provide contact to the cell membrane. Peptides with the same amino acids or amino acids with similar structure located at the same positions in the peptide chain, or positions in the peptide chain that are similar or equivalent to those of amino acids 69, 70, 75, 76, and 85 of azurin, should have the same or similar ability to contact specific cell membrane residues and enter cells. Once internalized, p28 inhibits cancer cell proliferation initially through a cytostatic mechanism. Thus, p18 and p28 account for the preferential entry of azurin into human cancer cells and a significant amount of the anti-proliferative and cytotoxic activity of azurin on human cancer cells, respectively.

In addition to entering cancer cells, p18 and p28 are able to enter tumors and mammalian organs, as is shown in FIGS. 16 through 53, which were obtained using the methods disclosed in Example 31. Surprisingly, p18 and p28 are also able to penetrate the blood-brain barrier and enter mammalian brains, as demonstrated by, for example, FIGS. 20A, 20B, 21B, 23, 24, 28, 30, 31A, 32B, 33, 34B, 35A-B, 37A-C, 38A-C, 40A, 42A, 43A, 45A-D, 46, 47B, 48A-B, and 50.

The peptides of the present invention can be used to introduce other molecules or compounds, such as DNA or RNA fragments, into mammalian cancer cells. The following describe non-limiting exemplary techniques and/or particular DNA or RNA fragments that can be introduced with the peptides of the present invention, and, in one embodiment, p18, which facilitate the entry of a linked molecule into a mammalian cancer cell. For example, the compounds of the invention, which may preferentially enter cells, can be used with gene therapy, RNAi approaches, hematopoietic gene transfer, homologous recombination, ribozyme technology, antisense technology, tumor immunotherapy and tumor suppressors, translational research, anti-gene therapy (antisense, siRNA & ribozymes), apoptosis, immunology and immunotherapy, DNA synthesis and repair.

Gene therapy involves the transfer of a foreign gene into a cancer cell, for example a tumor suppressor or inducer of apoptosis, under conditions suitable for expression of the gene. Once expressed, the gene product confers a beneficial effect on the tumor cell by either slowing its growth, inhibiting its metastatic potential, or killing it outright. Historically, the clinical effectiveness of cancer gene therapy has been limited by 1) lack of control of therapeutic gene expression within the tumor, and 2) selective targeting of the vector to the tumor. The compounds of the present invention address the selective targeting of tumor cells. Moreover, several strategies have been proposed for the control of gene expression. One strategy is transcriptional targeting in which the promoter regulating the therapeutic gene is activated by tumor-selective transcription factors. Examples include the use of the MUC-1 promoter in breast cancer and the CEA promoter in colon cancer (Kurihara et al., "Selectivity of a replication-component adenovirus for human breast carcinoma cells expressing the MUC1 antigen," *J. Clin. Invest.* 106(6): 763-771, 2000; Konishi et al., "Transcriptionally targeted in vivo gene therapy for carcinoembrionic antigen-producing adenocarcinoma," *J. Med. Sci.*, 48(3): 79-89, 1999).

Antisense techniques rely on the introduction of a nucleic acid molecule into a cell which typically is complementary to a mRNA expressed by the selected gene. The antisense molecule typically suppresses translation of the mRNA molecule and prevents the expression of the polypeptide encoded by the gene. Modifications of the antisense technique may prevent the transcription of the selected gene by the antisense molecule binding to the gene's DNA to form a triple helix; One particular antisense drug that can be used in accordance with the present invention is G3139 (also known as oblimersen; manufactured by Genta, Inc., Lexington, Mass.). Another particular antisense molecule that can be used is G4460 (also known as c-myb antisense manufactured by Genta, Berkeley Heights, N.J.).

RNA interference (RNAi) based molecules can also be attached to the peptides of the present invention. RNAi is generally mediated by double stranded RNA ("dsRNA"), short hairpin RNA ("shRNA") or other nucleic acid molecules with similar characteristics. These nucleic acid molecules are processed or cut into smaller pieces by cellular enzymes including Dicer and Drosha. The smaller fragments of the nucleic acid molecules can then be taken up by a protein complex (the RISC complex) that mediates degradation of mRNAs. The RISC complex will degrade mRNA that complementarily base pairs with the nucleic acid molecules it has taken up. In this manner, the mRNA is specifically destroyed, thus preventing encoded-for proteins from being made.

Ribozyme technologies rely on the introduction of a nucleic acid molecule into a cell which expresses a RNA molecule which binds to, and catalyses the selective cleavage of, a target RNA molecule. The target RNA molecule is typically a mRNA molecule, but it may be, for example, a retroviral RNA molecule.

Targeted gene deletion by homologous recombination, which requires two gene-inactivating events (one for each allele) is also a strategy that can be used with the present invention.

Particular therapies delivered in conjunction with the compounds of the present invention can also be directed against cancer-specific transcription complexes (CSTCs) that can control expression of proteins that are critical for cancer development. See, for example, United States Patent Application No. 2008/0027002 which is incorporated by reference herein for its teachings regarding cancer therapies directed against CSTCs.

Due to the high degree of structural similarity between cupredoxins, it is likely that cupredoxins other than azurin and truncations thereof will also be able to preferentially enter cancer cells via non-endocytotic and endocytotic pathways, and will further be able to inhibit the formation of premalignant lesions in mammals. Such cupredoxins may be found in, for example, bacteria or plants. Several cupredoxins are known to have pharmacokinetic activities similar to those of azurin from *Pseudomonas aeruginosa*. For example, rusticyanin from *Thiobacillus ferrooxidans* (SEQ ID NO: 4) can also enter macrophages and induce apoptosis. Yamada et al., Cell Cycle 3:1182-1187 (2004); Yamada et al., Cell. Micro. 7:1418-1431 (2005). Plastocyanin from *Phormidium laminosum* (SEQ ID NO: 3) and pseudoazurin form *Achromobacter cycloclastes* (SEQ ID NO: 5) also are cytotoxic towards macrophages. U.S. Pat. Pub. No. 20060040269, published Feb. 23, 2006. It is therefore contemplated that other cupredoxins may be used in the compositions and methods of the invention. Further, variants, derivatives, truncations, and structural equivalents of cupredoxins that retain the ability to inhibit the formation of cancer in mammals may also be used in the compositions and methods of the invention. These variants and derivatives may include, but are not limited to, truncations of a cupredoxin, conservative substitutions of amino acids and protein modifications disclosed herein, including but not limited to PEGylation and all-hydrocarbon stabling of α-helices.

Chemoprevention Through p53

The interaction of amino acids 50-77 of azurin (p28, SEQ ID NO: 2) and p53 was studied and is described in Examples 26 to 30 below. As disclosed herein, p28 penetrates and exhibits an anti-proliferative effect on human breast cancer cells that is mediated by p53, a tumor suppressor protein that becomes functionally active in response to stress and triggers either cell cycle arrest or cell death. Experiments using a series of GST-pull down assays, glycerol gradient centrifugation, microcalorimetric experiments, single molecule force spectroscopy, and computer modeling show that azurin binds within either the N-terminal or DNA binding domains of p53 and increases its intracellular levels. The results disclosed in Examples 26 to 30 and FIGS. 54-57 herein refine the binding site(s) for p28 to within amino acids 1-17, 24-31, 80-276 or 297-305, the N-terminal and DNA binding domains of p53.

Suggestions that the azurin binding domain for p53 includes a hydrophobic patch described by azurin Met44 and Met64 are supported by evidence that a disrupted hydrophobic patch mutant (mutant azurin M44KM64E) is less cytotoxic to human melanoma (Mel-2) cells than wt azurin. This shows that the p53 binding domain of the azurin molecule surrounds the hydrophobic patch. A recent docking simulation study demonstrated a significant loss of ~75 kJ/mol in the interaction free energy of the mutant complex with respect to wild type azurin, again indicating that the hydrophobic patch of azurin surrounding residues Met44 and Met64 is important for interaction with p53. As Met64 resides within the p53 binding site of p28 (amino acid 15 of p28), competition assays, mutant studies, and docking experiments clearly show that this is the azurin domain that binds to p53.

Figure 57A:
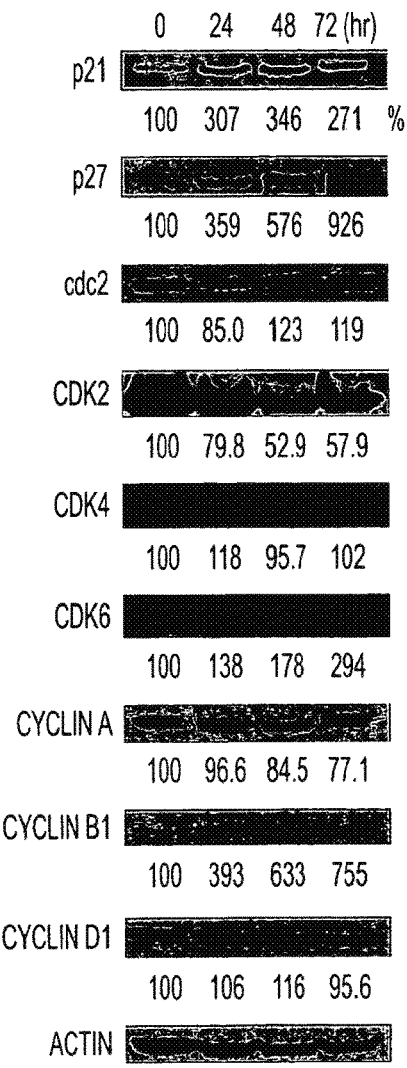
FIG. 57. Photographs depicting induction of the cyclin (CDK and CDKI) cascade by p28. MCF-7 (A) and MDD2 cells (B) were exposed to p28 (50 μM) for 24, 48 and 72 hr and protein levels determined by immunoblotting. Intracellular localization and relative level of p21 (C) and cyclin B1 (D) MCF-7 cells were cultured on cover slips with p28 for 72 h. p21 and cyclin B were stained with corresponding to the specific antibodies. (E) Phosphorylated cdc2 was estimated with an anti p-cdc2 antibody (Santa Cruz Biotechnology, CA). All results normalized by actin as an internal control FIG. 58. Pictures depicting protein structures. A) Azurin truncation with alpha-helical structure; B) Result of 70 ns simulation; C) Measurement of thioether bridge positions based on distances between Cα atoms in a simulated structure.

The tumor suppressor protein p53 is a predominantly nuclear protein that acts as a transcriptional regulator for many genes, including the 21 kDa protein p21/Waf1/Cip1, an inhibitor of cell cycle progression. Treatment of MCF-7 cells with p28 increased p53 levels, leading to higher intracellular levels of p21, a strong inhibitor of cyclin dependent kinase (CDK) activity, especially cdc2 and CDK2 that regulate cell cycle progression at $G_1$ and $G_2/M$, respectively. In the progression through the $G_2/M$ phase, cdc2 and CDK2 kinases are activated primarily in association with cyclin B and cyclin A, respectively. The CDK inhibitor p21 associates efficiently with cyclin A in $G_2/M$ arrested cells, although under the same conditions, cyclin B1 does not associate with p21 and the level of cyclin B1 increases continuously. This shows that the p28 induced $G_2/M$ arrest in MCF-7 cells is associated with inhibition of CDK2 and cyclin A (FIG. 57A).

The p28-induced increase in p21 in MCF-7 cells was also accompanied by a time-dependent increase in p27, another member of the Cip/Kip CDKI family. Hsu et al., 2008 recently demonstrated that induction of p53 increased both p21 and p27 promoter activity as determined by luciferase assay. Cellular and Molecular Life Sciences (CMLS), 2008. In addition, p53 DNA binding activity of the p21 and p27 promoters is activated by the p53 inducer, progesterone, which means that not only p21, but also p27 is transcriptionally regulated by p53. Collectively, data shows that p28 enhancement of p53 levels subsequently up-regulates p21 and p27, inducing a significant decrease in intracellular CDK2 and cyclin A levels in MCF-7 cells and inhibition of the cell cycle at $G_2/M$ (FIG. 57A). The reported lack of or inefficient association between cyclin B1 and p21, suggests the increase in cyclin B/cdc2 activity following exposure to p28 may reflect a similar pattern following a p28 induced increase in p21. An increase in phosphorylated cdc2 (inactive form) following exposure to p28 accompanied the increased cellular level of cyclin B1, suggesting the increase in the cdc2-cyclin B complex is reflected by the increase in cdc2 phosphorylation. A similar $G_2$ arrest in MCF-7 and MDA-MB-468 human breast cancer cells, accompanied by high levels of cytoplasmic cyclin B1, is induced by nocodazole, a known disruptor of microtubules, and transcriptional and translational activator of p21. Differentiation agents such as all-trans retinoic acid (ATRA) and sodium butyrate (SB) produce a similar phenomenon of growth inhibition and $G_1$ arrest in oral squamous carcinoma cells that correlates with the induction of $G_1$ phase cell cycle regulatory proteins CDK6, p21 and p27, and the inhibition of the $G_2$ phase cell cycle regulatory protein CDK2. Since p28 did not enhance p21 in MDD2 cells, and p27 appears absent in these cells, the levels of CDK2 and cyclin A were not significantly altered (FIG. 57B) and no inhibition of cell cycle occurred. Additional evidence for a p28 induced decrease in the CDK2 and cyclin A complex, a key regulator of cdc2 activity in human cells, causing a $G_1$ and $G_2/M$ arrest is found in the $G_2$ delay that follows cyclin A RNAi introduction to HeLa cells, which inactivates the CDK2-cyclin A complex causing cell cycle arrest in $G_2/M$.

Figure 57B:
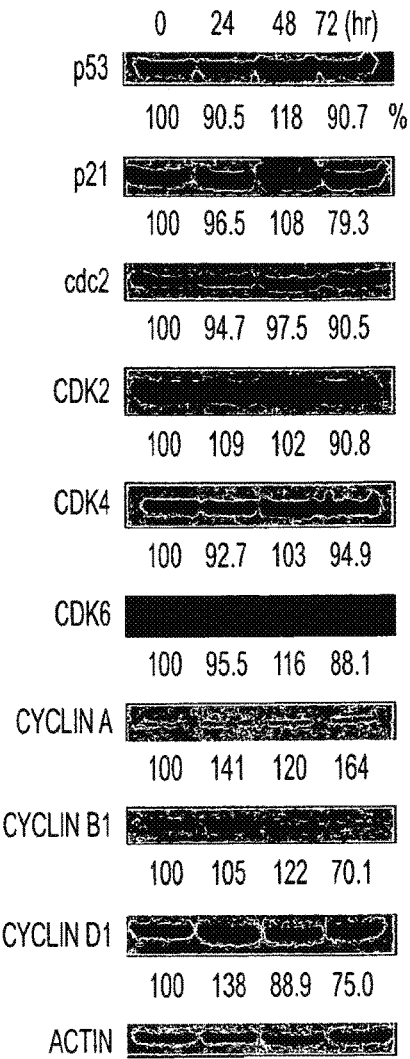

Although Cip/Kip family proteins such as p21 and p27 are potent inhibitors of cyclin A dependent CDK2, they also act as positive regulators of cyclin D-dependent kinases. Cip/Kip family proteins can stabilize CDK4 and CDK6. CDK4 is amplified and overexpressed in wide variety of tumors including breast, gliomas, sarcomas and carcinomas of the uterine cervix, whereas the CDK6 gene is amplified in certain type of malignancies including squamous cell carcinomas, gliomas and lymphoid tumors. Although, the initial or control level of CDK6 is lower than CDK4, CDK6, but not CDK4 levels are continuously elevated in MCF-7 cells exposed to p28. Again, there was no alteration in CDK4 and CDK6 in MDD2 cells where p53 and p21 did not increase in response to p28 (FIG. 57B). The Ink4 group, $p16^{Ink4a}$, $p15^{Ink4b}$, $p18^{Ink4c}$ and $p19^{Ink4d}$ of CDKIs specifically associates with and inhibits CDK4 and CDK6 which regulate cell cycle progression at $G_1$. Since the $p16^{Ink4a}$ gene is homozygously deleted in MCF-7 cells, Ink4 CDKI proteins should exhibit less of an inhibitory effect on CDK6 than CDK4, providing a rationale for the increase on CDK6 observed in CDK6 in the presence of essentially stable CDK4 levels.

Collectively, these results demonstrate that p28 binds to p53, increasing p53 levels that subsequently amplify antiproliferative activity through p21 and p27 inactivation of the CDK2-cyclin A complex, causing a $G_2/M$ cell cycle arrest in MCF-7 breast cancer cells in vitro and inhibition MCF-7 xenograft growth in athymic mice.

Compositions of the Invention

In certain embodiments, the invention provides for peptides that are cupredoxin(s) or variants, truncations, derivatives or structural equivalents of cupredoxin that inhibit the development of premalignant lesions in mammalian cells, tissues and animals. In other aspects, the invention further provides for peptides that are cupredoxin(s) or variants, truncations, derivatives or structural equivalents of cupredoxin that inhibit the development of cancer in mammalian cells, tissues and animals. In some embodiments, the peptide comprises the C-terminus of p28 (SEQ ID NO: 2), such as SEQ ID NO. 35, SEQ ID NO. 36, or SEQ ID NO. 37. In other embodiments, the peptide comprises one or more of the amino acids located at positions 69, 70, 75, 76, and 85 of SEQ ID NO: 1 in locations the same or similar to those of azurin.

Some embodiments of the invention further provide for peptides that are cupredoxin(s) or variants, truncations, derivatives or structural equivalents of cupredoxin that preferentially enter cancer cells. In further aspects, the invention provides for peptides that are cupredoxin(s) or variants, truncations, derivatives or structural equivalents of cupredoxin that preferentially enter cells by endocytotic pathways, including caveolae-mediated and Golgi mediated pathways, and have chemopreventive effects therein. In further embodiments, the peptide comprises or consists of the C-terminus of p28, such as SEQ ID NO. 35, SEQ ID NO. 36, or SEQ ID NO. 37. In other embodiments, the peptide comprises one or more of the amino acids located at positions 69, 70, 75, 76, and 85 of SEQ ID NO: 1 in locations the same or similar to those of azurin. In other embodiments, the peptide comprises the amino acids located at 69, 70, 75, 76, and 85 of SEQ ID NO. 1 in locations the same or similar to those of azurin.

In some embodiments, the peptide is isolated. In some embodiments, the peptide is substantially pure or pharmaceutical grade. In other embodiments, the peptide is in a composition that comprises, or consists essentially of, the peptide. In another specific embodiment, the peptide is non-antigenic and does not raise an immune response in a mammal, and more specifically a human. In some embodiments, the peptide is less that a full-length cupredoxin, and retains some of the pharmacologic activities of the cupredoxins. Specifically, in some embodiments, the peptide may retain the ability to inhibit the development of premalignant lesions in the mouse mammary gland organ culture. In other embodiments, the peptide retains the ability to directly and preferentially enter cells via, for example, caveolae-mediated endocytosis. In other embodiments, the peptide retains the ability to directly and preferentially enter cells and have chemopreventive effects therein.

In other aspects, the invention also provides compositions comprising at least one peptide that is a cupredoxin, or variant, derivative, truncation or structural equivalent of a cupredoxin that can preferentially enter cancer cells, specifically in a pharmaceutical composition. In specific embodiments, the pharmaceutical composition is designed for a particular mode of administration, for example, but not limited to, oral, intraperitoneal, or intravenous. Such compositions may be hydrated in water, or may be dried (such as by lyophilization) for later hydration. Such compositions may be in solvents other than water, such as but not limited to, alcohol.

Certain embodiments of the invention also provide compositions comprising peptides that are variants, derivatives, truncations or structural equivalents of cupredoxin that preferentially enter cancer cells and/or tumors in mammalian cells, tissues and animals. In some embodiments, the peptide is the C-terminus of p28, such as SEQ ID NO. 35 or SEQ ID NO. 36. In some embodiments, the peptide is p18 having SEQ ID NO. 25. In some embodiments, the peptide is a variant, derivative or structural equivalent of p18. In some embodiments, the composition is p18 coupled to DNA or RNA. In some embodiments, the DNA or RNA is a gene or a portion of a gene. In some embodiments, the DNA or RNA has a therapeutic effect once delivered. In some embodiments, the peptide is p28 having SEQ ID NO. 2. In some embodiments, the peptide is a variant, derivative, or structural equivalent of p28. In some embodiments, the composition is p28 coupled to DNA or RNA. In some embodiments, the DNA or RNA is a gene or a portion of a gene. In some embodiments, the DNA or RNA has a therapeutic effect once delivered.

Because of the high structural homology between the cupredoxins, it is contemplated that cupredoxins will have the same chemopreventive properties as azurin and p28. In some embodiments, the cupredoxin is, but is not limited to, azurin, pseudoazurin, plastocyanin, rusticyanin, auracyanin, stellacyanin, cucumber basic protein or Laz. In particularly specific embodiments, the azurin is derived from *Pseudomonas aeruginosa, Alcaligenes faecalis, Achromobacter xylosoxidans* ssp. *denitrificans I, Bordetella bronchiseptica, Methylomonas* sp., *Neisseria meningitides, Neisseria gonorrhea, Pseudomonas fluorescens, Pseudomonas chlororaphis, Xylella fastidiosa, Ulva pertussis* or *Vibrio parahaemolyticus*. In one embodiment, the azurin is from *Pseudomonas aeruginosa*. In other specific embodiments, the cupredoxin comprises an amino acid sequence that is SEQ ID NO: 1, 3-19.

Aspects of the invention include peptides that are amino acid sequence variants which have amino acids replaced, deleted, or inserted as compared to the wild-type cupredoxin. Variants of the invention may be truncations of the wild-type cupredoxin. In some embodiments, the peptide of the invention comprises a region of a cupredoxin that is less that the full length wild-type polypeptide. In some embodiments, the peptide of the invention comprises more than about 10 residues, more than about 15 residues or more than about 20 residues of a truncated cupredoxin. In some embodiments, the peptide comprises not more than about 100 residues, not more than about 50 residues, not more than about 40 residues, not more than about 30 residues or not more than about 20 residues of a truncated cupredoxin. In some embodiments, a cupredoxin has to the peptide, and more specifically SEQ ID NOS: 1, 3-19 as to the peptide of the invention, at least about 70% amino acid sequence identity, at least about 80% amino acid sequence identity, at least about 90% amino acid sequence identity, at least about 95% amino acid sequence identity or at least about 99% amino acid sequence identity.

In specific embodiments, the variant of cupredoxin comprises *P. aeruginosa* azurin residues 50-77 (p28, SEQ ID NO: 2), azurin residues 50-67 (p18, SEQ ID NO: 25), or azurin residues 36-88 (SEQ ID NO: 26). In other embodiments, the variant of cupredoxin consists of *P. aeruginosa* azurin residues 50-77 (SEQ ID NO: 2), azurin residues 50-67 (SEQ ID NO: 25), or azurin residues 36-88 (SEQ ID NO: 26). In other specific embodiments, the variant consists of the equivalent residues of a cupredoxin other that azurin. It is also contemplated that other cupredoxin variants can be designed that have a similar pharmacologic activity to azurin residues 50-77 (SEQ ID NO: 2), or azurin residues 36-88 (SEQ ID NO: 26). To do this, the subject cupredoxin amino acid sequence will be aligned to the *Pseudomonas aeruginosa* azurin sequence using BLAST, BLAST2, ALIGN2 or Megalign (DNASTAR), the relevant residues located on the *P. aeruginosa* azurin amino acid sequence, and the equivalent residues found on the subject cupredoxin sequence, and the equivalent peptide thus designed.

In one embodiment of the invention, the cupredoxin variant contains at least amino acids 57 to 89 of auracyanin B of *Chloroflexus aurantiacus* (SEQ ID NO: 20). In another embodiment, the cupredoxin variant contains at least amino acids 50-67 of *Pseudomonas aeruginosa* azurin (SEQ ID NO 25). In another embodiment of the invention, the cupredoxin variant contains at least amino acids 51-77 of *Pseudomonas syringae* azurin (SEQ ID NO: 21). In another embodiment of the invention, the cupredoxin variant contains at least amino acids 89-115 of *Neisseria meningitidis* Laz (SEQ ID NO: 22). In another embodiment of the invention, the cupredoxin variant contains at least amino acids 52-78 of *Vibrio parahaemolyticus* azurin (SEQ ID NO: 23). In another embodiment of the invention, the cupredoxin variant contains at least amino acids 51-77 of *Bordetella bronchiseptica* azurin (SEQ ID NO: 24).

The variants may also include peptides made with synthetic amino acids not naturally occurring. For example, non-naturally occurring amino acids may be integrated into the variant peptide to extend or optimize the half-life of the composition in the bloodstream. Such variants include, but are not limited to, D,L-peptides (diastereomer), (for example Futaki et al., J. Biol. Chem. 276(8):5836-40 (2001); Papo et al., Cancer Res. 64(16):5779-86 (2004); Miller et al, Biochem. Pharmacol. 36(1):169-76, (1987).; peptides containing unusual amino acids (for example Lee et al., J. Pept. Res. 63(2):69-84 (2004)), olefin-containing non-natural amino acid followed by hydrocarbon stapling (for example Schafmeister et al., J. Am. Chem. Soc. 122:5891-5892 (2000); Walenski et al., Science 305:1466-1470 (2004)), and peptides comprising ε-(3,5-dinitrobenzoyl)-Lys residues.

In other embodiments, the peptide of the invention is a derivative of a cupredoxin. The derivatives of cupredoxin are chemical modifications of the peptide such that the peptide still retains some of its fundamental activities. For example, a "derivative" of azurin can be a chemically modified azurin that retains its ability to preferentially enter cells via endocytotic or non-endocytotic pathways, as well as the ability to inhibit the development of premalignant lesions in mammalian cells, tissues or animals. Chemical modifications of interest include, but are not limited to, hydrocarbon stabling, amidation, acetylation, sulfation, polyethylene glycol (PEG) modification, phosphorylation and glycosylation of the peptide, and other methods disclosed herein. In addition, a derivative peptide maybe a fusion of a cupredoxin, or variant, derivative or structural equivalent thereof to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (for example Monk et al., BioDrugs 19(4):261-78, (2005); DeFreest et al., J. Pept. Res. 63(5):409-19 (2004)), N- and C-terminal modifications (for example Labrie et al., Clin. Invest. Med. 13(5):275-8, (1990)), and olefin-containing non-natural amino acid followed by hydrocarbon stapling (for example Schafmeister et al., J. Am. Chem. Soc. 122: 5891-5892 (2000); Walenski et al., Science 305:1466-1470 (2004)).

In some embodiments, the cupredoxin may be changed using methods that include, but are not limited to, those which decrease the hydrolysis of the peptide, decrease the deamidation of the peptide, decrease the oxidation, decrease the immunogenicity and/or increase the structural stability of the peptide. In some embodiments, the cupredoxin may be modified using methods that enhance its ability to preferentially enter cancer cells and/or have cytotoxic effects therein. It is contemplated that two or more of the modifications described herein may be combined in one modified cupredoxin derived peptide, as well as combinations of one or more modifications described herein with other modification to improve pharmacokinetic properties that are well know to those in the art. Many methods to design such variants and derivatives are well known in the art.

Biotransformation

One approach to improving the pharmacokinetic properties of peptides is to create variants and derivatives of the cupredoxin derived peptides that are less susceptible to biotransformation. Biotransformation may decrease the pharmacologic activity of the peptide as well as increase the rate at which it is eliminated from the patient's body. One way of achieving this is to determine the amino acids and/or amino acid sequences that are most likely to be biotransformed and to replace these amino acids with ones that are not susceptible to that particular transformative process.

In some embodiments, the cupredoxin derived peptides may include unnatural amino acids or modified amino acids. In some embodiments, the introduction of certain unnatural amino acids enhances the pharmcaokinetic properties of the cupredoxin derived peptide. Such introduction may be site-specific and may be done to avoid certain biochemical modifications in vivo. Exemplary unnatural amino acids include b-amino acids (e.g., b3 and b2), homo-amino acids, cyclic amino acids, aromatic amino acids, Pro and Pyr derivatives, 3-substituted Alanine derivatives, Glycine derivatives, Ring-substituted Phe and Tyr Derivatives, Linear Core Amino Acids and Diamino Acids. Such unnatural amino acids may be incorporated into peptides by site directed modification, ribosomal translation, or by chemical synthesis of the peptide. Each of these methods may be applied in synthesizing cupredoxin derived peptides.

For example, modified cupredoxin derived peptides may be synthesized by the use of wild-type Aminoacyl-tRNA synthetases (AARSs) with unnatural amino acids building for the production of unnatural cupredoxin variants. See Hartman, et al., PLoS One, 2(10): e972 (2007); Miranda, et al., J. Am. Chem. Soc. 129: 13153-13159 (2007). The specificity of the ribosomal translation apparatus limits the diversity of unnatural amino acids that may be incorporated into peptides using ribosomal translation. Over ninety unnatural building blocks that are AARS substrates have been uncovered including side chain and backbone analogs. Hartman, et al., PLoS One, 2(10): e972 (2007). Over fifty unnatural amino acids may be incorporated into peptides with high efficiency using an all-enzymatic translation system, with peptides containing up to thirteen different unnatural amino acids. Hartman, et al., PLoS One, 2(10): e972 (2007). In some embodiments, such amino acids may be incorporated in cupredoxin derived peptides.

One method of chemically modifying a cupredoxin or cytochrome c551 or variant, derivative, truncation, or structural equivalent thereof may be to follow the steps taken to design an anti-HIV small protein, CCL-5 (RANTES) with improved pharmaceutical properties by, for example, hydrophobic N-terminal modification, total protein-polymer conjugate chemicals synthesis, coded and noncoded amino acid mutagenesis, peptide backbone engineering, and site-specific polymer attachment. Anti-HIV proteins can be designed by incorporating natural and unnatural amino acid residues into CCL-5 analogues baring polymer substituents at varying attachment positions. Studies indicate that in vitro anti-HIV activity of polymer-modified CCL-5 derivatives correlates with CCR-5 signaling, so changes to the peptide should not disrupt CCR-5 activity. Miranda, et al., J. Am. Chem. Soc. 129: 13153-13159 (2007), the disclosure of which is incorporated in its entirety herein.

Other modifications may include the use of optically active α-amino acids. The use of optically active α-amino acids and their derivatives is being expanded for their use in pharmaceuticals, agrochemicals and as chiral ligands. In particular, chiral glycine and alanine equivalents plan an important role. At least one stereoselective strategy for constructing α-amino acids has been proposed, allowing for enantiopure α-amino acids in predetermined stereochemistry. Lu, et al. "Asymmetric Synthesis of α-amino acids: Preparation and alkylation of monocyclic iminolactones derived from α-Methyl trans-cinnamaldehyde" published on Internet on Sep. 11, 2008 (to be published in J. Org. Chem.), the disclosure of which is incorporated by reference herein. The modified cupredoxin derived peptides may be synthesized using the optically active α-amino acids to produce enantiomerically enriched iterations.

Hydrolysis is generally a problem in peptides containing aspartate. Aspartate is susceptible to dehydration to form a cyclic imide intermediate, causing the aspartate to be converted to the potentially inactive iso-aspartate analog, and ultimately cleaving the peptide chain. For example, in the presence of aspartic acid—proline in the peptide sequence, the acid catalyzed formation of cyclic imide intermediate can result to cleavage of the peptide chain. Similarly, in the presence of aspartic acid—glycine in the peptide sequence, the cyclic intermediate can be hydrolyzed either into the original aspartate form (harmless) or into the iso-aspartate analog. Eventually, all of the aspartate form can be completely converted into the iso-aspartate analog. Similarly sequences with serine can also be dehydrated to form a cyclic imide intermediate that can cleave the peptide chain.

Cleavage of the peptide may result in reduced plasma half-life as well as reduced specific pharmacologic activity of the peptide.

It is contemplated that substituting other amino acids for asparagine and/or serine in the sequence of the cupredoxin derived peptide may result in a peptide with improved pharmacokinetic properties such as a longer plasma half-life and increased specific activity of a pharmacologic activity of the peptide. In one contemplated variant, at one or more asparagine residues of the cupredoxin derived peptide may be replaced with another amino acid residue, and specifically a glutamic acid residue. In another contemplated variant, one or more serine residues of the cupredoxin derived peptide may be replaced with another amino acid residue, and specifically a threonine residue. In some variants of cupredoxin derived peptide, one or more asparagine residues and one or more serine residues are substituted. In some embodiments, conservative substitutions are made. In other embodiments, non-conservative substitutions are made.

Deamidation of amino acid residues is a particular problem in biotransformation. This base-catalyzed reaction frequently occurs in sequences containing asparagine-glycine or glutamine-glycine and follows a mechanism analogous to the aspartic acid-glycine sequence above. The de-amidation of the asparagine-glycine sequence forms a cyclic imide intermediate that is subsequently hydrolyzed to form the aspartate or iso-asparate analog of asparagine. In addition, the cyclic imide intermediate can lead to racemization into D-aspartic acid or D-iso-aspartic acid analogs of asparagine, all of which can potentially lead to inactive forms of the peptide.

It is contemplated that deamidation in the cupredoxin peptides may be prevented by replacing a glycine, asparagine and/or glutamine of the asparagine—glycine or glutamine—glycine sequences of the cupredoxin with another amino acid and may result in a peptide with improved pharmacokinetic properties, such as a longer plasma half-life and increased specific activity of a pharmacologic activity of the peptide. In some embodiments, the one or more glycine residues of the cupredoxin derived peptide are replaced by another amino acid residue. In specific embodiments, one or more glycine residues of the cupredoxin derived peptide are replaced with a threonine or an alanine residue. In some embodiments, the one or more asparagine or glutamine residues of the cupredoxin derived peptide are replaced by another amino acid residue. In specific embodiments, one or more asparagine or glutamine residues of the cupredoxin derived peptide are replaced with an alanine residue. In other specific embodiments, the glycine at residues 58 and/or 63 of P. aeruginosa azurin (SEQ ID NO: 1), or equivalent glycines of other cupredoxins, are replaced with an alanine or a threonine. In other specific embodiments, the methionine at residue 59 of P. aeruginosa azurin (SEQ ID NO: 1), or an equivalent methionine residue of another cupredoxin derived peptide, is replaced by an alanine residue. In other specific embodiments, the glycine at residue 63 of P. aeruginosa azurin (SEQ ID NO: 1), or an equivalent glycine residue of another cupredoxin derived peptide, is replaced by an threonine residue. In some embodiments, conservative substitutions are made. In other embodiments, non-conservative substitutions are made. In specific embodiments, the modified cupredoxin derived peptide of the invention comprises the following sequence, wherein the underlined amino acids are substituted into the wildtype Pseudomonas aeruginosa p28 sequence

LSTAADMQAVVTDTMASGLDKDYLKPDD    (SEQ ID NO: 38)

Reversible and irreversible oxidation of amino acids are other biotransformative processes that may also pose a problem that may reduce the pharmacologic activity, and/or plasma half-life of cupredoxin derived peptides. The cysteine and methionine residues are the predominant residues that undergo reversible oxidation. Oxidation of cysteine is accelerated at higher pH, where the thiol is more easily deprotonated and readily forms intra-chain or inter-chain disulfide bonds. These disulfide bonds can be readily reversed in vitro by treatment with dithiothreitol (DTT) or tris(2-carboxyethylphosphine) hydrochloride (TCEP). Methionine oxidizes by both chemical and photochemical pathways to form methionine sulfoxide and further into methionine sulfone, both of which are almost impossible to reverse.

It is contemplated that oxidation in the cupredoxin derived peptides may be prevented by replacing methionine and/or cysteine residues with other residues. In some embodiments, one or more methionine and/or cysteine residues of the cupredoxin derived peptide are replaced by another amino acid residue. In specific embodiments, the methionine residue is replaced with a leucine or valine residue. In other specific embodiments, one or more of the methionines at residues 56 and 64 of P. aeruginosa azurin (SEQ ID NO: 1), or equivalent methionine residues in other cupredoxin derived peptides, are replaced with leucine or valine. In some embodiments, conservative substitutions are made. In other embodiments, non-conservative substitutions are made. In specific embodiments, the cupredoxin peptides of the invention comprise one of the following sequences, wherein the underlined amino acid is substituted into the wildtype Pseudomonas aeruginosa p28 sequence:

LSTAADLQGVVTDGLASGLDKDYLKPDD    (SEQ ID NO: 39)
or
LSTAADVQGVVTDGVASGLDKDYLKPDD.   (SEQ ID NO: 40)

Another biotransformative process that may affect the pharmacologic activity, (such as the ability to preferentially enter cells), plasma half-life and/or immunogenicity of the cupredoxin derived peptides is diketopiperazine and pyroglutamic acid formation. Diketopiperazine formation usually occurs when glycine is in the third position from the N-terminus, and more especially if proline or glycine is in position 1 or 2. The reaction involves nucleophilic attack of the N-terminal nitrogen on the amide carbonyl between the second and third amino acid, which leads to the cleavage of the first two amino acids in the form of a diketopiperazine. On the other hand, pyroglutamic acid formation may be almost inevitable if glutamine is in the N-terminus. This is an analogous reaction where the N-terminal nitrogen attacks the side chain carbonyl carbon of glutamine to form a deaminated pyroglutamayl peptide analog. This conversion also occurs in peptide containing asparagine in the N-terminus, but to a much lesser extent.

It is contemplated that diketopiperazine and pyroglutamic acid formation may be decreased in cupredoxin derived peptides by replacing glycine in position 1, 2, or 3 from the N-terminus, proline in position 3 from the N-terminus, or asparagine at the N-terminus of the peptide with another amino acid residue. In some embodiments, a glycine in positions 1, 2, or 3 from the N-terminus of the cupredoxin derived peptide is replaced with another amino acid residue.

In specific embodiments, the glycine residue is replaced by a threonine or alanine residue. In another embodiment, a proline at position 3 from the N-terminus of the cupredoxin derived peptide is replaced with another amino acid residue. In specific embodiments, the proline is replaced by an alanine residue. In another embodiment, an asparagine at the N-terminus is replaced with another amino acid residue. In specific embodiments, the asparagine residue is replaced by a glutamine residue. In some embodiments, conservative substitutions are made. In other embodiments, non-conservative substitutions are made.

Another biotransformative process that may affect the pharmacologic activity, plasma half-life and/or immunigenicity of the cupredoxin derived peptide is racemization. This term is loosely used to refer to the overall loss of chiral integrity of the amino acid or peptide. Racemization involves the base-catalyzed conversion of one enantiomer (usually the L-form) of an amino acid into a 1:1 mixture of L- and D-enantiomers. One way to improve stability of the peptide in general is by making a retro-inverso (D-isomer) peptide. The double inversion of peptide structure often leaves the surface topology of the side-chain intact and has been used extensively to stabilize biologically active peptides. Snyder et al., PLoS Biol. 2:0186-0193 (2004). A D-amino acid substituted Tat is internalized into cells as well as the L-amino acid peptide. Futaki et al., J. Biol. Chem. 276:5836-5840 (2001); Huq et al., Biochemistry 38:5172-5177 (1999). In some embodiments, one or more amino acid residues of the cupredoxin derived peptide are replaced by the D-isomer of that amino acid residue. In other embodiments, all of the amino acid residues of the cupredoxin derived peptide are replaced with D-isomers of those residues. In one embodiment, the modified cupredoxin derived peptide is a retro-inverso (D-isomer) version of the cupredoxin derived peptide. In a specific embodiment, the modified cupredoxin derived peptide is

DDPKLYDKDLGSAMGDTVVGQMDAATSL    (SEQ ID NO: 41)

Other methods to protect a cupredoxin derived peptide from biotransformative degradation are N-acetylation and C-amidation. These derivatives may protect the peptide from degradation and may make the cupredoxin derived peptide more closely mimic the charge state of the alpha amino and carboxyl groups in the native protein. Peptides with the N-acetylation and/or C-amidation can be provided by commercial suppliers. In one embodiment of the invention, the N-terminus of the cupredoxin derived peptide may be acetylated. In another embodiment of the invention, the C-terminus of the cupredoxin derived peptides may be amidated. In one specific embodiment, the modified cupredoxin derived peptide is (SEQ ID NO: 42)
Acetylation-LSTAADMQGVVTDGMASGLDKDYLKPDD-amidation Cyclization is an additional manner of biotransformation that may be beneficial to therapeutic peptides including the cupredoxins as described herein. Cyclization may stabilize therapeutic peptides, allowing them to be stored longer, be administered at lower doses and be administered less frequently. Cyclization has been shown to protect peptides against peptidase and protease degradation. Cyclization can be done chemically or enzymatically. Enzymatic cyclization is generally less problematic than chemical cyclization, as chemical cyclization can lack in regio- and stereospecificity, can lead to multimerization in lieu of cyclization and can require complicated multistep processes. Indeed, it has been shown that thioether cyclization is more protective and stable than a disulfide bond against proteolytic enzymes.

Enzymatic cyclization has been shown in lantibiotics-(methyl)lanthionine-containing bacterial peptides. E.g., R. Rink, et al., "Lantibiotic Structures as Guidelines for the Design of Peptides That Can Be Modified by Lantibioitic Enzymes" 44 Biochem., 8873-82 (2005); R. Rink, et al., "Production of Dehydroamino Acid-Containing Peptides by Lactococcus lactis" 73:6 Applied and Environmental Microbiology, 1792-96 (2007); R. Rink, et al., "NisC, the Cyclase of the Lantibiotic Nisin, Can Catalyze Cyclization of Designed Nonlantibiotic Peptides" 46 Biochem., 13179-89 (2007) (each of which is hereby incorporated by reference in its entirety). Lantibiotics are produced by and inhibit the growth of gram-positive bacteria. In lantibiotics, dehydroalanine and dehydrobutyrine are created by enzyme mediated dehydration of serine and threonine residues. Cysteines are then enzymatically coupled to the dehydrated serine and threonine residues to form thioether cyclizations. Naturally occurring lantibiotics show such couplings via thioether bonds between residues that are up to 19 residues apart. Thioether ring formation depends upon the leader peptide. The location of the cyclization depends upon the cyclase mediated regio- and stereospecific ring closure and the positions of the dehydratable serine and threonine residues.

The best characterized of the lantibiotics is nisin—a pentacyclic peptide antiobiotic produced by Lactococcus lactis. Nisin is composed of four methyllanthionines, one lanthionine, two dehydroalanines, one dehydrobutyrine, and twenty-six unmodified amino acids. Nisin's five thioether cross-links are formed by the addition of cysteine residues to dehydroalanine and dehydrobutyrine residues that originate from serine and threonine. Nisin contains thioether-containing amino acids that are posttranslationally introduced by a membrane-associated enzyme complex. This enzyme complex includes: transporter NisT, serine and threonine dehydratase NisB, and cyclase NisC. NisB dehydrates serine and threonine residues, converting them into dehydroalanine and dehydrobutyrine, respectively. This is followed by NisC catalyzed enantioselective coupling of cysteines to the formed dehydroresidues. NisT facilitates the export of the modified prenisin. Another enzyme, NisP cleaves the nisin leader peptide from prenisin.

The cyclase NisC has been well characterized. Li et al, "Structure and Mechanism of the Lantibiotic Cyclase Involved in Nisin Biosynthesis" 311 Science, 1464-67 (2006) (hereby incorporated by reference in its entirety).

An analysis of cyclization in lantibiotics has led to the identification of amino acid sequences and characteristics in peptides that favor cyclization. It has been shown that the NisB enzyme dehydrates more often where certain amino acids flank the serine and threonine residues. It has been shown that cyclization occurs more often in lantibiotic propeptides where hydrophobic, nonaromatic residues are in proximity to the serine and threonine residues. The flanking residues of the modified cysteines are typically less hydrophobic than the flanking residues of the modified threonines and serines. Exceptions have been found, including hexapeptides VSPPAR (SEQ ID NO: 43), YTPPAL (SEQ ID NO: 44) and FSFFAF (SEQ ID NO: 45). The hexapeptides suggest that the presence of a proline at position 3 or 4 or having phenylalanine flanking both sides may prohibit dehydration. The rings are typically formed by coupling a dehydrated residue to a C-terminally located cysteine. However, rings may be formed by coupling a dehydrate residue to a N-terminally located cysteine.

It has also been shown that the nisin dehydrating and transport enzymes are not specific to nisin and may, in fact, be used to modify non-nisin peptides (and non-lantibiotic peptides). NisB has been shown to dehydrate serine and threonine residues in peptides such as human peptide hormones when such peptides are N-terminally fused to the lantibiotic leader peptide. On non-lantibiotic peptides, similar ring formation characteristics apply; namely, the extent of dehydration can be controlled by the amino acid context of the flanking region of the dehydratable serine and threonine residues. The presence of hydrophobic flanking residues (e.g., alanine and valine) around the serines and threonines allowed full dehydration and therefore enhanced thioether ring formation. The presence of an N-terminal aspartate and C-terminally flanked arginine prevented dehydration. It also shown that the presence of proline residues and phenylalanine residues is disfavorable for dehydration. Generally, the presence of hydrophilic flanking residues prevented dehydration of the serine and threonine residues. Hydrophobic flanking favors dehydration; hydrophilic flanking disfavors dehydration. Studies have shown that where dehydration does occur, the average hydrophobicity of the flanking residues of serines and threonine is positive—0.40 on the N-terminal side and 0.13 on the C-terminal side. Also, the average hydrophobicity of the residues flanking serines and threonines that are not dehydrated is negative—–0.36 on the N-terminal side and –1.03 on the C-terminal side. Deydration is not restricted by the presence of a series of flanking threonine residues and is not restricted by the distance between the nisin leader peptide and the residue to be dehydrated.

N is C has been shown to catalyze the regiospecific formation of thioether rings in peptides unrelated to naturally occurring lantibiotics. Generally, such peptides must be fused to the nisin leader peptide. In some cases, thioether rings may form spontaneously, for example where a dehydroalanine is spaced by two amino acids from a cysteine. Unlike spontaneous cyclization, N is C catalyzed cyclization is stereospecific for dehydrated pre-nisin. Consequently, the methyllanthionines and lanthionine in nisin are in the DL configuration. It is thought that cyclization in nonlantibiotic peptides will also be stereospecific These principles can be applied to the compounds described herein, including cupredoxins and variants and truncations thereof.

Thioether Bridges

In nature, lantibiotic-enzyme-induced thioether bridges occur with up to 19 amino acids under the bridge. Thioether bridges with 2 to 4 amino acids under the bridge are abundant.

Figure 58A:
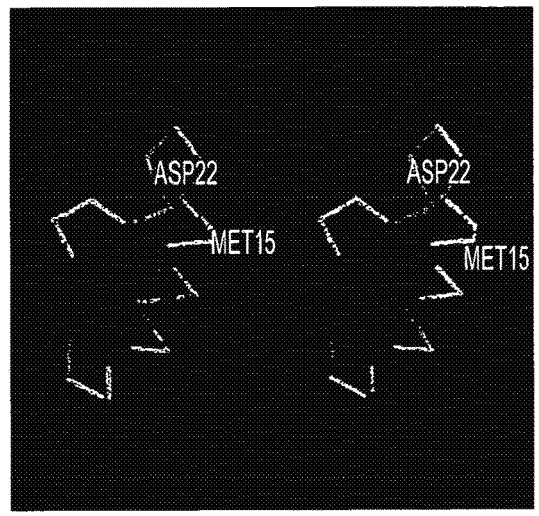
Figure 58B:
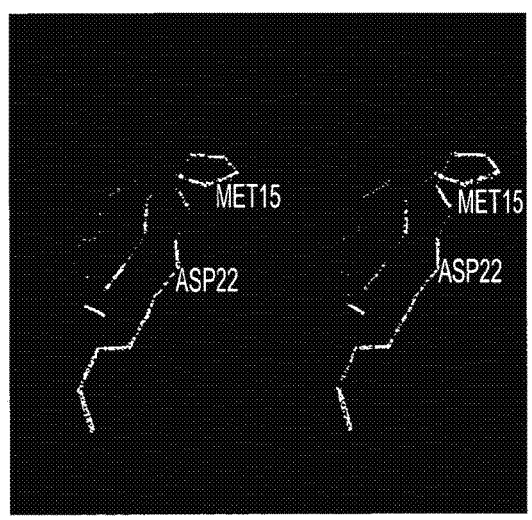
Figure 58C:
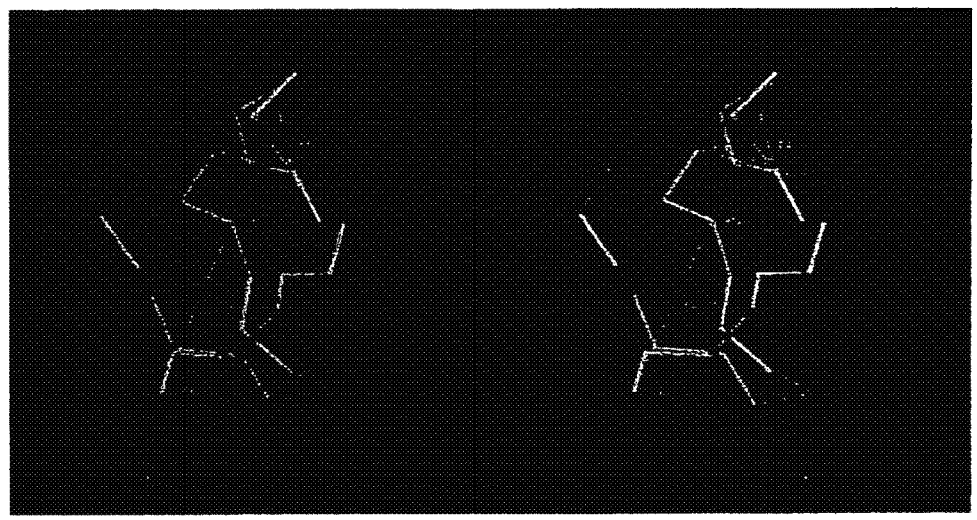

In some embodiments, the cupredoxin may be modified by introducing thioether bridges into the structure. The azurin truncation p28 (SEQ ID NO: 2), for example, may be modified using this method. Extended molecular dynamics simulations (70 ns) using software package GROMACS (www.gromacs.org) suggest that, at 37° C., the region of the p28 alpha helix from position 6 to 16 is unstable, and that the peptide tends to adopt a beta sheet conformation. FIG. 58, A and B. This, together with the fact that the part of the molecule presumed to be responsible for interaction with p53 remains solvent exposed, suggests that introduction of a thioether bridge in this region of the p28 peptide may not affect its functionality.

The amino acid sequence of p28 is SEQ ID NO: 2 (LSTAADMQGVVTDGMASGLDKDYLKPDD). The amino acid sequence known as p18 is SEQ ID NO: 25 (LSTAADMQGVVTDGMASG). The sequence SGLDKD (SEQ ID NO: 96) may interact with p53. Thioether bridges can be formed between Ser/Thr on the N-side to Cys on the C-side. The serine/threonine is dehydrated and subsequently coupled to the cysteine. Threonines are preferred since they are more easily dehydrated than serines. Generally, hydrophobic flanking residues (at least one) to the threonine are preferred since they enhance the extent of dehydration. Negatively charged amino acids, glutamate and aspartate, that are flanking residues have a strong negative effect on dehydration. Generally, hydrophilic flanking residues, especially glycin, do not favor dehydration. Preceding the Cys there is a slight preference for charged hydrophilic residues, especially glutamate/aspartate. Depending on the size of the thioether ring, the bulkiness of the amino acids that participate in the ring matters.

In one embodiment, the truncated azurin sequence is LSTAADMQGVVTDGMASGLDKDYLTPGC (SEQ ID NO: 46). A thioether bridge is formed between positions 25 and 28 of p28, and will be fully protected against carboxyetidases. Positions 2, 3 and 25 will be dehydrated, but neither the import sequence, nor the sequence thought to be relevant for interaction with p53, is altered by thioether ring introduction. As such, peptide activity should not be altered. The threonine is between two hydrophobic amino acids and hence is expected to be fully dehydrated by dehydratase, NisB, according to specific guidelines. See Rink et al., Biochemistry 2005. The same guidelines also predict cyclization involving positions 25 and 28 by cyclase NisC, especially because of the aspartate located before the cysteine.

In another embodiment, the truncated azurin sequence is LSTAADCQGVVTDGMASGLDKDYLKPDD (SEQ ID NO: 47) and the thioether bridge is formed between positions 3 and 7. The ring between position 3 and 7 mimics ring A of nisin and makes use of the existing threonine at position 2. The aspartate at position 6 will favor cyclization.

In another embodiment, the truncated azurin sequence is LSTAACMQGVVTDGMASGLDKDYLKPDD (SEQ ID NO: 48), and the threonine in position 2 is utilized to form a thioether bridge.

In another embodiment, two or more of the thioether rings in the truncated azurins described in the paragraphs above are combined into one peptide.

In another embodiment, many truncated azurin sequences can be created and screened for threonine rings by analyzing the peptides with a ring of one lanthionine and two to three additional amino acids under the sulfur bridge. This might involve one or combinations of the sequences below:

```
LSTACDMQGVVTDGMASGLDKDYLKPDD    (SEQ ID NO: 49)
LSTAATMQCVVTDGMASGLDKDYLKPDD    (SEQ ID NO: 50)
LSTAATMQGCVTDGMASGLDKDYLKPDD    (SEQ ID NO: 51)
LSTAANTQGCVTDGMASGLDKDYLKPDD    (SEQ ID NO: 52)
LSTAANTQGVCTDGMASGLDKDYLKPDD    (SEQ ID NO: 53)
LSTAADMTAVCTDGMASGLDKDYLKPDD    (SEQ ID NO: 54)
LSTAADMTAVVCDGMASGLDKDYLKPDD    (SEQ ID NO: 55)
LSTAADMQTVVCDGMASGLDKDYLKPDD    (SEQ ID NO: 56)
LSTAADMQTVVTCGMASGLDKDYLKPDD    (SEQ ID NO: 57)
```

-continued

```
LSTAADMQATVTCGMASGLDKDYLKPDD     (SEQ ID NO: 58)

LSTAADMQATVTDCMASGLDKDYLKPDD     (SEQ ID NO: 59)

LSTAADMQGVTADCMASGLDKDYLKPDD     (SEQ ID NO: 60)

LSTAADMQGVTADGCASGLDKDYLKPDD     (SEQ ID NO: 61)

LSTAADMQGVVTNGCASGLDKDYLKPDD     (SEQ ID NO: 62)
```

A practical approach would be to genetically make a large number of such sequences and select a group for purification on the basis of extent of modification and level of production.

In another embodiment, a thioether bridge is formed between a threonine at position 12 in p28 (SEQ ID NO: 2) and the c-terminus of the peptide. The distance between the Cα of position 13 and the aspartate at position 28 might be 17.52 angstroms, larger than 1.5 nanometers, implying significant alteration of the structure of the peptide. FIG. 58 C.

In another embodiment, the peptide sequence is LSTAADMQGVVTATMGSGLCKDYLKPDD (SEQ ID NO: 63), with a thioether bridge from position 14 to position 2 at a distance of 4.38 angstroms. The mutation of aspartate at position 13 to alanine favors dehydration of threonine at position 14. Mutation of alanine at position 16 to glycine completely prevents dehydration of serine at position 17 and enhances cyclization.

In another embodiment, the peptide sequence is LSTAADMQGVVTDLTASGLCKDYLKPDD (SEQ ID NO:64), with the thioether bridge from position 15 to position 20 at a distance of 5.83 angstroms. In this situation, mutation of glycine at position 14 to leucine favors dehydration of threonine at position 15.

Tertiary Structure Stabilization

The stability of the tertiary structure of the cupredoxin derived peptide will affect most aspects of the pharmacokinetics, including the pharmacologic activity, plasma half-life, and/or immunogenicity among others. See Kanovsky et al., Cancer Chemother. Pharmacol. 52:202-208 (2003); Kanovsky et al., PNAS 23:12438-12443 (2001). Peptide helices often fall apart into random coils, becoming more susceptible to protease attack and may not penetrate cell membrane well. Schafmeister et al., J. Am. Chem. Soc. 122:5891-5892 (2000). Therefore, one way to stabilize the overall structure of the peptide is to stabilize the α-helix structure of the peptide. The intra-molecular hydrogen bonding associated with helix formation reduces the exposure of the polar amide backbone, thereby reducing the barrier to membrane penetration in a transport peptide, and thus increasing related pharmacologic activities and increasing the resistance of the peptide to protease cleavage. Id. *Pseudomonas aeruginosa* azurin (SEQ ID NO: 1) has α-helices at residues 53-56, 58-64 and 68-70.

One method to stabilize an α-helix is to replace in the α-helix helix breaking amino acid residues such as glycine, proline, serine and aspartic acid, or helix neutral amino acid residues such as alanine, threonine, valine, glutamine, asparagine, cysteine, histidine, lysine or arginine, with helix forming residues, such as leucine, isoleucine, phenylalanine, glutamic acid, tyrosine, tryptophan and methionine or helix favoring amino acid residue substitutions, for example α-amino-isobutyric acid (Aib). See Miranda et al., J. Med. Chem., 51, 2758-2765 (2008), the disclosure of which is incorporated by reference herein. It is contemplated that the α-helix of cupredoxin derived peptides may be stabilized by replacing one or more glycine, proline, serine and/or aspartic acid residues with other amino acids. In specific embodiments, the glycine, proline, serine, aspartic acid, alanine, threonine, valine, glutamine, asparagine, cysteine, histidine, lysine and/or arginine residues are replaced by leucine, isoleucine, phenylalanine, glutamic acid, tyrosine, tryptophan, Aib and/or methionine residues. See Lee et al., Cancer Cell Intl. 11:21 (2005). In other specific embodiments, one or more serine or glutamine residues in the α-helices of a cupredoxin derived peptide may be substituted. In still more specific embodiments, the serine and/or glutamine residues in residues 53-56, 58-64 and 68-70 of *P. aeruginosa* azurin (SEQ ID NO: 1), or equivalent residues of other cupredoxin derived peptides, may be replaced. In another specific embodiment, the glutamine residue at amino acid residue 57 of *P. aeruginosa* azurin (SEQ ID NO: 1), or an equivalent residue of another cupredoxin derived peptide, may be replaced, more specifically replaced with tryptophan. In another specific embodiment, the threonine residue at amino acid residue 52 of *P. aeruginosa* azurin (SEQ ID NO: 1), or an equivalent residue of another cupredoxin derived peptide, may be replaced, more specifically replaced with tryptophan. In another specific embodiment, the threonine residue at amino acid residue 61 of *P. aeruginosa* azurin (SEQ ID NO: 1), or an equivalent residue of another cupredoxin derived peptide, may be replaced, more specifically replaced with tryptophan. In another specific embodiment, the glycine residue at amino acid residue 63 of *P. aeruginosa* azurin (SEQ ID NO: 1), or an equivalent residue of another cupredoxin derived peptide, may be replaced, more specifically replaced with tryptophan. In another specific embodiment, one or more threonine, glutamine or glycine residues at amino acid residues 52, 57, 61 or 63 of *P. aeruginosa* azurin (SEQ ID NO: 1), or an equivalent residue of another cupredoxin derived peptide, may be replaced, more specifically replaced with tryptophan. In specific embodiments, the cupredoxin peptide comprises one of the following sequences wherein the underlined amino acid is substituted into the wildtype *Pseudomonas aeruginosa* p28 sequence:

```
LSWAADMQGVVTDGMASGLDKDYLKPDD;   (SEQ ID NO: 65)

LSTAADMWGVVTDGMASGLDKDYLKPDD;   (SEQ ID NO: 66)

LSTAADMQGVVWDGMASGLDKDYLKPDD;   (SEQ ID NO: 67)

LSTAADMQGVVTDWMASGLDKDYLKPDD;   (SEQ ID NO: 68)

LSWAADMWGVVTDGMASGLDKDYLKPDD;   (SEQ ID NO: 69)

LSWAADMQGVVWDGMASGLDKDYLKPDD;   (SEQ ID NO: 70)

LSWAADMQGVVTDWMASGLDKDYLKPDD;   (SEQ ID NO: 71)

LSTAADMWGVVWDGMASGLDKDYLKPDD;   (SEQ ID NO: 72)

LSTAADMWGVVTDWMASGLDKDYLKPDD;   (SEQ ID NO: 73)

LSTAADMQGVVWDWMASGLDKDYLKPDD;   (SEQ ID NO: 74)
or

LSWAADMWGVVWDWMASGLDKDYLKPDD.   (SEQ ID NO: 75)
```

In other embodiments, equivalent amino acids in other cupredoxin derived peptides are substituted with tryptophan.

Another method to stabilize an α-helix tertiary structure involves using unnatural amino acid residues capable of π-stacking. For example, in Andrews and Tabor (Tetrahedron 55:11711-11743 (1999)), pairs of ε-(3,5-dinitrobenzoyl)-Lys residues were substituted into the α-helix region of a peptide at different spacings. The overall results showed that the i,(i+4) spacing was the most effective stabilizing arrangement. Increasing the percentage of water, up to 90%, increased the helical content of the peptide. Pairs of α-acyl-Lys residues in the same i,(i+4) spacing had no stabilizing effect, indicating that the majority of the stabilization arises from π-π interactions. In one embodiment, the cupredoxin derived peptide may be modified so that the lysine residues are substituted by ε-(3,5-dinitrobenzoyl)-Lys residues. In a specific embodiment, the lysine residues may be substituted by ε-(3,5-dinitrobenzoyl)-Lys in a i,(i+4) spacing.

Another method to stabilize an α-helix tertiary structure uses the electrostatic interactions between side-chains in the α-helix. When His-Cys or His-His residue pairs were substituted in into peptides in an i,(i+4) arrangement, the peptides changed from about 50% helical to about 90% helical on the addition of Cu, Zn or Cd ions. When ruthenium (Ru) salts were added to the His-His peptides, an exchange-inert complex was formed, a macrocyclic cis-[Ru—(NH$_3$)$_4$L$_2$]$^{3+}$ complex where L$_2$ are the side chains of two histidines, which improved the helix stability. Ghadiri and Fernholz, J. Am. Chem. Soc. 112, 9633-9635 (1990). In some embodiments, the cupredoxin derived peptides may comprise macrocyclic cis-[Ru—(NH$_3$)$_4$L$_2$]$^{3+}$ complexes where L$_2$ is the side chains of two histidines. In some embodiments, one or more histidine-cysteine or histidine-histidine residue pairs may be substituted an i,(i+4) arrangement into the α-helices of the cupredoxin derived peptide. In other embodiments, one or more histidine-cysteine or histidine-histidine residue pairs may be substituted an i,(i+4) arrangement in residues 53-56, 58-64 and 68-70 of P. aeruginosa azurin (SEQ ID NO: 1), or equivalent residues of other cupredoxin derived peptides. In some embodiments, the cupredoxin derived peptide may further comprise Cu, Zn, Cd and/or Ru ions.

Another method to stabilize an α-helix tertiary structure involves disulfide bond formation between side-chains of the α-helix. It is also possible to stabilize helical structures by means of formal covalent bonds between residues separated in the peptide sequence. The commonly employed natural method is to use disulfide bonds. Pierret et al., Intl. J. Pept. Prot. Res., 46:471-479 (1995). In some embodiments, one or more cysteine residue pairs are substituted into the α-helices of the cupredoxin derived peptide. In other embodiments, one or more cysteine residue pairs are substituted at residues 53-56, 58-64 and 68-70 of P. aeruginosa azurin (SEQ ID NO: 1), or equivalent residues of other cupredoxin derived peptides.

Another method to stabilize an α-helical tertiary structure involves the use of side chain lactam bridges. A lactam is a cyclic amide which can form from the cyclisation of amino acids. Side chain to side chain bridges have been successfully used as constraints in a variety of peptides and peptide analogues, such as amphipathic or model α-helical peptides, oxytocin antagonists, melanoptropin analogues, glucagon, and SDF-1 peptide analogues. For example, the Glucagon-like Peptide-1 (GLP-1) gradually assumes a helical conformation under certain helix-favoring conditions and can be stabilized using lactam bridging. Miranda et al., J. Med. Chem., 51, 2758-2765 (2008). These lactam bridges may be varied in size, effecting stability and binding affinity. Id. Such modifications improved the stability of the compounds in plasma. Id. Depending on the space between the cyclization sites and choice of residues, lactam bridges can be used to induce and stabilize turn or helical conformations. In some embodiments, one or more cupredoxin or variant analogues are prepared with lactam bridging between nearby amino acids (such as i to i+4 glutamic acid-lysine constraints). In some embodiments, the cupredoxin derived peptide may comprise such modifications to enhance α-helix content.

Another method to stabilize an α-helix tertiary structure is the all-carbon cross-link method. The all-hydrocarbon cross-link method is proven to increase the stabilization of helical structure, protease resistant and cell-permeability. Walensky et al., Science, 305, 1466-1470 (2004). α,α-disubstituted non-natural amino acids containing olefin-bearing tethers are incorporated into peptides. Ruthenium catalyzed olefin metathesis generates an all-hydrocarbon "staple" to cross-link the helix. Schafmeister et al., J. Am. Chem. Soc., 122, 5891-5892 (2000); Walensky et al., id. Non-natural amino acids containing olefin-bearing tethers may be synthesized according to methodology provided in Schafmeister et al. (id.) and Williams and Im (J. Am. Chem. Soc., 113:9276-9286 (1991)). In some embodiments, the cupredoxin derived peptides are stabilized by all-hydrocarbon staples. In specific embodiments, one or more pairs of α,α-disubstituted non-natural amino acids containing olefin-bearing tethers corresponding to the native amino acids are substituted into the α-helices of the cupredoxin derived peptide. In other embodiments, one or more pairs of α,α-disubstituted non-natural amino acids containing olefin-bearing tethers corresponded to the native amino acids are substituted into residues 53-56, 58-64 and 68-70 of P. aeruginosa azurin (SEQ ID NO: 1), or equivalent residues of other cupredoxin derived peptides.

In some embodiments, the modified cupredoxin derived peptide may comprise X$_1$SX$_2$AADX$_3$X$_4$X$_5$VVX$_6$DX$_7$X$_8$ASGLDKDYLKPDX$_9$ (SEQ ID NO: 76), where X$_1$ is L or acetylated-L, X$_2$ is T or W, X$_3$ is M, L or V, X$_4$ is Q or W, X$_5$ is G or A, X$_6$ is T or W, X$_7$ is G, T or W, X$_8$ is M, L or V, and X$_9$ is D or amidated-D. In other embodiments, the modified cupredoxin derived peptide may consist of X$_1$SX$_2$AADX$_3$X$_4$X$_5$VVX$_6$DX$_7$X$_8$ASGLDKDYLKPDX$_9$ (SEQ ID NO: 76), where X$_1$ is L or acetylated-L, X$_2$ is T or W, X$_3$ is M, L or V, X$_4$ is Q or W, X$_5$ is G or A, X$_6$ is T or W, X$_7$ is G, T or W, X$_8$ is M, L or V, and X$_9$ is D or amidated-D.

In other embodiments, the modified cupredoxin derived peptide may comprise X$_1$DPKLYDKDLGSAX$_2$X$_3$DX$_4$VVX$_5$X$_6$X$_7$DAAX$_8$SX$_9$ (SEQ ID NO: 77), where X$_1$ is D or acetylated-D, X$_2$ is M, L or V, X$_3$ is G, T or W, X$_4$ is T or W, X$_5$ is G or A, X$_6$ is Q or W, X$_7$ is M, L or V, X$_8$ is T or W, and X$_9$ is L or amidated-L. In other embodiments, the modified cupredoxin derived peptide may consist of X$_1$DPKLYDKDLGSAX$_2$X$_3$DX$_4$VVX$_5$X$_6$X$_7$DAAX$_8$SX$_9$ (SEQ ID NO: 77), where X$_1$ is D or acetylated-D, X$_2$ is M, L or V, X$_3$ is G, T or W, X$_4$ is T or W, X$_5$ is G or A, X$_6$ is Q or W, X$_7$ is M, L or V, X$_8$ is T or W, and X$_9$ is L or amidated-L. Specific peptides of interest are listed in Table 3.

PEGylation

Covalent attachment of PEG to drugs of therapeutic and diagnostic importance has extended the plasma half-life of the drug in vivo, and/or reduced their immunogenicity and antigenicity. Harris and Chess, Nature Reviews Drug Discovery 2:214-221 (2003). For example, PEG attachment has improved the pharmacokinetic properties of many therapeutic proteins, including interleukins (Kaufman et al., J. Biol. Chem. 263:15064 (1988); Tsutsumi et al., J. Controlled Release 33:447 (1995)), interferons (Kita et al., Drug Des. Delivery 6:157 (1990)), catalase (Abuchowski et al., J. Biol. Chem. 252:3582 (1977)), superoxide dismutase (Beauchamp et al., Anal. Biochem. 131:25 (1983)), and adenosine deanimase (Chen et al., Biochem. Biophys. Acta 660:293 (1981)), among others. The FDA has approved PEG for use as a vehicle or base in foods, cosmetics and pharmaceuticals, including injectable, topical, rectal and nasal formulations. PEG shows little toxicity, and is eliminated from the body intact by either the kidneys (for PEGs <30 kDa) or in the feces (for PEGs >20 kDa). PEG is highly soluble in water.

PEGylation of a therapeutic peptide may be used to increase the lifetime of the peptide in the bloodstream of the patient by reducing renal ultrafiltration, and thus reduce elimination of the drug from the body. Charge masking may affect renal permeation. Charge masking may be a consequence of the paramchemical modification of protein ionizable functional group, namely amines or carboxyls. In particular, the most common procedures for producing protein-PEG derivatives involves the conversion of protein amino groups into amides with the consequent loss of positive charges, and this can alter protein ultrafiltration. Since anionic macromolecules have been found to be cleared by renal ultrafiltration more slowly than neutral or positive ones, it could be expected that PEG conjugation to amino groups prolongs the permanence of the PEGylated peptide in the bloodstream.

Molecular size and globular ultrafiltration may also affect renal ultrafiltration of therapeutic peptides. The molecular weight cut off for kidney elimination of native globular proteins is considered to be about 70 kDa, which is close to the molecular weight of serum albumin. Thus, proteins with molecular weight exceeding 70 kDa are mainly eliminated from the body by pathways other than renal ultrafiltration, such as liver uptake, proteolytic digestion and clearance by the immune system. Therefore, increasing the size of a therapeutic peptide by PEGylation may decrease renal ultrafiltration of that peptide form the bloodstream of the patient.

Additionally, PEGylation of a therapeutic peptide may decrease the immunogenicity of that peptide, as well as protect the peptide from proteolytic enzymes, phagocytic cells, and other factors that require direct contact with the therapeutic peptide. The umbrella-like structure of branched PEG in particular has been found to give better protection than linear PEG towards approaching proteolytic enzymes, antibodies, phagocytic cells, etc. Caliceti and Veronese, Adv. Drug. Deliv. Rev. 55:1261-12778 (2003).

In some embodiments, the cupredoxin derived peptides of the invention are modified to have one or more PEG molecules covalently bonded to a cysteine molecule. The covalent bonding does not necessarily need to be a covalent bond directly from the PEG molecule to the cupredoxin derived peptide, but may be covalently bonded to one or more linker molecules which in turn are covalently bonded to each other and/or the cupredoxin derived peptide. In some embodiments, the cupredoxin derived peptide have site-specific PEGylation. In specific embodiments, the PEG molecule(s) may be covalently bonded to the cysteine residues 3, 26 and/or 112 of P. aeruginosa azurin (SEQ ID NO: 1). In other embodiments, one or more cysteine residues may be substituted into the cupredoxin derived peptide and is PEGylated. In some embodiments, the method to PEGylate the cupredoxin derived peptide may be NHS, reductive animation, malimid or epoxid, among others. In other embodiments, the cupredoxin derived peptides may be PEGylated on one or more lysine, cysteine, histidine, arginine, aspartic acid, glutamic acid, serine, threonine, or tyrosine, or the N-terminal amino group or the C-terminal carboxylic acid. In more specific embodiments, the cupredoxin derived peptides may be PEGylated on one or more lysines or N-terminal amino groups. In other embodiments, one or more lysine, cysteine, histidine, arginine, aspartic acid, glutamic acid, serine, threonine, or tyrosine residue are substituted into the cupredoxin derived peptides and are PEGylated. In other embodiments, the cupredoxin derived peptides may be PEGylated on one or more amino groups. In other embodiments, the cupredoxin derived peptides may be PEGylated in a random, non-site specific manner. In some embodiments, the cupredoxin derived peptides may have an average molecular weight of PEG-based polymers of about 200 daltons to about 100,000 daltons, about 2,000 daltons to about 20,000 daltons, or about 2,000 daltons to about 5,000 daltons. In other embodiments, the cupredoxin derived peptides may be comprised of one or more PEG molecules that is branched, specifically a branched PEG molecule that is about 50 kDa. In other embodiments, the cupredoxin derived peptides may comprise one or more linear PEG molecules, specifically a linear PEG molecule that is about 5 kDa.

In another embodiment, the peptide is a cupredoxin, or variant, structural equivalent, or derivative thereof that is a conjugate of Pep42, a cyclic 13-mer oligopeptide that specifically binds to glucose-regulated protein 78 (GRP78) and is internalized into cancer cells. The cupredoxin or variant, structural equivalent, or derivative of cupredoxin may be conjugated with Pep42 pursuant to the synthesis methods disclosed in Yoneda et al., "A cell-penetrating peptidic GRP78 ligand for tumor cell-specific prodrug therapy," Bioorganic & Medicinal Chemistry Letters 18: 1632-1636 (2008), the disclosure of which is incorporated in its entirety herein.

In another embodiment, the peptide is a structural equivalent of a cupredoxin. Examples of studies that determine significant structural homology between cupredoxins and other proteins include Toth et al. (Developmental Cell 1:82-92 (2001)). Specifically, significant structural homology between a cupredoxin and the structural equivalent may be determined by using the VAST algorithm. Gibrat et al., Curr Opin Struct Biol 6:377-385 (1996); Madej et al., Proteins 23:356-3690 (1995). In specific embodiments, the VAST p value from a structural comparison of a cupredoxin to the structural equivalent may be less than about $10^{-3}$, less than about $10^{-5}$, or less than about $10^{-7}$. In other embodiments, significant structural homology between a cupredoxin and the structural equivalent may be determined by using the DALI algorithm. Holm & Sander, J. Mol. Biol. 233:123-138 (1993). In specific embodiments, the DALI Z score for a pairwise structural comparison is at least about 3.5, at least about 7.0, or at least about 10.0.

It is contemplated that the peptides of the composition of invention may be more than one of a variant, derivative, truncation and/or structural equivalent of a cupredoxin. For example, the peptides may be a truncation of azurin that has been PEGylated, thus making it both a truncation and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. Scharmeister et al., J. Am. Chem. Soc. 122:5891-5892 (2000); Walensky et al., Science 305:1466-1470 (2004). Additionally, peptides that are structural equivalents of azurin may be fused to other peptides, thus making a peptide that is both a structural equivalent and a derivative. These examples are merely to illustrate and not to limit the invention. Variants, derivatives or structural equivalents of cupredoxin may or may not bind copper.

In some embodiments, the cupredoxin, or variant, derivative or structural equivalent thereof has some of the pharmacologic activities of the P. aeruginosa azurin, and specifically p28. In a specific embodiment, the cupredoxins and variants, derivatives and structural equivalents of cupredoxins that may inhibit prevent the development of premalignant lesions in mammalian cells, tissues or animals, and specifically but not limited to, mammary gland cells. The invention also provides for the cupredoxins and variants, derivatives and structural equivalents of cupredoxins that may have the ability to inhibit the development of mammalian premalignant lesions, and specifically but not limited to, melanoma, breast, pancreas, glioblastoma, astrocytoma, lung, colorectal, neck and head, bladder, prostate, skin and cervical cancer cells. Inhibition of the development of cancer cells is any decrease, or lessening of the rate of increase, of the development of premalignant lesions that is statistically significant as compared to control treatments.

Because it is now known that cupredoxins can preferentially enter cancer cells via endocytotic pathways, and can also inhibit the development of premalignant lesions and ultimately cancer in mammalian cells, tissues or animals, and specifically breast cells, and more specifically, mouse mammary gland cells, it is now possible to design variants and derivatives of cupredoxins that retain this activity. Such variants, derivatives and structural equivalents can be made by, for example, creating a "library" of various variants, derivatives and structural equivalents of cupredoxins and cupredoxin derived peptides and then testing each for preferential entry and/or chemopreventive activity, and specifically preferential entry and/or chemopreventive activity in the mouse mammary gland organ culture using one of many methods known in the art, such the exemplary method in Example 1. It is contemplated that the resulting variants, derivatives and structural equivalents of cupredoxins with chemopreventive activity and/or the ability to preferentially enter cells may be used in the methods of the invention, in place of or in addition to azurin or p28.

In some specific embodiments, the variant, derivative or structural equivalent of cupredoxin may inhibit the development of 7,12-dimethylbenz (a) anthracene (DMBA) induced premalignant lesions in a mouse mammary gland organ culture (MMOC) to a degree that is statistically different from a non-treated control. A peptide can be tested for this activity by using the MMOC model system is described in Example 1, or as in Mehta et al. (J Natl Cancer Inst 93:1103-1106 (2001)) and Mehta et al. (Meth Cell Sci 19:19-24 (1997)). Other methods to determine whether cancer development is inhibited another are well known in the art and may be used as well.

In some specific embodiments, the variant, derivative or structural equivalent of cupredoxin inhibits the development of mammary alveolar lesions (MAL) in the a MMOC model to a degree that is statistically different from a non-treated control. In some specific embodiments, the variant, derivative or structural equivalent of cupredoxin inhibits the development of mammary ductal lesions (MDL) in the a MMOC model to a degree that is statistically different from a non-treated control. A peptide can be tested for these activities by using the MMOC model system induced to form premalignant lesions by DMBA, as described in Example 1. Evaluation of development of premalignant lesions in a MMOC model system may be determined by morphometic analysis, or histopathological analysis, as provided in Example 1.

In some specific embodiments, the variant, derivative or structural equivalent can preferentially enter cancer cells and/or tumors in mammalian cells, tissues and animals. In some embodiments, the variant is a derivative or structural equivalent of p18. In some embodiments, the variant, derivative or structural equivalent can selectively enter cancer cells and/or tumors in mammalian cells, tissues and animals and deliver DNA or RNA. In some embodiments, the DNA or RNA is a gene or a portion of a gene. In some embodiments, the DNA or RNA has a therapeutic effect once delivered. In some embodiments, the variant is a derivative or structural equivalent of p28. In some embodiments, the variant, derivative or structural equivalent can selectively enter cancer cells and/or tumors in mammalian cells, tissues and animals and deliver DNA or RNA. In some embodiments, the DNA or RNA is a gene or a portion of a gene. In some embodiments, the DNA or RNA has a therapeutic effect once delivered.

Cupredoxins

These small blue copper proteins (cupredoxins) are electron transfer proteins (10-20 kDa) that participate in bacterial electron transfer chains or are of unknown function. The copper ion is solely bound by the protein matrix. A special distorted trigonal planar arrangement to two histidine and one cysteine ligands around the copper gives rise to very peculiar electronic properties of the metal site and an intense blue color. A number of cupredoxins have been crystallographically characterized at medium to high resolution.

The cupredoxins in general have a low sequence homology but high structural homology. Gough & Clothia, Structure 12:917-925 (2004); De Rienzo et al., Protein Science 9:1439-1454 (2000). For example, the amino acid sequence of azurin is 31% identical to that of auracyanin B, 16.3% to that of rusticyanin, 20.3% to that of plastocyanin, and 17.3% to that of pseudoazurin. See, Table 1. However, the structural similarity of these proteins is more pronounced. The VAST p value for the comparison of the structure of azurin to auracyanin B is $10^{-7.4}$, azurin to rusticyanin is $10^{-5}$, azurin to plastocyanin is $10^{-5.6}$, and azurin to psuedoazurin is $10^{-4.1}$.

All of the cupredoxins possess an eight-stranded Greek key beta-barrel or beta-sandwich fold and have a highly conserved site architecture. De Rienzo et al., Protein Science 9:1439-1454 (2000). A prominent hydrophobic patch, due to the presence of many long chain aliphatic residues such as methionines and leucines, is present around the copper site in azurins, amicyanins, cyanobacterial plastocyanins, cucumber basic protein and to a lesser extent, pseudoazurin and eukaryotic plastocyanins. Id. Hydrophobic patches are also found to a lesser extent in stellacyanin and rusticyanin copper sites, but have different features. Id.

TABLE 1

Sequence and structure alignment of azurin (1JZG) from
*P. aeruginosa* to other proteins using VAST algorithm.

| PDB | Alignment length[1] | % aa identity | P-value[2] | Score[3] | RMSD[4] | Description |
|---|---|---|---|---|---|---|
| 1AOZ A 2 | 82 | 18.3 | 10e−7 | 12.2 | 1.9 | Ascorbate oxidase |
| 1QHQ_A | 113 | 31 | 10e−7.4 | 12.1 | 1.9 | AuracyaninB |
| 1V54 B 1 | 79 | 20.3 | 10e−6.0 | 11.2 | 2.1 | Cytocrome c oxidase |
| 1GY2 A | 92 | 16.3 | 10e−5.0 | 11.1 | 1.8 | Rusticyanin |
| 3MSP A | 74 | 8.1 | 10e−6.7 | 10.9 | 2.5 | Motile Major Sperm Protein[5] |

TABLE 1-continued

Sequence and structure alignment of azurin (1JZG) from
*P. aeruginosa* to other proteins using VAST algorithm.

| PDB | Alignment length[1] | % aa identity | P-value[2] | Score[3] | RMSD[4] | Description |
|---|---|---|---|---|---|---|
| 1IUZ | 74 | 20.3 | 10e−5.6 | 10.3 | 2.3 | Plastocyanin |
| 1KGY E | 90 | 5.6 | 10e−4.6 | 10.1 | 3.4 | Ephrinb2 |
| 1PMY | 75 | 17.3 | 10e−4.1 | 9.8 | 2.3 | Pseudoazurin |

[1]Aligned Length: The number of equivalent pairs of C-alpha atoms superimposed between the two structures, i.e. how many residues have been used to calculate the 3D superposition.
[2]P-VAL: The VAST p value is a measure of the significance of the comparison, expressed as a probability. For example, if the p value is 0.001, then the odds are 1000 to 1 against seeing a match of this quality by pure chance. The p value from VAST is adjusted for the effects of multiple comparisons using the assumption that there are 500 independent and unrelated types of domains in the MMDB database. The p value shown thus corresponds to the p value for the pairwise comparison of each domain pair, divided by 500.
[3]Score: The VAST structure-similarity score. This number is related to the number of secondary structure elements superimposed and the quality of that superposition. Higher VAST scores correlate with higher similarity.
[4]RMSD: The root mean square superposition residual in Angstroms. This number is calculated after optimal superposition of two structures, as the square root of the mean square distances between equivalent C-alpha atoms. Note that the RMSD value scales with the extent of the structural alignments and that this size must be taken into consideration when using RMSD as a descriptor of overall structural similarity.
[5]*C. elegans* major sperm protein proved to be an ephrin antagonist in ocyte maturation. Kuwabara, Genes and Development 17: 155-161 (2003).

Azurin

The azurins are copper containing proteins of 128 amino acid residues which belong to the family of cupredoxins involved in electron transfer in certain bacteria. The azurins include those from *P. aeruginosa* (PA) (SEQ ID NO: 1), *A. xylosoxidans*, and *A. denitrficans*. Murphy et al., J. Mol. Biol. 315:859-871 (2002). The amino acid sequence identity between the azurins varies between 60-90%, these proteins showed a strong structural homology. All azurins have a characteristic β-sandwich with Greek key motif and the single copper atom is always placed at the same region of the protein. In addition, azurins possess an essentially neutral hydrophobic patch surrounding the copper site. Id.

Plastocyanins

The plastocyanins are soluble proteins of cyanobacteria, algae and plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 3 shows the amino acid sequence of plastocyanin from *Phormidium laminosum*, a thermophilic cyanobacterium. Another plastocyanin of interest is from *Ulva pertussis*.

Despite the sequence divergence among plastocyanins of algae and vascular plants (e.g., 62% sequence identity between the *Chlamydomonas* and poplar proteins), the three-dimensional structures are conserved (e.g., 0.76 Å rms deviation in the C alpha positions between the *Chlamydomonas* and *Poplar* proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths involving plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch. Redinbo et al., J. Bioenerg. Biomembr. 26:49-66 (1994).

Rusticyanins

Rusticyanins are blue-copper containing single-chain polypeptides obtained from a *Thiobacillus* (now called *Acidithiobacillus*). The X-ray crystal structure of the oxidized form of the extremely stable and highly oxidizing cupredoxin rusticyanin from *Thiobacillus ferrooxidans* (SEQ ID NO: 4) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. Walter, R. L. et al., J. Mol. Biol. 263:730-51 (1996).

Pseudoazurins

The pseudoazurins are a family of blue-copper containing single-chain polypeptide. The amino acid sequence of pseudoazurin obtained from *Achromobacter cycloclastes* is shown in SEQ ID NO: 5. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the mid-peptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Phytocyanins

The proteins identifiable as phytocyanins include, but are not limited to, cucumber basic protein, stellacyanin, mavicyanin, umecyanin, a cucumber peeling cupredoxin, a putative blue copper protein in pea pods, and a blue copper protein from *Arabidopsis thaliana*. In all except cucumber basic protein and the pea-pod protein, the axial methionine ligand normally found at blue copper sites is replaced by glutamine.

Auracyanin

Three small blue copper proteins designated auracyanin A, auracyanin B-1, and auracyanin B-2 have been isolated from the thermophilic green gliding photosynthetic bacterium *Chloroflexus aurantiacus*. The two B forms are glycoproteins and have almost identical properties to each other, but are distinct from the A form. The sodium dodecyl sulfate-polyacrylamide gel electrophoresis demonstrates apparent monomer molecular masses as 14 (A), 18 (B-2), and 22 (B-1) kDa.

The amino acid sequence of auracyanin A has been determined and showed auracyanin A to be a polypeptide of 139 residues. Van Dreissche et al., Protein Science 8:947-957 (1999). His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id. See exemplary amino acid sequence SEQ ID NO: 15 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. Bond et al., J. Mol. Biol. 306:47-67 (2001). With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. J. Biol. Chem. 267:6531-6540 (1992). See exemplary amino acid sequence SEQ ID NO: 16 for chain B of auracyanin from *Chloroflexus aurantiacus* (NCBI Protein Data Bank Accession No. 1QHQA).

Stellacyanin

Stellacyanins are a subclass of phytocyanins, a ubiquitous family of plant cupredoxins. An exemplary sequence of a stellacyanin is included herein as SEQ ID NO: 14. The crystal structure of umecyanin, a stellacyanin from horseradish root (Koch et al., J. Am. Chem. Soc. 127:158-166 (2005)) and cucumber stellacyanin (Hart et al., *Protein Science* 5:2175-2183 (1996)) is also known. The protein has an overall fold similar to the other phytocyanins. The ephrin B2 protein ectodomain tertiary structure bears a significant similarity to stellacyanin. Toth et al., Developmental Cell 1:83-92 (2001). An exemplary amino acid sequence of a stellacyanin is found in the National Center for Biotechnology Information Protein Data Bank as Accession No. 1JER, SEQ ID NO: 14.

Cucumber Basic Protein

An exemplary amino acid sequence from a cucumber basic protein is included herein as SEQ ID NO: 17. The crystal structure of the cucumber basic protein (CBP), a type 1 blue copper protein, has been refined at 1.8 Å resolution. The molecule resembles other blue copper proteins in having a Greek key beta-barrel structure, except that the barrel is open on one side and is better described as a "beta-sandwich" or "beta-taco". Guss et al., J. Mol. Biol. 262: 686-705 (1996). The ephrinB2 protein ectodomian tertiary structure bears a high similarity (rms deviation 1.5 Å for the 50 α carbons) to the cucumber basic protein. Toth et al., Developmental Cell 1:83-92 (2001).

The Cu atom has the normal blue copper NNSS' co-ordination with bond lengths Cu—N(His39)=1.93 A, Cu—S(Cys79)=2.16 A, Cu—N(His84)=1.95 A, Cu—S(Met89)=2.61 A. A disulphide link, (Cys52)-S—S-(Cys85), appears to play an important role in stabilizing the molecular structure. The polypeptide fold is typical of a sub-family of blue copper proteins (phytocyanins) as well as a non-metalloprotein, ragweed allergen Ra3, with which CBP has a high degree of sequence identity. The proteins currently identifiable as phytocyanins are CBP, stellacyanin, mavicyanin, umecyanin, a cucumber peeling cupredoxin, a putative blue copper protein in pea pods, and a blue copper protein from *Arabidopsis thaliana*. In all except CBP and the pea-pod protein, the axial methionine ligand normally found at blue copper sites is replaced by glutamine. An exemplary sequence for cucumber basic protein is found in NCBI Protein Data Bank Accession No. 2CBP, SEQ ID NO: 17.

Methods of Use

The invention provides methods to prevent malignancies in otherwise healthy patients comprising administering to the patient at least one peptide that is a cupredoxin, or variant, derivative or structural equivalent thereof, as described above. Chemopreventive therapies are based on the hypothesis that the interruption of processes involved in carcinogenesis will prevent the development of cancer. The cupredoxin *Pseudomonas aeruginosa* azurin and the truncated azurin peptide p28 are now known to inhibit the development of premalignant lesions, either by inhibiting the initial formation of premalignant lesions, or killing or inhibiting the growth of premalignant lesions that are present.

It therefore contemplated that a cupredoxin, or variant, truncation, derivative or structural equivalent thereof, as described above, with the ability to inhibit the development of premalignant lesions, may be used in chemopreventive therapies in otherwise healthy patients. Such otherwise healthy patients are, in some embodiments, patients at a higher risk to develop cancer than those in the general population. Cancers that may be prevented by treatment with the compositions of the invention include, but are not limited to, melanoma, breast, pancreas, glioblastoma, astrocytoma, lung, colorectal, neck and head, bladder, prostate, skin, and cervical cancer. In some embodiments, the patient may be human. In other embodiments, the patient is not human.

The invention further includes compositions and methods to preferentially enter cancerous cells. Cupredoxins, specifically azurin derivatives p18 and p28, are now known to enter cancerous cells via certain mechanisms described herein, including caveolae-mediated endocytosis, which may be mediated by the Golgi apparatus. It is therefore contemplated that a cupredoxin or variant, derivative, or structural equivalent thereof may be used to enter and kill cancer cells, and may also be used to transport cargo across cell membranes.

The invention further includes methods to study the development of cancer comprising contacting mammalian cells before or after induction with a carcinogen with a composition comprising cupredoxin, or a variant, derivative, truncation, or structural equivalent thereof and observing the development of the cells. In some embodiments, the cells are mouse mammary gland cells, while in others they are other cells that may become malignant in mammals.

Patients at a higher at risk to develop cancer than the general population may be patients with high risk features, patients with premalignant lesions, and patients that have been cured of their initial cancer or definitively treated for their premalignant lesions. See generally Tsao et al., CA Cancer J Clin 54:150-180 (2004). High risk features may be behavioral, genetic, environmental or physiological factors of the patient. Behavioral factors that predispose a patient to various forms of cancer include, but are not limited to, smoking, diet, alcohol consumption, hormone replacement therapy, higher body mass index, nulliparity, beta1 nut use, frequent mouthwash use, exposure to human papillomavirus, childhood and chronic sun exposure, early age of first intercourse, multiple sexual partners, and oral contraceptive use. Genetic factors that predispose a patient to various forms of cancer include, but are not limited to, a family history of cancer, gene carrier status of BRCA1 and BRCA2, prior history of breast neoplasia, familial adenomatous polyposis (FAP), hereditary nonpolyposis colorectal cancer (HN-PCC), red or blond hair and fair-skinned phenotype, xeroderma pigmentosum, and ethnicity. Environmental features that predispose a patient to various forms of cancer include, but are not limited to, exposure to radon, polycyclic aromatic hydrocarbons, nickel, chromate, arsenic, asbestos, chloromethyl ethers, benzo[a]pyrene, radiation, and aromatic amines from rubber or paint occupational exposure. Other miscellaneous factors that predispose a patient to various forms of cancer include, but are not limited to, chronic obstructive pulmonary disease with airflow obstruction, chronic bladder infections, schistosomiasis, older age, and immunocompromised status.

Additionally, patients at a higher risk of developing cancer may be determined by the use of various risk models that have been developed for certain kinds of cancer. For example, patients predisposed to breast cancer may be determined using the Gail risk model, or the Claus model, among others. See Gail et al., J Natl Cancer Inst 81:1879-1886 (1989); Cuzick, Breast 12:405-411 (2003); Huang et al., Am J Epidemiol 151:703-714 (2000).

Patients with premalignant lesions are at a higher risk to develop cancer than the general population. The presence of premalignant lesions in or on a patient may be determined by many methods that are well known to those in the art. Intermediate markers or biomarkers that originate from premalignant lesions may be measured in a patient to determine if the patient harbors premalignant lesions. Chromosomal abnormalities occur in tumor cells and the adjacent histologically normal tissues in the majority of cancer patients. Progression in chromosomal abnormalities parallels the phenotypic progression from premalignant lesion to invasive cancer. Thiberville et al., Cancer Res. 55:5133-5139 (1995). Therefore, chromosomal abnormalities associated with cancer may be used as intermediate markers to detect premalignant lesions in a patient. Common chromosomal abnormalities associated with cancer include, but are not limited to, allelic deletions or loss of heterozygosity (LOH) in tumor suppressor genes such as 3p (FHIT and others), 9p (9p21 for p16$^{INK4}$, p15$^{INK4B}$, and p19$^{ARF}$), 17p (17p13 for p53 gene and others) and 13q (13q14 for retinoblastoma gene Rb and others). Deletions in 3p and 9p are associated with smoking and the early stages of lung cancer. Mao et al., J. Natl. Cancer Inst. 89:857-862 (1997). Deletions affecting 3p, 5q, 8p, 17p and 18q are common change in epithelial cancers. See generally Tsao et al., CA Clin. Cancer J. Clin. 54:153 (2004). Other chromosomal mutations associated with cancer include those which activate oncogenes. Oncogenes whose presence may be used as intermediate markers include, but are not limited to, Ras, c-myc, epidermal growth factor, erb-B2 and cyclins E, D1 and B1. See generally id. at 154.

Other intermediate markers may be the products of genes up-regulated in premalignant cells and cancer cells. Genes that may be up-regulated in premalignant cells include, but are not limited to, cyclooxygenases COX-1 and COX-2, telomerase. Other biomarkers of cancer cells, and some premalignant cells, include, but are not limited to, p53, epidermal growth factor receptor (GFR), proliferating cell nuclear antigen (PCNA), RAS, COX-2, Ki-67, DNA aneuploidy, DNA polymerase-α, ER, Her2neu, E-cadherin, RARβ, hTERT, p16$^{INK4a}$, FHIT (3p14), Bcl-2, VEGF-R, HPV infection, LOH 9p21, LOH 17p, p-AKT, hnRNP A2/B1, RAF, Myc, c-KIT, cyclin D1, E and B1, IGF1, bcl-2, p16, LOH 3p21.3, LOH 3p25, LOH 9p21, LOH 17p13, LOH 13q, LOH 8p, hMSH2, APC, DCC, DPC4, JV18, BAX, PSA, GSTP1, NF-kB, AP1, D3S2, HPV infection, LOH 3p14, LOH 4q, LOH 5p, bladder tumor antigen (BTA), BTK TRAK (Alidex, Inc., Redmond Wash.), urinary tract matrix protein 22, fibrin degradation product, autodrine motility factor receptor, BCLA-4, cytokeratin 20, hyaluronic acid, CYFRA 21-1, BCA, beta-human chorionic gonadotropin, and tissue polypeptide antigen (TPA). See generally id. at 155-157.

Patients that have been cured of their initial cancers or have been definitively treated for their premalignant lesions are also at a higher risk to develop cancer than the general population. A second primary tumor refers to a new primary cancer in a person with a history of cancer. Second primary tumors are the leading cause of mortality in head and neck cancer Id. at 150. A second primary tumor is distinct from a metastasis in that the former originates de novo while the later originates from an existing tumor. Patients that have been cured of cancer or premalignant lesions of the breast, head and neck, lung, and skin are at a particularly high risk to develop second primary tumors.

The compositions comprising a cupredoxin or variant, derivative, truncation, or structural equivalent thereof can be administered to the patient by many routes and in many regimens that will be well known to those in the art. In specific embodiments, the cupredoxin, or variant, derivative or structural equivalent thereof is administered intravenously, intramuscularly, subcutaneously, topically, orally, or by inhalation. The compositions may be administered to the patient by any means that delivers the peptides to the site in the patient that is at risk of developing cancer. In specific embodiments, the cupredoxin or variant, derivative, truncation, or structural equivalent thereof is administered intravenously.

In one embodiment, the methods may comprise co-administering to a patient one unit dose of a composition comprising a cupredoxin or a variant, derivative, truncation, or structural equivalent of cupredoxin and one unit dose of a composition comprising another chemopreventive drug, in either order, administered at about the same time, or within about a given time following the administration of the other, for example, about one minute to about 60 minutes following the administration of the other drug, or about 1 hour to about 12 hours following the administration of the other drug. Chemopreventive drugs of interest include, but are not limited to, Tamoxifen, aromatase inhibitors such as letrozole and anastrozole (Arimidex®), retinoids such as N-[4-hydroxyphenyl]retinamide (4-HPR, fenretinide), nonsteriodal antiinflammatory agents (NSAIDs) such as aspirin and sulindac, celecoxib (COX-2 inhibitor), defluoromethylornithing (DFMO), ursodeoxycholic acid, 3-hydroxy-3-methylglutaryl coenzyme A reductase inhibitors, EKI-785 (EGFR inhibitor), bevacizumab (antibody to VEGF-receptor), cetuximab (antibody to EGFR), retinol such as vitamin A, beta-carotene, 13-cis retinoic acid, isotretinoin and retinyl palmitate, α-tocopherol, interferon, oncolytic adenovirus dl1520 (ONYX-015), gefitinib, etretinate, finasteride, indole-3-carbinol, resveratrol, chlorogenic acid, raloxifene, and oltipraz.

Compositions for Facilitating Entry of Compounds into Cancer Cells and Tumors

The present invention relates to methods and materials for delivering a cargo compound into a cell. Delivery of the cargo compound according to this invention is accomplished by the use of a suitable transport polypeptide. In one embodiment of the invention, the cargo compound is linked to the transport polypeptide. Suitable transport peptides include a cupredoxin, or a fragment of a cupredoxin containing a "cupredoxin entry domain". The term "cupredoxin entry domain" refers to a fragment of a cupredoxin that includes the amino sequence that is required for the entry of cupredoxin into a mammalian cancer cell. Cargo compounds delivered by the present invention include, but are not limited to, proteins, lipoproteins, polypeptides, peptides, polysaccharides, nucleic acids, including RNA, DNA and anti-sense nucleic acids, dyes, fluorescent and radioactive tags, microparticles or nanoparticles, toxins, inorganic and organic molecules, small molecules, and drugs (for example, chemopreventive drugs). In some embodiments, the drugs and toxins kill tumor cells.

In one embodiment of the invention, the cupredoxin is an azurin, such as azurin from *Pseudomonas aeruginosa* (SEQ ID NO: 1). In other embodiments of the invention, the cupredoxin is a plastocyanin, a rusticyanin, or a pseudoazurin, among others. In specific embodiments, the azurin is from *Pseudomonas aeruginosa, Pseudomonas syringa, Neisseria meningitides, Neisseria gonorrhoeae, Vibrio parahaemolyticus* or *Bordetella bronchiseptica*, among others.

In one embodiment, a cargo compound is delivered to kill or retard cell cycle progression in a cell, such as a cancer cell. Such a cancer cell can be, for example, an osteosarcoma cell, lung carcinoma cell, colon carcinoma cell, lymphoma cell, leukemia cell, soft tissue sarcoma cell or breast, liver, bladder or prostate carcinoma cell, among others. For example, the cargo compound can be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A, among others. In other embodiments, a biologically active fragment of one of the above classes of compounds is delivered. In another embodiment, the cargo compound is delivered in order to generate an image of the target tissue. For example, the target tissue can be a cancer and the cargo compound can be one commonly used to generate an image for detection by X-ray computed tomography (CT), Magnetic Resonance Imaging (MRI) and ultrasound. In these embodiments, the cargo compound is a gamma ray or positron emitting radioisotope, a magnetic resonance imaging contrast agent, an X-ray contrast agent, or an ultrasound contrast agent.

The invention further includes methods of selectively introducing DNA or RNA into a mammalian cancer cell. In such embodiments, the DNA or RNA is the cargo compound. In some embodiments, the method includes providing p18 or p28 coupled to DNA or RNA and introducing the compound into the body of a mammal. In some embodiments, the DNA or RNA is a gene or a fragment of a gene. In some embodiments, the DNA or RNA has a therapeutic effect once introduced into a mammalian cell.

Cupredoxin Entry Domain

The invention provides for a protein transduction domain that allows for the preferential entry of peptides into cancer cells, as well as transport of linked cargo into mammalian cancer cells but not non-cancerous cells. It has been discovered that cupredoxin proteins comprise a protein transduction domain, the cupredoxin entry domain, which facilitates the entry of linked cargo into mammalian cancer cells. In some embodiments, the entire cupredoxin protein can be used to facilitate the transport linked cargo selectively into cancer cells. In other embodiments, a portion of a cupredoxin can be used to transport linked cargo into cancer cells. In some embodiments, the cupredoxin entry domain consists of a region of a cupredoxin that is less that the full length wild-type protein. In some embodiments, the cupredoxin entry domain consists of more than about 10 residues, about 15 residues or about 20 residues of a cupredoxin. In some embodiments, the cupredoxin entry domain consists of not more than about 50 residues, about 40 residues or about 30 residues of a cupredoxin. In some embodiments, the cupredoxin entry domain has at least about 90% amino acid sequence identity, at least about 95% amino acid sequence identity or at least about 99% amino acid sequence identity to a cupredoxin.

In some embodiments, the cupredoxin entry domain is an azurin entry domain. In one embodiment of the present invention, azurin entry domain contains at least amino acids 50 to 77 of *Pseudomonas aeruginosa* azurin, p28 (SEQ ID NO: 2). In another embodiments of the invention, the cupredoxin entry domain contains at least amino acids 36 to 77 of *Pseudomonas aeruginosa* azurin (SEQ ID NO: 27). In another embodiment of the invention, the cupredoxin entry domain contains at least amino acids 36 to 89 of *Pseudomonas aeruginosa* azurin (SEQ ID NO: 28). In another embodiment of the invention, the cupredoxin entry domain contains at least amino acids 36 to 128 of *Pseudomonas aeruginosa* azurin (SEQ ID NO: 29). In yet another embodiment of the invention, the cupredoxin entry domain contains at least amino acids 50 to 67 of *Pseudomonas aeruginosa* azurin, p18 (SEQ ID NO: 25). In another embodiment of the invention, the cupredoxin entry domain contains at least amino acids 53 to 70 of *Pseudomonas aeruginosa* azurin (SEQ ID NO: 30). In yet another embodiment of the invention, the cupredoxin entry domain contains at least amino acids 53 to 64 of *Pseudomonas aeruginosa* azurin (SEQ ID NO: 31).

The Examples described herein, particularly Example 19, demonstrate that the C-terminal region of p28, not present on p18 (amino acids 50-67) is most likely to contact specific residues on the cell membrane and provide access to the cell. As such, in another embodiment of the invention, the cupredoxin entry domain is an azurin entry domain containing at least amino acids 66-77 of p28 (SEQ ID NO. 35). In another embodiment of the invention, the cupredoxin entry domain is an azurin entry domain containing at least amino acids 68-77 of p28 (SEQ ID NO. 36). In another embodiment of the invention, the cupredoxin entry domain is an azurin entry domain containing at least amino acids 67-77 of p28 (SEQ ID NO. 37). In another embodiment of the invention, the cupredoxin entry domain comprises one or more of the amino acids located at positions 69, 70, 75, 76, and 85 of SEQ ID NO. 2. In another embodiment, the cupredoxin entry domain comprises amino acids 69, 70, 75, 76, and 85 of SEQ ID NO. 2.

In another embodiment of the invention, the cupredoxin entry domain is an entry domain from a cupredoxin other than P. aeruginosa azurin. In different embodiments, the cupredoxin entry domain may be a fragment of plastocyanin from the cyanobacterium Phormidium laminosum (SEQ ID NO: 3), rusticyanin from Thiobacillus ferrooxidans (SEQ ID NO: 4); pseudoazurin from Achromobacter cycloclastes (SEQ ID NO: 5), azurin from Pseudomonas syringae (SEQ ID NO: 21), azurin from Neisseria meningitidis (SEQ ID NO: 10), azurin from Vibrio parahaemolyticus (SEQ ID NO: 8), or an auracyanin from Chloroflexus aurantiacus (SEQ ID NO: 15 and 16).

In another embodiment of the invention, the cupredoxin entry domain contains at least amino acids 57 to 89 of auracyanin B of Chloroflexus aurantiacus (SEQ ID NO: 20). In another embodiment of the invention, the cupredoxin entry domain contains at least amino acids 51-77 of Pseudomonas syringae azurin (SEQ ID NO: 21). In another embodiment of the invention, the cupredoxin entry domain contains at least amino acids 89-115 of Neisseria meningitidis Laz (SEQ ID NO: 22). In another embodiment of the invention, the cupredoxin entry domain contains at least amino acids 52-78 of Vibrio parahaemolyticus azurin (SEQ ID NO: 23). In another embodiment of the invention, the cupredoxin entry domain contains at least amino acids 51-77 of Bordetella bronchiseptica azurin (SEQ ID NO: 24).

Modification of a Cupredoxin Entry Domain

In another embodiment of the present invention, a cupredoxin entry domain is chemically modified or genetically altered to produce variants that retain the ability to preferentially enter and/or transport a cargo compound into a cell. For example, Example 14 shows that Pseudomonas aeruginosa azurin having proline residues introduced at positions 54, 61 and 70 retains its ability to enter UISO-Mel-2 cells.

In another embodiment, the cupredoxin entry domain comprises a conserved amino acid sequence DGXXXXXDXXYXKXXD (SEQ ID NO: 32) or DGXXXXDXXYXKXXD (SEQ ID NO: 33) where D is aspartic acid, G is glycine, Y is tyrosine, K is lysine and X is any amino acid. See Example 17.

Variants of a cupredoxin entry domain may be synthesized by standard techniques. Derivatives are amino acid sequences formed from native compounds either directly or by modification or partial substitution. Analogs are amino acid sequences that have a structure similar, but not identical, to the native compound but differ from it in respect to certain components or side chains. Analogs may be synthesized or from a different evolutionary origin.

Variants may be full length or other than full length, if the derivative or analog contains a modified amino acid. Variants of a cupredoxin entry domain include, but are not limited to, molecules comprising regions that are substantially homologous to the cupredoxin entry domain by at least about 65%, 70%, 75%, 85%, 90%, 95%, 98%, or 99% identity over an amino acid sequence of identical size or when compared to an aligned sequence in which the alignment is performed by a homology algorithm.

In another embodiment, the variants of a cupredoxin entry domain have a significant structural similarity to P. aeruginosa azurin residues 50-77, p28 (SEQ ID NO: 2). In other embodiments, the variants of a cupredoxin entry domain have a significant structural similarity to P. aeruginosa azurin residues 50-67, p18 (SEQ ID NO: 25). Examples of studies that determine significant structural homology between cupredoxins and other proteins include Toth et al. (Developmental Cell 1:82-92 (2001)). Specifically, significant structural homology between a variant of the cupredoxin entry domain and P. aeruginosa azurin residues 50-77 (SEQ ID NO: 2) is determined by using the VAST algorithm (Gibrat et al., Curr Opin Struct Biol 6:377-385 (1996); Madej et al., Proteins 23:356-3690 (1995)). In specific embodiments, the VAST p value from a structural comparison of a variant of the cupredoxin entry domain and P. aeruginosa azurin residues 50-77 (SEQ ID NO: 2) is less than about $10^{-3}$, less than about $10^{-5}$, or less than about $10^{-7}$. In other embodiments, significant structural homology between a variant of the cupredoxin entry domain and P. aeruginosa azurin residues 50-77 (SEQ ID NO: 2) can be determined by using the DALI algorithm (Holm & Sander, J. Mol. Biol. 233:123-138 (1993)). In specific embodiments, the DALI Z score for a pairwise structural comparison is at least about 3.5, at least about 7.0, or at least about 10.0.

Modifications to the cupredoxin entry domain can be made using methods known in the art such as oligonucleotide-mediated (site-directed) mutagenesis, alanine scanning, PCR mutagenesis, and the methods and techniques disclosed herein. Site-directed mutagenesis (Carter, Biochem J. 237:1-7 (1986); Zoller and Smith, Methods Enzymol. 154:329-50 (1987)), cassette mutagenesis, restriction selection mutagenesis (Wells et al., Gene 34:315-23 (1985)) or other known techniques can be performed on the cloned DNA to produce a cupredoxin entry domain variant nucleic acid. In addition, nucleotides encoding entry domains with structural similarity to that of the cupredoxin entry domains may be synthesized by methods that are well known in the art. Further, protein molecules that are wild type or variant cupredoxin entry domains may be synthesized by methods that are well known in the art.

Nucleic Acids Coding for a Cupredoxin Entry Domain and Complex of a Cupredoxin Entry Domain Linked to a Cargo Compound In another aspect, the present invention provides a nucleic acid molecule encoding a fusion protein comprising a cupredoxin entry domain linked to a cargo compound, where the cargo compound is a protein or peptide. The nucleic acid molecule according to the invention can be prepared by a combination of known techniques in the art. For instance, nucleic acid sequences for the cupredoxin entry domain and the cargo compound can individually be prepared by chemical synthesis or cloning. The nucleic acid sequences are then ligated in order with a ligase to give a nucleic acid molecule of interest.

Methods of Delivering a Cargo Compound Using a Cupredoxin Entry Domain

Many arginine-rich peptides are known to translocate through mammalian cell membranes and carry protein cargo compounds inside such cells. Suzuki, T., et al. J. Biol. Chem. 277:2437-43 (2002). For example, a short arginine-rich 11 amino acid (amino acids 47-57) segment of HIV Tat protein allows transport of cargo proteins into mammalian cells. Schwarze, S R., et al. Trends Cell Biol. 10:290-95 (2000). Synthetic entry domains that strengthen the alpha-helical content and optimize the placement of arginine residues have been shown to have enhanced potential as protein transduction domains. Ho, A., et al. Cancer Res. 61:474-77 (2001). In comparison, *P. aeruginosa* azurin has a single arginine residue.

In some embodiments, the present invention encompasses the use of those cupredoxin fragments that facilitate the entry of a cargo compound into a cell, such as p18 (SEQ ID NO. 25) and p28 (SEQ ID NO. 2). Such fragments may be determined by any method that identifies those fragments required for entry into a cell. In one such method, a cupredoxin fragment is linked to a marker substance and a test performed to determine whether the cupredoxin fragment enters a cell. Such methods may be used to identify suitable fragments of the cupredoxins discussed above.

In various embodiments of the present invention, the cargo compound is attached to a cupredoxin or a fragment thereof, such as azurin from *P. aeruginosa* (SEQ ID NO: 1); plastocyanin from the cyanobacterium *Phormidium laminosum* (SEQ ID NO: 3); rusticyanin from *Thiobacillus ferrooxidans* (SEQ ID NO: 4); or pseudoazurin from *Achromobacter cycloclastes* (SEQ ID NO: 5), a fragment of an azurin from *Pseudomonas syringae* (SEQ ID NO: 21), azurin from *Neisseria meningitidis* (SEQ ID NO: 10), azurin from *Vibrio parahaemolyticus* (SEQ ID NO: 19), azurin from *Bordelella bronchiseptica* (SEQ ID NO: 8), auracyanin A and B from *Chloroflexus aurantiacus* (SEQ ID NO. 15 and 16), among other azurin and azurin-like proteins. In other embodiments, the cargo is linked to a cupredoxin entry domain such as p28 (SEQ ID NO: 2), p18 (SEQ ID NO: 25), or any one of SEQ ID NOs: 35-37.

In various embodiments of the present invention, a cupredoxin entry domain delivers a cargo compound into a cell in vitro, ex vivo or in vivo. For example, delivery may be achieved in vitro by adding a complex of a cupredoxin entry domain and a cargo compound to a cell culture, such as a pap smear. Alternatively, delivery may be achieved ex vivo by adding the complex to a sample removed from a patient, for example, blood, tissue, or bone marrow, and returning the treated sample to the patient. Delivery may also be achieved by administration of the complex directly to a patient. The methods of the present invention may be used for therapeutic, prophylactic, diagnostic or research purposes. Cargo compounds delivered by the present invention include, but are not limited to, proteins, lipoproteins, polypeptides, peptides, polysaccharides, nucleic acids, including anti-sense nucleic acids, dyes, microparticles or nanoparticles, toxins, organic and inorganic molecules, small molecules, and drugs.

In one embodiment, a detectable substance, for example, a fluorescent substance, such as green fluorescent protein; a luminescent substance; an enzyme, such as β-galactosidase; or a radiolabelled or biotinylated protein is delivered to confer a detectable phenotype to a cell. Similarly, microparticles or nanoparticles labeled with a detectable substance, for example, a fluorescent substance, can be delivered. One example of suitable nanoparticles is found in U.S. Pat. No. 6,383,500, issued May 7, 2002, which is hereby expressly incorporated by reference. Many such detectable substances are known to those skilled in the art.

In some embodiments, the cargo compound is a detectable substance that is suitable for X-ray computed tomography, magnetic resonance imaging, ultrasound imaging or radionuclide scintigraphy. In these embodiments, the cargo compound is administered to the patient for purposes of diagnosis. A contrast agent is administered as a cargo compound to enhance the image obtained by X-ray CT, MRI and ultrasound. The administration of a radionuclide cargo compound that is targeted to tumor tissue via the cupredoxin entry domain can be used for radionuclide scinitigraphy. In some embodiments, the cupredoxin entry domain may contain the radionucleotide with or without a cargo compound. In other embodiments, the cargo compound is a gamma ray or positron emitting radioisotope, a magnetic resonance imaging contract agent, an X-ray contrast agent, or an ultrasound contrast agent.

Ultrasound contrast agents suitable for use as cargo compounds include, but are not limited to, a microbubble of a biocompatible gas, a liquid carrier, and a surfactant microsphere, further comprising an optional linking moiety, $L_n$, between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein expressly incorporated by reference. The term surfactant microsphere includes nanospheres, liposomes, vesicles and the like. The biocompatible gas can be air, or a fluorocarbon, such as a $C_3$-$C_5$ perfluoroalkane, which provides the difference in echogenicity and thus the contrast in ultrasound imaging. The gas is encapsulated or contained in the microsphere to which is attached the cupredoxin entry domain, optionally via a linking group. The attachment can be covalent, ionic or by van der Waals forces. Specific examples of such contrast agents include lipid encapsulated perfluorocarbons with a plurality of tumor neovasculature receptor binding peptides, polypeptides or peptidomimetics.

X-ray contrast agents suitable for use as cargo compounds include, but are not limited to, one or more X-ray absorbing or "heavy" atoms of atomic number 20 or greater, further comprising an optional linking moiety, $L_n$, between the cupredoxin entry domain and the X-ray absorbing atoms. The frequently used heavy atom in X-ray contrast agents is iodine. Recently, X-ray contrast agents comprised of metal chelates (e.g., U.S. Pat. No. 5,417,959) and polychelates comprised of a plurality of metal ions (e.g., U.S. Pat. No. 5,679,810) have been disclosed. More recently, multinuclear cluster complexes have been disclosed as X-ray contrast agents (e.g., U.S. Pat. No. 5,804,161, PCT WO91/14460, and PCT WO 92/17215).

MRI contrast agents suitable for use as cargo compounds include, but are not limited to, one or more paramagnetic metal ions, further comprising an optional linking moiety, $L_n$, between the cupredoxin entry domain and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

In another embodiment, a cargo compound is delivered to kill or retard cell cycle progression in a cell, such as a cancer cell. Such a cancer cell can be, for example, an osteosarcoma cell, lung carcinoma cell, colon carcinoma cell, lymphoma cell, leukemia cell, soft tissue sarcoma cell or breast, liver, bladder or prostate carcinoma cell. For example, the cargo compound can be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A. In other embodiments, a biologically active fragment of one of the above classes of compounds is delivered.

In yet another embodiment, the cargo compound is a nucleic acid. In some embodiments the nucleic acid codes for one of the above classes of compounds. In yet another embodiment, the cargo compound is a drug used to treat cancer. Such drugs include, for example, 5-fluorouracil; Interferon α; Methotrexate; Tamoxifen; and Vincristine. The above examples are provided for illustration only, many other such compounds are known to those skilled in the art. In other embodiments, the nucleic acid is useful for gene therapy.

Cargo compounds suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; $5\alpha$-reductase inhibitors; inhibitors of $17\beta$-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol™), docetaxel (Taxotere™), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, caminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents useful as cargo compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The above other therapeutic agents, when employed as cargo compounds with the compounds of the present invention, may be used, for example, in those amounts indicated in the Physicians' Desk Reference (PDR) or as otherwise determined by one of ordinary skill in the art.

Pharmaceutical Compositions Containing a Cupredoxin Entry Domain

Pharmaceutical compositions containing, comprising, or consisting of a cupredoxin entry domain, as well as pharmaceutical compositions containing complex of a cupredoxin entry domain linked to a cargo compound, can be manufactured in any conventional manner, e.g., by conventional mixing, dissolving, granulating, dragee-making, emulsifying, encapsulating, entrapping, or lyophilizing processes. The complex can be readily combined with a pharmaceutically acceptable carrier well-known in the art. Such carriers enable the preparation to be formulated as a tablet, pill, dragee, capsule, liquid, gel, syrup, slurry, suspension, and the like. Suitable excipients can also include, for example, fillers and cellulose preparations. Other excipients can include, for example, flavoring agents, coloring agents, detackifiers, thickeners, and other acceptable additives, adjuvants, or binders.

Such compositions can be used in, for example, the detection or imaging of a cell type or in the treatment of a condition related to cell death or in the prevention thereof. The compositions can be administered in an amount sufficient to prevent or treat a condition related to resistance to cell death. As used herein, the term "a condition related to resistance to cell death" refers to a disease, state, or ailment characterized by at least a tendency for prolonged cell life when compared with a healthy cell of like kind as determined by a reasonable, skilled physician or clinician. Typically, the host organism is a mammal, such as a human or animal.

Administration of Compositions Containing a Cupredoxin Entry Domain

Compositions containing a cupredoxin entry domain can be administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary administration). The compositions and pharmaceutical formulations thereof can be administered in any amount effective to achieve its intended purpose. When administrated to treat a condition related to resistance to cell death, the composition is administered in a therapeutically effective amount. A "therapeutically effective amount" is an amount effective to prevent development of, or to alleviate the existing symptoms of, the subject being treated. Determination of a therapeutically effective amount is well within the capability of those skilled in the art.

The appropriate dosage will, of course, vary depending upon, for example, the compound containing the cupredoxin entry domain employed, the host, the mode of administration and the nature and severity of the conditions being treated or diagnosed. However, in one embodiment of the methods of the present invention, satisfactory treatment results in humans are indicated to be obtained at daily dosages from about 0.001 to about 20 mg/kg of body weight of the compound containing the cupredoxin entry domain. In one embodiment, an indicated daily dosage for treatment in humans may be in the range from about 0.7 mg to about 1400 mg of a compound containing the cupredoxin entry domain conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days. Dosing can be continuous, intermittent or a single dose, using any applicable dosing form, including tablet, patches, i.v. administration and the like. More specifically, the composition is administered in a therapeutically effective amount. In specific embodiments, the therapeutically effective amount is from about 0.01-20 mg/kg of body weight. In specific embodiments, the dose level is about 10 mg/kg/day, about 15 mg/kg/day, about 20 mg/kg/day, about 25 mg/kg/day, about 30 mg/kg/day, about 35 mg/kg/day, about 40 mg/kg/day, about 45 mg/kg/day or about 50 mg/kg/day.

The method of introducing compounds containing the cupredoxin entry domain to patients is, in some embodiments, co-administration with other drugs known to treat cancer. Such methods are well-known in the art. In a specific embodiment, the compounds containing the cupredoxin entry domain are part of an cocktail or co-dosing containing or with other drugs for treating cancer. Such drugs include, for example, those listed herein and specifically 5-fluorouracil; Interferon α; Methotrexate; Tamoxifen; and Vincristine. The above examples are provided for illustration only, many other such compounds are known to those skilled in the art.

Nucleic acid molecules encoding a cupredoxin entry domain or a fusion protein combining a either entry domain and a cargo compound can be inserted into vectors and used as gene therapy vectors. Gene therapy vectors can be delivered to a subject by, for example, intravenous injection, local administration (Nabel et al., U.S. Pat. No. 5,328,470 1994. USA), or by stereotactic injection (Chen et al., Proc Natl Acad Sci USA, vol. 91, pp 3054-57 (1994)). The pharmaceutical preparation of a gene therapy vector can include an acceptable diluent or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

In one aspect, the composition is delivered as DNA such that the complex is generated in situ. In one embodiment, the DNA is "naked," as described, for example, in Ulmer et al., Science 259:1745-49 (1993) and reviewed by Cohen, Science 259 1691-92 (1993). The uptake of naked DNA may be increased by coating the DNA onto a carrier, e.g. a biodegradable bead, which is efficiently transported into the cells.

In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of the composition. In expression vectors, the introduced DNA is operably-linked to elements such as promoters that signal to the host cell to transcribe the inserted DNA. Some promoters are exceptionally useful, such as inducible promoters that control gene transcription in response to specific factors. Operably-linking a composition polynucleotide to an inducible promoter can control the expression of the wt-azurin entry domain composition polypeptide or fragments. Examples of classic inducible promoters include those that are responsive to α-interferon, heat shock, heavy metal ions, and steroids such as glucocorticoids (Kaufman, *Methods Enzymol.* 185: 487-511 (1990)) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, enhancer elements, promoters, and transcription termination sequences.

Kits Comprising a Cupredoxin Entry Domain-Cargo Compound Complex

In another aspect, the invention provides kits containing one or more of the following in a package or container: (1) a reagent comprising a cupredoxin entry domain on its own, such as p18 or p28, or linked to a cargo compound; (2) a reagent containing a pharmaceutically acceptable adjuvant or excipient; (3) a vehicle for administration, such as a syringe; (4) instructions for administration. Embodiments in which two or more of components (1)-(4) are found in the same container are also contemplated.

Pharmaceutical Compositions Comprising Cupredoxin, a Cupredoxin Entry Domain, a Cupredoxin Entry Domain—Cargo Compound Complex, or Variant, Derivative or Structural Equivalent Thereof Pharmaceutical compositions comprising cupredoxin or variant, derivative or structural equivalents thereof, can be manufactured in any conventional manner, e.g., by conventional mixing, dissolving, granulating, dragee-making, emulsifying, encapsulating, entrapping, or lyophilizing processes. The substantially pure or pharmaceutical grade cupredoxin or variants, derivatives and structural equivalents thereof can be readily combined with a pharmaceutically acceptable carrier well-known in the art. Such carriers enable the preparation to be formulated as a tablet, pill, dragee, capsule, liquid, gel, syrup, slurry, suspension, and the like. Suitable carriers or excipients can also include, for example, fillers and cellulose preparations. Other excipients can include, for example, flavoring agents, coloring agents, detackifiers, thickeners, and other acceptable additives, adjuvants, or binders. In some embodiments, the pharmaceutical preparation is substantially free of preservatives. In other embodiments, the pharmaceutical preparation may contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising a cupredoxin or variant, derivative or structural equivalent thereof used in the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., id. In some embodiments, the composition comprising a cupredoxin or variant, derivative or structural equivalent thereof can be formulated and used directly as injectibles, for subcutaneous and intravenous injection, among others. The injectable formulation, in particular, can advantageously be used to treat patients that are appropriate for chemopreventive therapy. The composition comprising a cupredoxin or variant, derivative or structural equivalent thereof can also be taken orally after mixing with protective agents such as polypropylene glycols or similar coating agents.

When administration is by injection, the cupredoxin or variant, derivative or structural equivalent thereof may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the cupredoxin or variant, derivative or structural equivalent thereof may be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide.

When administration is by intravenous fluids, the intravenous fluids for use administering the cupredoxin or variant, derivative or structural equivalent thereof may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 2.

TABLE 2

Composition of Common Crystalloid Solutions

| Solution | Other Name | [Na$^+$] | [Cl$^-$] | [Glucose] |
|---|---|---|---|---|
| D5W | 5% Dextrose | 0 | 0 | 252 |
| ⅔ & ⅓ | 3.3% Dextrose/ 0.3% saline | 51 | 51 | 168 |
| Half-normal saline | 0.45% NaCl | 77 | 77 | 0 |
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L K$^+$ and 3 mmol/L Ca$^{2+}$.

When administration is by inhalation, the cupredoxin or variant, derivative or structural equivalent thereof may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the proteins and a suitable powder base such as lactose or starch.

When administration is by topical administration, the cupredoxin or variant, derivative or structural equivalent thereof may be formulated as solutions, gels, ointments, creams, jellies, suspensions, and the like, as are well known in the art. In some embodiments, administration is by means of a transdermal patch. When administration is by suppository (e.g., rectal or vaginal), cupredoxin or variants and derivatives thereof compositions may also be formulated in compositions containing conventional suppository bases.

When administration is oral, a cupredoxin or variant, derivative or structural equivalent thereof can be readily formulated by combining the cupredoxin or variant, derivative or structural equivalent thereof with pharmaceutically acceptable carriers well known in the art. A solid carrier, such as mannitol, lactose, magnesium stearate, and the like may be employed; such carriers enable the cupredoxin and variants, derivatives or structural equivalent thereof to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a cupredoxin or variant, derivative or structural equivalent thereof allow for the release of cupredoxin or variant, derivative or structural equivalent thereof over extended periods of time, such that without the sustained release formulation, the cupredoxin or variant, derivative or structural equivalent thereof would be cleared from a subject's system, and/or degraded by, for example, proteases and simple hydrolysis before eliciting or enhancing a therapeutic effect.

The half-life in the bloodstream of the peptides of the invention can be extended or optimized by several methods well known to those in the art. The peptide variants of the invention may include, but are not limited to, various variants that may increase their stability, specific activity, longevity in the bloodstream, and/or decrease immunogenicity of the cupredoxin, while retaining the ability of the peptide to inhibit the development of premalignant lesions in mammalian cells, tissues and animals. Such variants include, but are not limited to, those which decrease the hydrolysis of the peptide, decrease the deamidation of the peptide, decrease the oxidation, decrease the immunogenicity, increase the structural stability of the peptide or increase the size of the peptide. Such peptides also include circularized peptides (see Monk et al., BioDrugs 19(4):261-78, (2005); DeFreest et al., J. Pept. Res. 63(5):409-19 (2004)), D,L-peptides (diastereomer), Futaki et al., J. Biol. Chem. February 23; 276(8):5836-40 (2001); Papo et al., Cancer Res. 64(16):5779-86 (2004); Miller et al., Biochem. Pharmacol. 36(1):169-76, (1987)); peptides containing unusual amino acids (see Lee et al., J. Pept. Res. 63(2):69-84 (2004)), N- and C-terminal modifications (see Labrie et al., Clin. Invest. Med. 13(5):275-8, (1990)), hydrocarbon stapling (see Schafmeister et al., J. Am. Chem. Soc. 122:5891-5892 (2000); Walenski et al., Science 305:1466-1470 (2004)) and PEGylation.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of Cupredoxin or Variant, Derivative or Structural Equivalent Thereof The cupredoxin or variant, derivative or structural equivalent thereof, such as p18 or p28, can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) or vitreous administration. The pharmaceutical formulations thereof can be administered in any amount effective to achieve its intended purpose. More specifically, the composition is administered in a therapeutically effective amount. In specific embodiments, the therapeutically effective amount is generally from about 0.01-20 mg/day/kg of body weight.

The compounds comprising cupredoxin or variant, derivative or structural equivalent thereof are useful for the prevention of cancer, alone or in combination with other active agents and/or cargo compounds. The appropriate dosage will, of course, vary depending upon, for example, the compound of cupredoxin or variant, derivative or structural equivalent thereof employed, the host, the mode of administration and the nature and severity of the potential cancer. However, in general, satisfactory results in humans are indicated to be obtained at daily dosages from about 0.01-20 mg/kg of body weight. An indicated daily dosage in humans is in the range from about 0.7 mg to about 1400 mg of a compound of cupredoxin or variant, derivative or structural equivalent thereof conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days or over. Alternatively, dosing can be continuous using patches, i.v. administration and the like.

The exact formulation, route of administration, and dosage is determined by the attending physician in view of the patient's condition. Dosage amount and interval can be adjusted individually to provide plasma levels of the active cupredoxin or variant, derivative or structural equivalent thereof, with or without a cargo compound, which are sufficient to maintain therapeutic effect. Generally, the desired cupredoxin or variant, derivative or structural equivalent thereof is administered in an admixture with a pharmaceutical carrier selected with regard to the intended route of administration and standard pharmaceutical practice.

In one aspect, the cupredoxin or variant, derivative or structural equivalent thereof is delivered as DNA such that the polypeptide is generated in situ. In one embodiment, the DNA is "naked," as described, for example, in Ulmer et al., (Science 259:1745-1749 (1993)) and reviewed by Cohen (Science 259:1691-1692 (1993)). The uptake of naked DNA may be increased by coating the DNA onto a carrier, e.g., biodegradable beads, which are then efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cupredoxin. In expression vectors, the introduced DNA is operably-linked to elements such as promoters that signal to the host cell to highly transcribe the inserted DNA. Some promoters are exceptionally useful, such as inducible promoters that control gene transcription in response to specific factors. Operably-linking a cupredoxin and variants and derivatives thereof polynucleotide to an inducible promoter can control the expression of the cupredoxin and variants and derivatives thereof in response to specific factors. Examples of classic inducible promoters include those that are responsive to α-interferon, heat shock, heavy metal ions, and steroids such as glucocorticoids (Kaufman, Methods Enzymol. 185: 487-511 (1990)) and tetracycline. Other desirable inducible promoters include those that are not endogenous to the cells in which the construct is being introduced, but, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated. In addition, the peptides of the present invention, including in one embodiment, p18, may be used as a vector to selectively deliver therapeutic compounds into cancer cells or tumors.

Vector choice is dictated by the organism or cells being used and the desired fate of the vector. In general, vectors comprise signal sequences, origins of replication, marker genes, polylinker sites, enhancer elements, promoters, and transcription termination sequences.

Kits Comprising Cupredoxin, or Variant Derivative Or Structural Equivalent Thereof In one aspect, the invention provides regimens or kits comprising one or more of the following in a package or container: (1) a pharmacologically active composition comprising at least one cupredoxin or variant, derivative or structural equivalent thereof, (2) an additional chemopreventive drug, (3) apparatus to administer the biologically active composition to the patient, such as a syringe, nebulizer etc.

When a kit is supplied, the different components of the composition may be packaged in separate containers, if appropriate, and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampoules may contain lyophilized cupredoxin and variants, derivatives and structural equivalents thereof, or buffers that have been packaged under a neutral, non-reacting gas, such as nitrogen. Ampoules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampoules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributor of the kit, or supplied as electronic mail.

Modification of Cupredoxin, Cupredoxin Entry Domains and Variants, Derivatives and Structural Equivalents Thereof Cupredoxin or variant, derivative or structural equivalents thereof may be chemically modified or genetically altered to produce variants and derivatives as explained above. Such variants and derivatives may be synthesized by standard techniques. Cupredoxin entry domains may be similarly modified.

In addition to naturally-occurring allelic variants of cupredoxin, changes can be introduced by mutation into cupredoxin coding sequence that incur alterations in the amino acid sequences of the encoded cupredoxin that do not significantly alter the ability of cupredoxin to inhibit the development of premalignant lesions. A "non-essential" amino acid residue is a residue that can be altered from the wild-type sequences of the cupredoxin without altering pharmacologic activity, whereas an "essential" amino acid residue is required for such pharmacologic activity. For example, amino acid residues that are conserved among the cupredoxins are predicted to be particularly non-amenable to alteration, and thus "essential."

Amino acids for which conservative substitutions that do not change the pharmacologic activity of the polypeptide can be made are well known in the art. Useful conservative substitutions are shown in Table 3, "Preferred substitutions." Conservative substitutions whereby an amino acid of one class is replaced with another amino acid of the same type fall within the scope of the invention so long as the substitution does not materially alter the pharmacologic activity of the compound.

TABLE 3

Preferred substitutions

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the pharmacologic activity. Residues are divided into groups based on common side-chain properties as denoted in Table 4. Non-conservative substitutions entail exchanging a member of one of these classes for another class. Substitutions may be introduced into conservative substitution sites or more specifically into non-conserved sites.

TABLE 4

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-350 (1987)), cassette mutagenesis, restriction selection mutagenesis (Wells et al., Gene 34:315-323 (1985)) or other known techniques can be performed on the cloned DNA to produce the cupredoxin variant DNA.

Known mutations of cupredoxins can also be used to create variant cupredoxin to be used in the methods of the invention. For example, the C112D and M44KM64E mutants of azurin are known to have cytotoxic and growth arresting activity that is different from the native azurin, and such altered activity can be useful in the treatment methods of the present invention.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof.

EXAMPLES

Example 1. Effect of Peptide p28 on DMBA-Induced Mammary Lesions in the MMOC Model The mouse mammary gland organ culture (MMOC) model allows evaluating efficacy of potentially chemopreventive agents against development of mammary alveolar lesions (MAL) or mammary ductal lesions (MDL) in response to DMBA. DMBA under appropriate incubation conditions form either MAL or MDL based on the hormonal milieu in the medium. Hawthorne et al., Pharmaceutical Biology 40: 70-74 (2002); Mehta et al., J. Natl. Cancer Inst. 93: 1103-1106 (2001). Estrogen and progesterone-treated glands in culture develop ductal lesions whereas aldosterone and hydrocortisone-treated glands form estrogen and progesterone-independent alveolar lesions. Mammary glands not exposed to a carcinogen or chemopreventive agent, undergo structural regression in the absence of growth-promoting hormones, whereas treatment with DMBA for the 24-hr period between days 3 and 4 prevents the regression of structures caused by deprivation of hormones. It is assumed that this is because the glands have lost normal hormonal responsiveness and now have altered their course of development. Generating mammary adenocarcinoma by transplanting transformed cells into syngeneic mice has proved the premalignant preneoplastic nature of these unrepressed areas.

The thoracic pair of mammary glands was excised aseptically from each Balb/c mouse, and the glands were divided into several groups. The effects of p28 were evaluated at 4 different dilutions in the medium. Carcinogen treated glands without the test agent served as a measure to determine percent incidence in the absence of a chemopreventive agent. An additional control was included to serve as a positive control for chemoprevention. Azurin was included in the medium at 50 µg/ml concentration. For alveolar lesions (MAL) stained glands were evaluated for the incidence of lesions (glands containing any lesions as compared to total number of glands in a given treatment group). For the ductal lesions (MDL) similar protocol was adapted, however, as indicated below in the methods section the hormonal combination is different for alveolar and ductal lesions. The glands were fixed in formalin and then processed for histopathology. The sections are stained with eosin and hematoxelene and evaluated under microscope. Here the multiplicity of ductal lesions between the control and the treatment groups are compared.

Organ Culture Procedure.

The experimental animals used for the studies were young, virgin BALB/c female mice 3 to 4 weeks of age obtained from Charles River, Wilmington, Mass. The mice were treated daily by subcutaneous injections with 1 µg estradiol-17β+1 mg progesterone for 9 days. This treatment is a prerequisite inasmuch as animals not pretreated with steroids fail to respond to hormones in vitro. The entire culture procedure is described in detail. Jang et al., Science 275:218-220 (1997); Mehta, Eu. J. Cancer 36:1275-1282 (2000); Mehta et al., J. Natl. Cancer Inst. 89:212-219 (1997); Mehta et al., J. Natl. Cancer Inst. 93:1103-1106 (2001).

Briefly, the animals were killed by cervical dislocation, and the thoracic pair of mammary glands were dissected out on silk rafts and incubated for 10 days in serum free Waymouth MB752/1 medium (5-glands/5 ml/dish). The medium was supplemented with glutamine, antibiotics (penicillin and streptomycin 100 units/ml medium) and growth-promoting hormones, 5 µg insulin (I), 5 µg prolactin (P), 1 µg aldosterone (A) and 1 µg hydrocortisone (H) per ml of medium for the protocol to induce mammary alveolar lesions (MAL). For induction of ductal lesions (MDL), the medium contained 5 µg/ml, 5 µg/ml P, 0.001 µg/ml estradiol 17β and 1 µg/ml progesterone (Pg). Mehta et al., J. Natl. Cancer Inst. 93:1103-1106 (2001). The carcinogen, DMBA (2 µg/ml) was added to the medium between days 3 and 4. For the present study, DMBA was dissolved in DMSO at a final concentration of 4 mg/ml, and 50 µg I was added to 100 ml medium resulting in 2 µg/ml final concentrations. The control dishes contained DMSO as vehicle.

On day 4, DMBA is removed from the medium by rinsing the glands in fresh medium and transferring them to new dishes containing fresh medium without DMBA. After 10 days of incubation, the glands were maintained for another 14 days in the medium containing only 1 (5 µg/ml). During the entire culture period, the glands were maintained at 37° C. under 95% $O_2$ and 5% $CO_2$ environment. The chemopreventive agent was included in the medium during the first ten days of growth-promoting phase. The test peptide p28 was evaluated at 4 concentrations ranging from 12.5 µg/ml to 100 µg/ml. Azurin was evaluated at 50 µg/ml in the medium. The peptide was dissolved in sterile water and filtered prior to use. The medium was changed three times per week (Monday, Wednesday and Friday). At the end of the exposure, the glands were fixed in formain. Results were analyzed by Chi-square analysis and Fisher's Exact Test.

Morphometic Analysis of MAL.

For examination of MAL, the glands were stained in alum carmine, and evaluated for the presence of the lesions. The glands were scored for the presence or absence of mammary lesions, severity of lesions per gland, and toxicity of the agent. The glands stored in xylene were evaluated for the presence or absence, incidence, and severity of mammary lesions for each gland under a dissecting microscope. Mammary glands were scored as positive or negative for mammary lesions, and the percent incidence was determined as a ratio of glands exhibiting lesions and the total number of glands in that group. Dilation of ducts or disintegration of mammary structure because of treatment with chemopreventive agent was considered a toxic effect. The data were subjected to statistical analysis for the incidence to determine the effectiveness of the potential chemopreventive agents.

Figure 2:
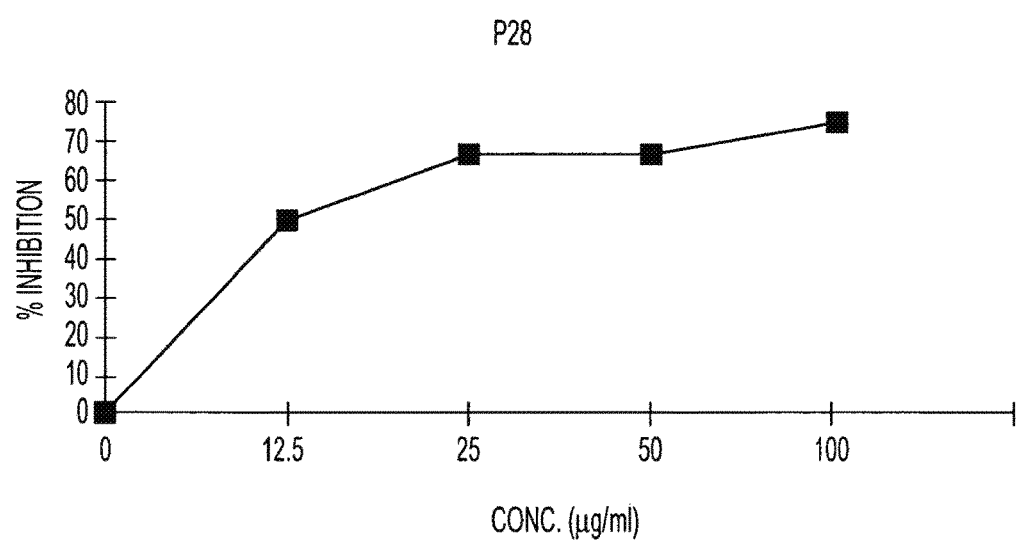
FIG. 2 depicts a graph showing the efficacy of p28 against DMBA-induced mammary alveolar lesions.

FIG. 1A shows a representative photograph of alveolar lesions in a DMBA treated gland and its comparison with a gland that was treated with DMBA along with a chemopreventive agent. The effects of p28 on the development of alveolar lesion are shown in FIGS. 1B-1F and summarized in FIG. 2. The peptide p28 inhibited MAL formation by 67% at 25 µg/ml concentration. Increasing concentration further up to 100 µg/ml did not enhance the efficacy of the peptide. The comparison of the peptide with azurin indicated that p28 was as effective as azurin for MAL development. Azurin at 50 µg/ml concentration resulted in a 67% inhibition. Statistical analyses indicated that the effect of p28 was statistically significant compared to DMBA control at concentrations greater than 12.5 µg/ml ($p<0.01$, Fisher's Exact Test; Chi Square analysis).

Histopathological Evaluation of MDL.

For MDL, the glands were processed for histopathological evaluations. The glands were sectioned longitudinally into 5-micron sections and stained with eosin hematoxeline. The longitudinal section of each gland was divided into several fields and each field was evaluated for ductal lesions. Mehta et al., J. Natl. Cancer Inst. 93:1103-1106 (2001). Briefly, the entire gland is evaluated under the scope; smaller glands will have fewer total fields as compared to larger glands. Thus, each gland will have variable number of fields. Often the number of sections through the ducts also varies greatly from gland to gland. This results in the variable number from group to group. Fields containing ductal hyperplasia or atypia were determined and were compared with total number of field evaluated for each gland. No discrimination is made between the hyperplasia or atypia and severely occluded glands. Any field containing any of these histological patterns was considered positive for the lesion. The treatment groups were compared with the controls for the severity and percent inhibition was calculated.

Figure 4:
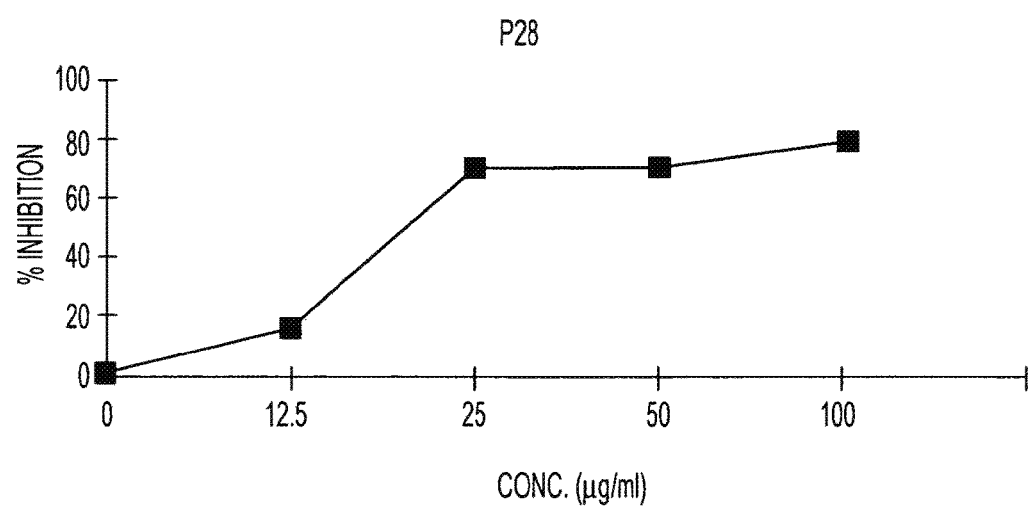
FIG. 4 depicts a graph showing the efficacy of p28 against DMBA-induced ductal lesions FIG. 5. Diagram showing the localization of the α-helix in wt-azurin as well as in the wt-azurin 50-77 protein transduction domain. Replacement of three amino acids in the azurin 50-77 domain by proline residues is indicated.

FIG. 3 shows a representative ductal lesion. DMBA induces ductal lesions varying from hyperplasia, atypia to complete occlusion of the ducts. A ratio of ductal lesions/total number of ductal sections was determined. Again, 12.5 µg/ml concentration of p28 suppressed only 15% of the MDL formation. However, at 25 µg/ml there was a significant inhibition of the lesions comparable to that observed with 50 µg/ml azurin. The efficacy of p28 at concentrations greater than 12.5 µg/ml was statistically significant ($p<0.01$, Fishers Exact Test). These results are summarized in FIG. 4. Often effects of chemopreventive agents can be differentiated between the MAL and MDL. For example tamoxifen inhibited the development of MDL but not MAL. It is interesting to note that azurin and p28 inhibited both estrogen and progesterone-dependent ductal lesions as well as independent alveolar lesions.

This example indicates that both p28 and azurin can prevent the development of precancerous lesions in breast tissue. Thus, p28 and azurin may be used as chemopreventive agents in mammalian patients.

Example 2. Selective Penetration of Cancer Cells by Cupredoxins and Derivative Peptides as Potential Vectors for Gene Delivery Azurin, a member of the cupredoxin family of proteins, isolated from *Pseudomonas aeruginosa*, enters cancer cells and induces a p53-mediated apoptosis in vitro and in vivo. The selectivity of penetration of cationic and anionic cupredoxins and derived peptides as potential vectors for gene delivery was evaluated. The following cupredoxins were tested: azurin (14 kDa, pI 5.7), rusticyanin (17 kDa, pI 8.0), and plastocyanin (11 kDa, pI 5.4). The results indicated that azurin had the most selective penetration.

25 amino acid (a.a.) fragments of azurin (azu) were synthesized and evaluated for their penetration into a variety of cancer and histologicaly matched normal cells. Confocal microscopic and flow cytometric (FACS) analysis demonstrated that an 18 amino acid (1.7 kDa, azu 50-67) fragment (p18) labeled with Alexafluor 568 (800 Da) selectively penetrated human melanoma (Mel-2,7,29), breast (MCF-7), ovarian (SK-OV3), pancreatic (CAPAN-2), glioblastoma (LN-229), astrocytoma (CCF-STTG1), prostate (LN-CAP), and kidney (ACHN-CRL1611) cell lines, but not their respective controls. LDH release and hemolysis assays showed that p18 did not disrupt cancer cell membrane structure during penetration or produce hemolysis of human erthrocytes, suggesting that p18 penetrates human cancer cells without disrupting membrane structure. Pretreatment of Mel-2 cells with specific inhibitors of cell internalization (cytochalasin D; inhibition of actin polymerization, taxol; inhibition of microtubule depolymerization, chlorpromazine; inhibition of clathrin-mediated endocytosis, sodium azide; metabolic inhibition, or staurosporine; cell cycle inhibition) had a negligible effect on the penetration of p18. However, incubation of Mel-2 cells with nystatin (caveolae formation inhibitor) and brefeldin A (golgi apparatus disrupter) significantly inhibited the penetration of p18, suggesting that endocytic processes may, in part, be involved in the penetration of p18. Imaging of p18 labeled with an infrared dye ($\lambda_{em}$ 800 nm) in athymic mice bearing xenografted melanoma tumors clearly demonstrated selective uptake in primary s.c. tumors and distant organ metastases without accumulating in normal organs and tissues. As such, the peptides of the present invention, including in one embodiment, p18 appear to have significant utilization as a non-viral vector for gene (or any DNA/RNA fragment) therapy.

Example 3—Plasmid Constructions

Figure 5:
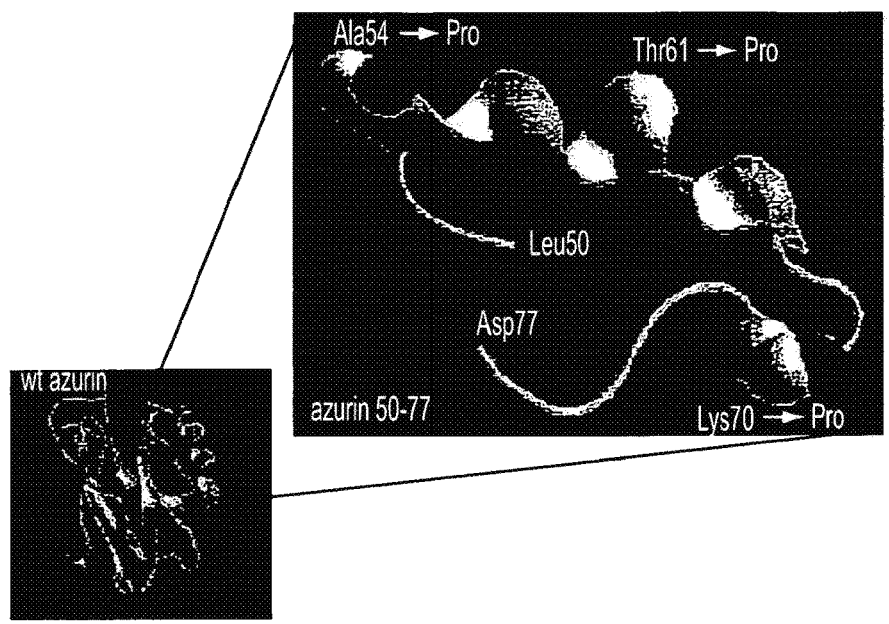

Plasmids expressing fusion glutathione S-transferase (GST)-truncated wt-azurin (azu) derivatives were constructed by a polymerase chain reaction using proofreading DNA polymerase. FIG. 5 shows a schematic representation of various truncated wt-azurin constructs. For pGST-azu 36-128, an amplified PCR fragment was introduced into the BamHI and EcoRI sites of the commercial GST expression vector pGEXSX (Amersham Biosciences, Piscataway, N.J. 08855). The fragment was amplified with pUC19-azu as a template and primers, 5'-C<u>GGGATCC</u> CCG GCA ACC TEC CGA AGA ACG TCA TGGGC-3' (SEQ ID NO: 78) and 5'-CG<u>GAATTC</u> GCA TCA CTT CAG GGT CAG GG-3' (SEQ ID NO: 79), where the additionally introduced BamHI and EcoRI sites are underlined respectively. Carboxyl-terminus truncation of azu gene was cumulatively performed by introducing a stop codon using QuickChange site-direct mutagenesis kit (Stratagene, La Jolla, Calif. 92037).

For pGST-azu 36-50, pGST-azu 36-77 and pGST-azu 36-89, stop codons were introduced into Ser51, Ser78, and Gly90, respectively. The plasmid carrying pGST-azu 36-128 was used as template DNA. Three sets of oligonucleotides for site-direct mutagenesis are shown as follows. For pGST-azu 36-50:5'-GGC CAC AAC TGG GTA CTG TGA ACC GCC GCC GAC ATG CAG-3' (SEQ ID NO: 80), and 5'-CTG CAT GTC GGC GGC GGT TCA CAG TAC CCA GTT GTG GCC-3' (SEQ ID NO: 81). For pGST-azu 36-77: 5'-CCT GAA GCC CGA CGA CTG ACG TGT CAT CGC CCA CAC C-3' (SEQ ID NO: 82) and 5'-GGT GTG GGC GAT GAC ACG TCA GTC GTC GGG CTT CAG G-3' (SEQ ID NO: 83). For pGST-azu 36-89: 5'-CCA AGC TGA TCG GCT CGT GAG AGAAGG ACT CGG TGA CC-3' (SEQ ID NO: 84), and 5'-GGT CAG CGA GTC CTT CTC TCA CGA GCC GAT CAG CTT GG-3' (SEQ ID NO: 85). The plasmids pGST-azu 50-77 and pGST-azu 67-77 were generated by PCR using pGST-azu 36-77 as a template DNA.

Amplified PCR fragments, azu 50-77 and azu 67-77, were obtained using forward primers 5'-C<u>GGGATCC</u> TGA GCA CCG CCG CCG ACA TGC AGG G-3' (SEQ ID NO: 86) and 5'-CG<u>GGGATCC</u> CCG GCC TGG ACA AGG ATT ACC TGA AGC CCG-3' (SEQ ID NO: 87), where the additionally introduced BamHI site is indicated by underlining. The reverse primer, 5'-CG<u>GAATTC</u> GCA TCA CTT CAG GGT CAG GG-3', was utilized in both cases (SEQ ID NO: 88).

The plasmid carrying gst-azu 50-77 was used for generating pGST-azu 50-66 by introduction of a stop codon in Gly67 using oligonucleotides as follows: 5'-GAC GGC ATG GCT TCC TGA CTG GAC AAG GAT TAC C-3' (SEQ ID NO: 89), and 5'-GGT AAT CCT TGT CCA GTC AGG AAG CCA TGC CGTC-3' (SEQ ID NO: 90). The green fluorescent protein gene (gfp) encoding the green fluorescent protein was also amplified by PCR. Forward and reverse primers used were 5'-C<u>GGGATCC</u> CCA TGG TGA GCA AGGGCG-3' (SEQ ID NO: 91) and 5'-CG<u>GAATTC</u> CTT GTA CAG CTC GTC CAT GCC G-3' (SEQ ID NO: 92) containing BamHI and EcoRI sites at the 5' end of each oligonucleotides. The resultant PCR fragment was ligated into the pGEXSX vector for creating pGST-GFP. For the preparation of plasmid DNA carrying gst-gfp-azu 50-77, the azu 50-77 gene was amplified by PCR with pGST-azu 50-77 as a template and primers 5'-CCG<u>CTCGAG</u> CCT GAG CAC CGC CGC CATGCA GGG-3' (SEQ ID NO: 93) and 5'-TTTTCCTTTTGC<u>GGCCGC</u> TCA GTC GTC GGG CTT CAG GTA ATC C-3' (SEQ ID NO: 94), where the introduced Xho I and Not I sites are underlined respectively. Purified azu 50-77 fragment was introduced into pGST-GFP at Xho 1 and Not 1 unique restriction enzyme sites Example 4—Purification of Proteins Wt-azurin and M44KM64E mutant azurin were prepared and purified as described by Yamada, T. et al. Proc. Natl. Acad. Sci. USA, vol. 101, pp. 4770-75 (2004), and in copending U.S. patent application Ser. No. 10/720,603, the contents of which are incorporated by this reference. Briefly, the wt-azurin gene was amplified by PCR according to the method described by Kukimoto et al., FEBS Lett, vol. 394, pp 87-90 (1996). PCR was performed using genomic DNA from *P. aeruginosa* strain PAO1 as a template DNA.

The amplified DNA fragment of 545 bp, digested with HindIII and PstI, was inserted into the corresponding sites of pUC19 so that the azurin gene was placed down-stream of the lac promoter to yield an expression plasmid pUC19-azuA. *E. coli* JM109 was used as a host strain for expression of the azurin gene. The recombinant *E. coli* strain was cultivated in 2YT medium containing 50 μg ml$^{-1}$ ampicillin, 0.1 mM IPTG; and 0.5 mM CuSO$_4$ for 16 h at 37° C. to produce azurin.

For preparation of the M44KM64E mutant azurin, site-directed mutagenesis of the azurin gene was performed using a QuickChange site-directed mutagenesis kit (Stratagene, La Jolla, Calif.). Mutations were confirmed by DNA sequencing.

Plasmid DNA, pET9a carrying the rus gene encoding the cupredoxin rusticyanin from *Acidithiobadilus ferrooxidans*, was obtained from Dr. Kazuhiko Sasaki, Central Research Institute of Electric Power Industry, Chiba, Japan.

Rusticyanin was isolated from *E. coli* BL21 (DE3) harboring the rus gene using the method of Sasaki, K., et al. Biosci. Biotechnol. Biochem., vol. 67, pp. 1039-47 (2003) with some modifications. Briefly, acetic acid buffer (pH 4.0) and CM-Sepharose (Sigma Chemicals, St. Louis, Mo. 63178) were used instead of beta-alanin buffer (pH 4.0) and TSK-gel CM-650 column (Tosoh Bioscience, LLC, Montgomeryville, Pa. 18936). Two other purified cupredoxins, plastocyanin from *Phormidium laminosum* and pseudoazurin from *Achromobacter cycloclastes* were obtained from Dr. Beatrix G. Schlarb-Ridley, University of Cambridge, UK and Dr. Christopher Dennison, University of Newcastle Upon Tyne, UK, respectively.

All recombinant GST-fusion derivatives were purified as follows: *E. coli* BL21 cells were used as the host strain. After induction with 0.4 mM IPTG at early log phase of growth in L broth, GST-fusion proteins were purified from cell extracts by using Glutathione Sepharose 4B affinity chromatography and Sephadex 75 gel-filtration column with PBS (Amersham Biosciences, Piscataway, N.J. 08855). Purified proteins, wt azurin and GST-derivatives or other cupredoxins, labeled with ALEXA FLUOR® (Molecular Probes, Inc., Eugene, Oreg. 97402) were isolated according to manufacturer's instructions. Unbound free fluorescent chemical was removed by gel-filtration column.

Example 5—Cell Cultures

J774 and UISO-Mel-2 cells (available from Frederick Cancer Research and Development Center, Frederick, Md. U.S.A.) were cultured as described in Yamada, T. et al. Infect. Immun. vol. 70, pp. 7054-62 (2002); Goto, M., et al. Mol. Microbiol. vol. 47, pp. 549-59 (2003); and Yamada, T., et al. Proc. Natl. Acad. Sci. USA vol. 99, pp. 14098-103 (2002), the contents of which are incorporated by reference. Human normal fibroblast cells (stock culture collection of the Department of Surgical Oncology, University of Illinois at Chicago (UIC), Chicago) were cultured in MEM with Eagle's salt containing 2 mM L-glutamine, 0.1 mM MEM essential amino acids and supplemented with 10% heat inactivated fetal bovine serum, 100 Units/ml penicillin and 100 μg/ml streptomycin. MCF-7 and MOF-10F cells were cultured as described in Punj et al. *Oncogene* 23:2367-78 (2004).

Example 6—Co-culture of J774, UISO-Mel-2 and Fibroblast Cells and Confocal Microscopy J774, UISO-Mel-2, and fibroblast cells were cultured on individual cover slips. After overnight incubation, the cells were washed with fresh media and all three cell lines were placed on a culture dish containing 200 μg/ml of wt-azurin conjugated with ALEXA FLUOR® 568. The cells were then incubated for 0.5 or 3.5 h at 37° C. under 5% $CO_2$.

For preparation of microscope samples, cells were cultured on cover-slips overnight at 37° C. Cultured cells were placed at 37° C. or 4° C. for 2 h before protein treatment. Pre-warmed 37° C. fresh media or ice-cold 4° C. fresh media were mixed with red-fluorescent (labeled with ALEXA FLUOR® 568) cupredoxins or GST-fusion derivatives, and incubated with the cells. The cells were washed with PBS, and fixed with methanol at –20° C. for 5 min. After washing with PBS twice and the addition of mounting media containing 1.5 μg/ml 4',6-diamidino-2-phenylindole (DAPI) for staining nuclei (VECTASHILD, Vector, Burlingame, Calif.), images were taken by a confocal microscope.

Example 7—Entry of Cupredoxins into J774 Cells

Wt-azurin, its mutant variant M44KM64E, plastocyanin, pseudoazurin and rusticyanin were incubated with J774 cells as in Example 6 and the cells examined using confocal microscopy. In these experiments, the cupredoxins were conjugated with ALEXA FLUOR® 568 to fluoresce red and incubated with the J774 cells for 1 hr at 37° C. at a concentration of 200 μg/ml, and in a separate experiment wild type azurin and rusticyanin were incubated with J774 cells for 1 hr at 37° C. at a concentration of about 6 to 7 μM. The nucleus was stained blue with DAPI. A control without the proteins was maintained. In all cases, the cupredoxins were seen to enter into the cytosol of J774 cells. In similar experiments, auracyanin A and B enter preferentially to MCF7 cancer cells and not non-cancerous control cells.

Example 8—Entry of Wt-azurin and Rusticyanin into Various Cell Types

Wt-azurin exhibits a reduced cytotoxic activity towards MCF-10F cells as contrasted with the MCF-7 cells. Punj et al. Oncogene 23:2367-2378 (2004). J774, peritoneal macrophages, mast cells, human breast cancer MCF-7 and human normal epithelial MCF-10F cells (stock culture collection of the Department of Surgical Oncology, University of Illinois at Chicago (UIC), Chicago) were treated and examined as in Example 5 and tested to determine if wt-azurin could enter such cells.

Wt-azurin was internalized in J774 cells during 45 mm incubation. However, it was internalized very inefficiently in peritoneal macrophages or mast cells. Even after 6 hr incubation, such cells showed only limited entry. Similarly, while wt-azurin entered the breast cancer MCF-7 cells efficiently, it showed an extremely reduced rate of entry in the normal mammary MCF-10F cells.

Alexa Fluor®-conjugated azurin entered efficiently in UISOMel-2 and MCF-7 cancer cells but not in the normal mammary MCF 10A1 cells. Alexa Fluor®-conjugated rusticyanin, however, not only entered the cytosol of UISO-Mel-2 and MCF-7 cancer cells, but also in the normal MCF 10A1 cells. Unlike in the cancer cells where rusticyanin was evenly distributed in the cytosol, in MCF10A1 cells, much of the rusticyanin was sequestered in the perinuclear space surrounding the nucleus.

Example 9—Wt Azurin-Mediated Cytotoxicity and Growth Inhibition

To further assess the specificity of entry of wt-azurin in various cells, the entry of Alexa fluor-conjugated wt-azurin in J774, UISO-Mel-2 and normal fibroblast cells was determined during incubation at 37° C. for 30 min and 3.5 hr. Wt-azurin was seen to enter rapidly in J774 and UISO-Mel-2 cells in 30 mm; very little wt-azurin was seen in the cytosol of fibroblasts during this period. After 3.5 hr of incubation, only small amounts of wt-azurin were found in the fibroblasts.

A 3(4,5 dimethylthiazol-2-yl-2,5 tetrazolium bromide) (MTT) assay was performed for the measurement of the cytotoxicity of wt-azurin as described by Yamada, T., et al. *Infect, Immun.* 70:7054-62 (2002), Goto, M., et al. *Mol. Microbiol.* 47:549-59 (2003), and in co-pending U.S. patent application Ser. No. 10/720,603, filed Nov. 24, 2003, the contents of which are incorporated by reference. FIG. 1(b) shows that significant wt-azurin-mediated cytotoxicity was observed only with J774 and UISO-Mel-2 cells during 24 hr incubation.

M44KM64E mutant azurin showed very little apoptosis-inducing activity in J774 cells but at 1 mg/ml concentration significantly inhibited (about 95%) cell cycle progression at the $G_1$ to S phase. Cell cycle progression was analyzed by flow cytometry, as described by Hiraoka, Y. et al., *Proc. Natl. Acad. Sci. USA*, vol. 101:6427-32 (2004) and Yamada, T. et al. *Proc. Natl. Acad. Sci. USA* 101:4770-75 (2004), the contents of which are incorporated by reference. FIG. 1(a) shows that when the fibroblasts were treated with 500 μg/ml or 1 mg/ml of M44KM64E mutant azurin, the extent of inhibition of cell cycle progression was about 20%.

Example 10—Microinjection of Wt-azurin into Fibroblast and MCF-10F Cells

Wt-azurin was microinjected into fibroblast and MCF-10F cells as using the method described by Punj, V., et al., *Oncogene* 23:2367-78 (2004). Cells were examined for induction of apoptosis, leading to nuclear DNA condensation and fragmentation. Significant nuclear DNA (labeled blue with DAPI) condensation and fragmentation were observed in microinjected single cells after 5 hr incubation with wt-azurin, but not during a 30 min. incubation with azurin.

Example 11—Internalization of Wt-azurin Fusion Derivatives at 37° C.

A series of GST fusions of wt-azurin truncated at both the N- and the C-terminal were prepared and purified as in Example 1 (FIGS. 2(a) and 2(b). Using ALEXA FLUOR® 568 conjugated wt-azurin, GST and GST-azu fusion derivatives, internalization in J774 cells at 37° C. during 1 hr incubation was examined using the method described in Example 5. The nucleus was stained blue with DAPI.

While wt-azurin was internalized, GST remained at the periphery of the cells and was not internalized. GST-azu 36-128 and GST-azu 36-89 were internalized, as was GST-azu 36-77. Further truncations, however, demonstrated that while GST-azu 50-77 was internalized, GST-azu 36-50 was highly inefficient and appeared to form clumps on the surface.

Example 12—Internalization of Azurin Fusion Derivatives at 4° C.

Internalization of wt-azurin and the GST-azu fusion derivatives in J774 cells incubated at 4° C. was examined. At 4° C., internalization of wt-azurin inside J774 cells during 1 hr incubation was severely impaired. Similar impairment was also seen with GST-azu 36-128 and GST-azu 36-89. The shorter GST-azu 36-77, GST-azu 50-77, GST-azu 50-66 and GST-azu 67-77 demonstrated severe impairment of internalization at 4° C.

Figure 6A:
FIGS. 6(A), (B) and (C). (A) Diagram showing construction of a GST-GFP-azu 50-77 fusion protein. The gfp gene was introduced at the 3'-end of the gst gene (for GST-GFP) and the azu 50-77 fragment was then ligated at the 3'-end of the gfp gene in frame to produce the GST-GFP-azu 50-77 fusion protein. GST-GFP-azu 50-77 was purified as a single fusion protein from the cell lysates. Purified proteins were run on SDS-PAGE and detected by Coomassie Blue staining (6(B) and also by Western blotting using anti-azurin antibody (6(C)).
Figures 6B, 6C:
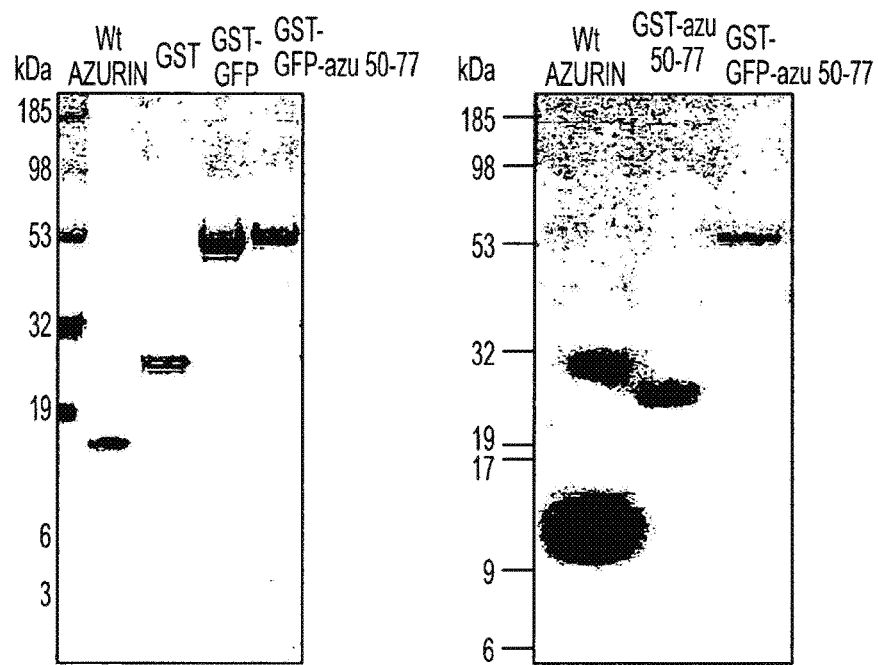

Example 13—Energy-Dependent Internalization of the GST-GFP-azu 50-77 Fusion Protein in J774 and Melanoma UISO-MeI-2 Cells GST was fused with GFP to make a GST-GFP fusion derivative. Additionally, azu 50-77 was fused to the GST-GFP ($M_r$ 53 kDa) fusion protein (FIG. 6(*a*)). The mobility of the purified GST, GST-GFP and GST-GFP-azu 50-77 fusion derivatives was examined on SDS-PAGE (FIG. 6(*b*)). Detection was by Coomassie Blue staining and Western blotting using anti-azurin antibody (FIG. 6(*c*))

Figures 7A, 7B, 7C:
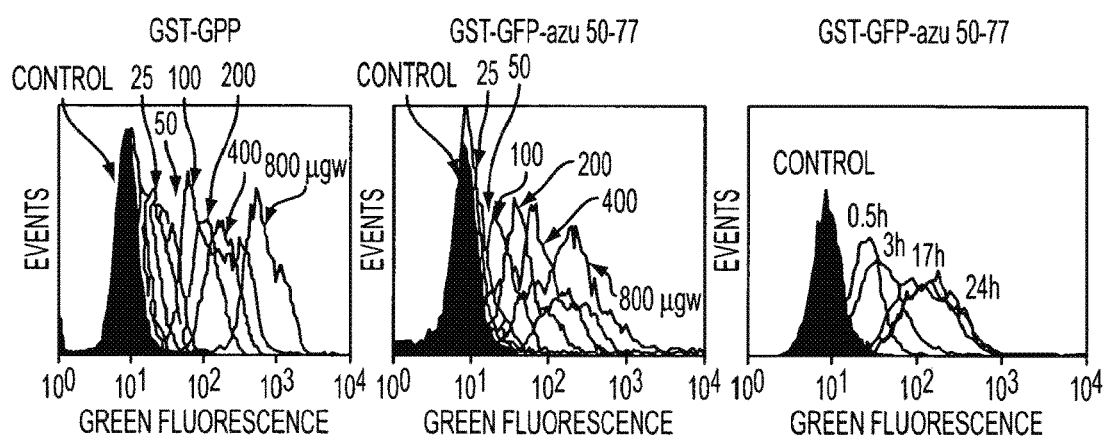
FIGS. 7(A), (B) and (C). Diagrams showing a kinetic study for the internalization of GST-Green Fluorescent Protein (GFP) and GST-GFP-azurin fusion proteins. Green fluorescence was assayed in J774 cells treated with various concentrations of GST-GFP (10(a)) or GST-GFP-azu 50-77 (10(b)) at 37° C. for 1 hr. Ten thousand cells were analyzed by flow cytometry. (c) Time-dependence of internalization of GST-GFP-azu 50-77. J774 cells were incubated with 200 µg/ml GST-GFP-azu 50-77 for indicated times at 37° C. and analyzed by flow cytometry.

Flow cytometric determination of J774 cells treated with varying concentrations of GST-GFP showed that this protein does bind to J774 cells. Flow cytometric separation of J774 cells treated with increasing concentrations of GST-GFP-azu 50-77 fusion protein demonstrated significantly reduced fluorescence than GST-GFP alone (FIG. 7). It is to be noted that internalization of GFP in mammalian cells is known to lead to loss of fluorescence. This reduction of fluorescence is also apparent when J774 cells are treated with 200 μg/ml of GST-GFP-azu 50-77 fusion protein and incubated for increasing periods of time at 37° C.

To determine if there is any difference in the binding and internalization profile of GST-GFP and GST-GFP-azu 50-77, both J774 and UISO-Mel-2 cells were incubated with GST-GFP and GST-GFP-azu 50-77 at 37° C. and at 4° C. The green fluorescence was localized using confocal microscopy. In J774 cells, GST-GFP fusion protein bound to the surface and was not internalized both at 37° C. and at 4° C. In contrast, GST-GFP-azu 50-77 was found to be internalized at 37° C., but not at 4° C. In UISO-Mel-2 cells, the GST-GFP fusion protein was retained on the surface both at 37° C. and at 4° C. In contrast, similar to J774 cells, GST-GFP-azu 50-77 fusion protein was seen to be internalized at 37° C. but not at 4° C.

Example 14—Wt-azurin Entry into Mammalian Cells by a Cell Membrane Penetration and an Endocytic Mechanism If wt-azurin entry is solely dependent on receptor-mediated endocytosis, it could be blocked by protonophore carbonyl cyanide m-chlorophenylhydrazone (CCCP), a mitochondrial uncoupler of energy generation, or preincubation with unlabeled azurin or other cupredoxins that block the receptors. J774 and UISO-MeI-2 cells were incubated with the cupredoxins at 10 fold excess concentration for 2 hr at 4° C., the cells washed thoroughly to remove the cupredoxins, and incubated with ALEXA FLUOR® 568-conjugated azurin for 1 hr at 37° C. There was as much internalized azurin as in cells not treated with the cupredoxins. The effects of cytochalasin D (available from Sigma-Aldrich, St. Louis, Mo. 63195), a known inhibitor of receptor-mediated endocytosis that disrupts the cellular microfilament network, and Brefeldin A (available from Sigma-Aldrich, St. Louis, Mo. 63195), which is known to disrupt the Golgi apparatus and inhibit classical vesicle-mediated secretion, were also tested. CCCP at 20 pM concentration significantly reduced the uptake of azurin in UISO-MeI-2 cells as did 0.25 to 0.5 μM cytochalasin D. Brefeldin A, on the other hand, had no significant effect.

Example 15—Entry of a GST-PEDIII-azu 50-77 Fusion Derivative into UISO-Mel-2 Cells A GST-fusion of *Pseudomonas aeruginosa* exotoxin A domain III (PEDIII) was constructed as described by Hwang, J. et al., *Cell* 48:129-36 (1987); Reiter, Y. and Pastan, I., *Trends Biotechnol.* 16:513-20 (1998). This GST-PEDIII fusion derivative contained amino acids 381-613 of the exotoxin A. PEDIII is known to harbor ADP-ribosyl transferase activity and inhibits cellular protein synthesis in eukaryotic cells by inhibiting eukaryotic elongation factor 2.

Figure 8A:
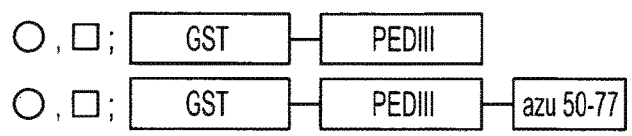
FIGS. 8(A), (B) and (C). (A) Diagram showing the exotoxin A domain III (amino acids 405-613), as well as part of domain 1b (amino acids 381-404), fused to GST (GST-PEDIII) as earlier described for the GST-GFP fusion. The azu 50-77 fragment was then ligated to the carboxyl end of GST-PEDIII (GST-PEDIII-azu 50-77), using PCR. (B) The fusion proteins were purified by glutathione Sepharose 4B column gel filtration column chromatography and run on SDS-PAGE for size determination. (C) Diagram showing action of GST-PEDIII-azu 50-77 fusion protein in UISO-Mel-2 cancer cells and in normal fibroblast (FBT) cells, as determined by PEDIII-mediated cytotoxicity. Various concentrations, as indicated, of GST-PEDIII and GST-PEDIII-azu 50-77 were incubated with UISO-Mel-2 and FBT cells for 24 h, after which the cell viability was determined by MTT assay.
Figure 8B:
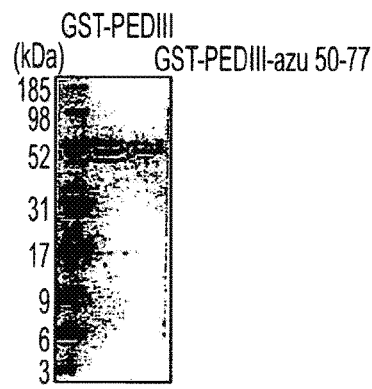
Figure 8C:
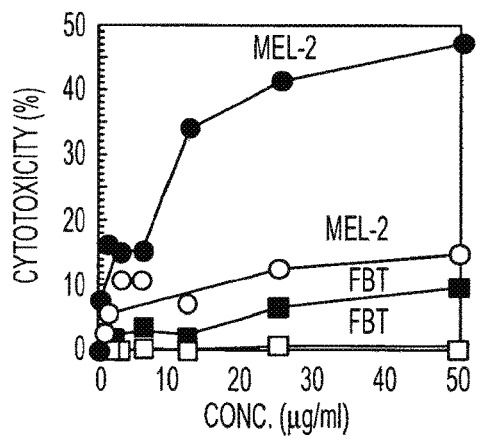

Using PCR as described for the GST-GFP-azu 50-77, the azu 50-77 sequence was introduced to the carboxyl end of the GST-PEDIII fusion protein (FIG. 8(*a*)). These two fusion proteins (GSTPEDIII and GST-PEDIII-azu 50-77) were purified by glutathione-sepharose 4B column chromatography as 52 and 54 kDa proteins (FIG. 8(*b*)). UISO-Mel-2 and normal fibroblast (FBT) cells were then incubated for 24 h at 37° C. with various concentrations of these proteins and the extent of cell death measured by MTT assay as described in Example 9.

While GST-PEDIII demonstrated only low cytotoxicity, the GST-PEDIII-azu 50-77 fusion protein had high cytotoxicity because of efficient entry to UISO-Mel-2 cells (FIG. 8(*c*)). In contrast, the fusion proteins demonstrated a low level of cytotoxicity towards the fibroblast cells.

Example 16—Destabilization of the α-helix in wt-Azurin has no Substantial Effect on its Internalization in UISO-Mel-2 Cells To examine if the α-helix plays a role in azurin entry, three helix-destabilizing proline residues were introduced in positions 54, 61 and 70 of wt-azurin (FIG. 6) and examined the entry of the full length A54PT61PK70P mutant azurin into UISO-Mel-2 cells. Single and double mutations in these positions were also constructed and tested for entry. The A54PT61PK70P mutant azurin was prepared by site-directed mutagenesis of the azurin gene using the QuickChange site-directed mutagenesis kit (Stratagene, La Jolla, Calif.).

The mutants were incubated at 200 μg/ml with UISO-Mel-2 cells for 1 hr at 37° C., after which the fluorescence was localized by confocal microscopy. In all cases, the ALEXA FLUOR® 568-conjugated mutant azurins entered UISO-Mel-2 cells. Similarly, when the GST-GFP-azu 50-77 fusion protein, as well as its triple A54PT61PK70P azu mutant variant, were examined for entry in UISO-Mel-2 cells, no significant difference was observed.

Example 17—Entry of a GST-PEDIII-Rusticyanin Fusion Derivative into UISO-Mel-2 Cells A GST-fusion of *Pseudomonas aeruginosa* exotoxin A domain III (PEDIII) and was constructed as in Example 15. Using PCR as described for the GST-GFP-azu 50-77, full-length rusticyanin sequence was introduced to the carboxyl end of the GST-PEDIII fusion protein. The fusion protein was purified by glutathione-sepharose 4B column chromatography. UISO-Mel-2 and FBT cells were then incubated for 24 h at 37° C. with various concentrations of the fusion protein and the extent of cell death measured by MTT assays as described in Example 7.

Figure 9:
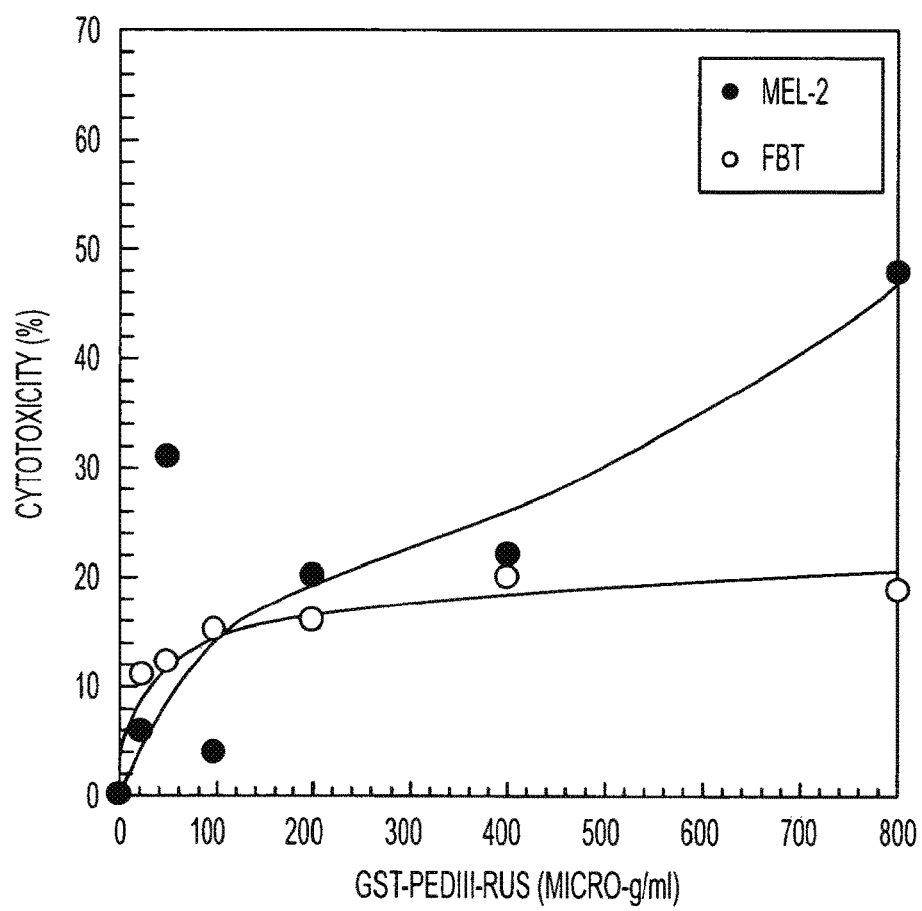
FIG. 9. Diagram showing PEDIII-mediated cytotoxicity of GST-PEDIII-rusticyanin fusion protein against UISO-Mel-2 cancer cells and FBT cells. Various concentrations, as indicated, of GST-PEDIII and GST-PEDIII-azu 50-77 were incubated with UISO-Mel-2 and FBT cells for 24 h, after which the cell viability was determined by MTT assay.

The GST-PEDIII-rusticyanin fusion protein exhibited high cytotoxicity against UISO-Mel-2 cells (FIG. 9). In contrast, the fusion protein demonstrated only a low level of cytotoxicity towards the FBT cells.

Example 18—Entry of p18 and p28 Into Human Cell Lines

Cell Culture and Cell Lines:

Human cancer and non-cancer (immortalized and non-immortalized) cell lines were obtained from ATCC [lung cancer (A549 and NCI-H23 adenocarcinoma), normal lung (CCD-13Lu), prostate cancers (DU145 and LN-CAP), normal prostate (CRL11611), breast cancer (MCF-7), normal breast (MCF-10A), colon cancer (HCT116), normal colon (CCD33Co), fibrosarcoma (HT1080), and ovarian cancer (SK-OV3 adenocarcinoma)]. Normal fibroblasts isolated from skin were established. Normal ovarian cells (HOSE6-3) were donated by Dr. S. W. Tsao (University of Hong Kong). Melanoma lines (UISO-Mel-2, 23, 29) were established and characterized. All cells except UISO-Mel-2 were cultured in MEM-E (Invitrogen, Carlsbad, Calif.) supplemented with 10% heat-inactivated fetal bovine serum (Atlanta Biological Inc., Lawrenceville, Ga.), 100 units/ml penicillin and 100 µg/ml streptomycin at 37 C in 5% CO2 or air.

Proliferation Assays/Cell Growth:

Melanoma cells were seeded (four replicates) in flat bottom 24 well plates (Becton Dickinson, Franklin Lakes, N.J.) at a density of 12×103 cells/well. After 24 hrs media was changed and fresh p18, p28, azurin or a similar volume of media without peptide (eight replicates) added daily for 72 hr. Cells were then counted in a Beckman Coulter (Z 1 coulter particle counter). Values represent the mean±SD of 4 replicates.

MITT Assay:

Melanoma cells were seeded at a density of 2000 cells/well in flat-bottomed 96 well plates (Becton Dickinson, Franklin Lakes, N.J.) and allowed to attach for 24 hrs. Freshly prepared peptide (10 µl) or culture medium was then added to each well. After 24 hrs, medium was changed and p18, p28 or azurin added daily. After 72 hr incubation, 10 µl of MTT reagent (Trevigen, Gaithersburg, Md.) was added to each well, the samples incubated for 3 hr, RT/sig 100 µl of detergent added to each well, and the samples incubated for an additional 3 hr at 37° C. Absorbance was measured with a SpectraMax 340 plate reader (Molecular Devices Corporation, Sunnyvale, Calif.) and percent change in the absorbance at 570 nm in treated cells relative to untreated controls determined. Values represent the mean±SD. Significance between control and treated groups was determined by Student's t-test.

Peptide Synthesis:

All azurin derived peptides including p18, Leu$^{50}$-Gly$^{67}$ LSTAADMQGVVTDGMASG (SEQ ID NO. 25), p28 Leu$^{50}$-Asp$^{77}$ LSTAADMQGVVTDGMASGLDKDYLKPDD (SEQ ID NO. 2), p18b Val$^{60}$-Asp$^{77}$ VTDGMASGLDKDYLKPDD (SEQ ID NO. 34), MAP, Mastoparan-7, and poly arginine (Arg$_8$) (SEQ ID NO: 95) were synthesized by C S Bio, Inc. (Melo Park, Calif.). Peptides were received as lyophilized powder aliquoted and stored at −20° C. in air-tight desiccators. All peptides were subsequently analyzed by mass spectrometry and reverse phase HPLC as >95% purity and mass balance.

Predictive Modeling for Azurin Peptides:

GENETYX software (ver. 6.1) was used to generate Robson structure models for azurin derived peptides. Garnier, J., Osguthorpe, D. J., and Robson, B., J Mol Biol, 120: 97-120 (1978). The MAPAS Software was used to predict a given protein structure for strong membrane contacts and define regions of the protein surface that most likely form such contacts. Sharikov, Y. et al, Nat Methods, 5: 119 (2008). If a protein, i.e., azurin, has a membranephilic residue score (MRS)>3, membranephilic area score (MAS)>60%, and coefficient of membranephilic asymmetry ($K_{mpha}$)>2.5, there is a high probability that the protein has a true membrane-contacting region.

Peptide/Protein Labeling:

Peptides were dissolved in 1 ml PBS mixed with Alexafluor 568 dye (Molecular Probes, Eugene, Oreg.) at a 1:2 protein:dye ratio, 100 µl sodium bicarbonate added, and the mixture incubated overnight at 4° C. with continuous stirring. Labeled peptide was separated from free dye by dialyzing against cold-PBS using Slide-A-Lyzerg Dialysis Cassettes 1000 MWCO for p12 and 2000 MWCO for others (Pierce Biotechnology, Rockford, Ill.).

Cell Penetration/Confocal Analysis:

Cells were seeded on glass coverslips and allowed to attach overnight at 37° C. under 5% $CO_2$. Cells were rinsed with fresh media and incubated at 37° C. for 2 hrs in pre-warmed media containing Alexafluor 568 labeled azurin peptides (20 µM) or Arg8 (SEQ ID NO: 95) (5 µM), or media alone. Following incubation, coverslips were rinsed 3× with PBS, cells fixed in 2.5% formalin for 5 min, and washed 2× in PBS, once in d.i. $H_2O$, and coverslips mounted in media containing 1.5 µg/ml DAPI for nuclear counter staining (VECTASHIELD® Vector Laboratories, Burlingame Calif.). Cellular uptake and distribution were photographed under an inverted confocal laser scanning microscope (Model LC510, Carl Zeiss Inc., Gottingen, Germany).

Peptide co-localization with lysosomes or mitochondria was determined by incubating cells growing on a glass coverslip for 2 hrs at 37° with Alexafluor 568 labeled azurin or peptides. Mitrotracker (MitroTracker® Green FM Invitrogen Corporation, Carlsbad, Calif.) or lysotracker (LysoTracker® Green DND-26 Invitrogen Corporation, Carlsbad, Calif.) was added (final concentration 1 µM) for the last 30 mins of incubation. Cells were rinsed 3× with PBS, fixed in 2.5% formalin for 5 mins, washed 2× with PBS and incubated in 0.1% Triton-X100 in PBS for 15 min. Cells were then incubated with 1 µg/ml rabbit anti-human golgin 97 or anti-human caveolin I (Abcam, Cambridge, Mass.) in PBS with 1% BSA. After 1 hr incubation at 4° C., coverslips were washed once with PBS, incubated 10 min in PBS containing Alexafluor 468 conjugated goat anti-rabbit antibody, washed 2× in PBS and once in d.i.H20. Coverslips were then mounted in media containing 1.5 µg/mlDAPI for nuclear counter staining. Colocalization (yellow) of Alexafluor 568 (red) and Alexafluor 468 (green) was analyzed and photographed.

UISO-Mel-2 cells on coverslips were preincubated in MEM-E containing 100 µg/ml heparin sulfate (Sigma-Aldrich, St. Louis, Mo.) for 30 min and p18, p28 or Arg$_8$ (SEQ ID NO: 95) added to bring the final concentration to 20 µM. After 1 hr, coverslips were washed, fixed, and analyzed as described above.

Cell Penetration by FFACS:

Cells (1.0×10$^6$/500 µl PBS) were incubated for 2 hrs at 37° C. with Alexafluor 568 labeled p18 or p28 (20 µM), Arg$_8$ (SEQ ID NO: 95) (5 µM), or media alone, washed 3× in PBS, fixed in 2.5% formalin for 5 min, washed twice in PBS, resuspended in 200 µl PBS, and passed through a screen to obtain a single cell suspension. Samples were analyzed with a MoFlo Cell Sorter (Dako, Glostrup, Denmark) $\lambda_{ex}$ 568 nm and λ$_{em}$ 603 nm and the fold increase of the mean fluorescence intensity over background levels calculated. Results represent mean fluorescence of three separate experiments.

Entry Inhibitors:

UISO-Mel-2 cells (3×10$^5$ per 300 μl), maintained in phenol red-, serum-free MEM-E at 37° C., were pretreated with inhibitors, including: Chloropromazine (inhibitor of clathrin-mediated endocytosis, 10 μg/ml, 60 min); Amiloride (macropinocytosis inhibitor, 50 μM, 30 min); Nystatin (50 μg/ml, 30 min); Methyl-β-cyclodextrin (MβCD, 5 mM, 60 min); Filipin (inhibitor of caveolae-mediated endocytosis, 3 μg/ml, 60 min); Taxol (microtubule stabilizer, 20 μM, 30 min); Staurosporine (cell cycle inhibitor, 250 nM, 10 min); Sodium azide (metabolic inhibitor, 1 mM, 60 min); Oauabain (ATPase-dependent Na+/K+ pump inhibitor, 50 mM, 60 min); Brefeldin A (BFA; Golgi apparatus disruptor, 100 μM, 60 min); Wortmannin (early endosome inhibitor, 100 nM, 30 min); Monensin (inhibits at late endosome/lysosome, 10 μM, 60 min); Nocodazole (inhibits caveosome formation, 10 μM, 60 min); Cytochalasin D (actin filament and microtubule disruptor, 5 μM, 30 min); Benzyl 2-acetamido-2-deoxy-α-D-galactopyranoside (Bn-GalNac; O-linked glycosylation inhibitor, 3 mM, 48 hrs); Tunicamycin (N-linked glycosylation inhibitor, 20 μg/ml, 48 hrs); and Neuraminidase (cleave sialic acid residues from proteins, IU/ml, 30 min). Final concentrations were derived from the dose response curves of individual inhibitors. Alexafluor 568 labeled p18 or p28 (20 μM) were then added, incubated for 1 hr, and the cells washed, fixed and prepared for flow cytometric analysis as described above.

Cell Membrane Toxcity Assays/LDH Leakage Assay:

An LDH leakage assay was performed according to the manufacturer's instructions (CytoTox-One, Promega, Wis.) with 100 μl of UISO-Mel-2 cells (5×10$^3$). Cells without peptides/proteins were used as a negative control. Experiments were carried out in triplicate (data represent mean±SEM).

Hemolysis Assay:

Human whole blood samples (2-3 ml) were centrifuged for 10 min at 100×g, and the pellets washed once with PBS and once with HKR buffer pH7.4 (18). Cell pellets were then resuspended in HKR buffer to 4% erythrocytes, 50 μl transferred to a 1.5 ml tube with 950 μl of peptides, azurin (5, 50 and 100 μM) or 0.1% Triton X-100 in HRK buffer to completely disrupt the RBC membrane. MAP and Mastoparan7 (Bachem California, Inc., Torrance, Calif.) were used as positive controls. After 30 min incubation at 37° C. with rotation, tubes were centrifuged for 2 min at 1000×g, 300 μl of supernatants transferred to a 96-well plate and absorbance recorded at 540 nm.

Kinetics of Entry:

UISO-Mel-2 cells (5×10$^5$ cells) in 1.5 ml tubes were suspended in MEME media without phenol red. Reactions were started by adding either Alexa fluor 568-conjugated p18 at 0, 10, 20, 50, 100, 150 and 200 μM for 5, 10, 15 and 20 sec., or Alexafluor 568-conjugated p28 at 1, 10, 25, 50, 100, 150 and 200 μM for 30, 60, 90 and 120 see on ice. After incubation, 1 ml of cold-PBS was added to the 250 μl reaction in mixture. Cells were centrifuged twice at 600×g for 2 min at 4° C. At least 10,000 fixed cells were analyzed by flow cytometry in each reaction and their background and relative fluorescence calculated.

$^{125}$I Labeling of Azurin and Competition Assays:

Peptide binding and entry was determined using a whole cell assay with UISO-Mel-2 cells in HEPES solution (50, 000 cells/ml), were incubated for 30 min at 37° C. with increasing concentrations (0-175 nM) of radiolabeled azurin in the presence/absence of 1000 fold excess of unlabeled p18, p28, or azurin, then washed 3 times with ice cold PBS, and radioactively remaining in the cell pellet counted using a gamma counter. Radioactivity in cells incubated with $^{125}$I azurin alone was considered total binding; radioactivity in the presence of unlabeled azurin, p18, or p28 was considered nonspecific binding. Specific binding was determined by subtracting nonspecific binding from total binding and Scatchard plots generated.

Example 19—Domain of p28 Responsible for Preferential Entry into Cancer Cells

Figure 10A:
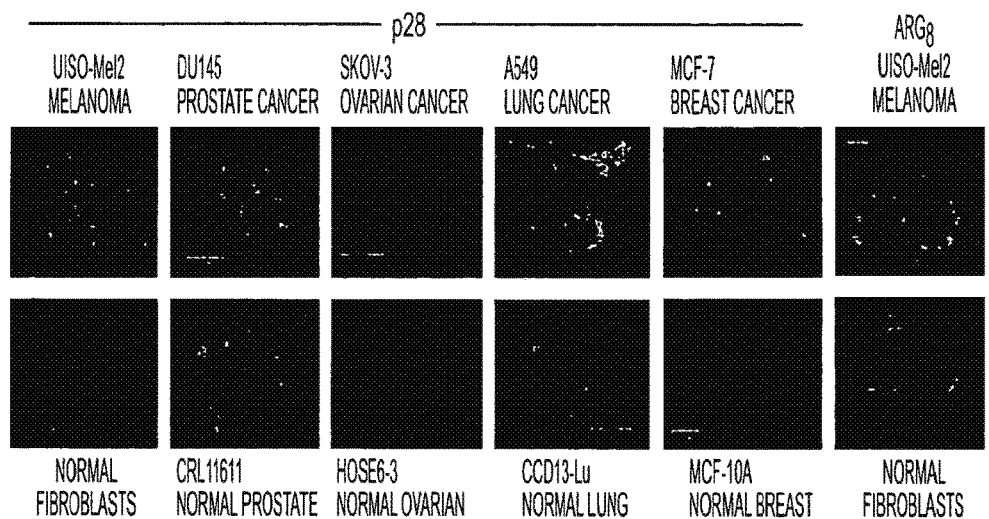
FIGS. 10, (A), (B) (C) and (D). Depicts photographs showing penetration of azurin derived peptides, p18 and p28, into cancer cell lines of diverse histogenesis and their normal counterparts. (A) and (B) Photos showing penetration of Alexafluor 568 labeled p28 or p18 after 2 hrs at 37° C. The cationic Args was used as a control. (C) Graphs depicting flow cytometric analysis of the penetration of Alexafluor 568 labeled p28 or p18 into the same cell lines after 2 hrs at 37° C. (D) Graphs depicting fold increase over fluorescence from normal cells. Similar observations of p28 or p18 entry into 4 melanoma cell lines show a several fold increase over fluorescence from normal cells.
Figure 10B:
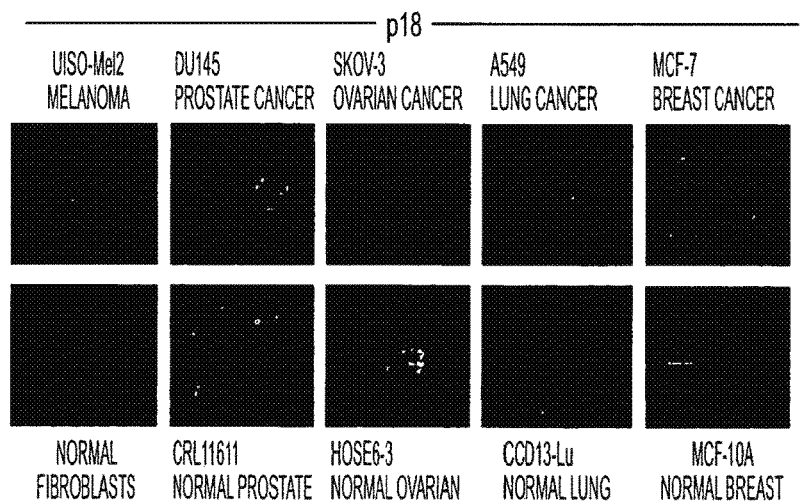

Initial data from peptide-GST constructs defined amino acids 50-77 of azurin as a PTD for cell penetration, which fits well with structural evidence for an-helical region encompassing residues 54-67 of azurin stabilizing the azurin molecule. Confocal analyses initially suggested that p28 and p18 of p28/azurin (FIG. 10A and B) penetrated human melanoma, prostate, lung, breast and ovarian cancer cells with relatively similar efficiency, but did not penetrate histologically matched normal cell lines to the same degree (FIG. 10A and B). A singular exception was CCD13-Lu, a cell line derived from lung fibroblasts. The cationic Args was rapidly and efficiently taken up into fibroblasts (FIG. 10A) and all other normal cell lines tested (data not shown).

Figure 10C:
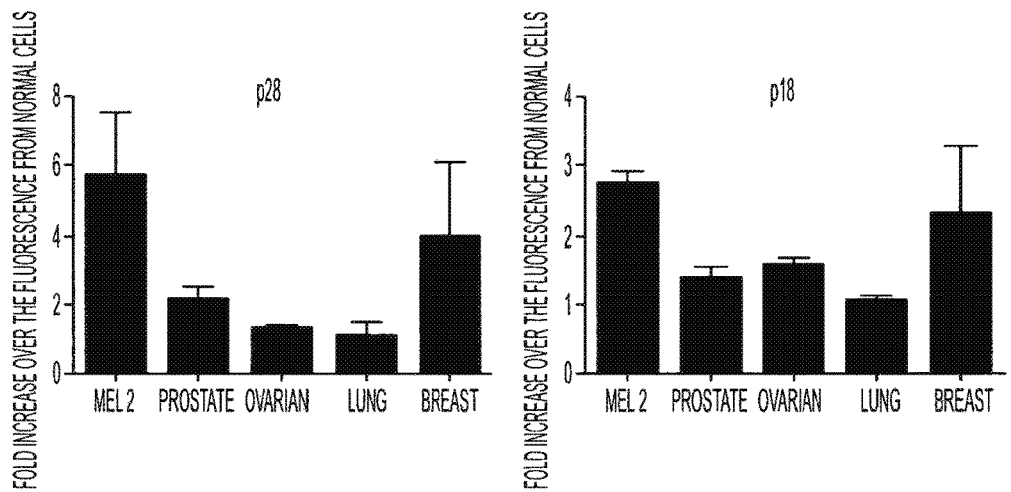
Figure 10D:
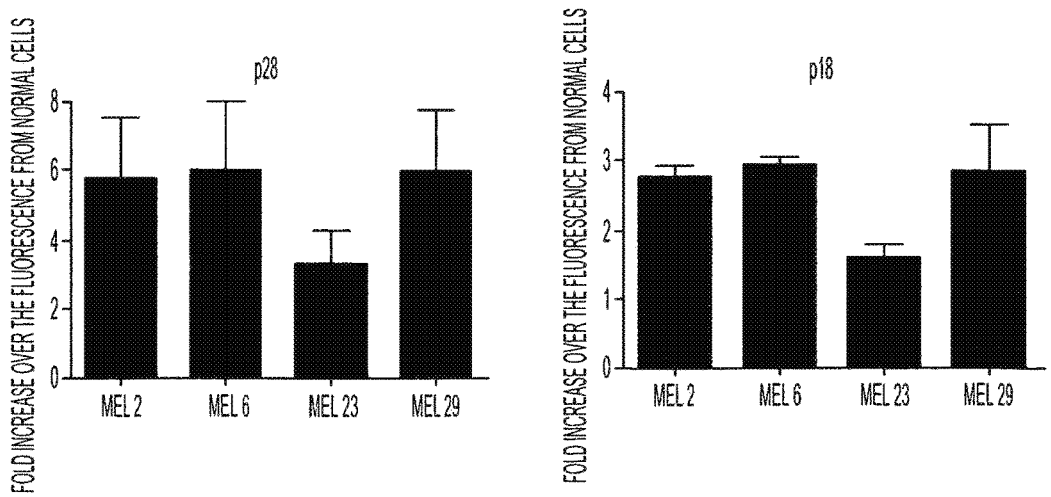

These observations were confirmed by a more sensitive FACs analyses (FIG. 10C) where p28 fluorescence was about 0.5-6 and p1 8 about 0.5-3 fold higher than the corresponding normal cell line, with the exception of lung cancer. A similar pattern in intracellular fluorescence intensity was observed within a histopathologic subtype, melanoma, where the relative intensity of p18 was about 50% of that observed with p28 (FIG. 10D). Fluorescence intensity over background was also consistently lower in normal and cancer cell pairs exposed to p18 than p28 (data not shown), again showing less p18 entered individual cells. In all cases, the degree of entry of p18 and p28 into either cancer or normal cells was significantly less than that observed with Args, where no preference for entry was observed (FIG. 10A and B). The predicted Robson structure (data not shown) of p18 suggests that the C-terminal amino acids form a partial f3-sheet. This and the shorter length of p18, which lacks the hydrophilic C-terminal 10 amino acids (amino acids 68-77) of p28, shows that p18, as a putative PTD for azurin, has a more rapid entry into cancer and normal cells via a non-endocytotic over an endocytotic or membrane receptor mediated process. MAPAS data {MRS 3.74, MAS 87.1, K$_{mpha}$ 2.37) show that amino acids 69, 70, 75, 76, 85 of azurin provide the best opportunity for membrane contact, demonstrating that the C-terminal region of p28, not present on p18 (amino acids 50-67) contacts specific residues on the cell membrane, irrespective of a cell's status.

Figure 11A:
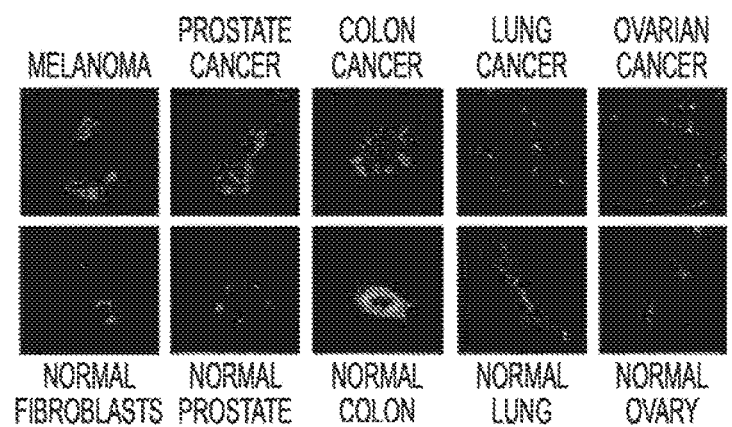
FIG. 11, (A) and (B). Depicts photographs showing entry of azu 60-77 (p18b) and azu 66-77 (p12) into cancer and normal cells. Cells were incubated with alexafluor 568 labeled p18b (A) or p12 (B) at 37° C. for 2 hrs and images recorded by confocal microscopy.
Figure 11B:
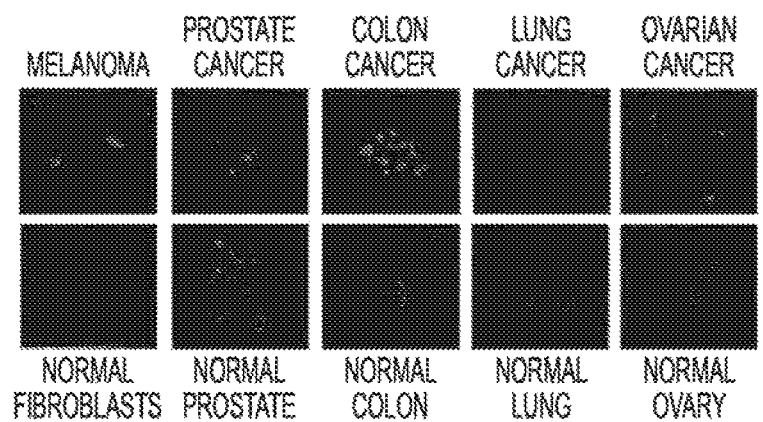

The preferential penetration of p18 and p28 was confirmed by exposing the same cell lines to azurin 60-77 (p18b), or amino acids 66-77 (p12), the C-terminal 12 amino acids of p28 (FIG. 11A, B). Here, the preferential penetration observed with p18 and p28 was completely abolished. p18b (theoretical pI 4.13) has a short α-helix and partial β-sheet, and is extremely hydrophilic which together may negate preferential entry. p12 (theoretical pI 4.33) lacks a secondary α-helical structure, but is also hydrophilic suggesting overall hydrophilicity may be a major contributor to the decrease in selectivity of cell penetration.

Example 20—Cell Penetration is not a Result of Membrane Disruption

Figure 12A:
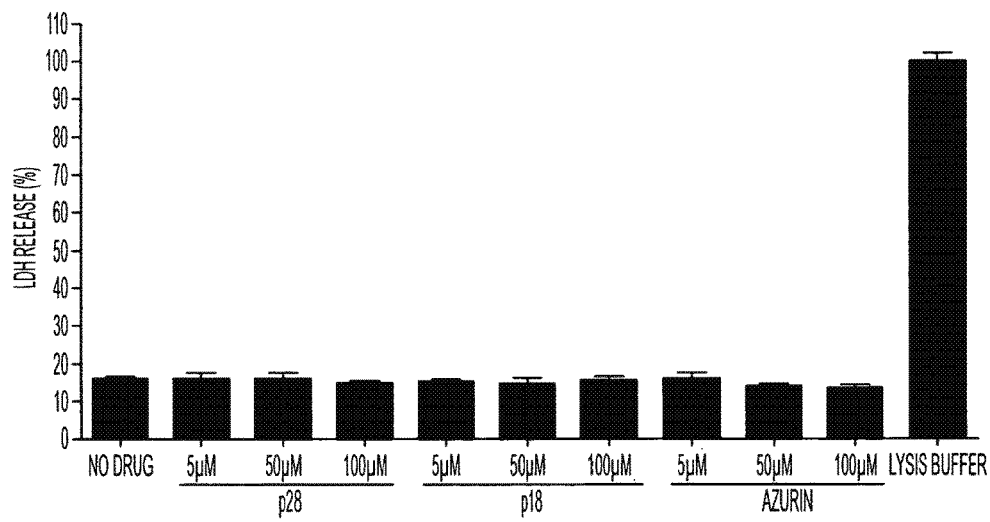
FIG. 12, (A) and (B). Graphs depicting cellular membrane toxicity of azurin and its peptides. (A) LDH leakage assay of UISOMel-2 cells exposure for 10 min to different concentrations of p28, p18 and azurin at 37° C. A standard lysis buffer (cytotox-one reagent) was included as a positive control. Changes in fluorescence following exposure were measured at $\lambda_{ex}$ 560 nm and $\lambda_{em}$ 590 nm. Lysis buffer was defined as 100% LDH release. Data represent % of positive fluorescence of control. Data are shown as mean±SEM. (B) Hemoglobin leakage from human erythrocytes incubated with p28, p18 and azurin. Human erythrocytes were incubated with peptide for 30 min at 37° C. and absorbance at 540 nm determined. Hemoglobin release following 0.1% Triton X-100 was defined as 100% hemoglobin release. Data represent mean±SEM of triplicate determinations.
Figure 12B:
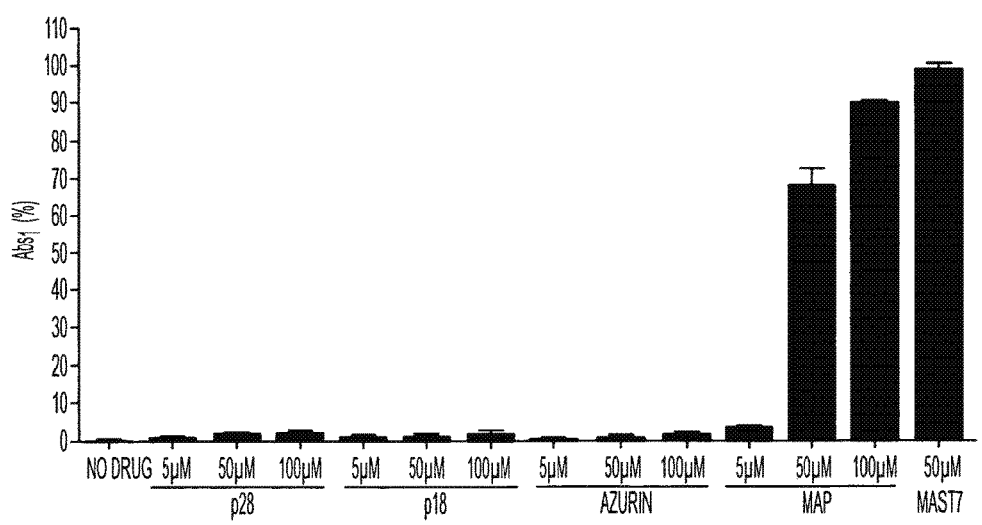

Cell penetration by azurin, p28, and p18 does not result from membrane disruption. An LDH leakage assay using UISO-Mel-2 cells in the presence of 5-100 µM p28, p18 or azurin (FIG. 12A) suggested that neither peptide nor azurin entered cells by altering plasma membrane integrity (18). The lack of membrane disruption was confirmed by determining the hemolytic activity of azurin, p28, and p18 on human erythrocytes against the receptor mimetic MAP and mast cell degranulating peptide mastoparan 7, which translocates cell membranes as an amphipathic alpha-helix, and activates heterotrimeric G proteins. Mastoparan 7 caused complete cell lysis at 25 µM, while azurin, p28, and p18 had no hemolytic effect when compared to control (no peptide) (FIG. 12B).

Example 21—p18/p28 Penetration is Energy Dependent and Saturable

Figure 13A:
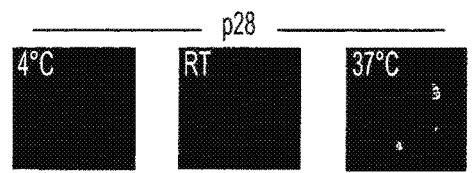
FIG. 13, (A), (B), (C) and (D). Depicts photographs showing temperature dependent and competitive internalization of p28 and p18 into UISO-Mel-2 cells. Penetration of Alexafluor 568 labeled p28 (A) or p18 (B) at 2011M was evaluated by confocal microscopy at different temperatures. (C) and (D) Confocal analysis of entry of Alexafluor 568 labeled p28 (C) or p18 (D) at 5 µM into UISO-Mel-2 cells after 30 min at 37° C. in the presence/absence of unlabeled peptide (200 fold excess).
Figure 13B:
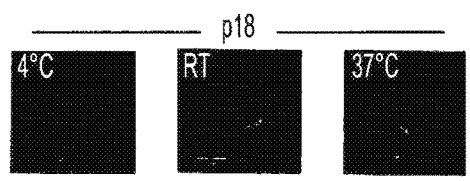
Figure 13C:
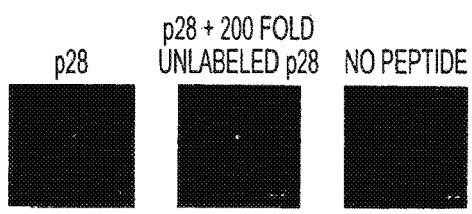
Figure 13D:
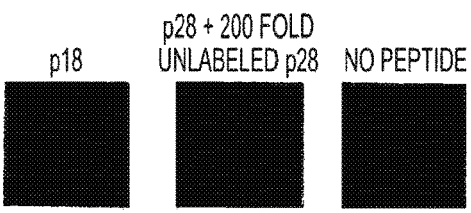

The penetration of p28 (FIG. 13A) and p18 (FIG. 13B) into UISO-Mel-2 cells is temperature dependent. Cell penetration and intracellular transport occurs relatively slowly over 3 hr at 4° C., while entry and intracellular transport through various compartments is rapid at 22 and 37° C. as p18 and p28 were present in the nucleus of UISO-Mel-2 cells within 2 hrs post exposure. The penetration of 5 µM p28 (FIG. 13C) or p18 (FIG. 13D) into UISO-Mel-2 cells after 30 min in the presence of a 200 fold excess of unlabeled peptide was severely curtailed, suggesting that entry was a saturable process and specific receptors or cell surface proteins or specific residues were, at least in part, responsible for initial entry.

Example 22—Kinetics of p28 and p18

The kinetics of p28 and p18 entry into UISO-Mel-2 cells relative to human fibroblasts was calculated after incubation, when cells were fixed and mean fluorescence intensity (MFI) determined. The $K_m$ and $V_{max}$ of each peptide were calculated by plotting peptide concentration (µM) vs velocity (MFI/sec) or by Scatchard analysis. Although the penetration of azurin fragments 50-67 (p18: Vmax 2.46, Km 101.6) and 50-77 tp28: Vmax 1.87, Km 159.1) into cancer and normal cells (Vmax 2.88, Km 102.1 and Vmax 1.89, Km 166.0, respectively) differs significantly from each other, with p18 entering ~42% faster, the rate of the entry of each peptide into normal and cancer cells is virtually identical. The increase in amount of fluorescence following exposure of cancer cells to p28 relative to p18 is likely due to the increase in the amount of p28 entering malignant cells. $^{125}$I azurin and p18 bound to UISO-Mel-2 cells with a similar affinity. In contrast, significantly more p28 ($K_d$ 2.5 µm, Bmax 3.0 pm) bound to UISO-Mel-2 cells with a higher affinity when exposed for a longer period of time (20 min vs 2 min) at a higher temperature (37° C. vs 4° C.) than either p18 ($K_d$ 18 min, Bmax 0.51 pm) or azurin ($K_d$ 10 nm and 0.48 pm). These results show that azurin, p28, and p18 all bind with relatively high affinity and capacity to a site on the cancer and normal cell surface prior to entry, but may enter via more than one mechanism.

Example 23—p18/p28 Penetration Involves Caveolae and the Golgi Complex

Figure 14A:
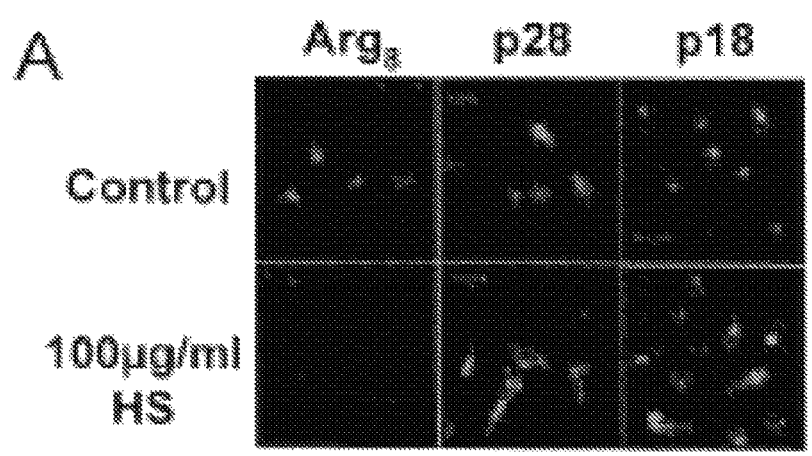
FIG. 14, (A), (B), (C) and (D). (A) Depicts photographs showing confocal analysis of 28, p18 (20 μM) and Arg$_8$ (SEQ ID NO: 95) (10 μM) entry into UISO-Mel-2 cells after 1 hr at 37° C. in the presence/absence of heparin sulfate (100 μg/ml). (B) Graphs showing flow cytometric analysis of p28 or p18 entry in the presence of inhibitors. Cell fluorescence intensity in the absence of inhibitor (control) was considered as 100%. (C) Graphs depicting FRCS analysis of p28 and p18 entry into fibroblasts in presence of inhibitors. (D) Depicts photographs showing colocalization of p18 and p28 with caveolin I (Panel 1). UISO-Mel-2 cells were incubated with Alexafluor 568 labeled p18 or p28 (20 μM) or media for 2 hrs at 37° C. Cells were fixed and processed for anti-caveolin 1 immunostaining. Confocal analysis of entry of Alexafluor 568 labeled p18 or p28 (20 μM) into UISO-Mel-2 cells after 2 hrs at 37° C. followed by antigolgin 97 antibodies (Panel 2). Colocalization of Alexafluor 568 labeled azurin, p28 and p18 (red) with mitotracker (green) (Panel 3) and Lysotracker (green) (Panel 4) dyes in UISO-Mel-2 cells. Cells were incubated at 37° C. with 20 μM azurin, p28, p18 or media only. After 90 min incubation, mitotracker/lysotracker probes were added and cells incubated for 30 min. Cells were counterstained with DAPI (blue). Colocalization of azurin, p28 or p18 appears as a yellow florescence.

As a class, cationic CPPs such as pTat and $Arg_8$ (SEQ ID NO: 95) enter cells by initially binding to anionic, sulfated proteoglycans prior to endocytosis. Incubation of p28 and p18 and $Arg_8$ (SEQ ID NO: 95) with UISO-Mel-2 cells under serum free conditions in the presence/absence of 100 µg/ml heparin sulfite (HS) significantly reduced the amount of intracellular $Arg_8$ (SEQ ID NO: 95), but did not alter the entry of either p28 or p18 (FIG. 14A). The penetration of p18 and p28 into UISO-Mel-2 cells in the presence or absence of a specific inhibitor of O-linked glycosylation, BnGalNac, and neruaminidase, which cleaves sialic acid residues, was further characterized (FIG. 14B), and no inhibition of penetration was observed. However, tunicamycin, an inhibitor of N-linked glycosylation, significantly reduced the penetration of p18 and p28 across the cell membrane.

The entry of p18 and p28 into UISO-Mel-2 cells was also analyzed using inhibitors of energy dependent transport mechanisms, i.e., ATP. Sodium azide (FIG. 14B) and ouabain ($Na^+K^+$ ATPase pump) did not significantly inhibit the penetration of either peptide suggesting non endocytosic pathways might also be involved in the penetration of these peptides. Chlorpromazine (CPZ), a specific inhibitor of clathrin mediated endocytosis, also had no effect on penetration, nor did the macropinocytosis inhibitor amiloride. (FIG. 14B). Stabilization of microtubules with taxol had no effect on penetration, but disruption of actin filaments and macropinocytosis with Cytochalasin D produced a small (~20%), reproducible inhibition of the penetration of p18 and p28. The lack of effect of amiloride suggests that the inhibitory activity of Cytochalasin D is probably through its effect on actin filaments.

Inhibition of the cell cycle with staurosporine did not block penetration, suggesting that penetration was not cell cycle specific. The lack of effect of staurosporine on p18 and p28 penetration of the cancer cell plasma membrane also suggests that a Src kinase/tyrosine kinase dependent pathway was not involved in penetration, was dynamin independent, and hence independent of caveolae budding. Neither p18 nor p28 co-localized with flotillin-1 (data not shown) a protein that resides within the plasma membrane and in a specific population of endocytic intermediates, again arguing against a role for flotillin and dynamin in internalization. In contrast, nocodazole, which disrupts caveolae transport and inhibitors of cholesterol mobilization and hence, caveolae-mediated endocytosis, inhibited penetration 50-65%.

The intracellular disposition of p18 and p28 was then analyzed using wortmannin, an inhibitor of early endosome formation, monensin, which inhibits late endosome/lysosome, and brefeldin A (BFA), a disrupter of the Golgi apparatus. Wortmannin did not block the intracellular accumulation of either p18 or p28 suggesting that, unlike cholera toxin, a caveolae to early endosome pathway is not involved in the intracellular trafficking of p18 and p28. The lack of early endosome involvement in the intracellular trafficking of p18 and p28 also suggests that clathrin mediated endocytosis is not involved in internalization of these peptides.

Figure 14C:
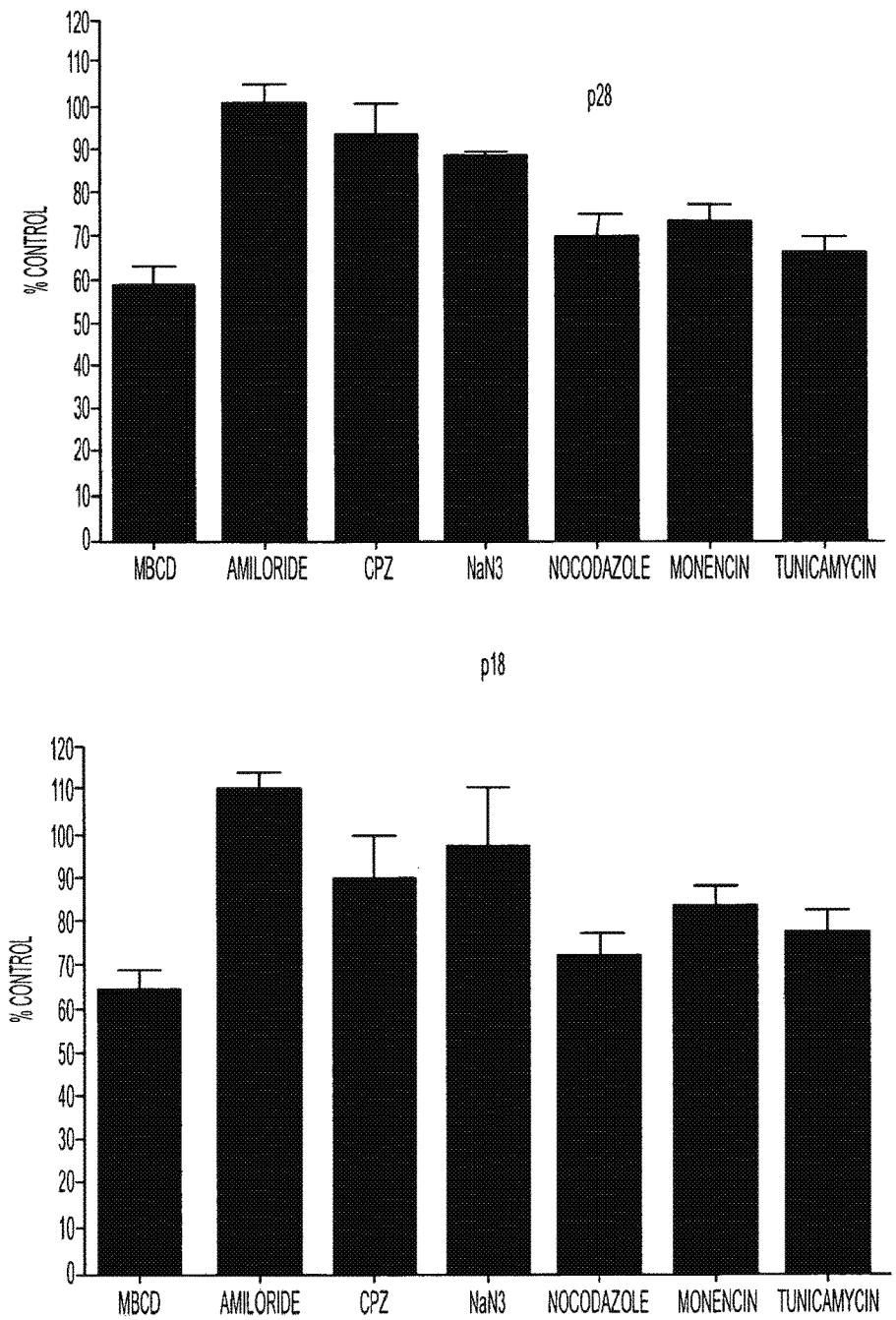
Figure 14D:
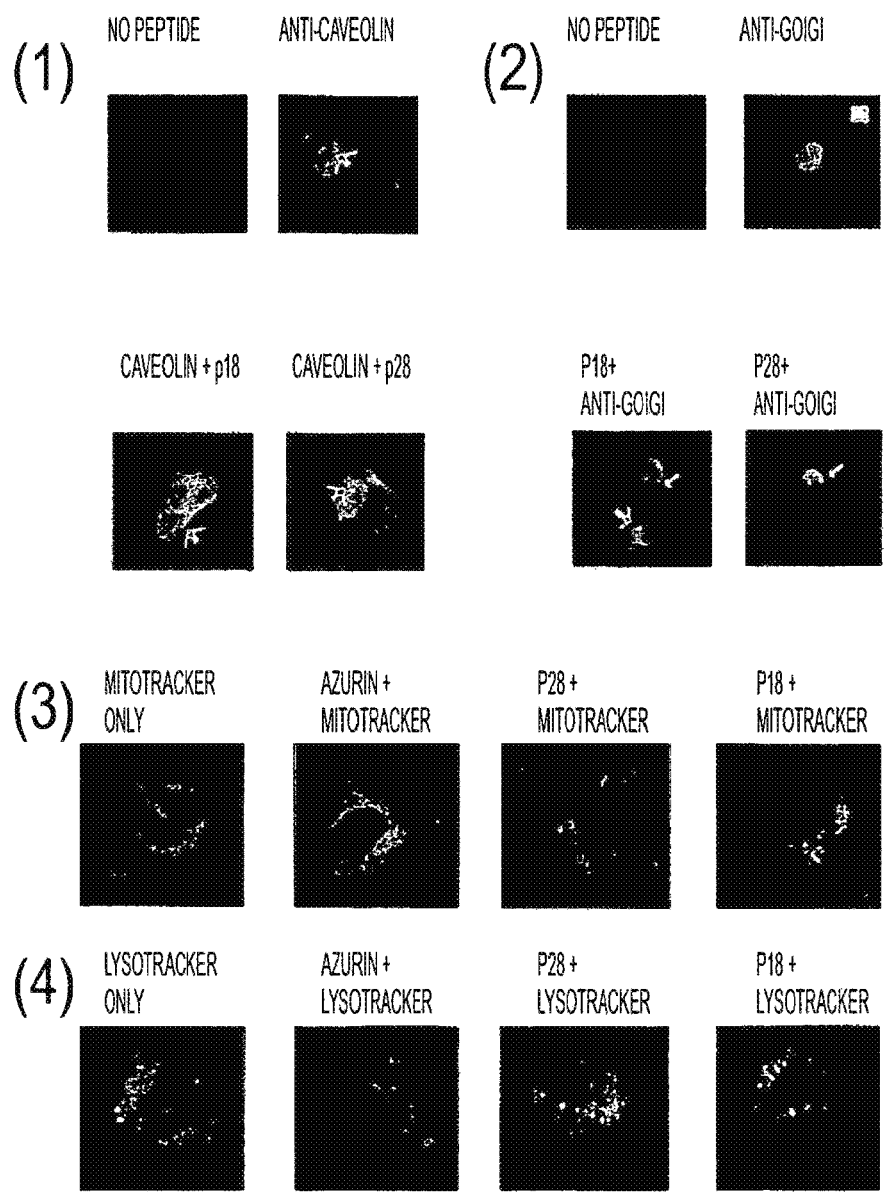

However, monensin (FIG. 14B) and BFA reduced the intracellular accumulation of both peptides with a greater inhibitory effect on p28 (~30%) than p18 (~10%) (FIG. 14B). The penetration of p28 and p18 into fibroblasts was also inhibited by MβCD, nocodazole, monensin and tunicamycin, but not by amiloride, sodium azide, and CPZ (FIG. 14C). This shows that at least one mechanism of entry into cancer and normal cells is similar, but additional preferential accumulation into cancer cells may be a function of the number of common membrane receptors or structures, i.e., caveolae (FIG. 14D, panels 1, 2). Alexafluor 568 labeled p18 and p28 co-localized with caveolin-1 and golgin 97 antibodies (FIG. 14D panels 1,2). This confirms that these organelles are involved in the intracellular trafficking of p18 and p28. Interestingly, azurin, but neither p18 nor p28 colocalized with mitochondrial specific fluorescence (FIG. 14D panel 3). In contrast, p28 and azurin, but not p18, co-localized with lysosomes (FIG. 14D panel 4).

Example 24—Functional Analysis of p28 and p18

Figure 15A:
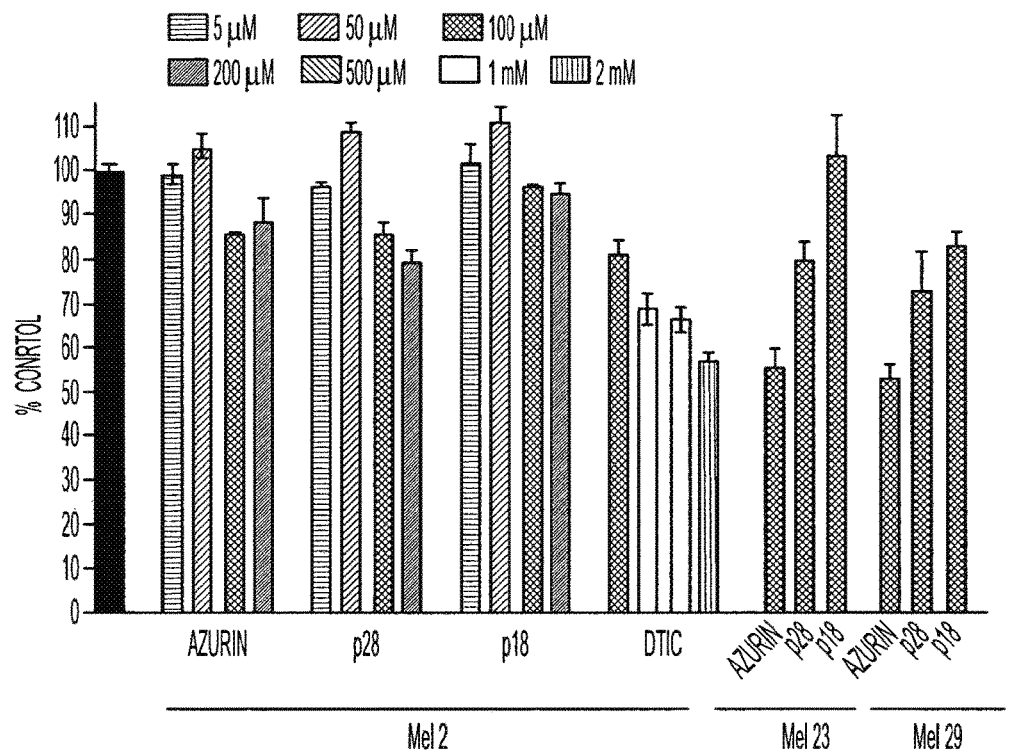
FIG. 15, (A) and (B). Graphs depicting UISO-Mel-2 cells that were incubated with increasing concentrations of azurin, p28, or p18 at 37° C. for 72 hrs. MTT (A); Direct cell count (B). Cell viability (MTT) or cell number in control wells were considered as 100%. Data represent mean±SEM.
Figure 15B:
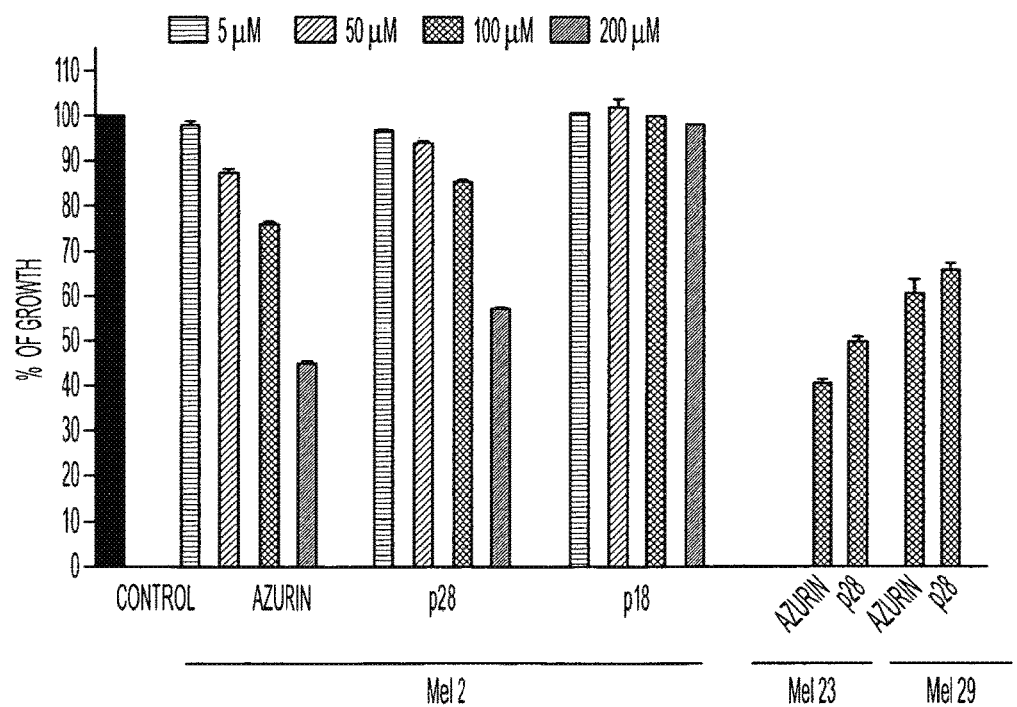
Figure 16A:
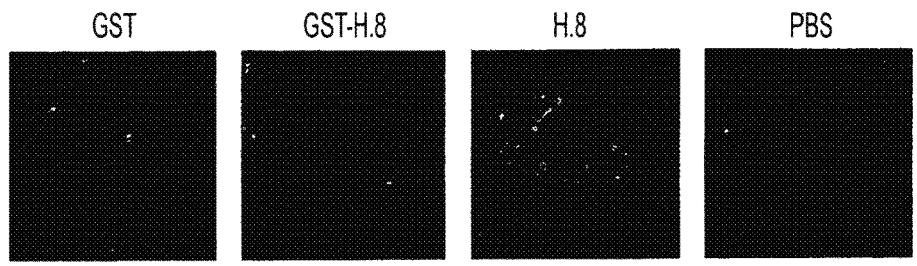
FIG. 16, (A) through (H). Depict photographs showing uptake of compounds by cells, taken using a confocal microscope after treatment of cells with proteins and/or buffer. (A) Human brain tumor LN-229 cells were pretreated with 20 μM of unlabeled proteins or PBS buffer for 2 hours, then washed three times using PBS buffer. All buffer was discarded and then 20 μM of Alex568-Paz was added for 30 minutes at 37° C. (B) The LN-229 cells were then treated with 20 μM of unlabeled proteins or PBS buffer and 20 μM of Alex568-Paz for 30 minutes at 37° C. (C) Another group of human brain tumor LN-229 cells were pretreated with 10 μM unlabeled proteins or PBS buffer for 2 hours, then washed three times using PBS buffer. All buffer was discarded and then 10 μM of Alex568-Paz was added for 30 minutes at 37° C. (D) The LN-229 cells were then treated with 10 μM unlabeled proteins or PBS buffer and 10 μM of Alex568-Paz for 30 minutes at 37° C. (E) Human brain tumor LN-229 cells were treated with 20 μM of unlabeled proteins or PBS buffer and 20 μM of Alex568-Paz for 30 minutes at 37° C. (F) Human brain tumor LN-229 cells were treated with 20 μM of Alex568-H.8 for 30 minutes at 37° C. (G) Human brain tumor LN-229 cells were treated with 20 μM Alex568-proteins for 30 minutes at 37° C. (H) Human breast adenocarcinoma MCF-7 cells were treated with 20 μM of Alex568-proteins for 30 minutes at 37° C.
Figure 16B:
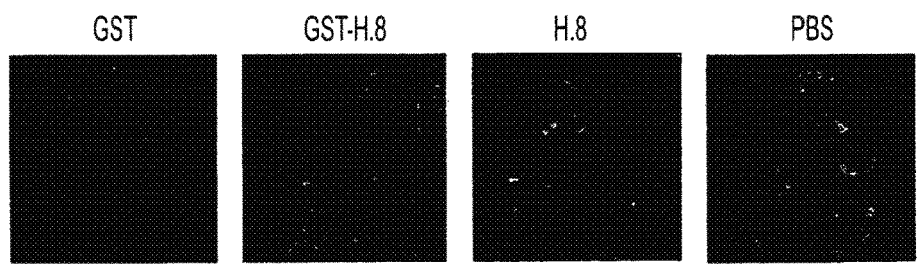
Figure 16C:
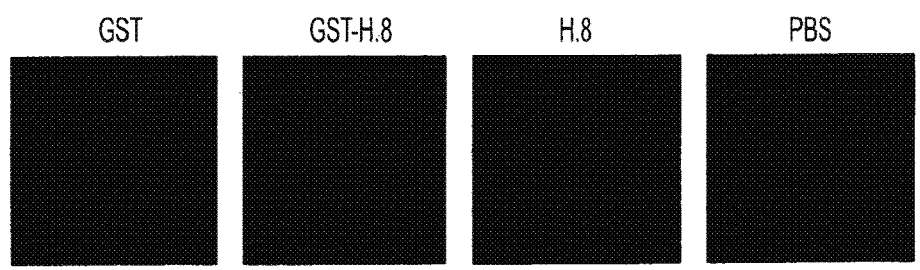
Figure 16D:
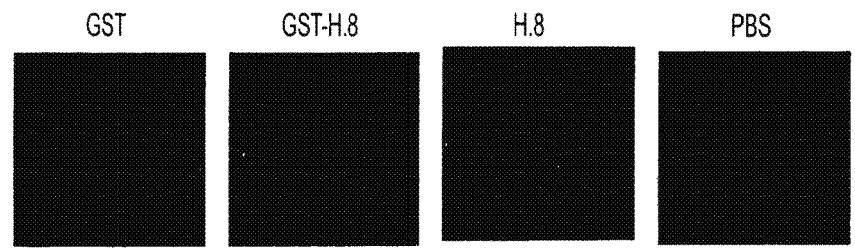
Figure 16E:
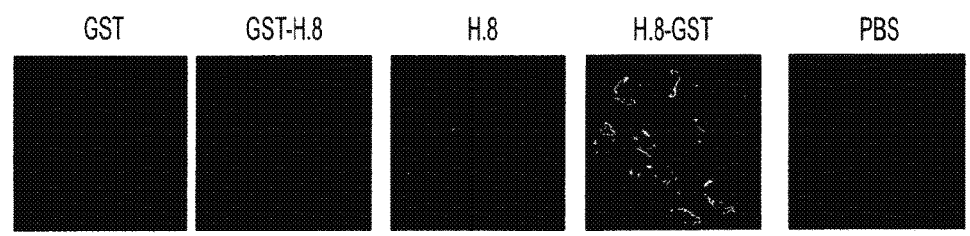
Figure 16F:
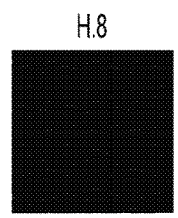
Figure 16G:
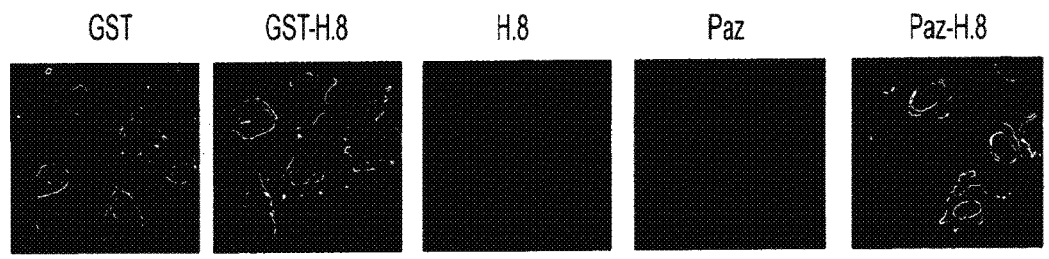
Figure 16H:
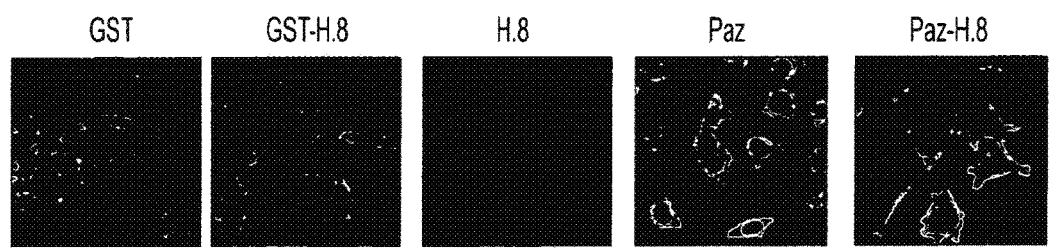

Azurin inhibits the growth of several human cancer cell lines in vitro and in vivo. FIGS. 15A and B illustrate the effect of p18 and p28 relative to azurin and dacarbazine (DTIC) on UISO-Mel-2 cells as determined by MTT and cell count. After 72 hrs exposure, azurin decreased ($p<0.5$) cell survival at 100 and 200 μM-15% (FIG. 15A). p28 had inhibited cell survival 14 and 22% ($p<0.05$) at 100 and 200 μM, respectively. In contrast, p18 had no effect, while dacarbazine (DTIC) produced a significant dose-related decrease on UISO-Mel-2 survival. Azurin and p28 (200 μM) also significantly decreased the survival of UISO-Mel-23 and 29 cells. p18 had no effect on UISO-Mel-2 cell proliferation. The apparent increase (~30-35%; UISO-Mel-2) in p28 and azurin inhibition of melanoma cell proliferation, as measured by direct cell counting, suggests that the inhibitory effect may reside primarily at the level of cell cycle with apoptosis subsequent to any delay. Although p18 penetrated cancer cells preferentially, unlike p28, it had virtually no inhibitory activity on cell proliferation. This result demonstrates that the cytostatic and cytotoxic activity of p28 lies in the C-terminal 10-12 amino acids of the sequence.

Example 25—Azurin and p28 Binding and Entry into Cells

Figures 17A, 17B, 17C:
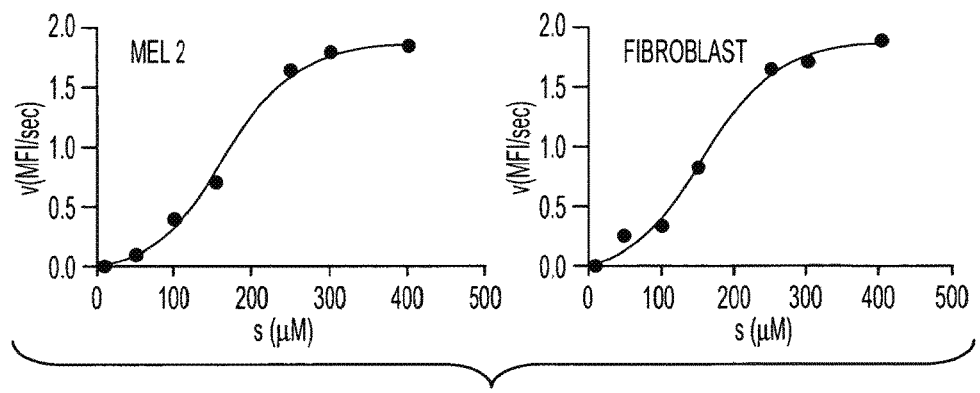
FIG. 17, (A) through (C). Graphs and charts depicting peptide binding and entry into cells. (A) UISO-Mel-2 or fibroblast cells (3×10$^5$ cells) were suspended in MEME media without phenol red. Reactions were started by adding Alexafluor 568-conjugated p28 at 10, 50, 100, 150, 250, 300 and 400 μM for 30, 60, 90 and 120 see on ice. Cells were analyzed by flow cytometry. (B) The K$_m$ and V$_{max}$ were calculated by plotting peptide concentration (μM) vs velocity (MFI/sec). (C) Peptide binding and entry was determined using whole Mel2 cells (50,000 cells/ml), were incubated for 30 min at 37° C. with increasing concentrations (0-175 nM) of radiolabeled azurin in the presence/absence of 1000 fold excess of unlabeled p28, or azurin, and radioactivity remaining in the cell pellet counted using a gamma counter. Radioactivity in cells incubated with $^{125}$I azurin alone was considered total binding; radioactivity in the presence of unlabeled azurin or p28 was considered nonspecific binding. Specific binding was determined by subtracting nonspecific binding from total binding and Scatchard plots generated.
Figure 18A:
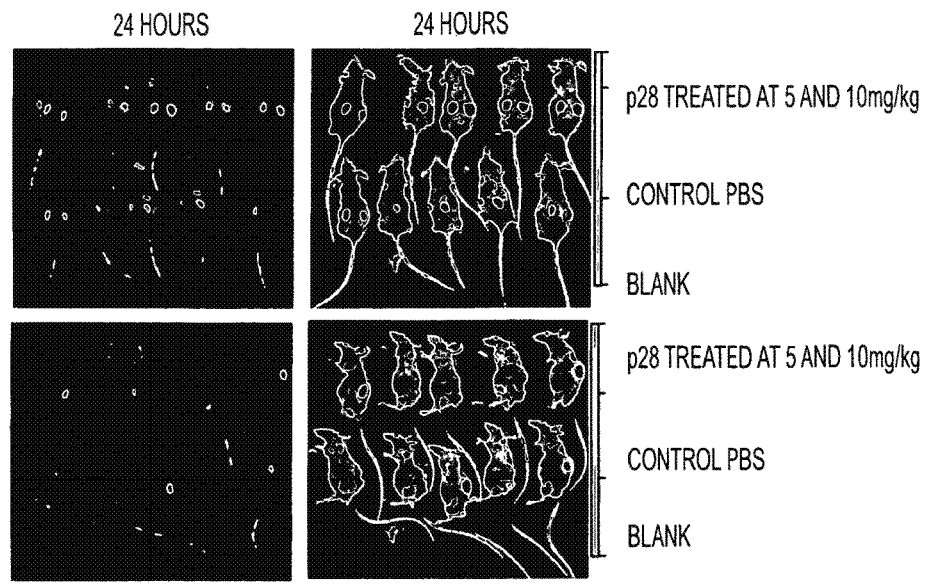
FIG. 18, (A) through (C). Depict side and back photographs of mice with melanoma MEL-23 tumors taken after injection with p28 dye complex at 60 μmolar concentration in 250 μL scans and after injection with control PBS at (A) 24 hours and (B) 48 hours. (C) depics side and back photographs of mice with melanoma MEL-23 tumors taken after injection with p28 at 200 μM concentration at 24 and 48 hours.
Figure 18B:
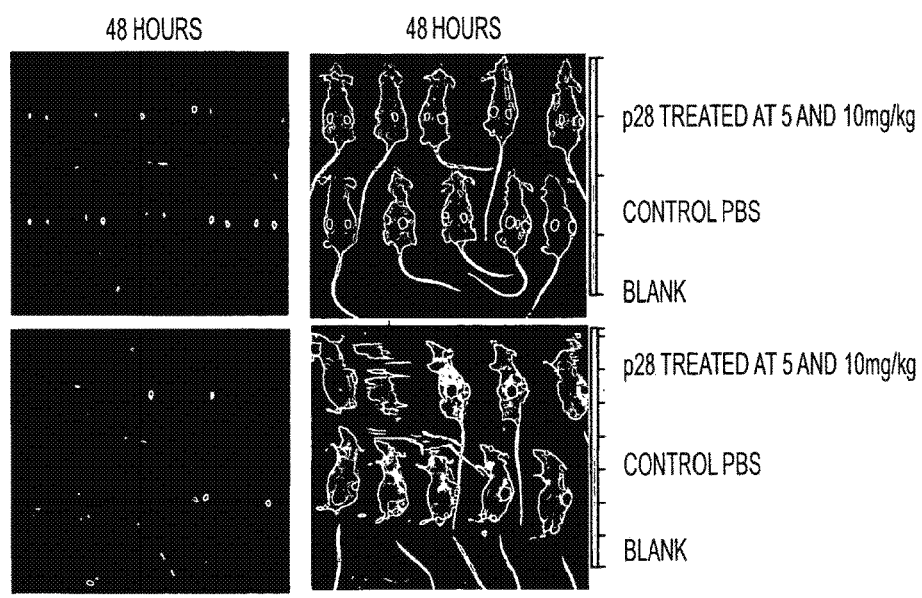
Figure 19A:
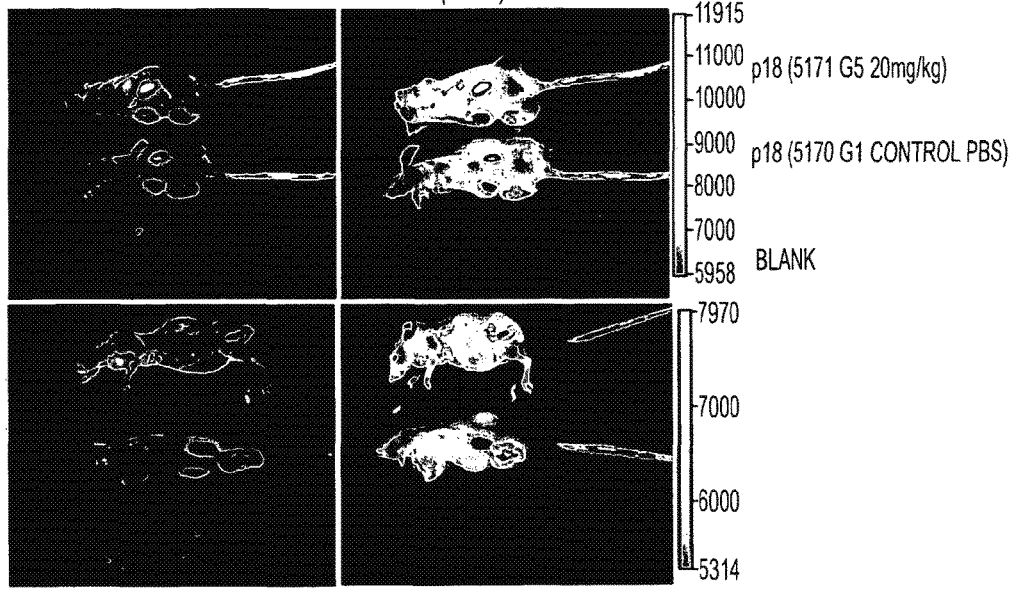
FIG. 19, (A) through (C). Depict side and back photographs of mice with melanoma MEL-23 tumors taken after injection with p18 at 60 μmolar concentration at (A) 17 hours, (B) 24 hours, and (C) 46 hours. (C) also depicts photographs of mouse organs, including the heart, lung, liver, kidney, spleen, and brain, taken 46 hours after injection of p18.
Figure 19B:
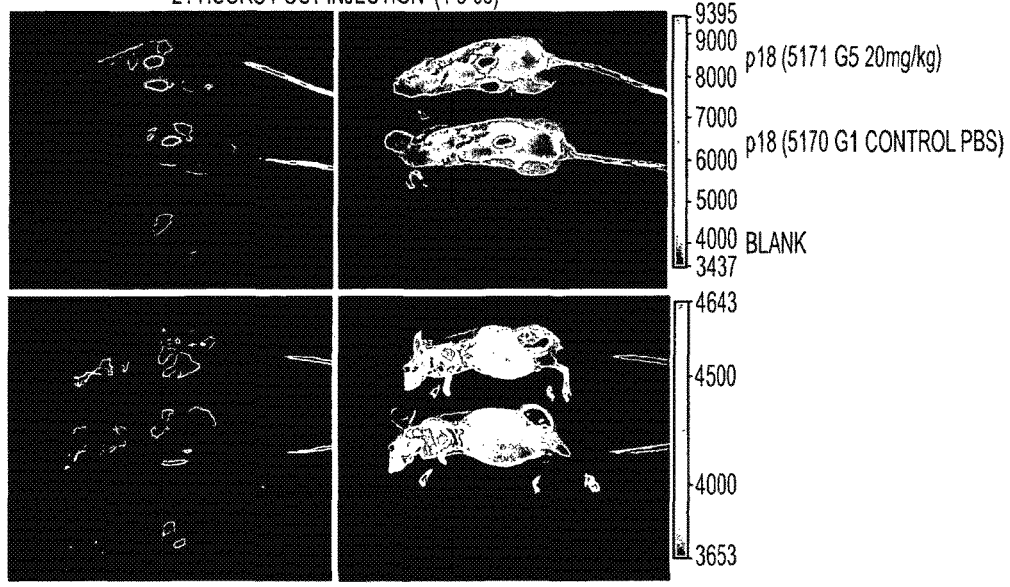
Figure 19C:
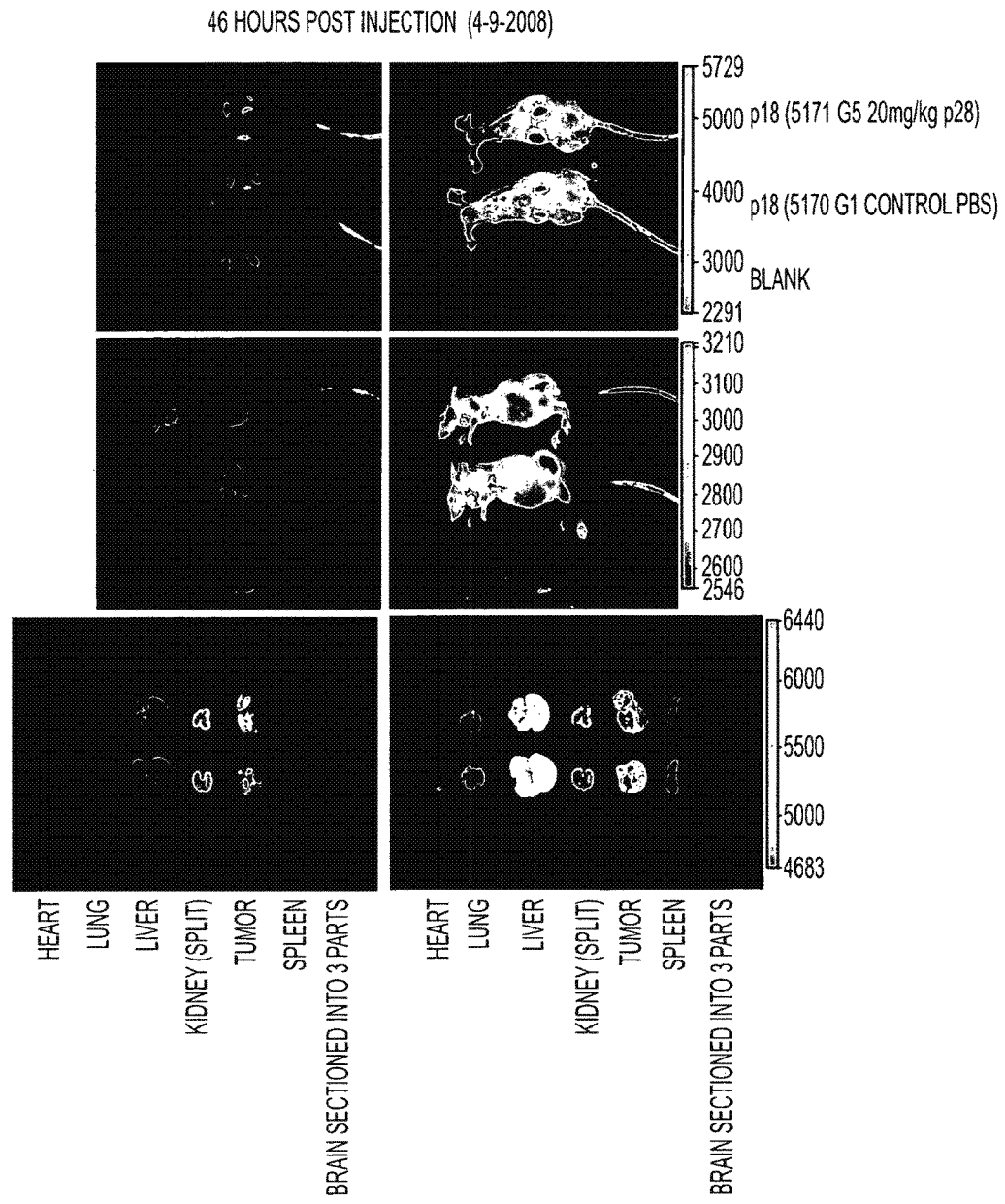
Figure 20A:
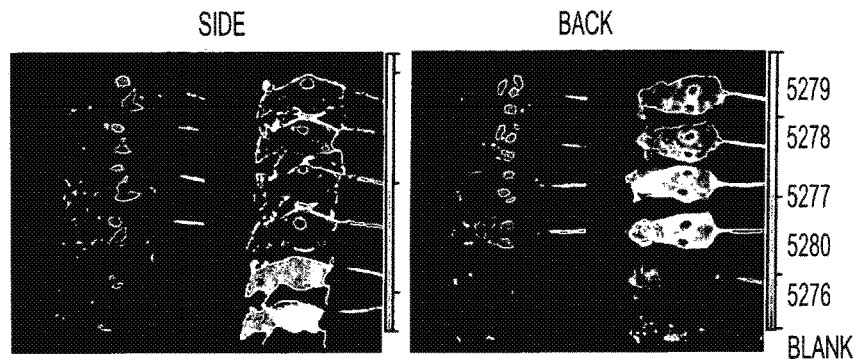
FIG. 20, (A) and (B). (A) Depicts side and back photographs of mice with tumors taken 12 hours after injection with p18, p28, and arg-8 (SEQ ID NO: 95) at 60 μmolar concentration. (B) Depicts photographs of mouse organs, including mouse brains, taken 12 hours after injection with p18, p28, and arg-8 (SEQ ID NO:95).
Figure 20B:
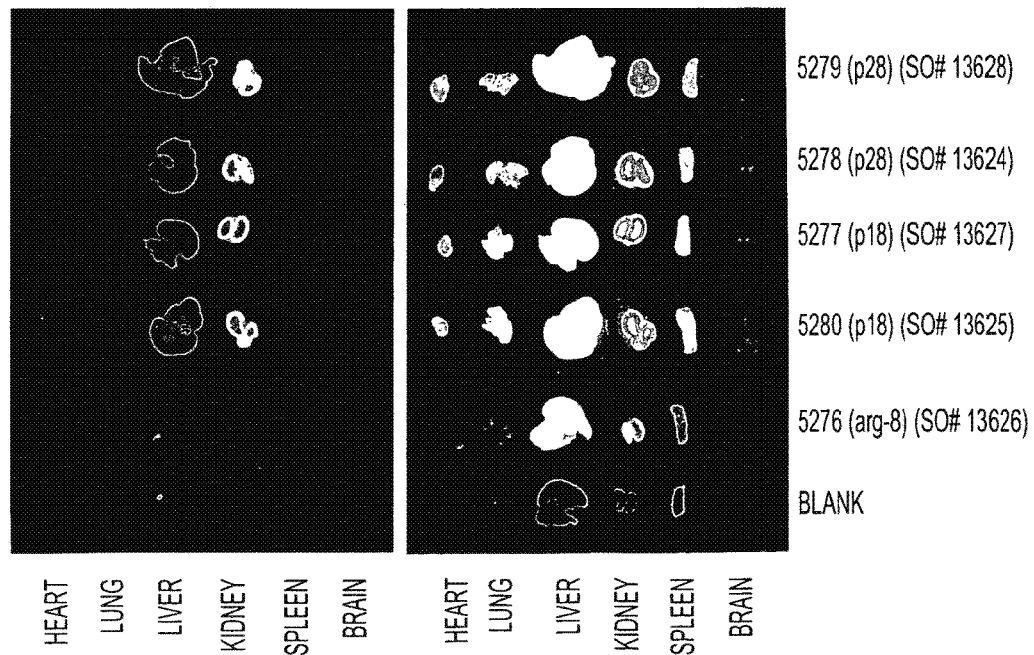
Figure 21A:
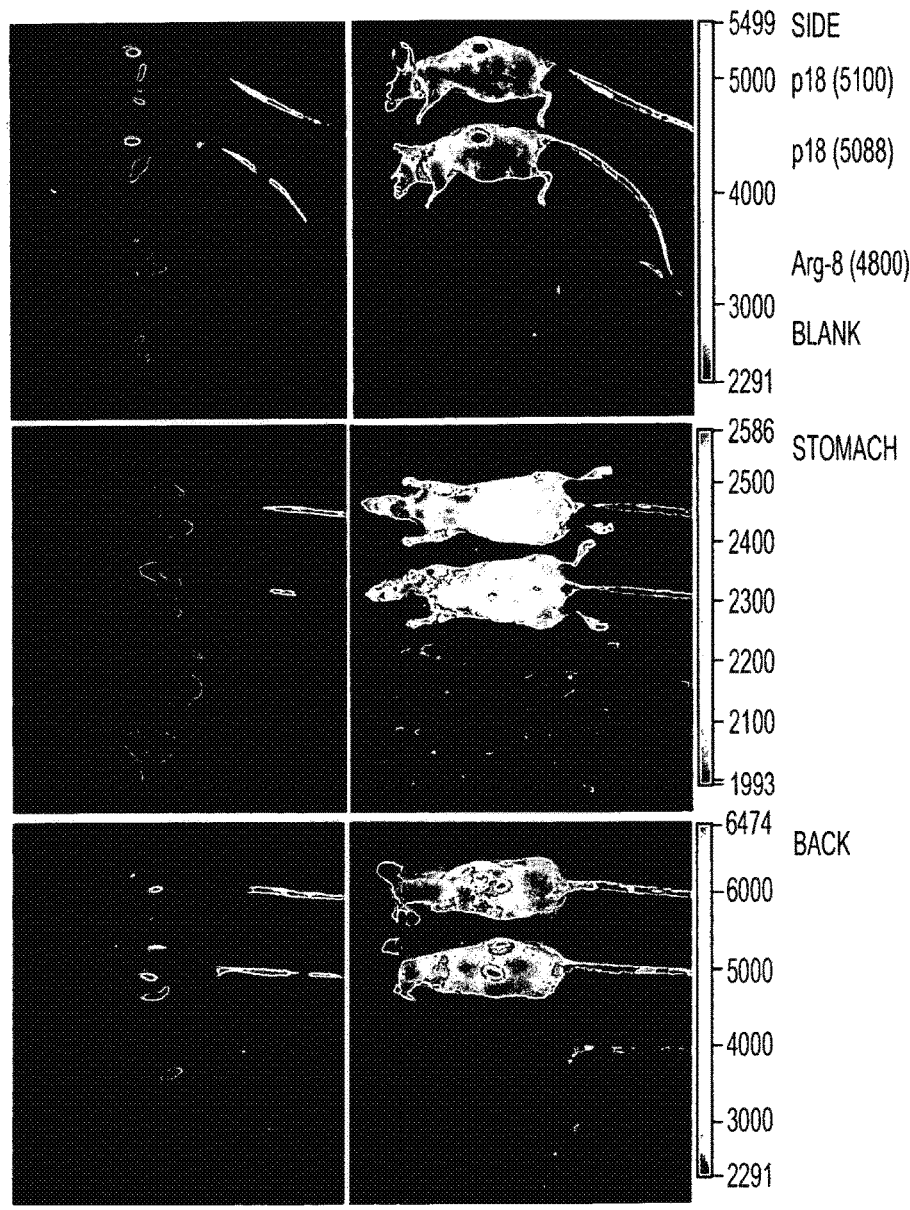
FIG. 21, (A) and (B). (A) Depicts side and back photographs of mice with melanoma MEL-6 tumors taken 40 hours after injections of 600 μM concentrations of p18 and arg-8 (SEQ ID NO: 95) into tail veins. Animals treated with p18 received 0.5 million cells, and animals treated with arg-8 (SEQ ID NO: 95) received 1 million cells. (B) Depicts photographs of mouse organs taken 40 hours after injections of 600 μM concentrations of p18 and arg-8 (SEQ ID NO: 95).
Figure 21B:
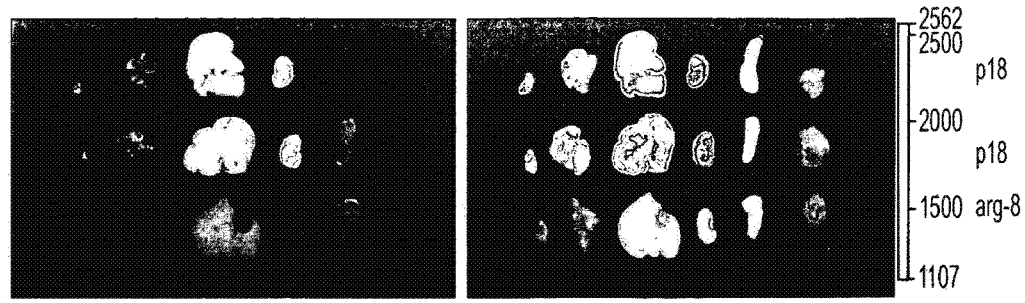
Figure 22A:
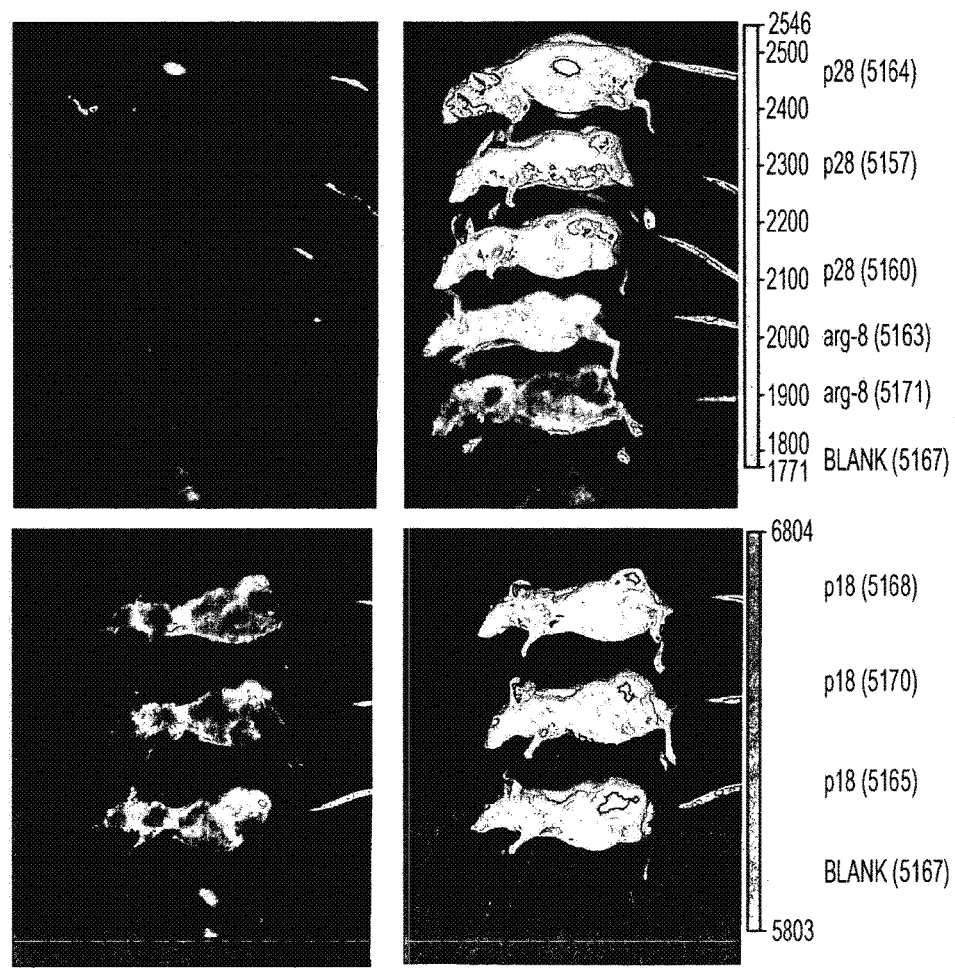
FIG. 22, (A) and (B). (A) Depicts side and back photographs of mice with melanoma MEL-23 tumors taken 16 hours after injections of 60 μM of p28, p18, and arg-8 (SEQ ID NO: 95). (B) Depicts side and back photographs of mice with melanoma MEL-23 tumors taken 24 hours after injections of 60 μM concentrations of p28, p18, and arg-8 (SEQ ID NO: 95).
Figure 22B:
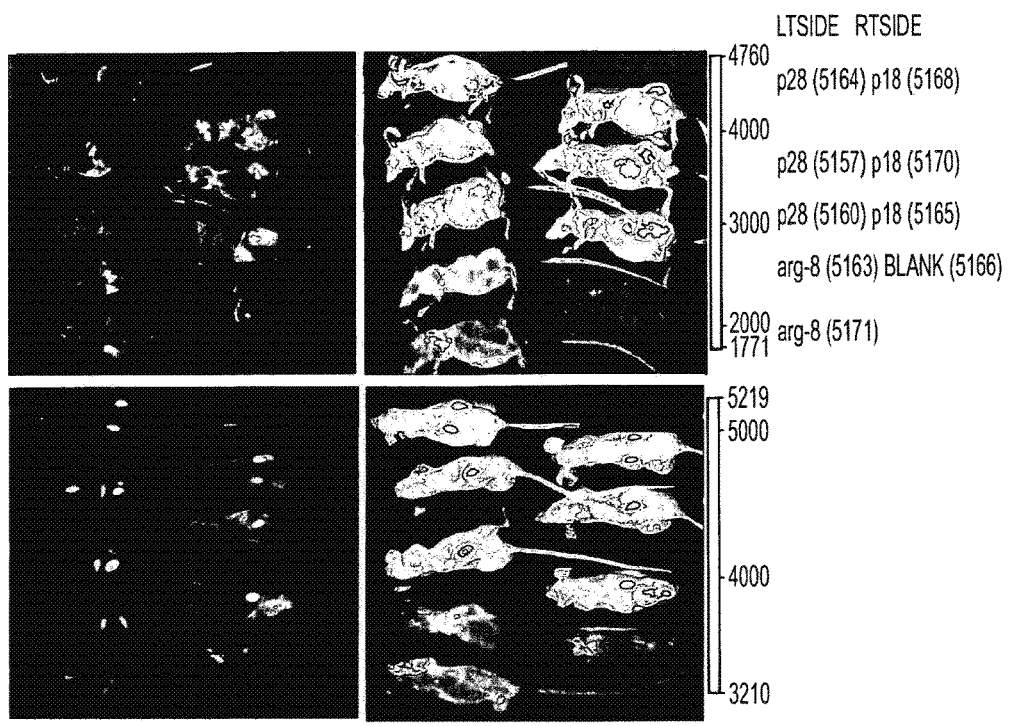
Figure 23:
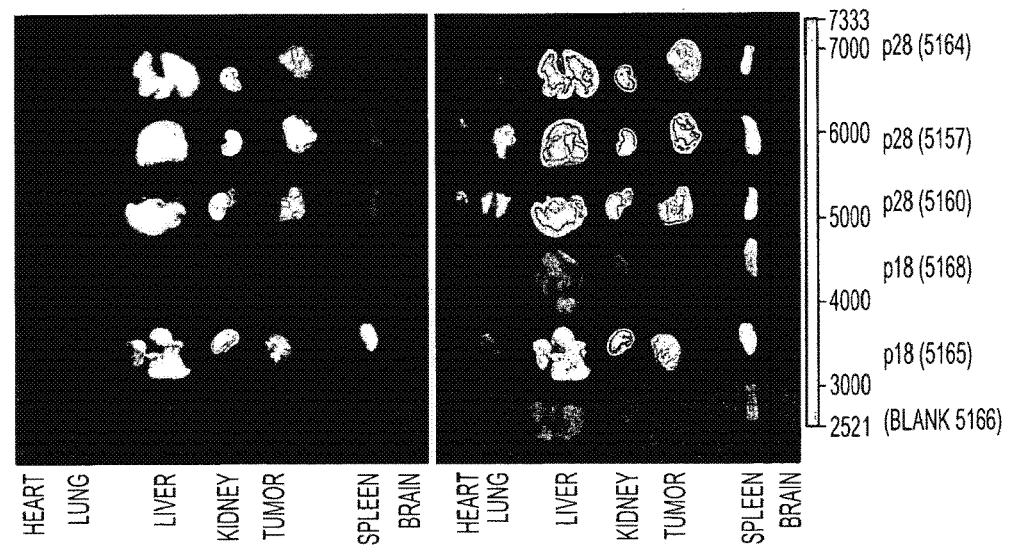
FIG. 23. Depicts photographs of mouse organs taken 48 hours after injection of 60 μM concentrations of p28 and p18 dye peptide complex into mice with melanoma MEL-23.
Figure 24:
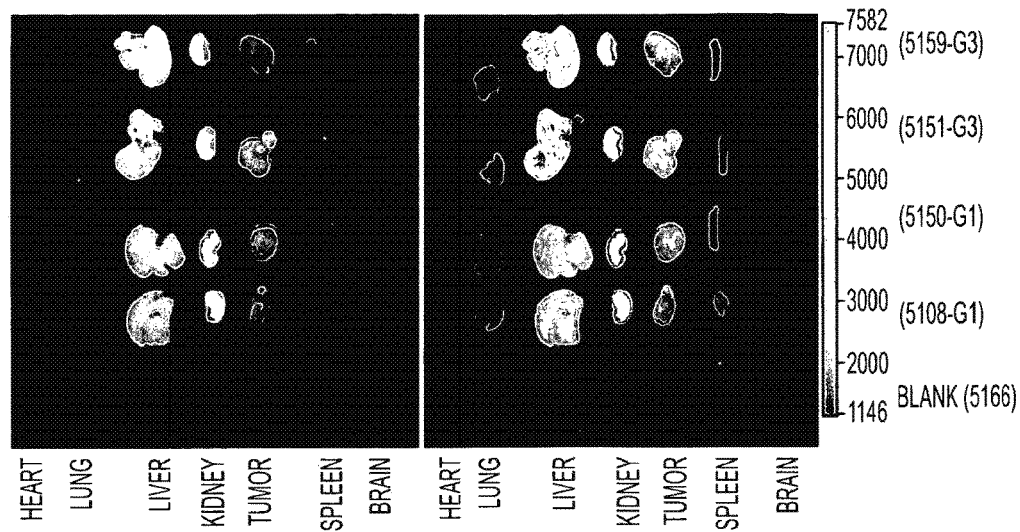
FIG. 24. Depicts photographs of mouse organs taken 24 hours after injection of 60 μM concentrations of p28 into mice with MEL-23 tumors and organs.
Figure 25:
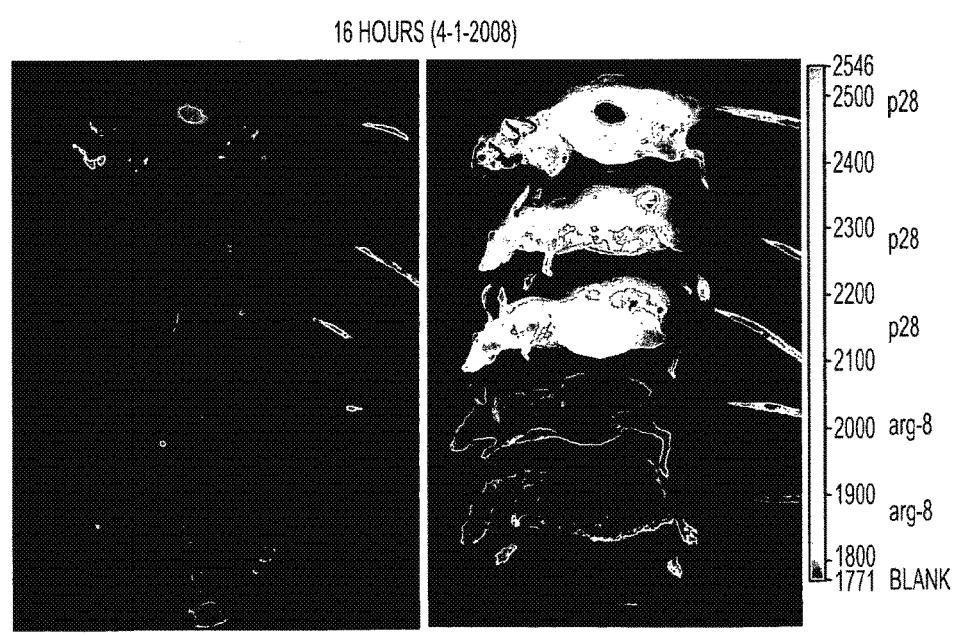
FIG. 25. Depicts side and back photographs of mice with melanoma MEL-23 tumors taken 16 hours after injections of 60 μM concentrations of p28 and arg-8 (SEQ ID NO: 95).
Figure 26:
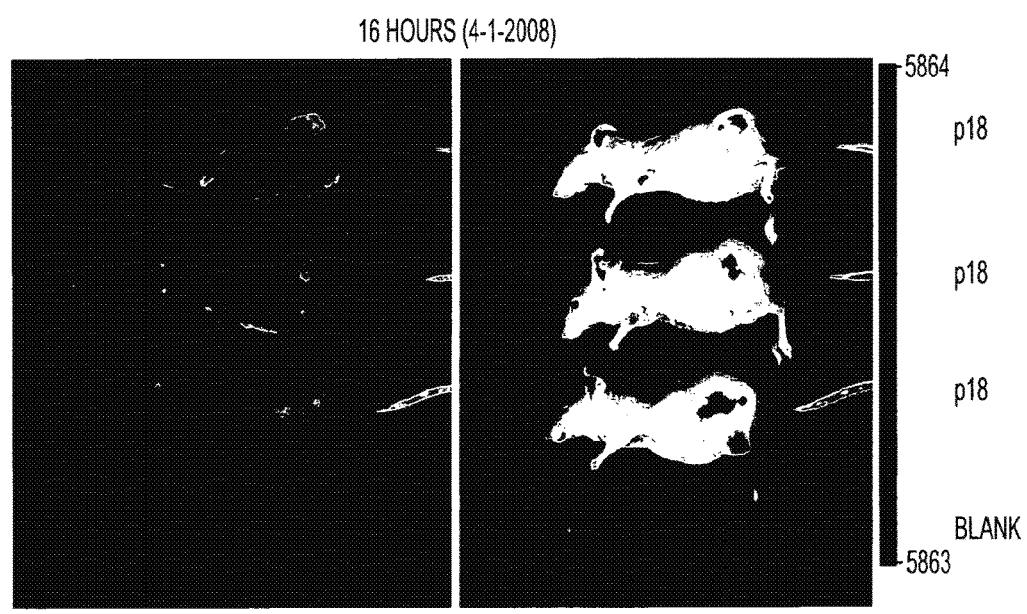
FIG. 26. Depicts side and back photographs of mice with melanoma MEL-23 tumors taken 16 hours after injections of 60 μM concentrations of p18.
Figure 27:
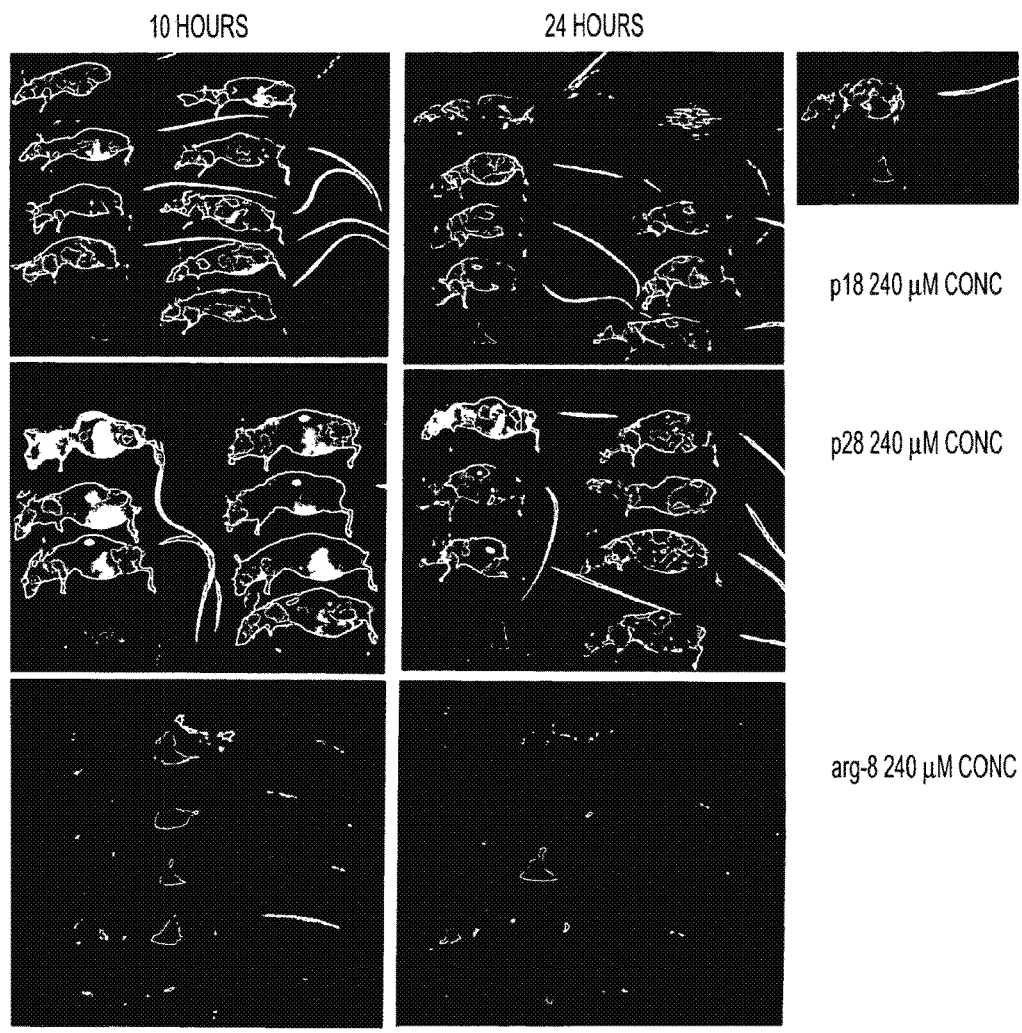
FIG. 27. Depicts side photographs of mice with tumors taken 10 and 24 hours after high dose treatment with 240 μM concentrations of p18, p28, and arg-8 (SEQ ID NO: 95).
Figure 28:
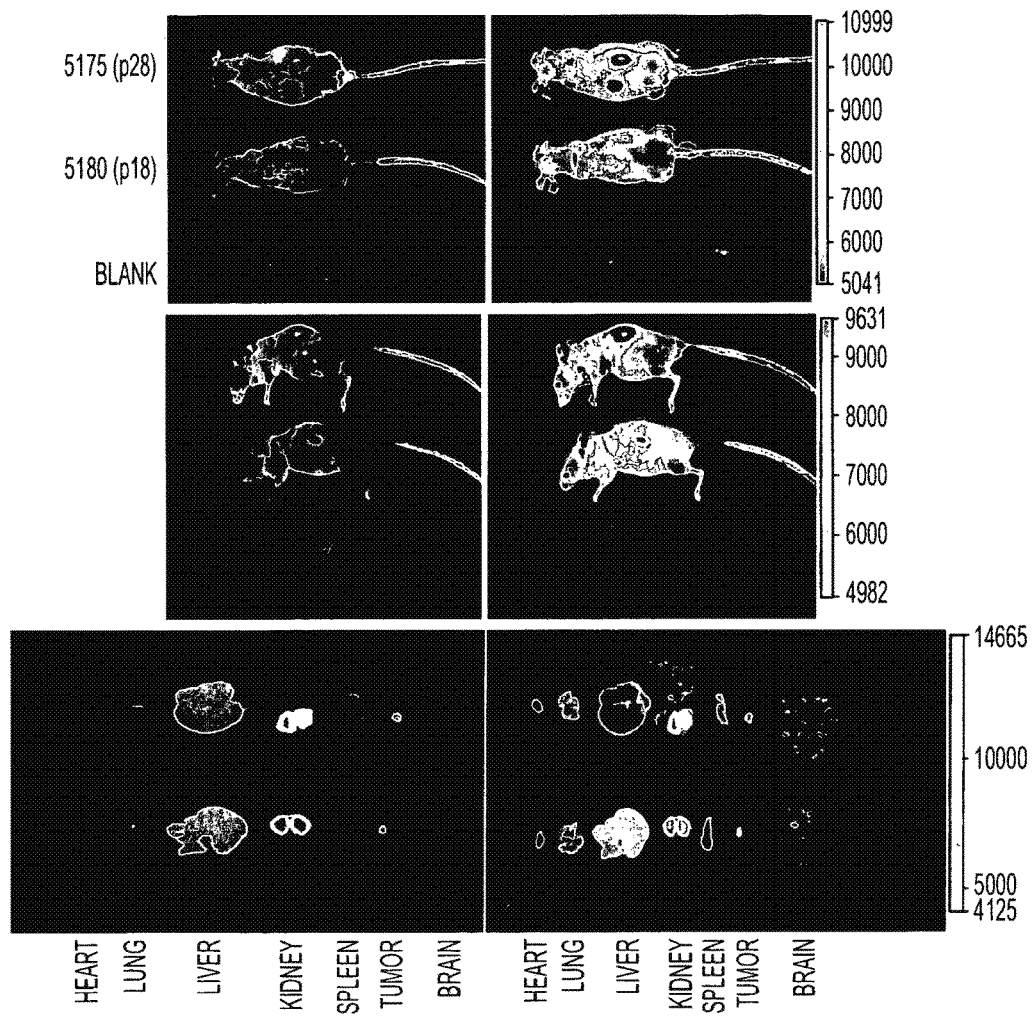
FIG. 28. Depicts side and back photographs of mice with MCF-7 tumors and organs taken 28 hours after high dose treatment with 240 μM concentrations of p18, p28, and arg-8 (SEQ ID NO: 95). Also depicts photographs of mouse organs with MCF-7 taken 28 hours after high dose treatment with 240 μM concentrations of p18, p28, and arg-8 (SEQ ID NO: 95).
Figure 29:
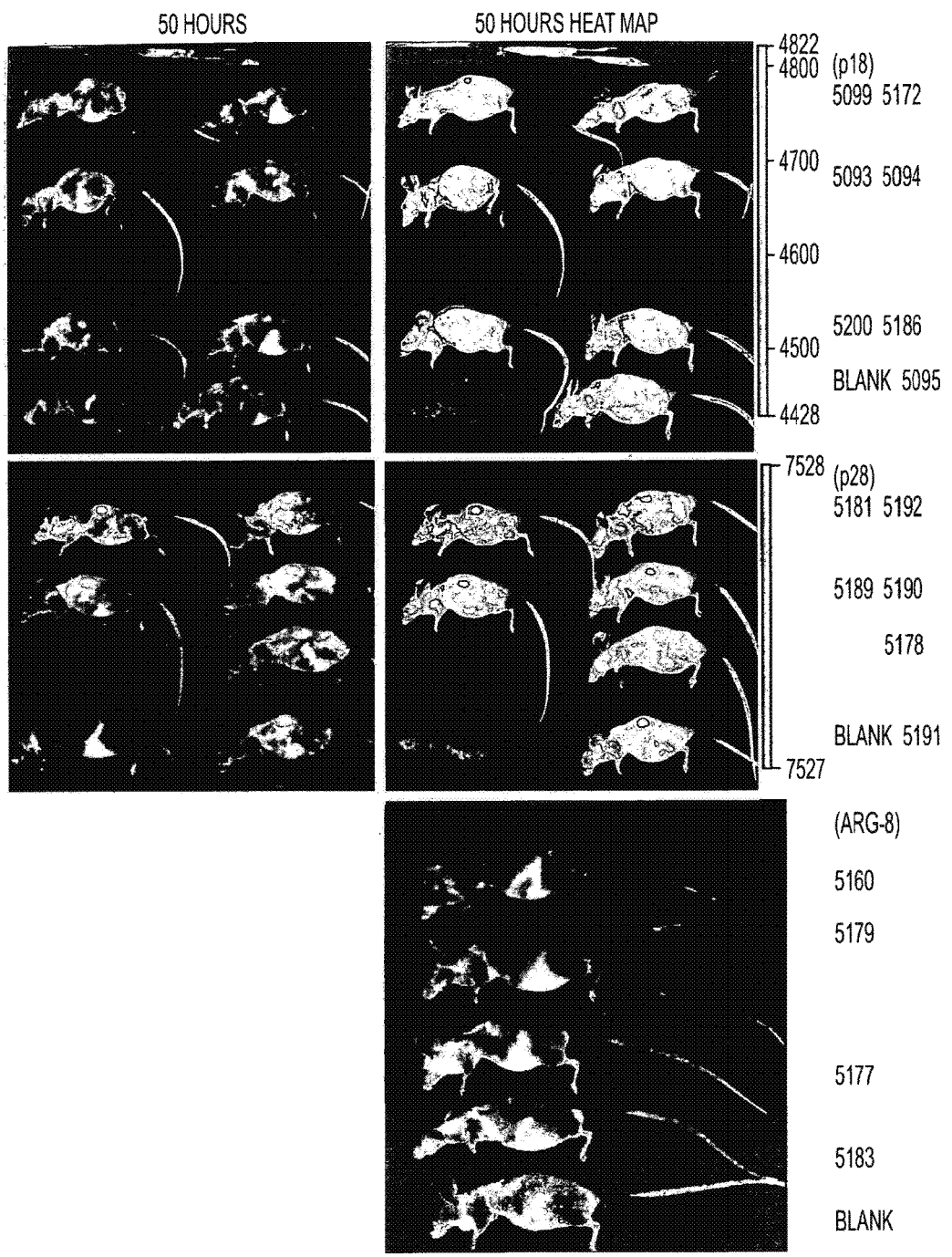
FIG. 29. Depicts side and back photographs of mice with tumors taken 50 hours after high dose treatment with 240 μM concentrations of p18, p28, and arg-8 (SEQ ID NO: 95).
Figure 30:
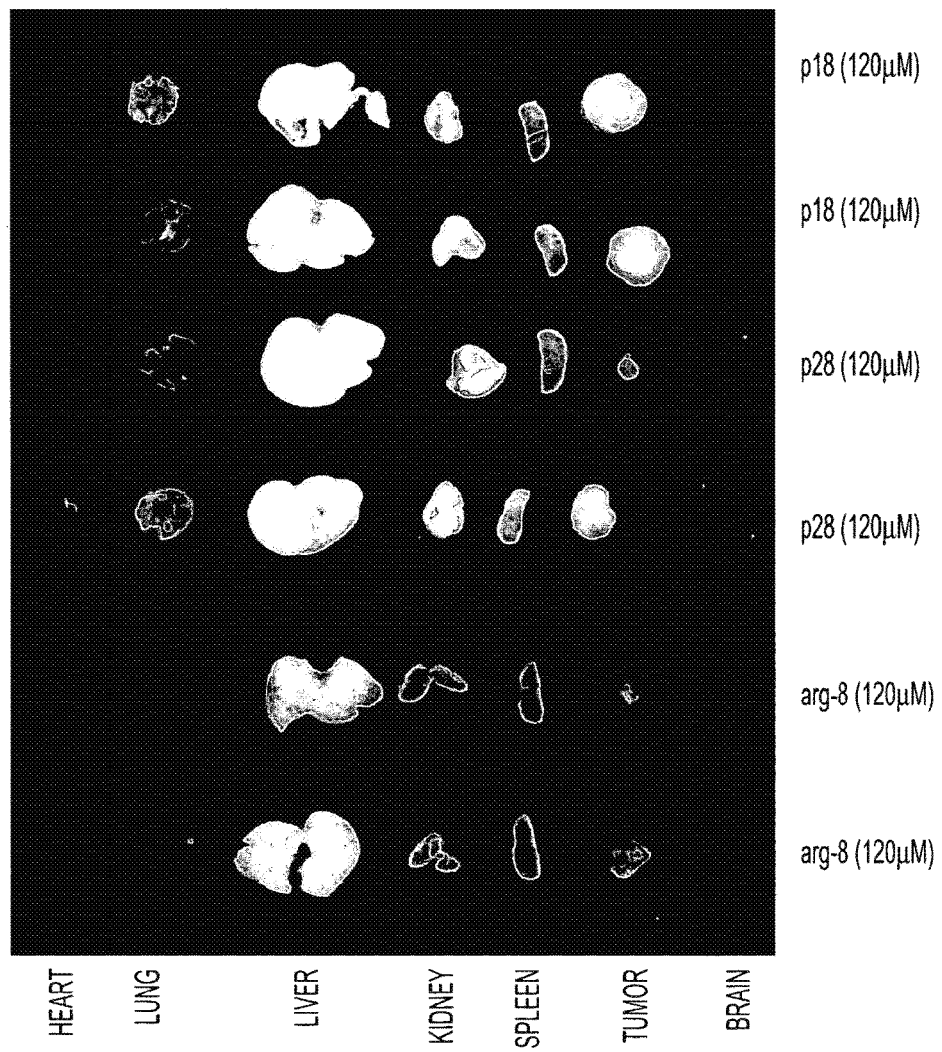
FIG. 30. Depicts photographs of mouse organs taken 24 hours after injection of 120 μM concentrations of p18, p28, and arg-8 (SEQ ID NO: 95) into the tail veins of mice with HCT-116 tumors and organs.
Figure 31A:
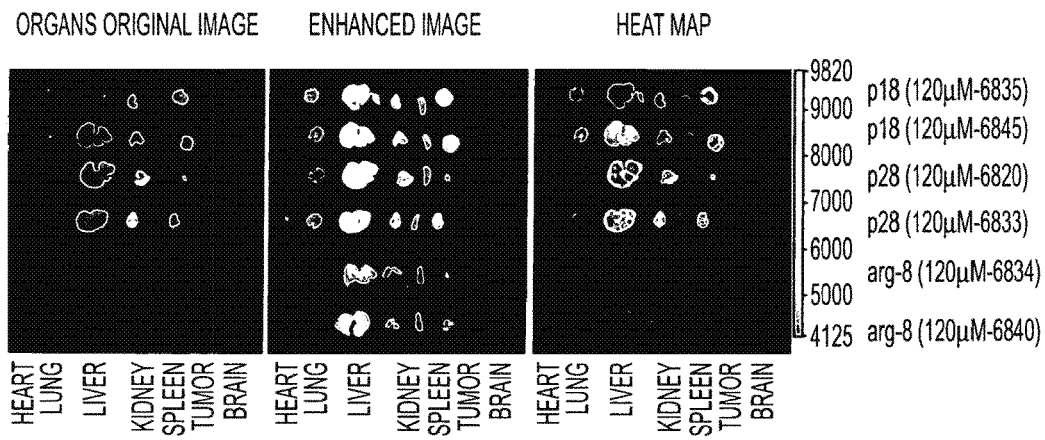
FIG. 31, (A) and (B). (A) Depicts photographs of mouse organs taken 24 hours after injection of 120 μM concentrations of p18, p28, and arg-8 (SEQ ID NO: 95) into the tail veins of mice with HCT-116 tumors and organs. (B) Depicts side photographs of mice with HCT-116 tumors taken 21 hours after injection of 120 μM concentrations of p18, p28, and arg-8 (SEQ ID NO: 95) into their tail veins.
Figure 31B:
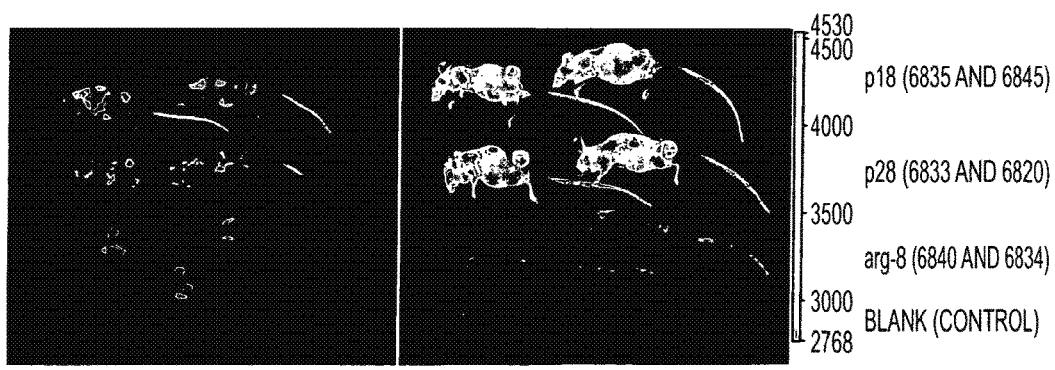
Figure 32A:
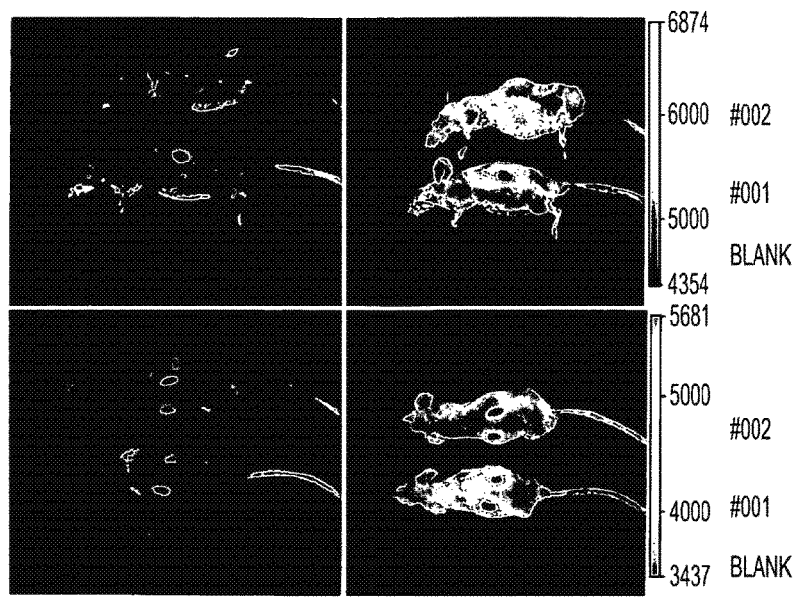
FIG. 32, (A) and (B). (A) Depicts side and back photographs of mice with HCT-116 24 hours after injection with 120 μM concentrations of p28, 47 days after injection of 1 million cells into tail veins. (B) Depicts photographs of mouse organs taken from mice with HCT-116 4 hours after injection with 120 μM concentrations of p28, 47 days after injection of 1 million cells into tail veins.
Figure 32B:
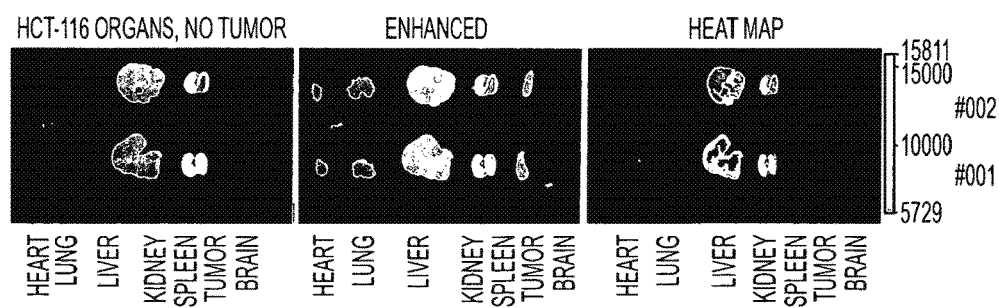
Figure 33:
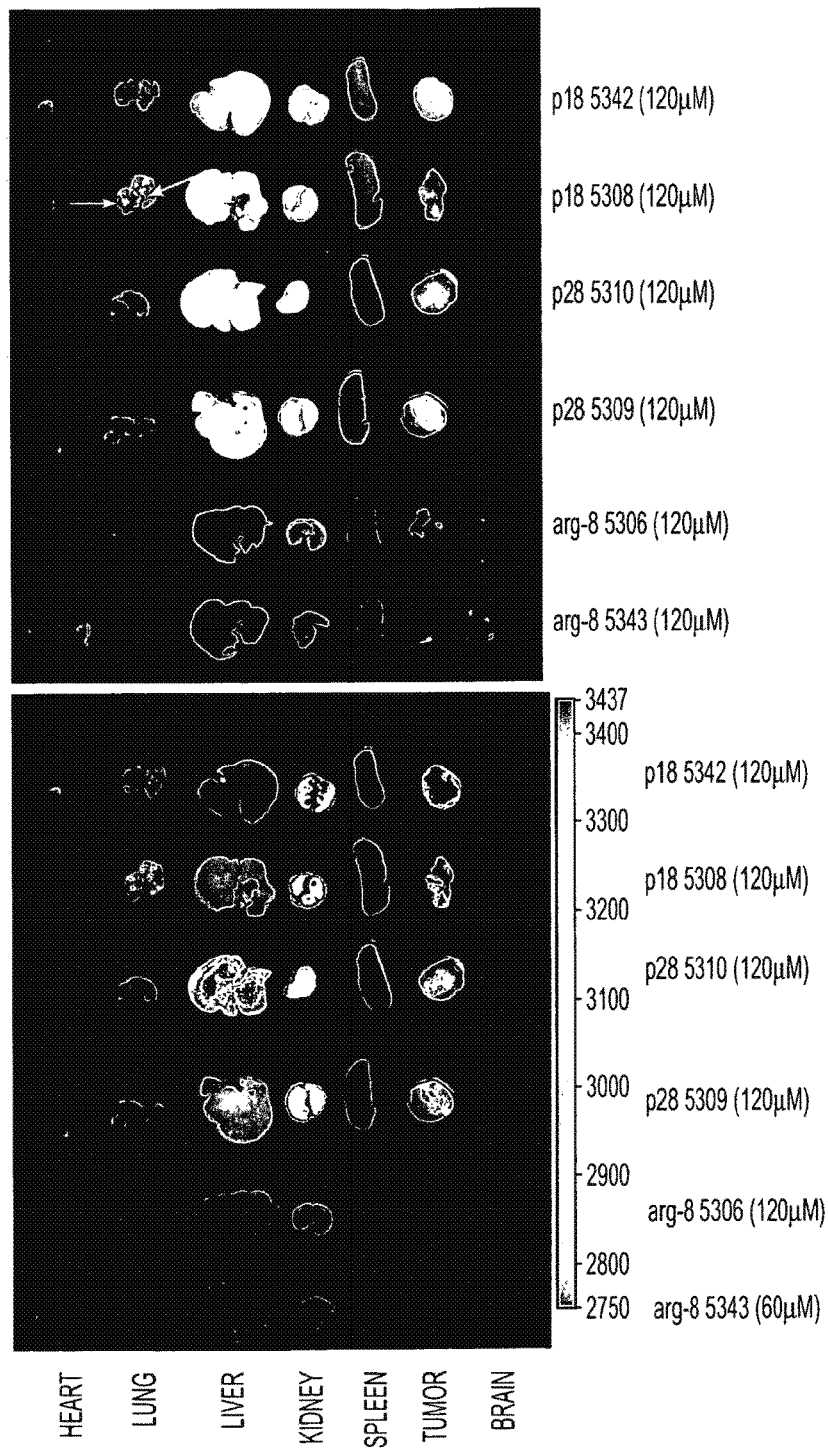
FIG. 33. Depicts photographs of organs from MEL-6 mice taken 24 hours after treatment with 120 μM concentrations of p18, p28, and arg-8 (SEQ ID NO: 95).
Figure 34A:
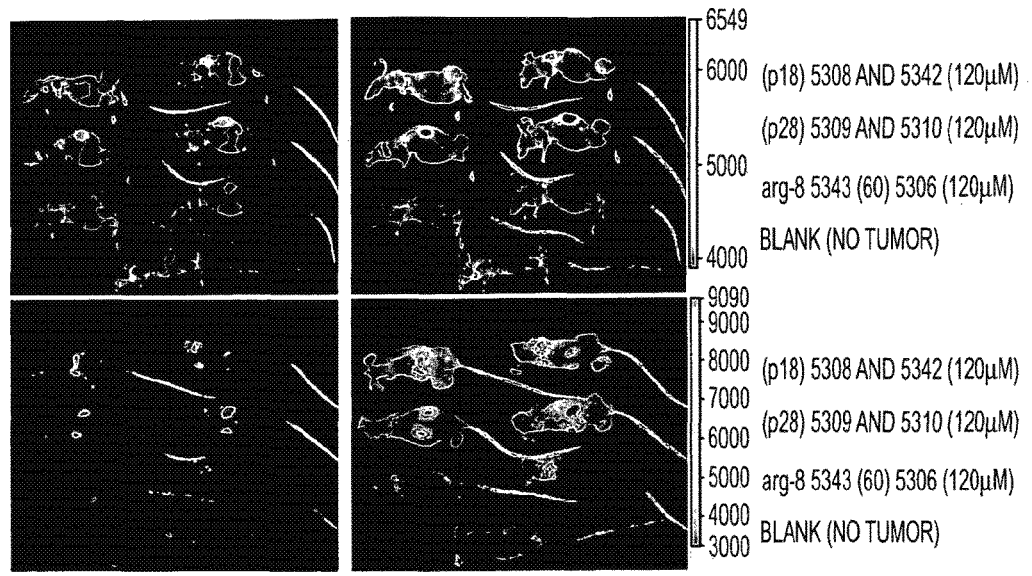
FIG. 34, (A) and (B). (A) Depicts side and back photographs of MEL-6 mice taken 22 hours after injection of 120 μM concentrations of p18, p28, and arg-8 (SEQ ID NO: 95), and 60 60 μM concentration of arg-8 (SEQ ID NO: 95). (B) Depicts photographs of MEL-6 mouse organs after treatment with 120 μM concentrations of p18, p28, and arg-8 (SEQ ID NO: 95), and 60 μM concentration of arg-8 (SEQ ID NO: 95).
Figure 34B:
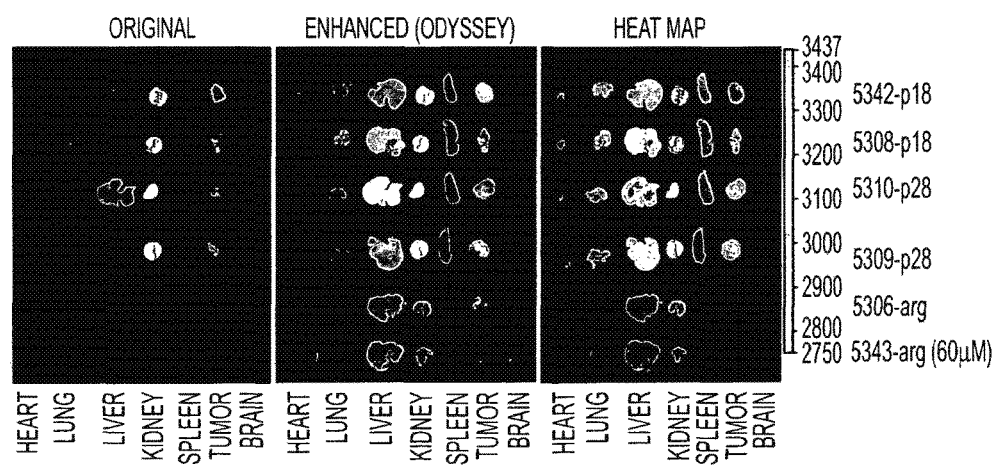
Figure 35B:
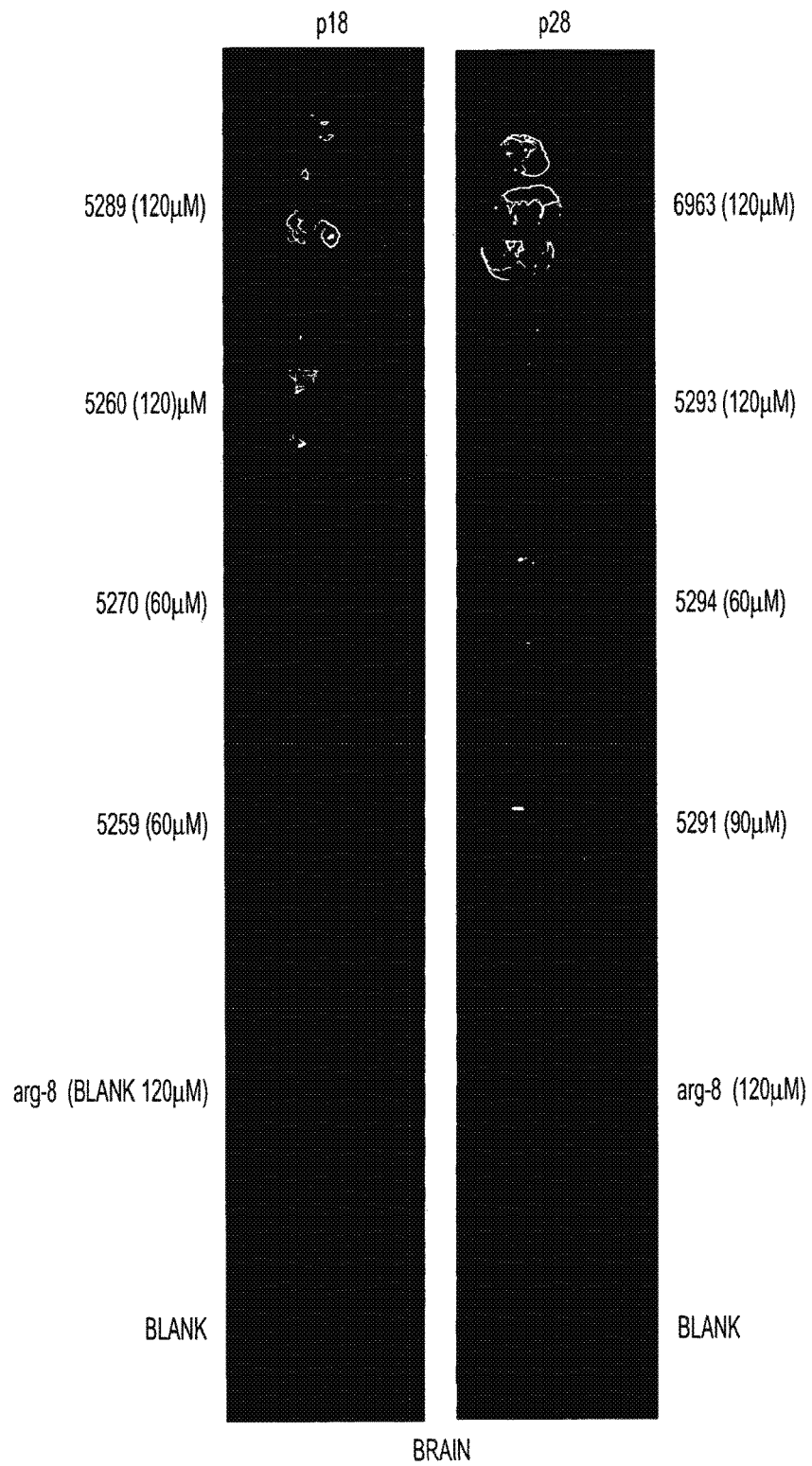
FIG. 35, (A) and (B). (A) Depicts photographs of organs from HT-1080 mice taken 22 hours after treatment with 60 and 120 μM concentrations of p18, p28, and arg-8 (SEQ ID NO: 95). (B) Depicts side-by-side photographs of brains from HT-1080 mice taken 22 hours after treatment with 60 and 120 μM concentrations of p18, p28, and arg-8 (SEQ ID NO: 95), demonstrating the differences between uptake of p18 and p28 into the brain.
Figure 36:
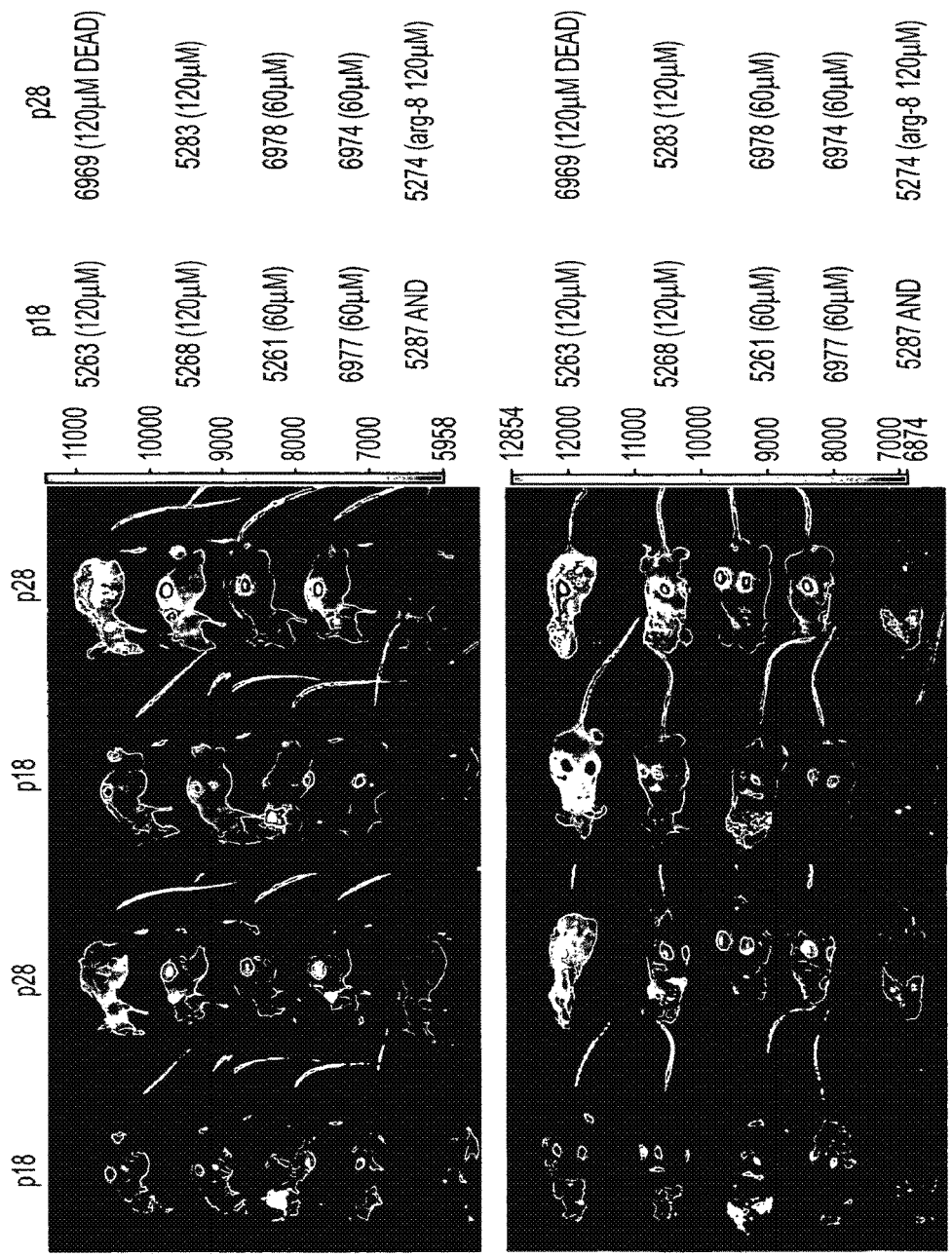
FIG. 36. Depicts side and back photographs of HT-1080 mice during Doxorubicin vs. p28 study taken 16 hours after treatment with 60 and 120 μM concentrations of p18, p28, and arg-8 (SEQ ID NO: 95).
Figure 37A:
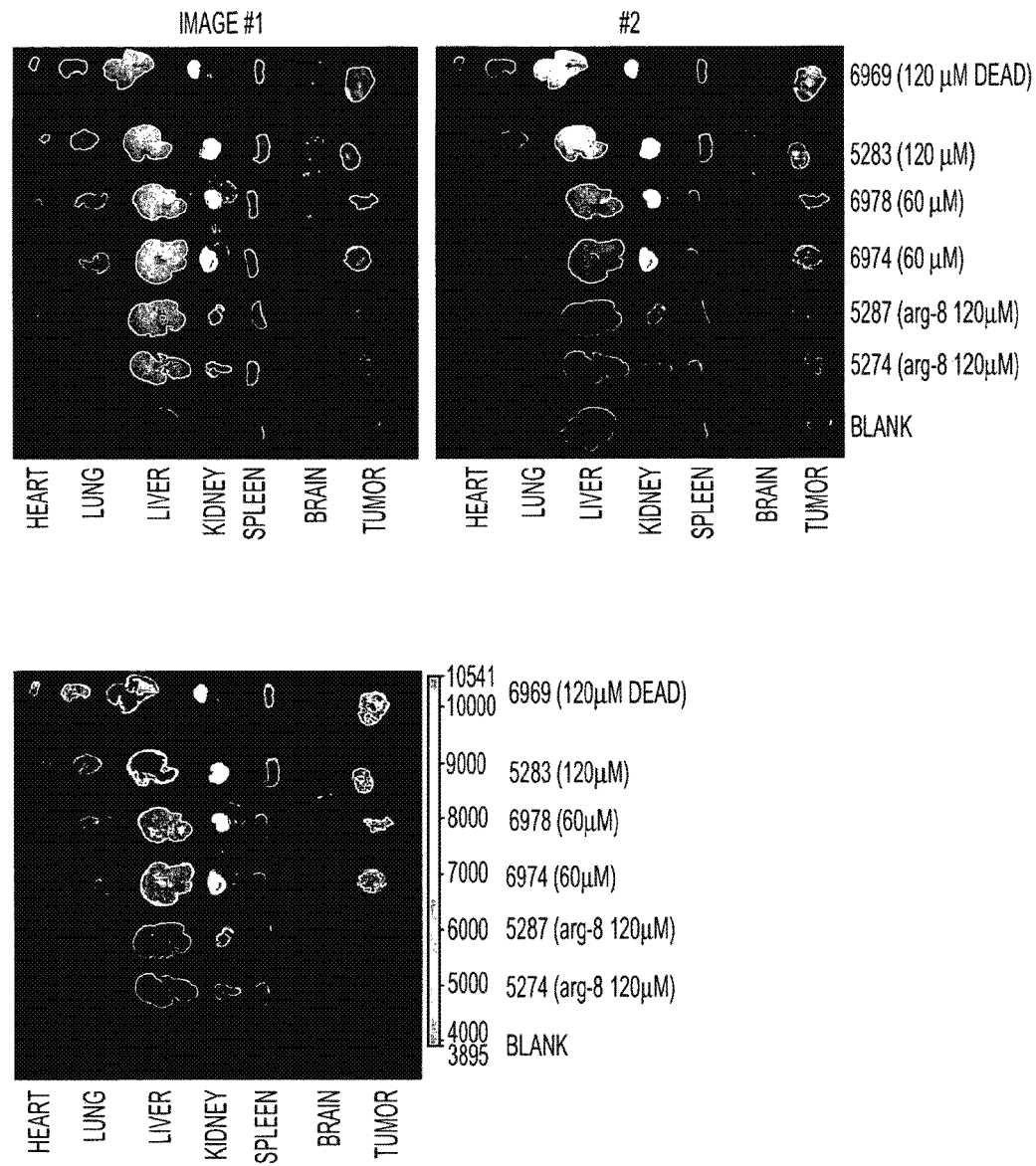
FIG. 37, (A) and (B). (A) Depicts photographs of organs from HT-1080 mice taken 22 hours after treatment with 60 and 120 μM concentrations of p28 and arg-8 (SEQ ID NO: 95). (B) Depicts side-by-side photographs of brains from HT-1080 mice taken 22 hours after treatment with 60 and 120 μM concentrations of p28 and arg-8 (SEQ ID NO: 95).
Figure 37B:
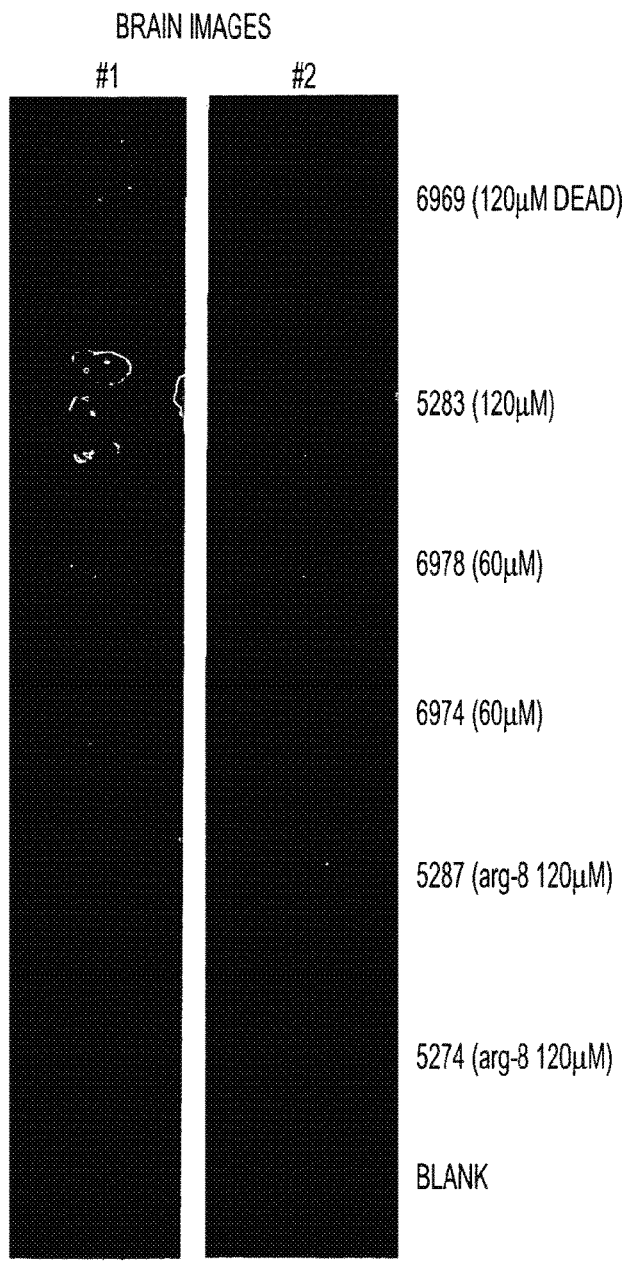
Figure 38A:
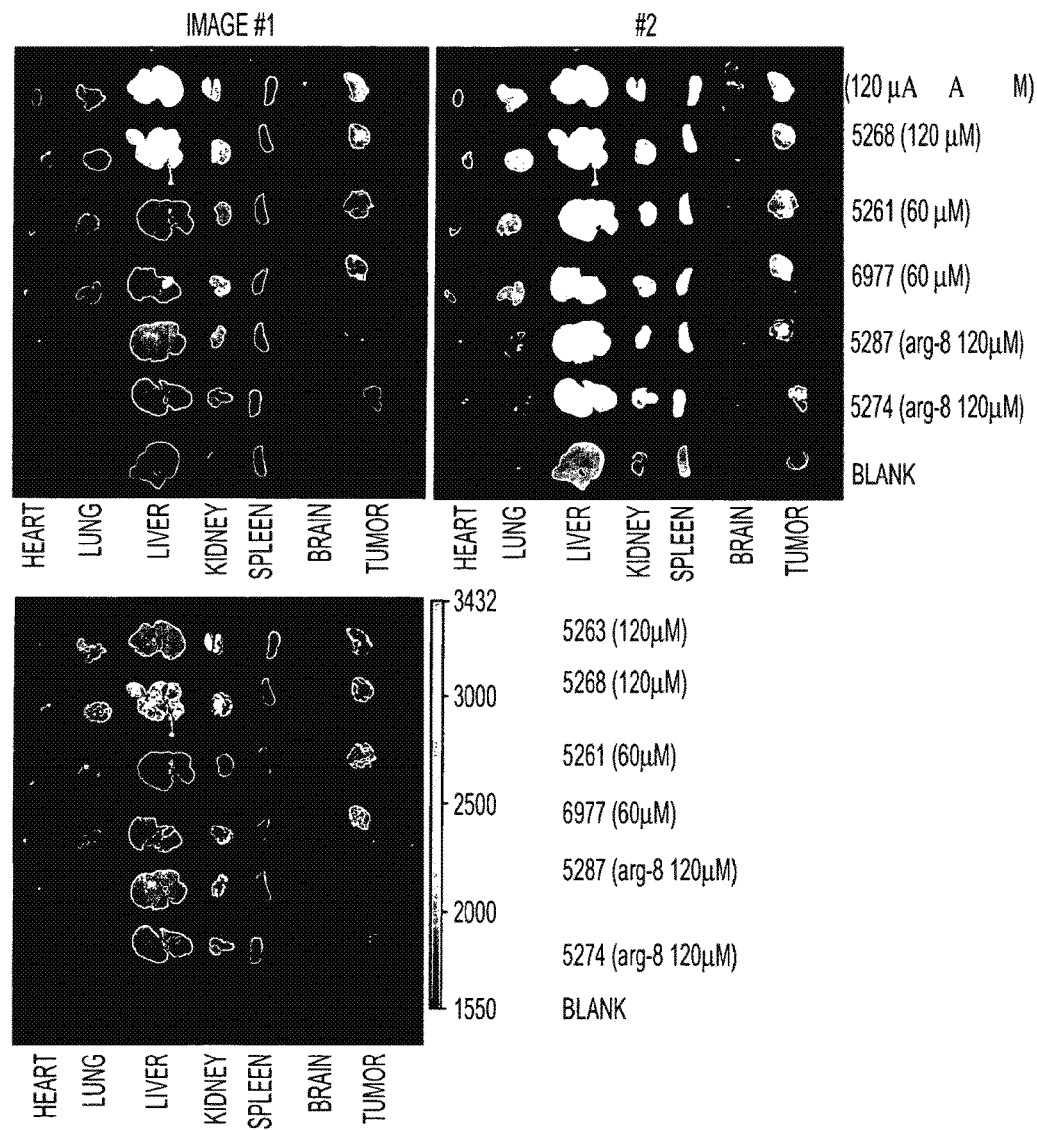
FIG. 38, (A) and (B). (A) Depicts photographs of organs from HT-1080 mice taken 22 hours after treatment with 60 and 120 μM concentrations of p18 and arg-8 (SEQ ID NO: 95). (B) Depicts side-by-side photographs of brains from HT-1080 mice taken 22 hours after treatment with 60 and 120 μM concentrations of p18 and arg-8 (SEQ ID NO: 95).
Figure 38B:
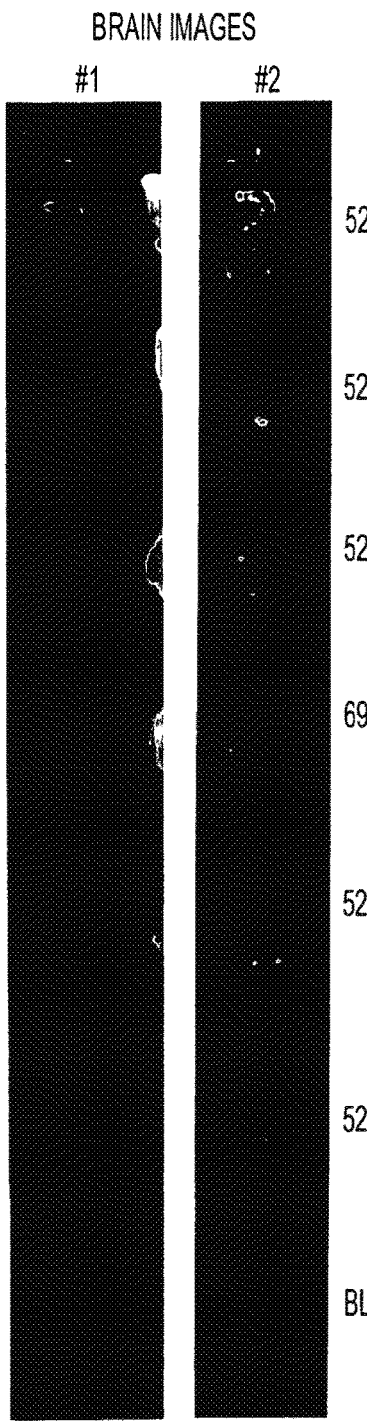
Figure 40A:
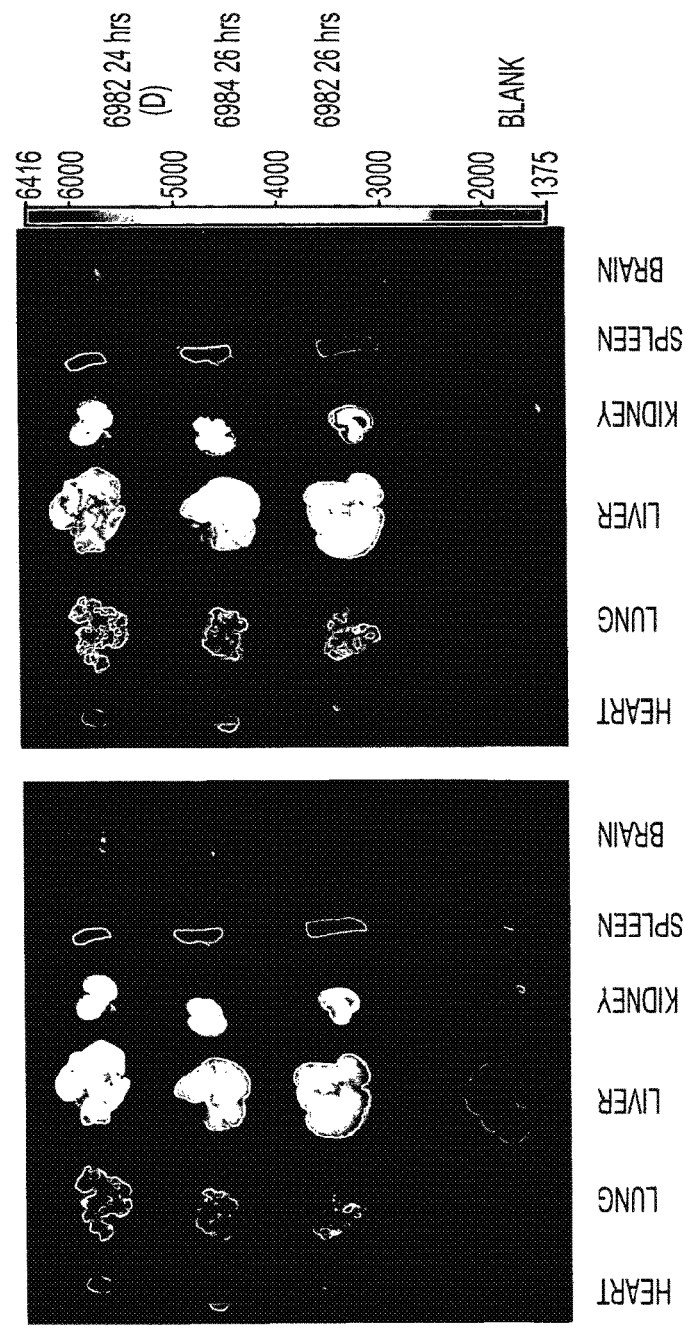
FIG. 40, (A) and (B). (A) Depicts photographs of organs from HT-1080 mice in an animal study, whereby 1×10$^6$ cells are injected into tail veins (43 days) and all treated mice have lung metastases, taken 24 and 26 hours after 60 μM concentrations of p28 injected into tail veins. Animal 6982 was dead when photographed. (B) Depicts side and back photographs of HT-1080 mice in an animal study, whereby 1×10$^6$ cells are injected into tail veins (43 days), taken 22 hours after 60 μM concentrations of p28 injected into tail veins. Animal 6982 was dead when photographed.
Figure 40B:
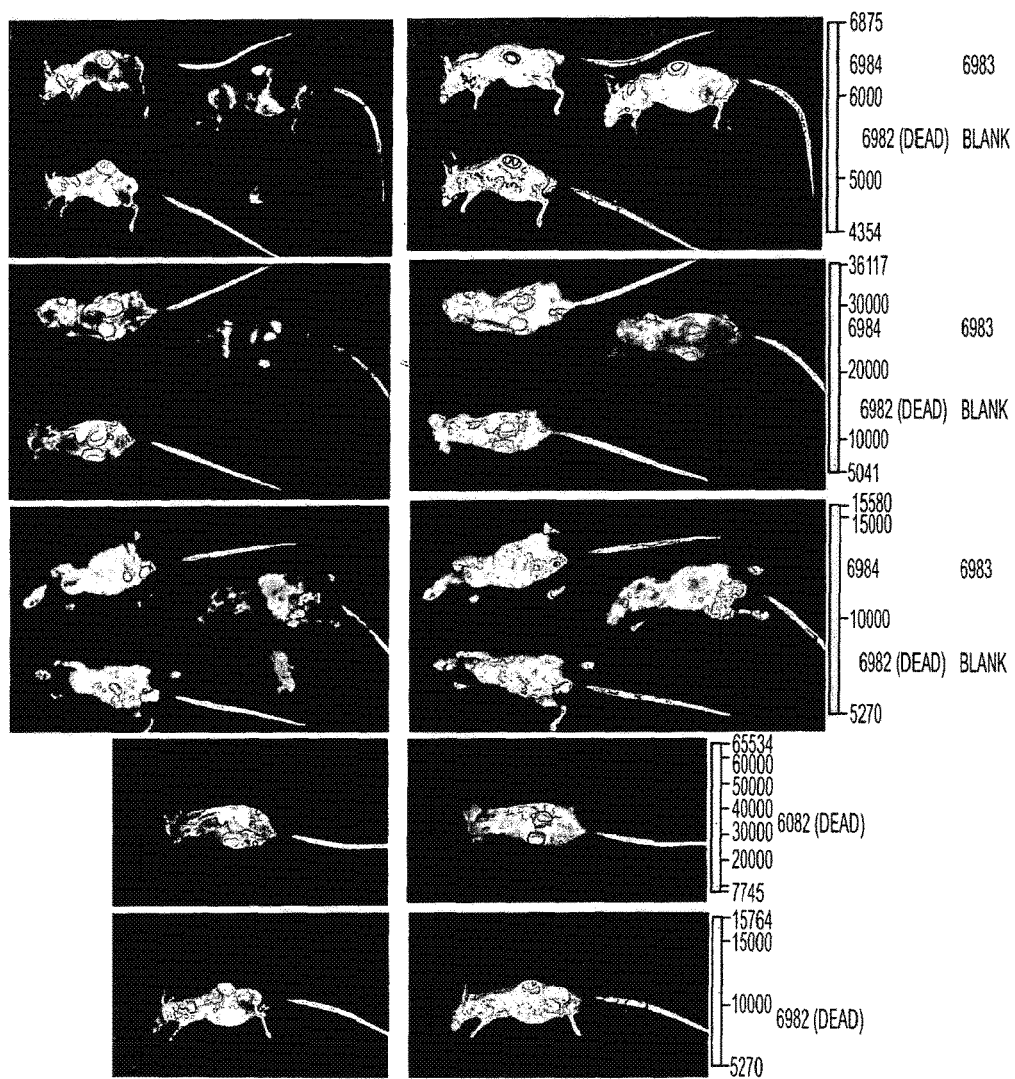
Figure 41:
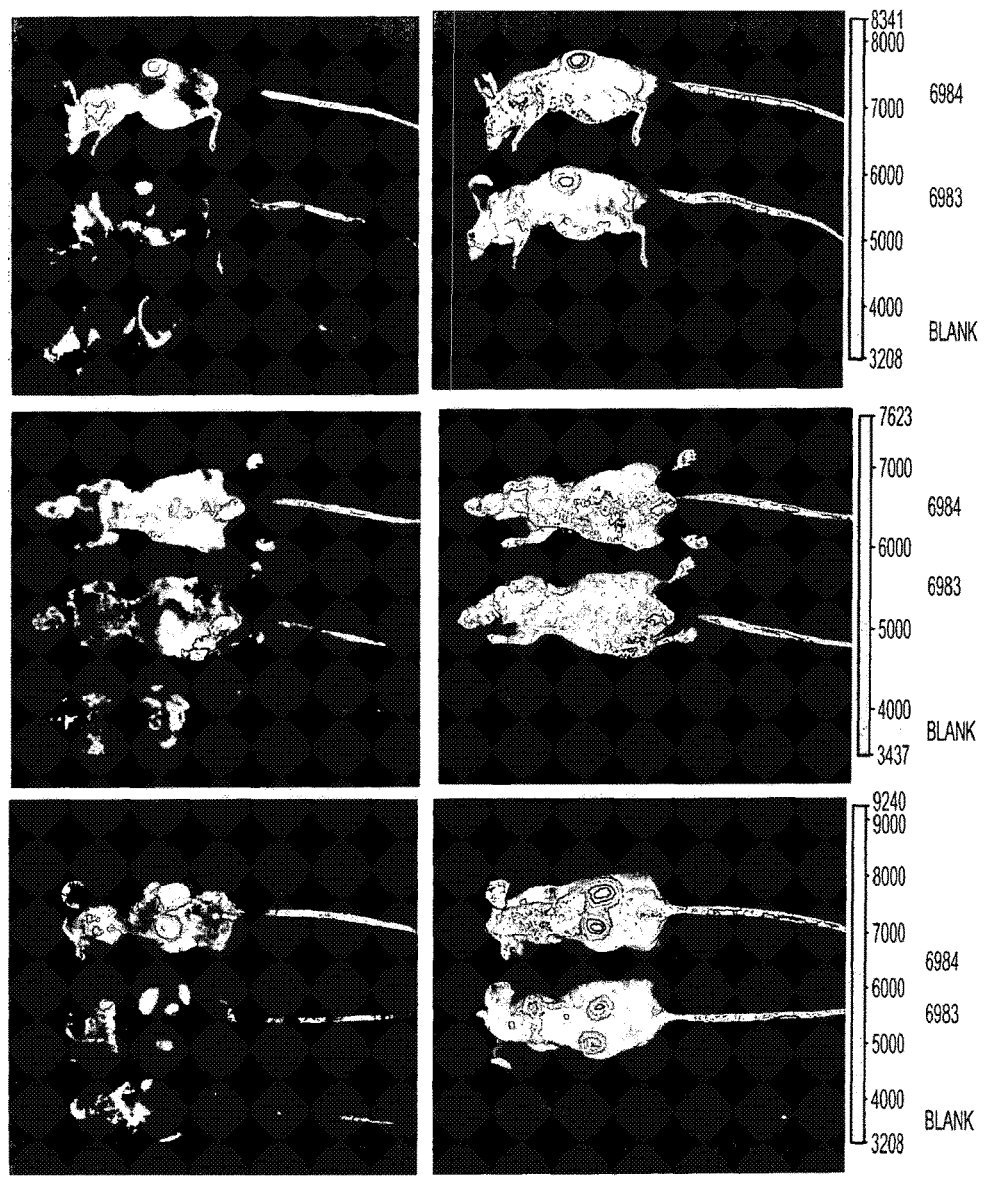
FIG. 41. Depicts side and back photographs of HT-1080 mice in an animal study, whereby 1×10$^6$ cells are injected into tail veins (43 days), taken 26 hours after 60 μM concentrations of p28 injected into tail veins.
Figure 42A:
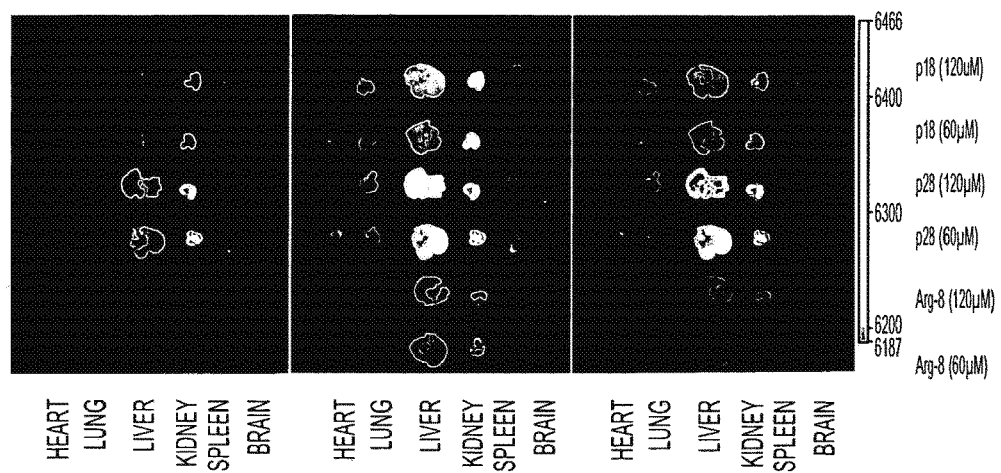
FIG. 42, (A) and (B). Depicts photographs of (A) organs from mice and (B) back views of mice in Balb-C peptide study taken 12 hours after treatment with 60 and 120 μM concentrations of p18, p28, and arg-8 (SEQ ID NO: 95).
Figure 42B:
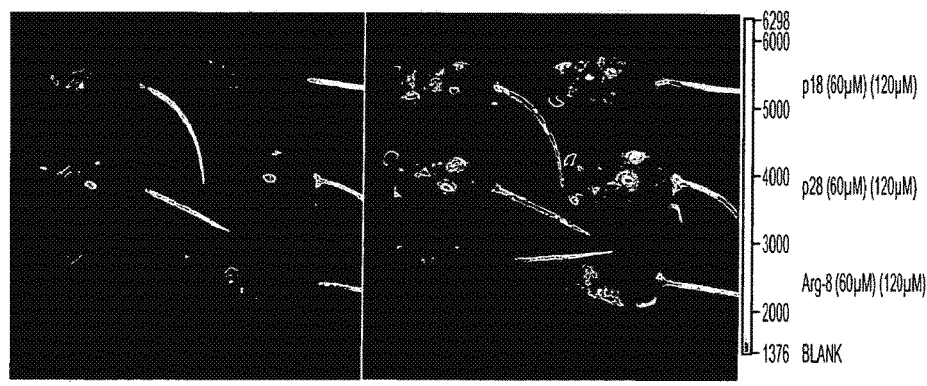
Figure 43A:
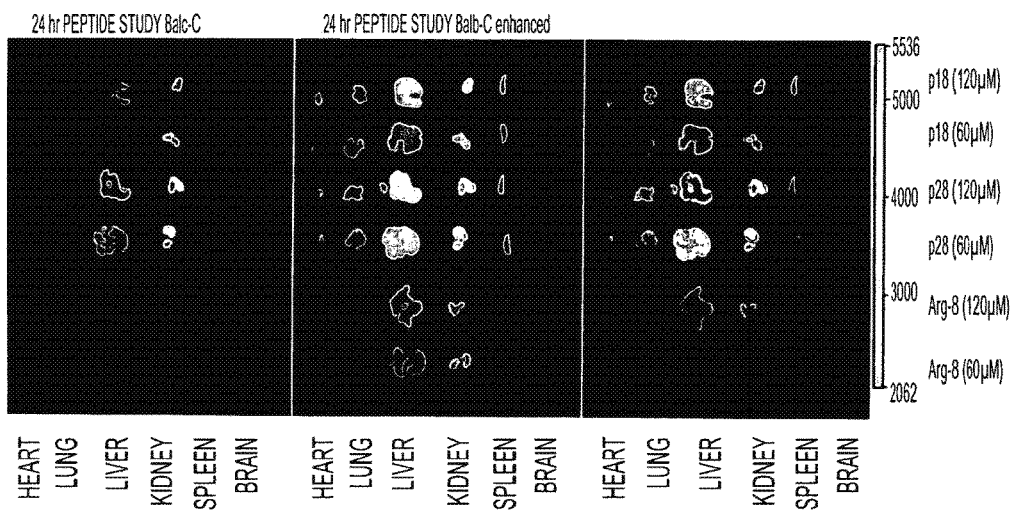
FIG. 43, (A) and (B). Depicts photographs of (A) organs from mice and (B) side views of mice in Balb-C peptide study taken 24 hours after treatment with 60 and 120 μM concentrations of p18, p28, and arg-8 (SEQ ID NO: 95).
Figure 43B:
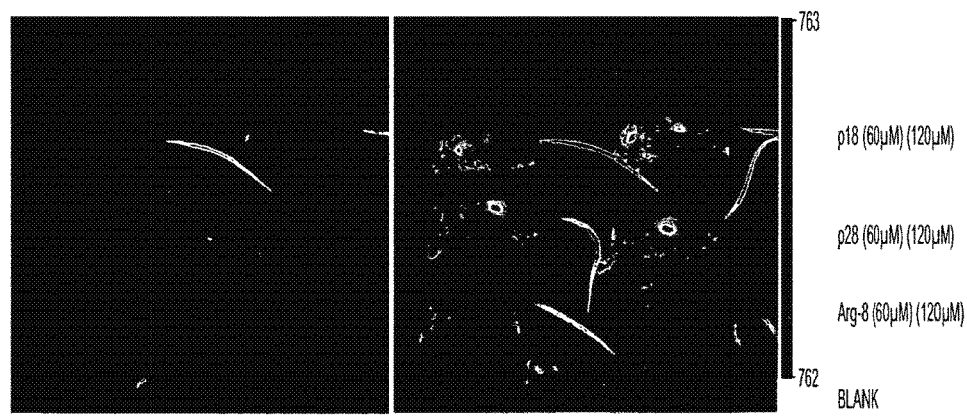
Figure 44:
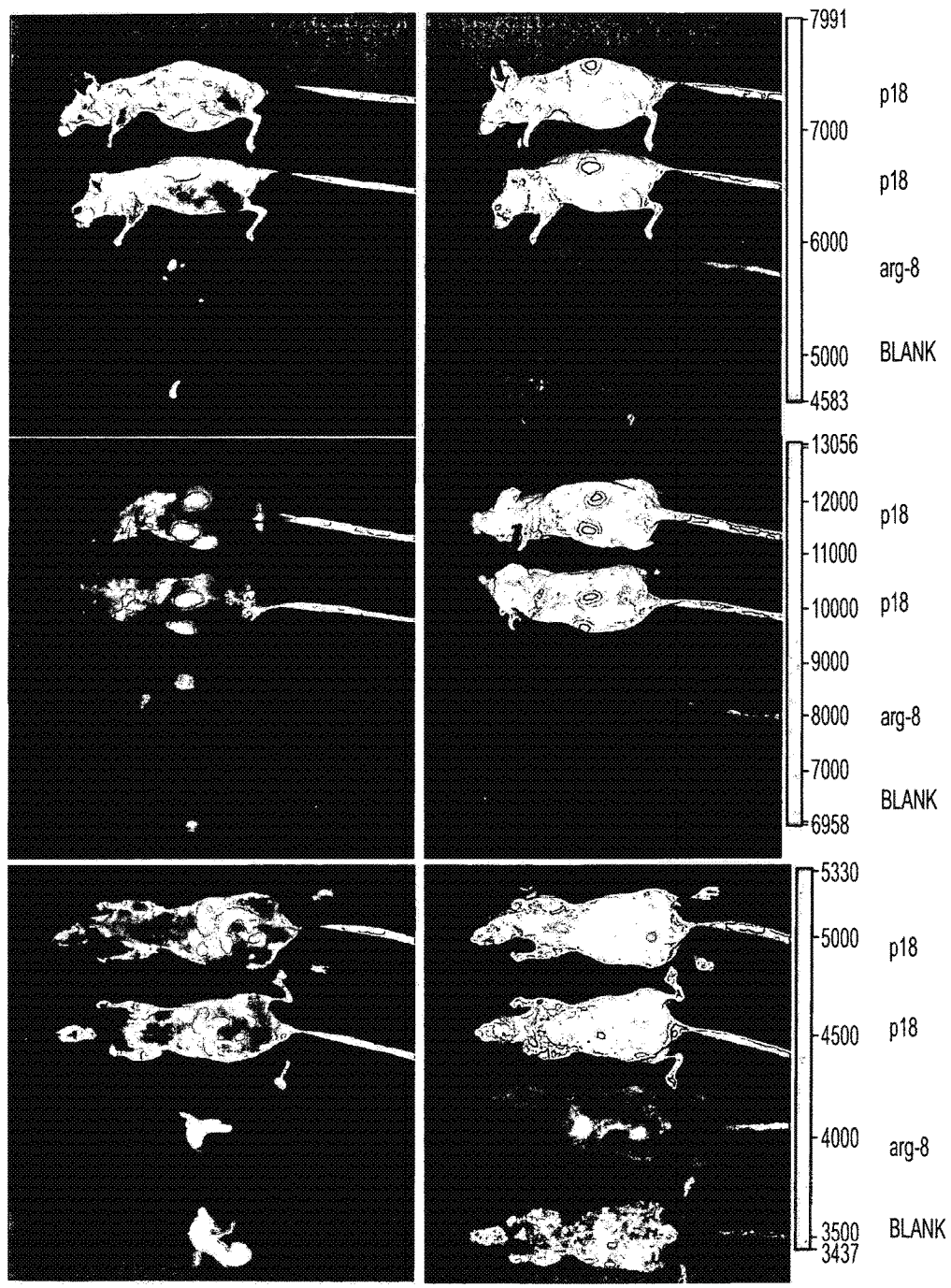
FIG. 44. Depicts side and back photographs of MEL-6 mice (0.5 million cells injected via tail vein) 16 hours after injection into tail veins of 60 μM concentrations of p18 and arg-8 (SEQ ID NO: 95).
Figure 45A:
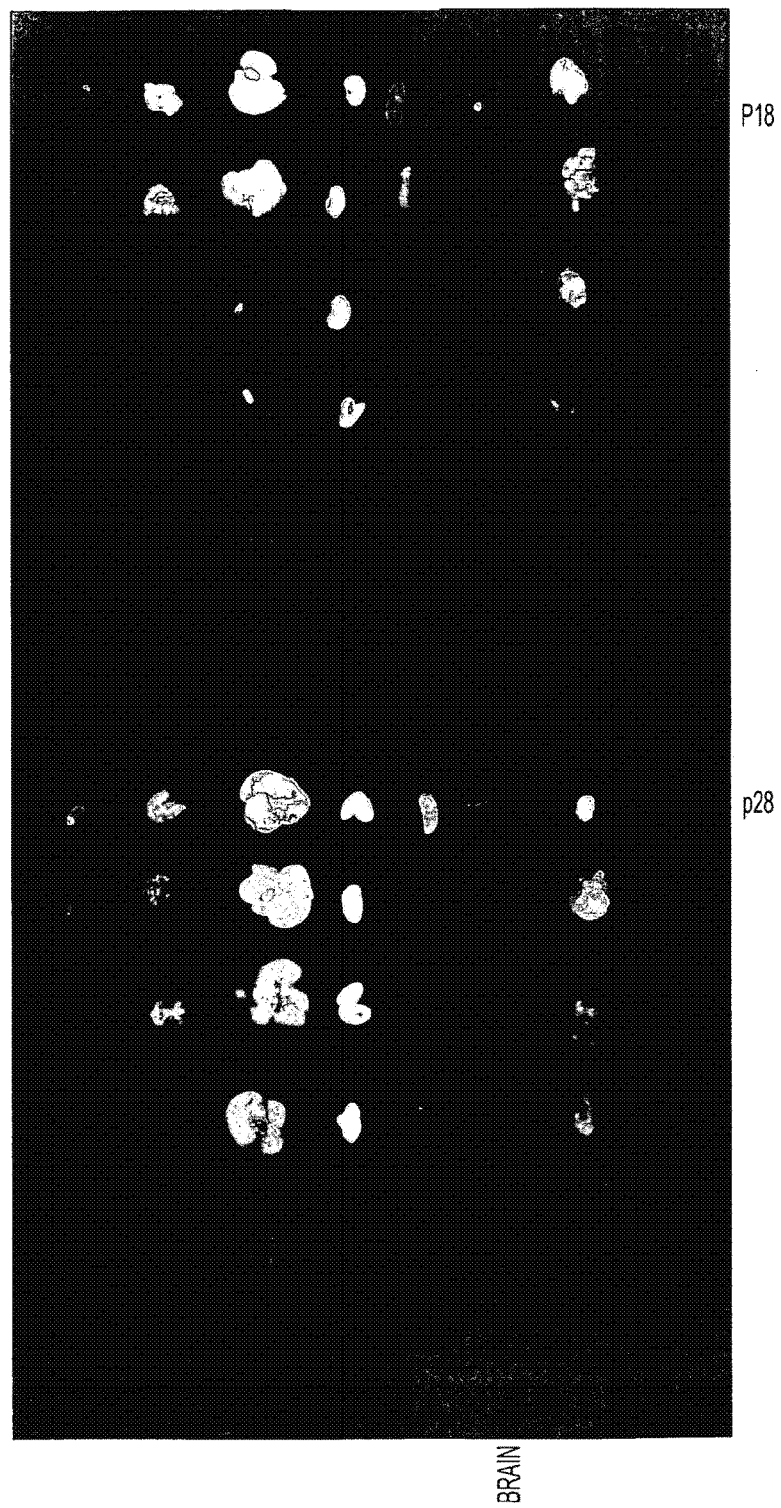
FIG. 45, (A) through (D). Depicts photographs of mouse organs, and specifically mouse brains, after treatment with p18 and p28.
Figure 45C:
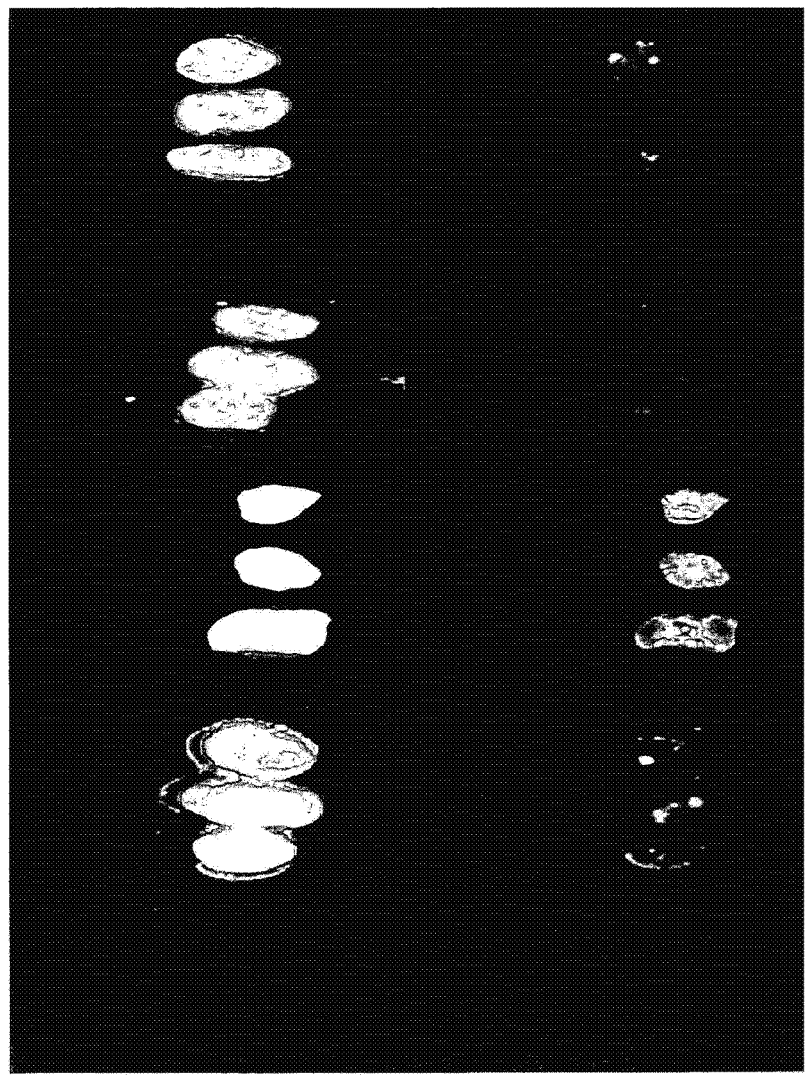
Figure 45D:
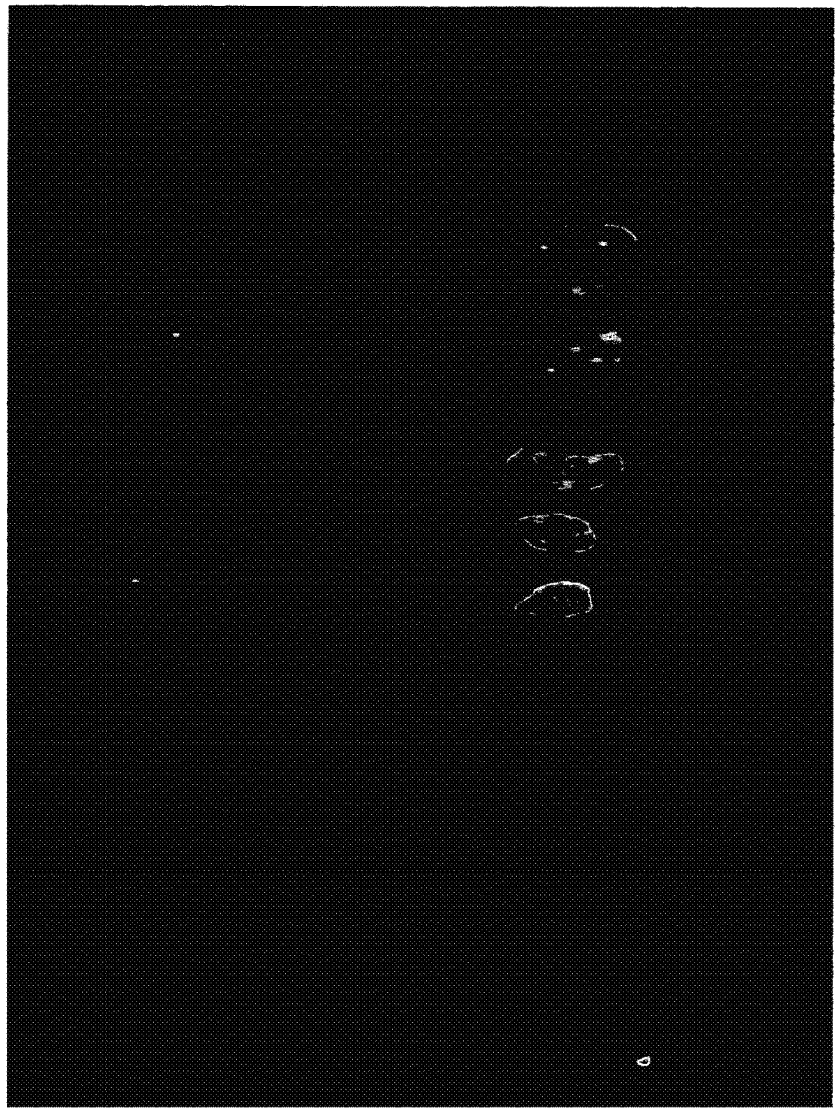
Figure 46:
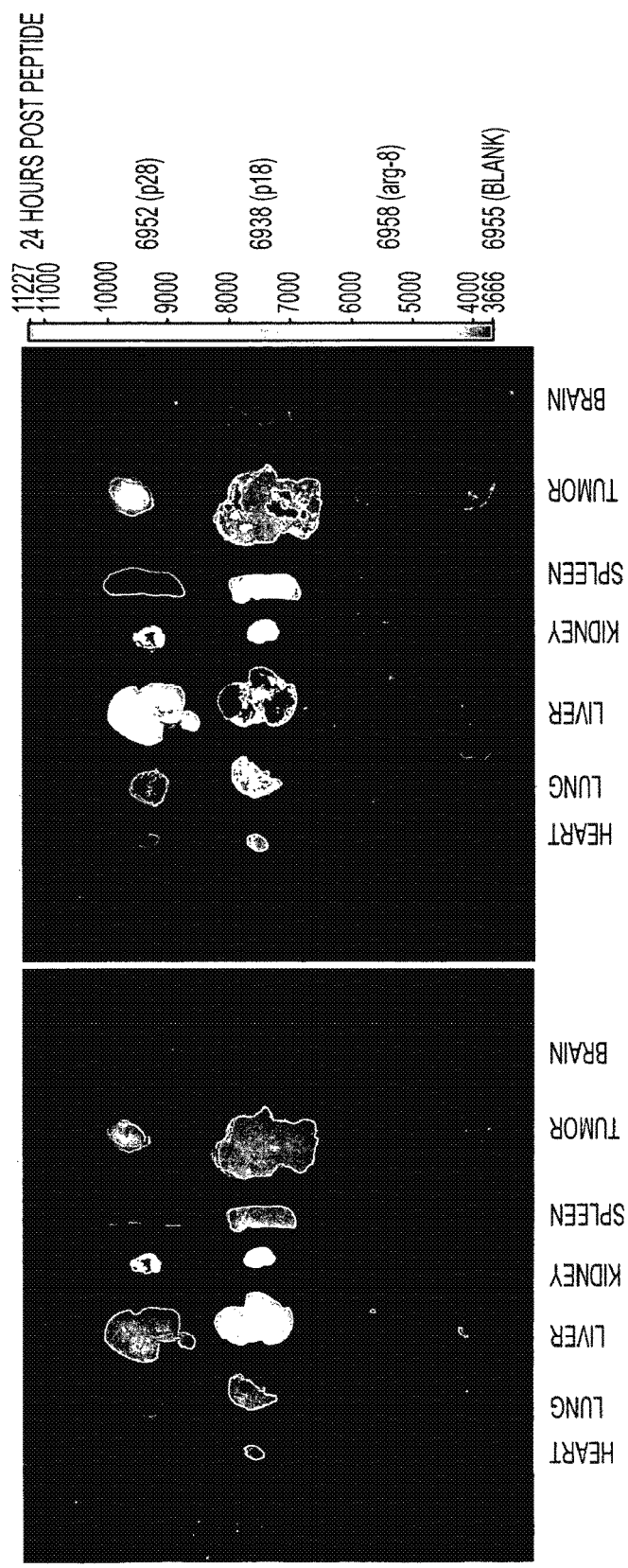
FIG. 46. Depicts photographs of organs from MEL-6 mice taken 24 hours after treatment with p28, p18, and arg-8 (SEQ ID NO: 95).
Figure 47A:
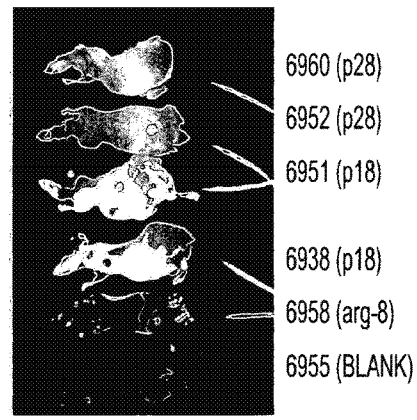
FIG. 47, (A) through (C). (A) Depicts side and back photographs of MEL-6 mice 3 hours after injection with 60 μM concentrations of p18, p28, and arg-8 (SEQ ID NO: 95). (B) Depicts side and back photographs of MEL-6 mice, and photographs of organs from MEL-6 mice, taken 22 hours after injection with 60 μM concentrations of p18, p28, and arg-8 (SEQ ID NO: 95). (C) Depicts photographs of organs from MEL-6 mice 24 hours after injection with 60 μM concentrations of p18, p28, and arg-8 (SEQ ID NO: 95).
Figure 47B:
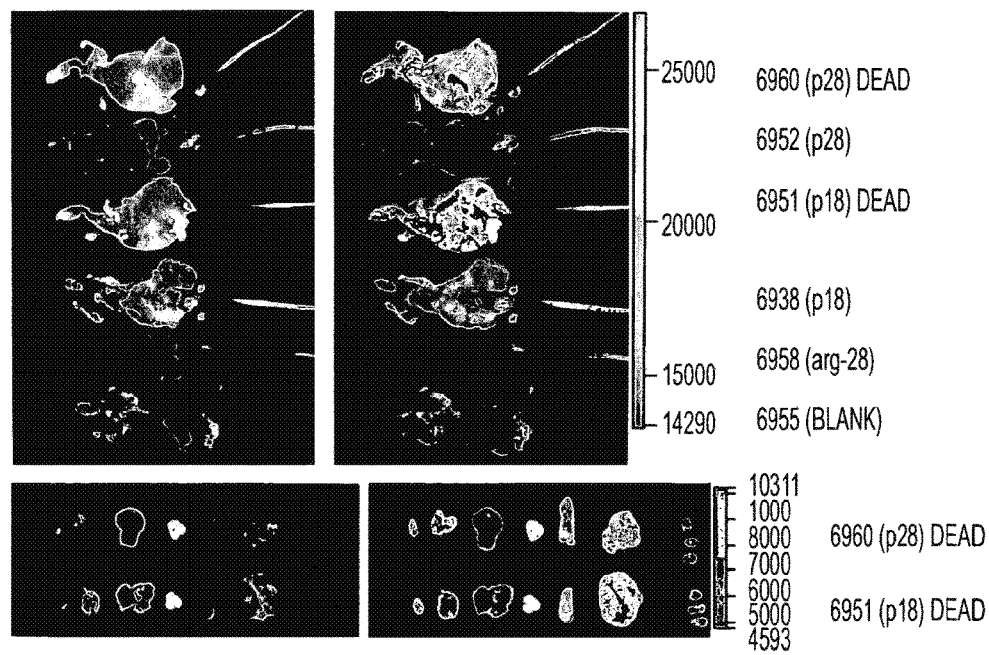
Figure 47C:
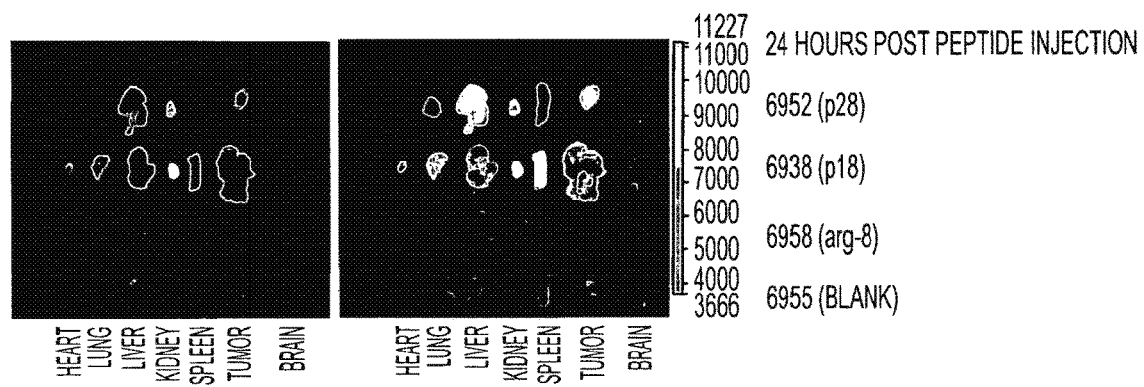
Figure 48B:
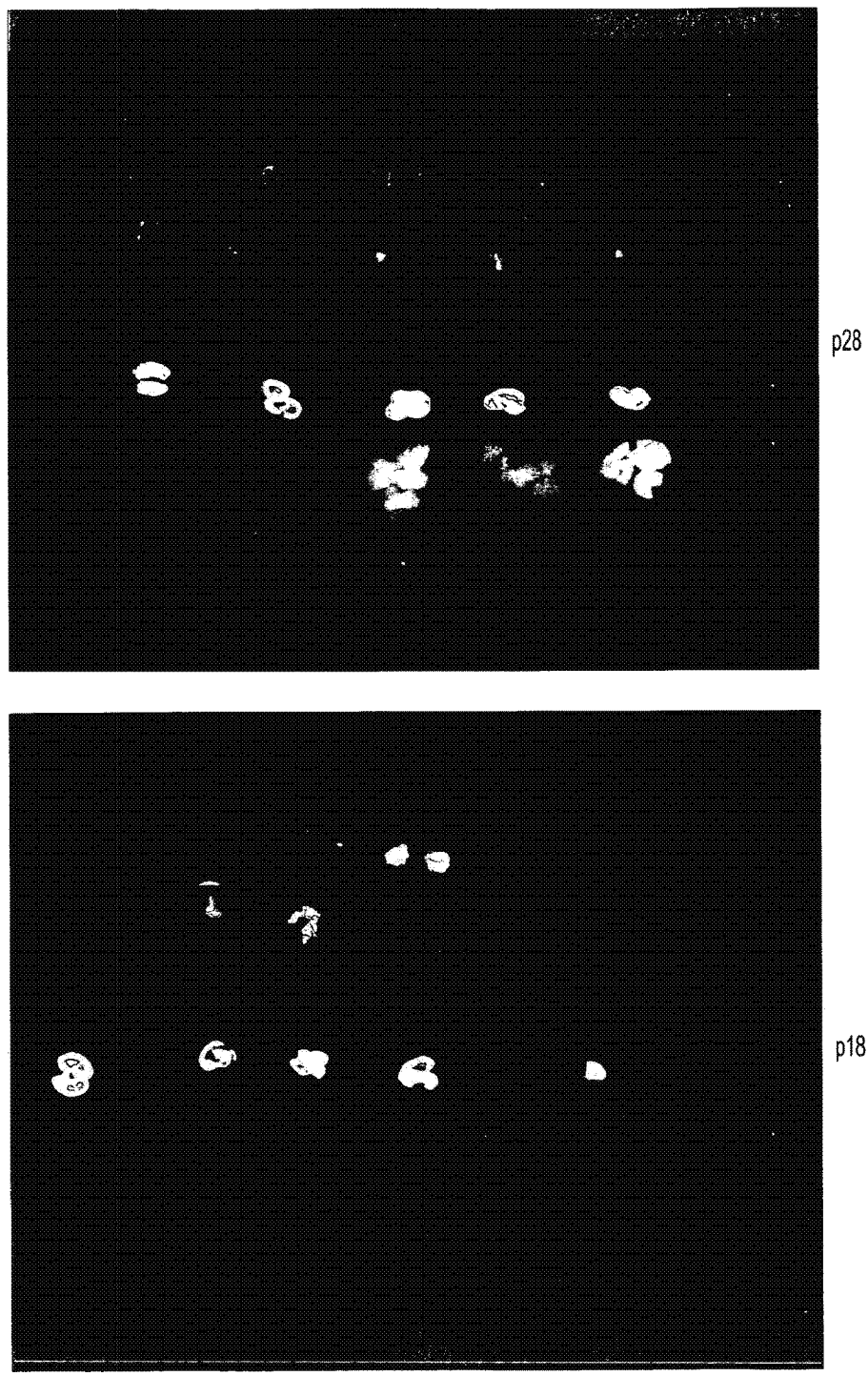
FIG. 48, (A) and (B). Depict uptake of p18 and p28 into (A) mouse brains and (B) mouse organs).
Figure 49:
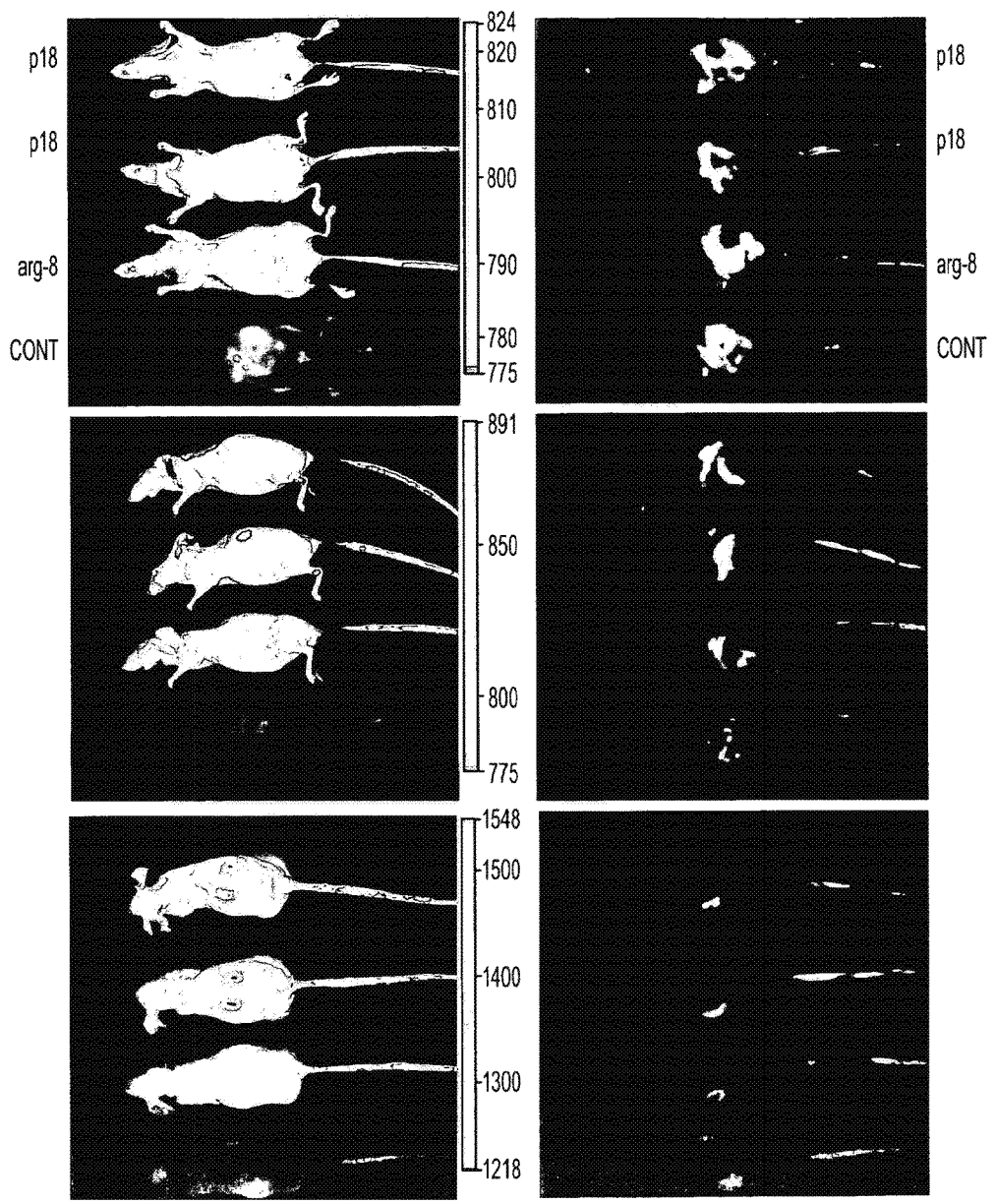
FIG. 49. Depicts side and back photographs of MEL-6 mice in study whereby 0.5 million cells injected I.V. into tail vein (44 days post), taken 120 hours after injection into tail vein of 24 μM concentrations of p18 and arg-8 (SEQ ID NO: 95).
Figure 50:
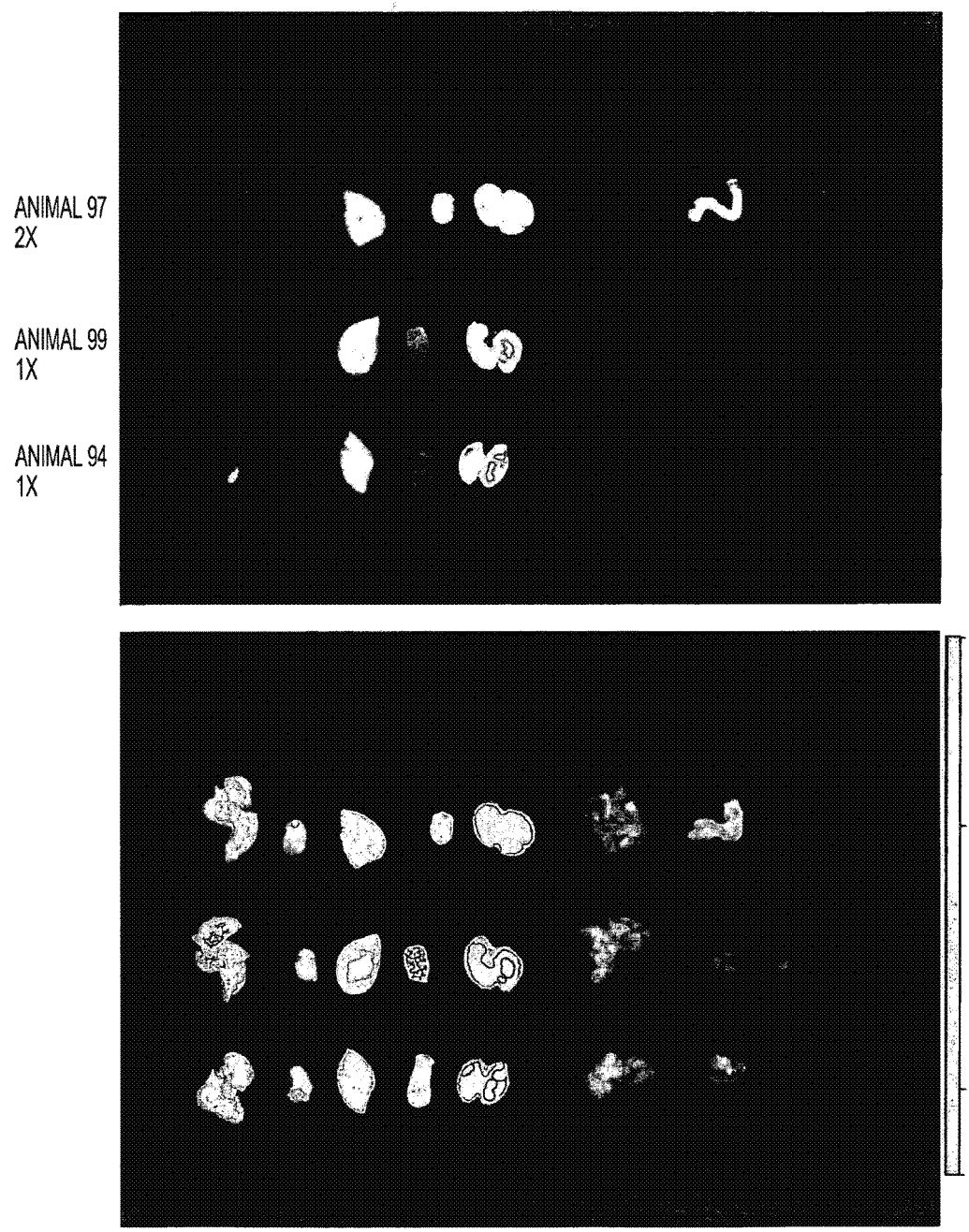
FIG. 50. Depicts photographs of organs from MEL-6 mice taken 168 hours after treatment with p18.
Figure 51:
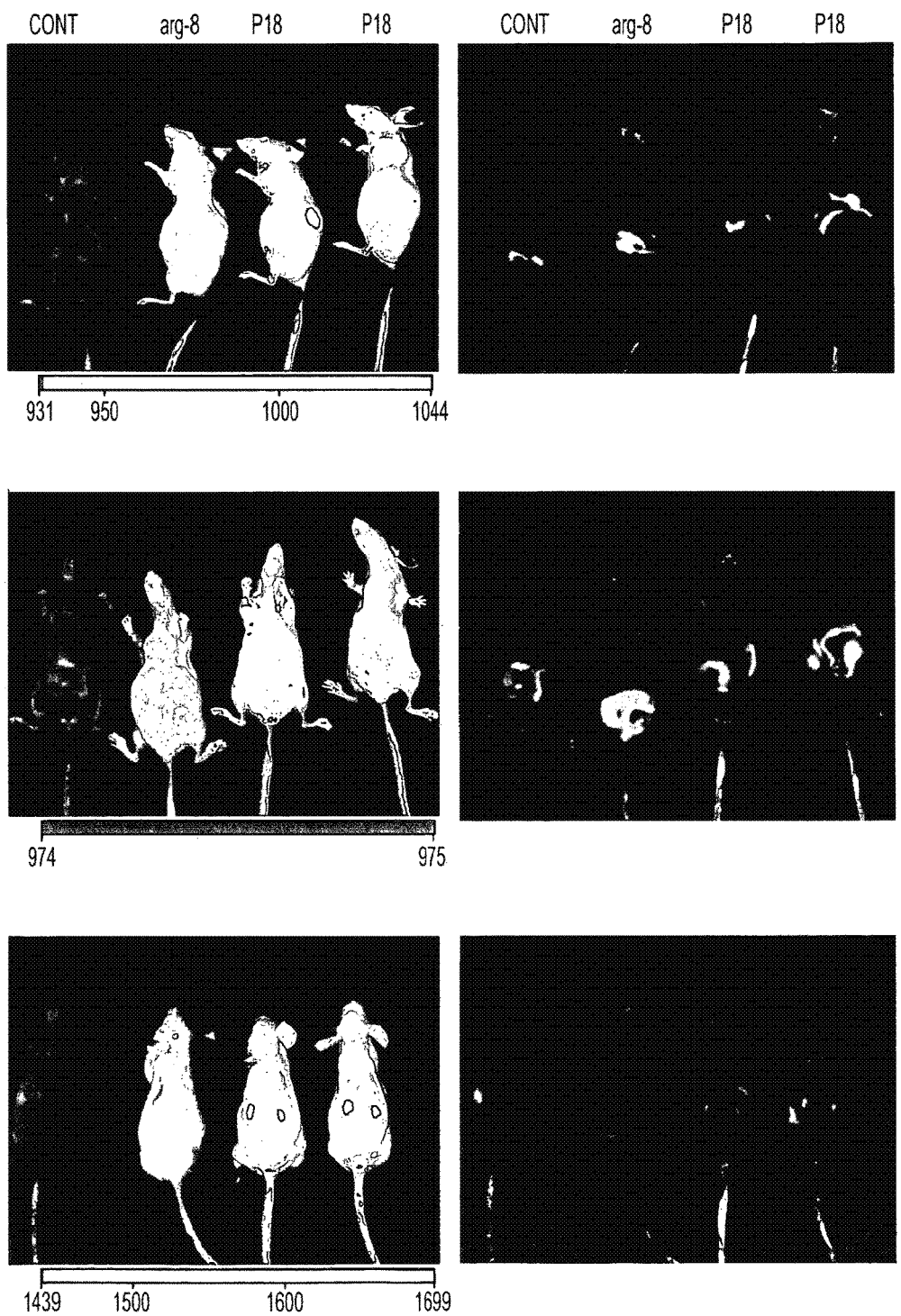
FIG. 51. Depicts side and back photographs of MEL-6 mice taken 72 hrs after injection of arg-8 (SEQ ID NO: 95) and p18, 41 days post injection of cells.
Figure 52:
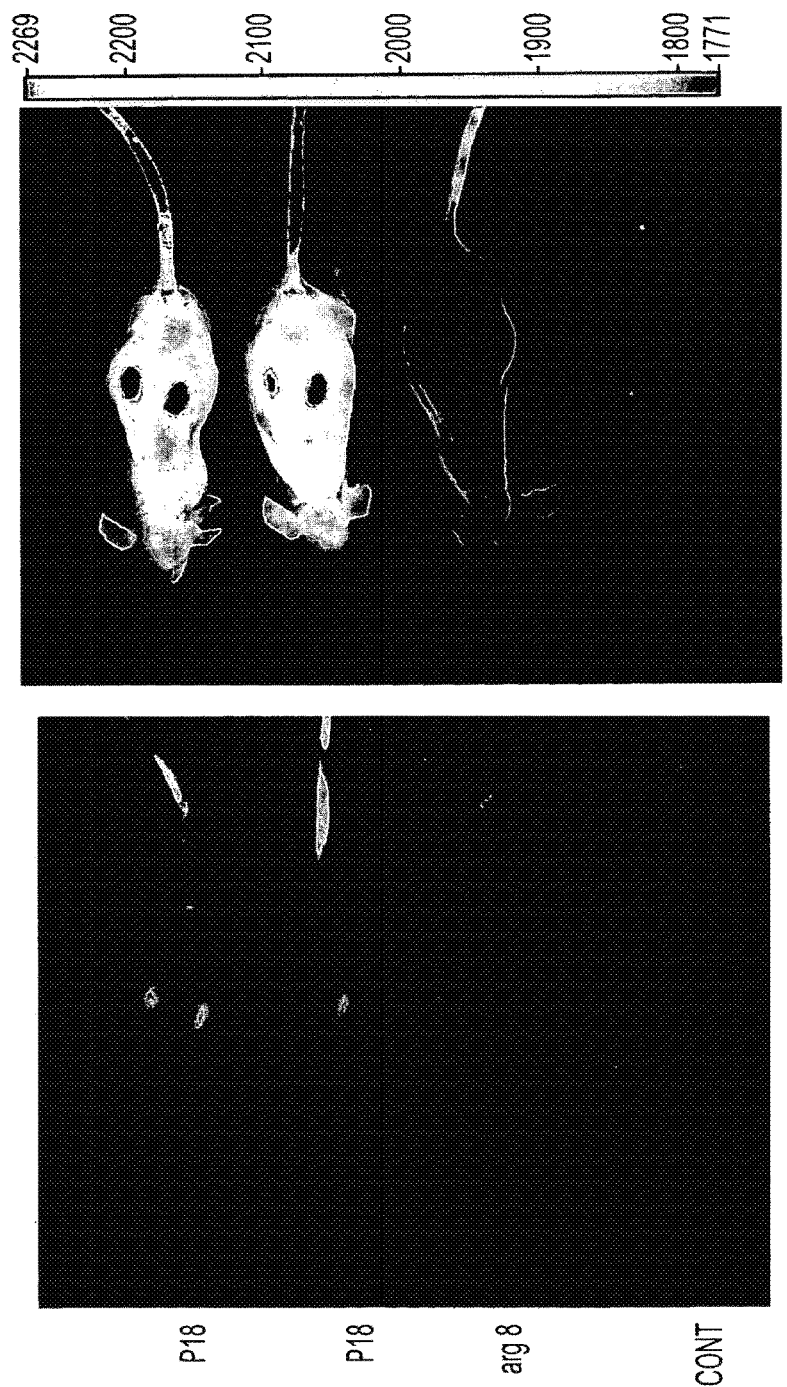
FIG. 52. Depicts back photographs of mice taken after injection of arg-8 (SEQ ID NO: 95) and p18.
Figure 53:
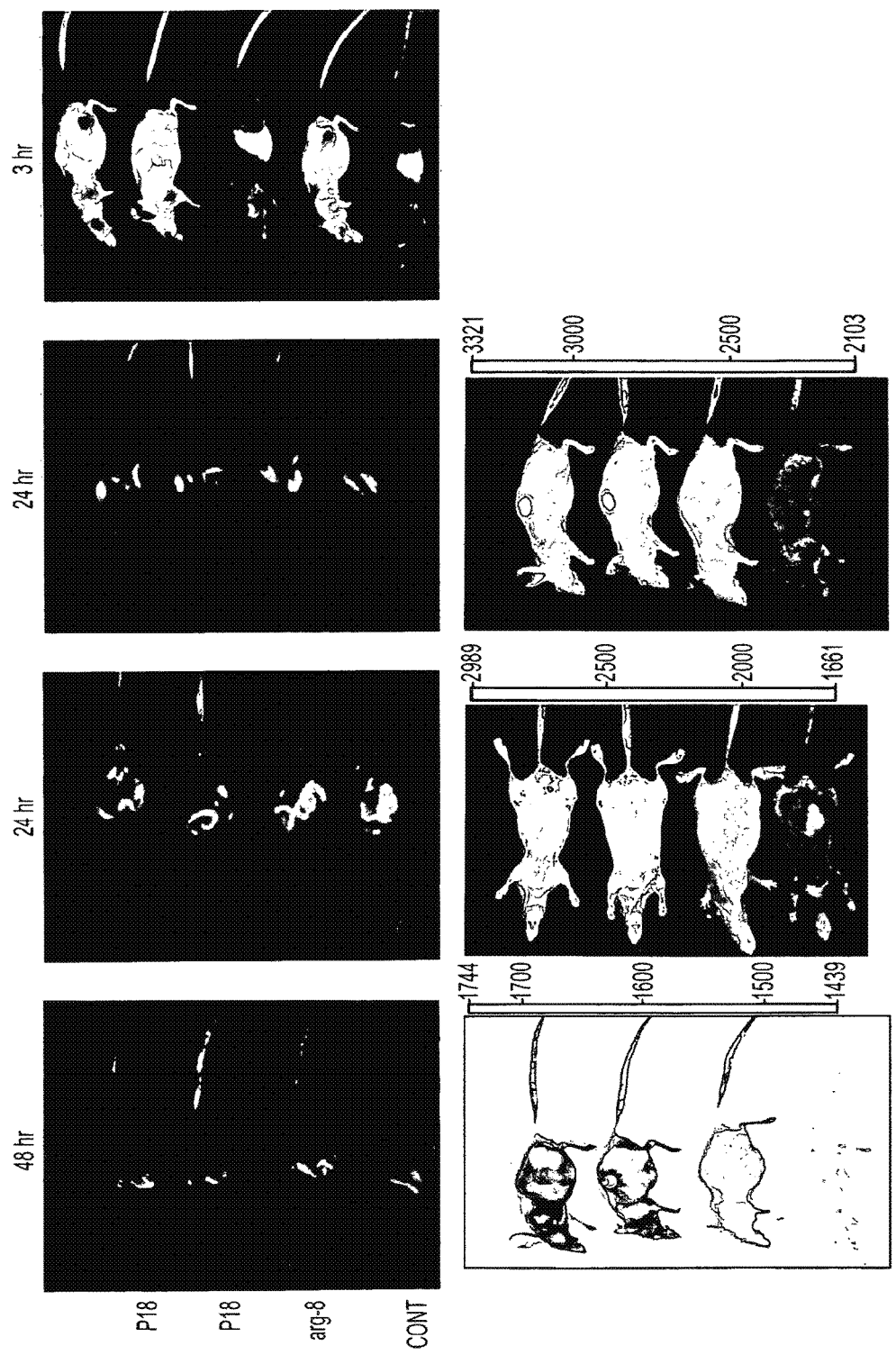
FIG. 53. Depicts side and front photographs of mice taken 3, 24, and 48 hours after injection of arg-8 (SEQ ID NO: 95) and p18.

UISO-Mel-2 or fibroblast cells ($3 \times 10^5$ cells) were suspended in MEME media without phenol red. Reactions were started by adding Alexafluor 568-conjugated p28 at 10, 50, 100, 150, 250, 300 and 400 μM for 30, 60, 90 and 120 sec on ice. Cells were analyzed by flow cytometry. The uptake of the peptides into the cells are shown in the graphs of FIG. 17A. The Km and Vmax were calculated by plotting peptide concentration (μM) vs velocity (MFI/sec). These calculations are depicted in FIG. 17B. Peptide binding and entry was determined using whole Mel2 cells (50,000 cells/ml), were incubated for 30 min at 37° C. with increasing concentrations (0-175 nM) of radiolabeled azurin in the presence/absence of 1000 fold excess of unlabeled p28, or azurin, and radioactivity remaining in the cell pellet counted using a gamma counter. The results are depicted in FIG. 17C. Radioactivity in cells incubated with $^{125}$I azurin alone was considered total binding; radioactivity in the presence of unlabeled azurin or p28 was considered nonspecific binding. Specific binding was determined by subtracting nonspecific binding from total binding and Scatchard plots generated.

Example 26—Inhibition of Cancer Growth Through p53 Using Azurin-Derived Peptides: Materials and Methods Cell culture.

Human breast cancer cell lines, MCF-7 (p53 wt), obtained from ATCC (Manassas, Va.) and MDD2 (p53 dominant negative) from Dr. Andrei V. Gudkov (Lerner Research Institute, Cleveland, Ohio) were cultured in MEM-E (Invitrogen, Carlsbad, Calif.) containing 2 mM L-glutamine, 0.1 mM essential amino acids supplemented with 10% heat inactivated fetal bovine serum, 100 Units/ml penicillin and 100 μg/ml streptomycin.

Bacterial Culture and Isolation of Azurin.

*Escherichia coli* JM109 was used as the host strain for production of wild type azurin. Culture conditions and protein purification steps were as described in Yamada, et al., Infect Immun, 70:7054-7062 (2002) and Goto, et al., Mol Microbiol, 47:549-449 (2003).

Peptide Synthesis.

All azurin-derived peptides including p18, Leu$^{50}$-Gly$^{67}$ LSTAADMQGVVTDGMASG (SEQ ID NO: 25), p28 Leu$^{50}$-Asp$^{77}$ (SEQ ID NO: 2) LSTAADMQGVVTDG-MASGLDKDYLKPDD, p18b Val$^{60}$-Asp$^{77}$ (SEQ ID NO: 34) VTDGMASGLDKDYLKPDD, p12 Gly$^{66}$-Asp$^{77}$ SGLDKDYLKPDD (SEQ ID NO: 35), and poly arginine (Arg$_8$) (SEQ ID NO: 95) were synthesized by CS Bio, Inc. (Menlo Park, Calif.) as >95% purity and mass balance.

Proliferation Assays.

Cells were seeded in MEM-E in quadruplicate into 24-well plates (Becton Dickinson, Franklin Lakes, N.J.) at a density of $12 \times 10^3$ cells/well and incubated in the presence of 5, 50, 100 and 200 μM p28 for 24, 48 and 72 hr. Media was changed daily. Control wells received MEM-E without p28 (8 replicates). Doxorubicin (10 μM) was used as positive control (Z1 coulter; Beckman Coulter Inc., Fullerton, Calif.). Values represent (%) of control. Significance between control and treated groups was determined by Student's t-test.

MTT Assay:

MCF-7 cells were seeded at a density of 2000 cells/well (quadruplicate) allowed to attach for 24 hrs, and freshly prepared peptide (10 μl) or MEM-E added to each well. After 24 hrs, medium and p18, p28, azurin or doxorubicin were added daily. After incubation, 10 μl of MTT reagent (Trevigen, Gaithersburg, Md.) was added to each well, the samples incubated for 3 hr at RT, 100 μl of detergent added to each well, and incubated for an additional 3 hr at 37° C. Absorbance (570 mm) was measured (SpectraMax 340 plate reader, Molecular Devices Corporation, Sunnyvale, Calif.) and percent change in treated cells determined. Significance $p<0.05$) between control and treated groups was determined by Student's t-test.

Xenograft Model.

Estradiol pre-treated (0.72 mg/pellet, 60-day release; Innovative Research, Sarasota, Fla.) female athymic mice (Harlan; 4-5 weeks old) received $3 \times 10^6$ MCF-7 cells s.c. in the right flank and randomized into control and experimental groups prior to treatment. Control animals received PBS/castor oil i.p. Paclitaxel, 15 μmmol/kg in PBS/castor oil was injected i.p. on days 10, 14, 21 and 25 post-tumor cell inoculation, or p28, 5 or 10 mg/kg in sterile PBS i.p. daily was injected for 30 days. Tumor volume was determined 3×/week. Body weights were measured twice weekly. Mice were necropsied on day 31 and all tumors collected for histopathology and immunocytochemistry. Significance ($p<0.05$) between control and treated groups was determined by Student's t-test.

Immunocytochemistry.

BrdU, 50 mg/kg body wt, was injected i.p., 2 hrs prior to necropsy. Tumor cell nuclei labeled with BrdU were identified with an anti-BrdU monoclonal antibody (Beckon Dickinson, Franklin Lakes, N.J.). p53 expression was quantified in formalin fixed, 5μ paraffin sections treated with 10 mM citrate buffer in a pressure cooker for 6 min. Cooled slides were treated with 3% $H_2O_2$ for 10 min to block endogenous peroxidase, covered with blocking serum for 10 min, and exposed to p53 antibody (DO-1, Santa Cruz Biotechnology, Santa Cruz, Calif.) for 2 hrs at room temperature. Rat anti-mouse IgG2a was used as the second antibody. Cells expressing p53 were identified using a Vectastain Elite ABC kit (Vector Laboratories, Burlingame, Calif.) and 3,3'-diaminobenzidine tetrahydrochloride (Sigma Aldrich, St. Louis, Mo.). Slides were counterstained with hematoxylin. Ten non-overlapping fields (250 cells/field) from each tumor periphery were screened (40×) for p53 labeled cells.

Confocal Microscopy:

Cells were seeded overnight on glass cover slips at 37° C. under 5% $CO_2$, rinsed with fresh media, and incubated at 37° C. for 2 hr in pre-warmed media containing Alexa Fluor 568 labeled peptides (20 μM), $Arg_8$ (SEQ ID NO: 95) (5 μM), or media alone. After incubation, cover slips were rinsed 3× with PBS, fixed in 2.5% formalin for 5 min, washed 2× in PBS, once in d.i.$H_2O$, and mounted in media containing 1.5 μg/ml DAPI to counter stain nuclei (VECTASHIELD®, Vector Laboratories). Cyclin B1 and p21 staining were determined in fixed cells, permiabilized by methanol and acetone, washed with PBS and incubated with anti-p21 or cyclin B at a 1:200 dilution (Santa Cruz Biotechnology). Secondary antibody conjugated Alexa Fluor 568 was used at 1:100 dilution. Cellular uptake and intracellular distribution were determined using an inverted confocal laser scanning microscope (Model LC510, Carl Zeiss Inc., Gottingen, Germany).

Kinetics:

MCF-7 and MDD2 cells ($3 \times 10^5$ cells) were suspended in MEM-E without phenol red. Reactions were started by adding Alexa Fluor 568-conjugated p28 at 1, 10, 25, 50, 100, 150 and 200 μM for 30, 60, 90 and 120 sec on ice. After incubation, 1 ml of cold-PBS was added to the reaction mixture and cells centrifuged 2× at 600×g for 2 min at 4° C. At least 10,000 fixed cells were analyzed for each time point and concentration by flow cytometry and their background and relative fluorescence calculated.

Cell Cycle Analysis.

MCF-7 and MDD2 cells were incubated with 50 μM of p28 for 48 and 72 hr at 37° C., washed twice with phosphate-buffered saline (PBS) and fixed with 70% ethanol at −20° C. Fixed cells were washed twice with PBS and stained by 50 μg/ml of propidium iodide (PI) in PBS containing 20 μg/ml of RNase A. Flow cytometry (EPICS Elite ESP, Beckman Coulter, Fullerton, Calif.) was used to determine DNA content. A minimum of ten thousand cells were collected in each experiment.

Immunoblotting.

MCF-7 and MDD2 cells were cultured with 50 μM p28 for 0, 24, 48 and 72 hr. and whole cell lysates prepared according to the methods described earlier (3). Cell lysates for phosphorylated cdc2 (p-cdc2) was prepared in 10 mM NaF, 137 mM NaCl, 1 mM $NaVO_4$, 10 mM EDTA, 1% NP-40, 1 mM DTT and proteinase inhibitors (Sigma Aldrich). Antibodies against p53, p27, CDKs, cyclins (Santa Cruz Biotechnology), p21 (Invitrogen) were used according to the suppliers' instructions. Actin expression was determined with a monoclonal actin antibody (Santa Cruz Biotechnology) and protein bands visualized using ECL reagent (Santa Cruz Biotechnology).

Anti-p28 Antibody.

A cysteine was introduced at the N-terminus of p28 (CS Bio Inc., Menlo Park, Calif.), and then the peptide was conjugated with Keyhole limpet hemocyanin through the thiol groups of the cysteine residue, the complex was inoculated intradermally and subcutaneously, and a polyclonal antibody specific for 11-28 amino acids of p28 (amino acids 60-77 of azurin) in rabbits (New Zealand White, Covance, Mich.) was generated. Antibody titer was determined by direct ELISA using p28 (0-3 μg/well). An antibody dilution of 1:140,000 was sufficient to give a reproducible change in absorbance of 0.5 at 450 nm after 15 min incubation with substrate (1-Step PNPP, Pierce, Rockford, Ill.) at 25° C., when 96 well-plates (Nunc, Rochester, N.Y.) were coated with 1 μg/well p28.

GST Pull-Down Assay.

p28 binding to p53 was assayed using a GST pull down assay essentially as described in Punj, et al, Oncogene 23:2367-2378 (2004). Purified GST-p28 (10 and 20 μg/reaction), GST-MDM2 (20 μg/reaction) and GST alone (20 μg/reaction) were bound to Glutathione Sepharose 4B beads (GE Healthcare, N.J.) and unbound peptide removed by washing 2× with PBS. Whole cell lysates of MCF-7 cells were generated with PBS/0.1% Triton X-100 containing proteinase inhibitor cocktail (Sigma-Aldrich) on ice for 15 min, and centrifuged at 14000 r.p.m. for 30 min at 4° C. Resultant supernatants were mixed with beads, incubated for 2 hr at 4° C., washed 2× with PBS to remove unbound cell lysate and then boiled in SDS-sample buffer prior to loading on 10% SDS-PAGE. Membranes were incubated with skim milk (5%) in TBST (Tris/0.05% Tween20) and polyclonal p53 antibody (FL-393, Santa Cruz Biotechnology) in 5% skim milk at 4° C., washed 3× with TBST, secondary rabbit IgG-HRP antibody (Sigma-Aldrich) added, incubated for 1 hr at room temperature (r/t), and washed 3× with TBST.

Potential binding sites on p53 were identified as follows. Interaction at the MDM2 binding site (amino acids 18-23) of p53 was analyzed using a GST-pull down assay in the presence of p28 (10-50 molar excess) and p53 bands detected by immunoblotting (IB). Three different anti-p53 antibodies, Pab 1801 (32-79 amino acids; Santa Cruz Biotechnology), ab 2433 (277-296-amino acids; Abeam Inc., Cambridge, Mass.) and Pab1802 (306-393-amino acids; Santa Cruz Biotechnology), that represent the broadest coverage of the p53 protein available, were each reacted with GST-p53 immobilized beads in the presence of p28. After incubation, samples were washed 2× with PBS to remove unbound p28, boiled in native PAGE sample buffer (Tri/glycerol/BPB) and loaded on 5% Native-PAGE. Samples were transferred to PVDF membrane by electroblotting (0.2 Amp for 1 hr), membranes blocked with skim milk (5%) in TBST and incubated with a polyclonal antibody to p28 (1:5000 dilution) in 5% skim milk at 4° C. After washing with TBST, HRP-conjugated rabbit anti-IgG antibody (1:7000 dilution, Santa Cruz Biotechnology) was applied. p28 bands were visualized using ECL reagent. Binding domains on p28 were identified using a competition assay between p28 and the p28 fragments p12, p18 and p18b for GST-p53 (20 μg/reaction) immobilized on Glutathione Sepharose 4B beads. Reactions were incubated for 2 hr at 4° C., washed 2× with PBS to remove unbound p28, then boiled in native PAGE sample buffer (Tri/glycerol/BPB) and loaded on 5% Native-PAGE. Proteins were transferred to a PVDF membrane by electro blotting (0.2 Amp for 1 hr), blocked, and incubated with the polyclonal antibody to p28 at 4° C. for 16 hr. p28 bands were visualized with ECL reagent. Band intensity was determined using Gel & Graph Digitizing Software, UN-SCAN-IT™ (Silk Scientific Inc., Orem, Utah) and the ratio of specific protein/actin calculated. Numbers displayed below each protein band are relative percentage of the protein babd intensity immediately prior to treatment (0 hr expressed as 100%).

p53 DNA-Binding Activity.

Nuclear fractions (Nuclear Extraction kit, Active Motif, Carlsbad, Calif.) were isolated from MCF-7 cells after incubation with either 50 μM p28 or azurin at for 24 h according to the manufacturers' instructions. Nuclear extract supernatants were collected by centrifugation at 14,000 rpm for 10 min at 4° C. Protein concentrations were determined using the Bradford method. DNA-binding activity of p53 was measured using a TransAM p53 kit (Active Motif). Briefly, 40 µl of binding buffer containing DTT and poly[d (I-C)] was introduced to each well to prevent non-specific binding to the p53 consensus oligonucleotide. Nuclear extracts were applied to each well, with $H_2O_2$-treated or buffer only as positive and negative controls, respectively, and incubated 1 hr r/t. Wells were washed 3× and 100 µl of p53 antibody (1:1000 dilution) applied and incubated at r/t for 1 hr. After washing, secondary antibody conjugated with HRP was added, samples incubated for 1 hr and developed for 3 min in the dark. p53 binding to DNA was determined by absorbance at 450 and 655 nm.

Figure 54A:
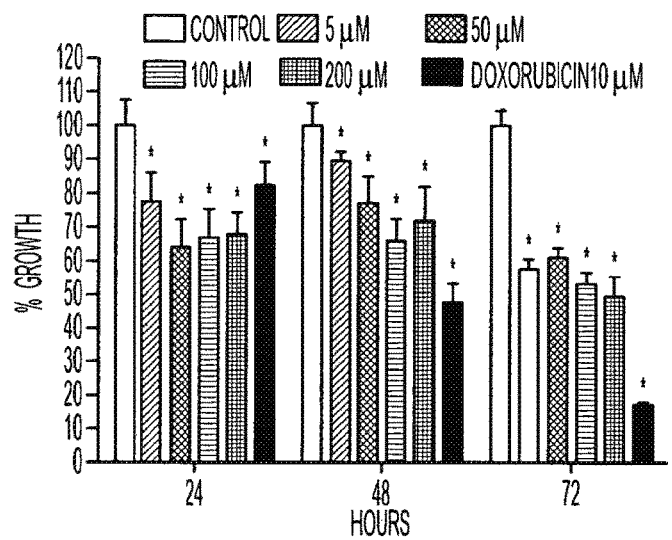
FIG. 54. Graphs depicting growth inhibition of human breast cancer cells by p28. MCF-7 cells were incubated with p28 (0-200 μM) at 37° C. for 24, 48 and 72 h. Cell count (A) and MTT assays (B). Doxorubicin (10 μM) was used as a positive control. Cell number or viability of control wells were considered as 100%. Data represent mean % of control±SEM. *, p<0.05. (C) Inhibition of MCF-7 xenograft growth by p28. A minimum of 10 mice per group were treated with paclitaxel 15 μmol/kg i.p. on days 10, 14, 21 and 25 or 5 or 10 mg/kg p28 i.p. daily for 30 days. Bars represent Mean±SEM. *, p<0.05.
Figure 54B:
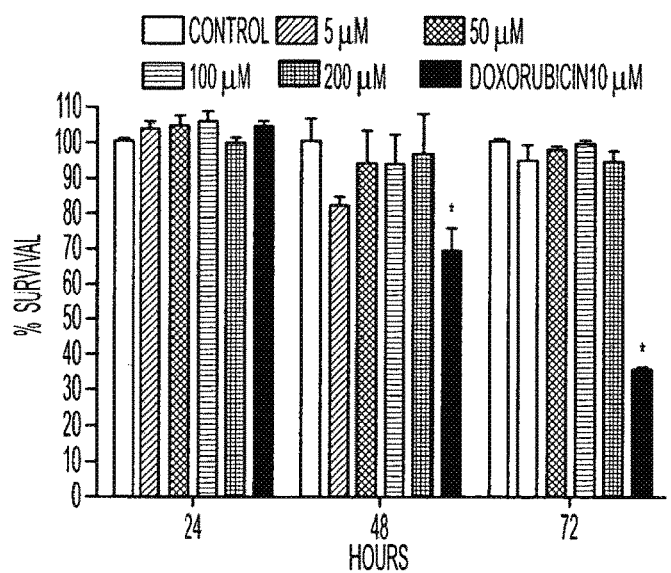
Figure 54C:
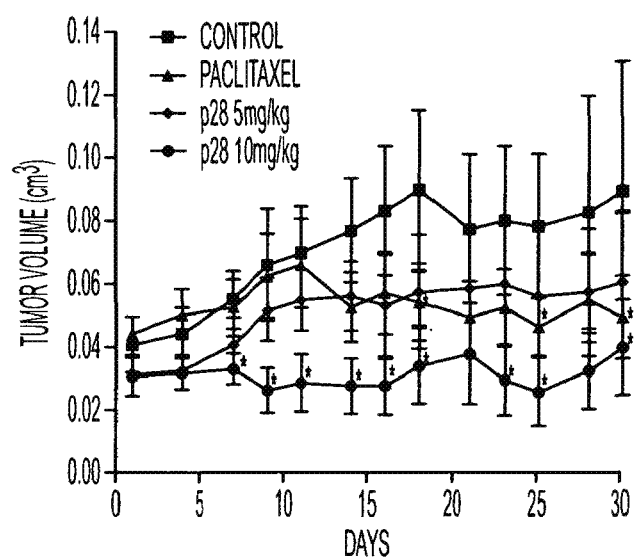

Example 27—Effect of p28 Treatment on the Growth of Human Cancer Cells In Vitro and In Vivo Azurin exerts its anti-cancer activity through induction of a p53-mediated apoptosis. FIGS. 54 A and B show the effect of p28 and doxorubicin on wt p53 (positive) MCF-7 cells as determined by direct cell count and MTT assay. p28 initially inhibited the proliferation of MCF-7 cells in vitro (FIG. 54A) in a dose and time related manner producing a significant decrease (p<0.05) in cell number ~23% at 5 µM and 36% at 50-200 µM after 24 hr exposure. Doxorubicin (DNA intercalating agent) also significantly inhibited cell growth in time-dependent manner. Cell survival determined by MTT assay was not significantly altered by p28, while doxorubicin exhibited a significant time related decrease in MCF-7 cell survival (FIG. 54B). p28 also produced a significant dose related decrease in the volume of xenografted MCF-7 cells in athymic mice over a daily, 30-day i.p. exposure (FIG. 54C), decreasing tumor volume (p<0.05) to that observed with Paclitaxel®, without inducing either a loss in body weight or behavioral change. By day 30, 10 mg/kg p28 daily i.p. inhibited MCF-7 growth to a greater extent (~20%) than 15 µmol/kg Paclitaxel® on days 10, 14, 21 and 25 post-tumor cell inoculation. The reduction in BrdU labeling associated with the p28-induced decrease in tumor volume suggested cell cycle was inhibited (Table 5). In contrast, the reduction in BrdU labeling and tumor volume was accompanied by a slight increase in nuclear p53-staining in p28 and a significant increase in the Paclitaxel® treated group compared to control (Table X).

TABLE 5

BrdU and p53 in MCF-7 xenograft tumors

|  | N | BrdU (%) | p53 (%) |
|---|---|---|---|
| Control | 7 | 21.0 ± 2.7 | 15.6 ± 0.82 |
| p28 (5 mg/kg) | 4 | 17.6 ± 0.75* | 15.8 ± 0.51 |
| p28 (10 mg/kg) | 3 | 16.1 ± 1.4* | 17.7 ± 0.92 |
| Paclitaxel | 6 | 9.0 ± 1.8** | 25.4 ± 0.65** |

All tumors were collected on day 31 post treatment. Values represent Mean ± SEM.
*p < 0.025;
**p < 0.01 from respective control; student's T-test.

Example 28—Inhibition of Cell Cycle Progression by p28

Figure 55A:
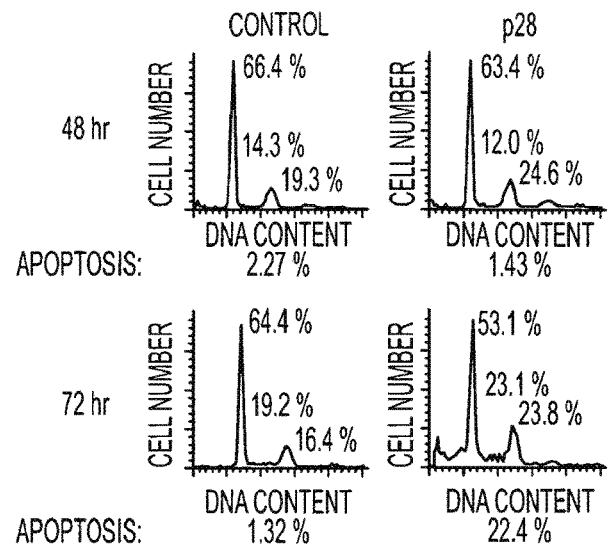
FIG. 55. (A) and (B) are graphs depicting FACS analyses of cell cycle and penetration of breast cancer cells by p28. MCF-7 (A) and MDD2 cells (B) were treated with p28 (50 μM) for 48 and 72 hr. Cells were stained with propidium iodide and analyzed by flow cytometry as described in Yamada, et al., Proc Natl Acad Sci USA, 101:4770-4775 (2004). The percentage of cells in the $G_1$, S, $G_2$/M and sub-$G_1$ (apoptosis) phases are indicated. (C) contains photographs depicting MCF-7 and MDD2 cells cultured on cover slips overnight in phenol-red free MEM, which were treated with 20 μM p28 or 10 μM of the cationic (positive control) peptide, octaarginine ($Arg_8$) (SEQ ID NO: 95), for 2 hr at 37° C. Red-Alexa fluor 56
Figure 55B:
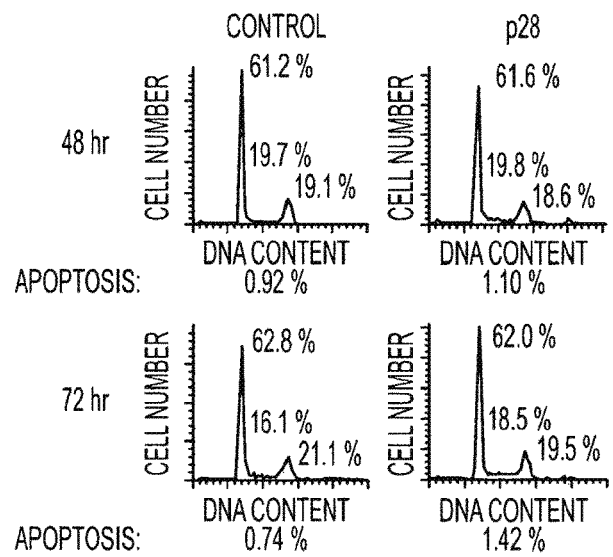
Figure 55C:
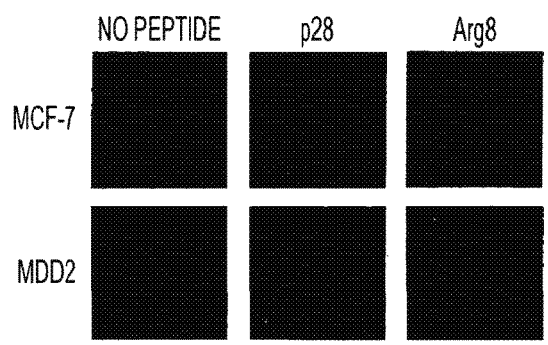

Cell cycle analysis of the two isogenic breast cancer cell lines, MCF-7 (p53 wt) and MDD2 (p53 dominant negative), revealed an increased cell population at the $G_2/M$ phase after exposure to p28 for 48-72 hrs and subsequent induction of apoptosis at 72 hrs in MCF-7 cells (FIG. 55A). There was essentially no inhibition of cell cycle progression or apoptosis in p28-treated MDD2 cells (FIG. 55B). The lack of cell cycle inhibition and apoptosis in p28-treated MDD2 cells (FIG. 55B) was not due to a difference in p28 entry into MDD2 cells (FIG. 55C) or difference in $V_{max}$ (MCF-7: 1.83 MFI/sec, MDD2: 2.21 MFI/sec) or $K_m$ (MCF-7: 144.3 µM, MDD2: 147.9 µM).

Example 29—p53 Levels are Elevated by p28

Figure 56A:
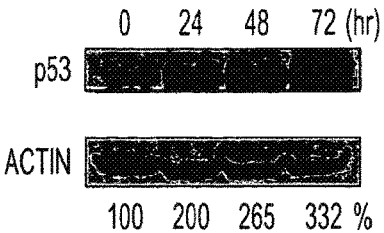
FIG. 56. Interaction of p28 with p53. (A)-(D) are photographs depicting p53 and p28 levels in cells. (A) p53 levels in MCF-7 cells with time after incubation with p28. (%) increase relative to p53 level immediately prior to treatment (0 hr as 100%). (B) GST pull-down assay demonstrating complex formation between GST-p28 and p53. Left to right GST-p28 (10 and 20 μg/reaction), GST-MDM2 and GST alone. p53 was detected by immunoblotting (IB) using anti-p53 antibody. (C) p53 was pulled down by GST-MDM2 in the presence of a molar excess of p28 (upper). Three different anti-p53 antibodies, Pab 1801 (32-79 amino acids), ab 2433 (277-296 amino acids) and Pab1802 (306-393 amino acids) reacted with GST-p53 immobilized beads in the presence of p28. p28 detected by IB using an anti-p28 antibody (lower). (D) Competition for p28 binding to GST-p53 by a molar excess of p28 fragments p12, p18 and p18b. Relative amount of binding (p28 alone expressed as 100%). M: p28 marker. (E) is a graph depicting p53 DNA-binding in MCF-7 nuclear extracts after exposure to p28 or azurin. Nuclear extracts of $H_2O_2$-treated MCF-7 cells served as an internal control. The p53-oligonucleotide complex was quantified with a monoclonal antibody to p53. Data are expressed as Mean±SEM of triplicates.
Figure 56B:
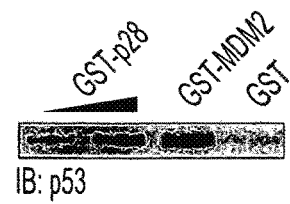
Figure 56C:
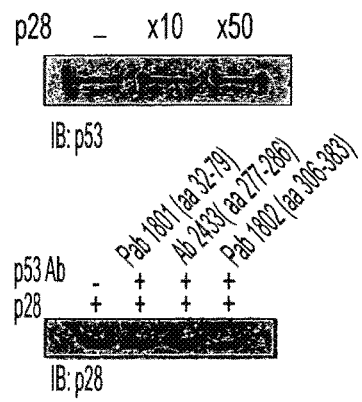

Azurin forms a complex with p53 and elevates intracellular p53 levels in MCF-7 cells. The intracellular level of p53 in MCF-7 cells also significantly increased with time post exposure to p28 (FIG. 56). A GST pull-down assay suggested p28 binds to p53 (FIG. 56B). Here, GST-p28 and GST-MDM2 successfully pulled down p53 from MCF-7 cell lysates, but GST alone did not. Molar increases of p28 did not compete for binding with GST-MDM2 (FIG. 56C) suggesting that amino acids 18-23 of p53 were not a preferred binding site for p28. An additional GST-pull down assay in the presence or absence of p53 antibodies, which recognize different motifs of the p53 protein (amino acids 32-79, 277-296 and 306-393), did not block p28 binding to p53, suggesting that p28 binds to a region of p53 outside these recognition sites (FIG. 56C).

Figure 56D:
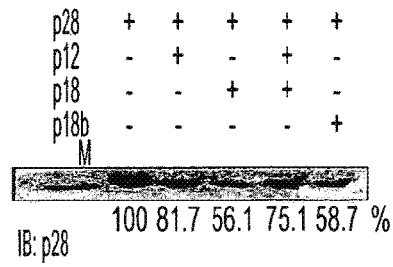

When Sepharose 4B-glutathione beads immobilized with GST-p53 protein were incubated with p28 and either amino acids 66-77, amino acids 50-67, or amino acids 60-77 of azurin, (p28 fragments p12, p18 and p18b) respectively, significant amounts of p28 were displaced by p18 and p18b, but only weakly when p12 was used as the competitor (FIG. 56D). These results suggest that maximal binding to p53 occurs within amino acids 11-28 of p28 (amino acids 60-77 of azurin).

Figure 56E:
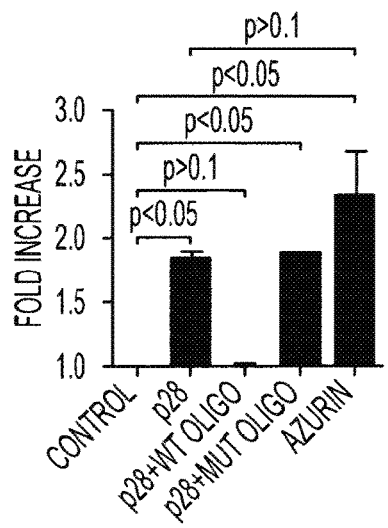

As p28 enhances intracellular levels of p53, the DNA-binding activity of p53 obtained from MCF-7 cell nuclear extracts treated with p28 or azurin was also examined. p53 DNA-binding activity in the nuclear fraction of MCF-7 cells treated by p28 and azurin was 1.8 and 2.3 fold higher than control (p>0.1, p28 vs azurin). The p53 wt consensus, but not the mutated oligonucleotide sequence, completely blocked the p28 induced increase in p53, confirming that the p53 in nuclear extracts of MCF-7 cells binds specifically to the consensus oligonucleotide sequence for wt p53 (FIG. 56E).

Example 30—Modulation of Cell Cycle Related Proteins by p28

Figure 57C:
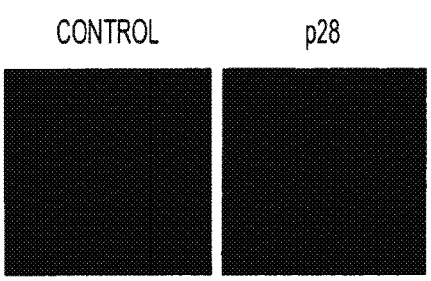
Figure 57D:
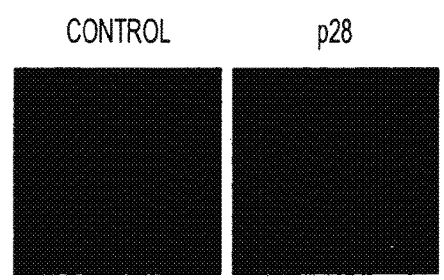
Figure 57E:
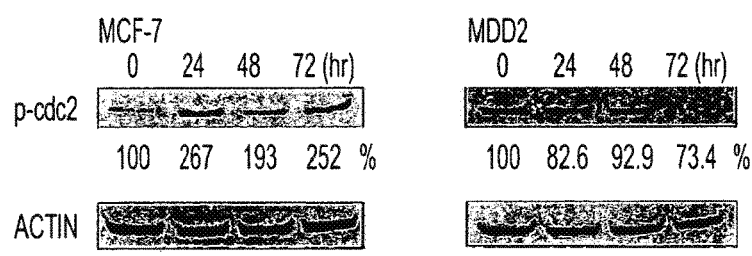

Upregulation of the CDK inhibitors (CDKIs), $p^{21}$ and p27, blocks cell cycle progression. p28 increased intracellular levels of p21, p27, CDK6 and cyclin B1 over control in MCF-7 cells with time post-exposure (FIG. 57A). The levels of CDK2 and cyclin A, essential proteins in the mitotic process, subsequently decreased with time post-exposure in p28 treated MCF-7 cells (FIG. 57A). In contrast, p53, cdc2, CDK2, CDK4 and CDK6 essentially remained constant in MDD2 cells (FIG. 57B), while cyclin A and cyclin B1 (48 hrs) increased slightly. Since p21 can be expressed by a p53-independent pathway in MDD2 cells, p21 remained detectable. p28 did not alter the level of p21, however (FIG. 57B). In contrast, p27 was not detectable in untreated or p28 exposed MDD2 cells. The increased levels of p21 and cyclin B1 in MCF-7 cells detected by immunoblotting in response to p28 are reflected by their increase in nuclear and cytosolic compartments, respectively (FIGS. 57C and D). Exposure of MCF-7 cells to p28 also induced the accumulation of phosphorylated cdc2 (p-cdc2), the inactive form of cdc2. The level of p-cdc2 did not increase following exposure of MDD2 cells to p28 (FIG. 57E).

Example 31—Imaging p18 and p28 Entry into Mouse Organs

Small animal in vivo imaging has important significance in biological studies, including human cancer research. The ability to track and visualize a tagged biological probe allows researchers to visualize biological processes and deduce mechanisms of action and efficacy. Imaging can be used to directly visualize trafficking of near infrared labeled peptides of the cupredoxin class of proteins, including azurin and the azurin fragments p28 and p18, to primary and metastatic tumor sites in xenograft bearing nude mice. J Biomed Optics 10:054010-1-11, 2005; J Amer Soc Exp Neuother 2:215-225, 2005; Topics Curr Chem 222:1-29, 2002

Procedure.

Athymic nude mice bearing Mel2 xenograft tumors were monitored until tumor size reached 0.5 cm$^3$. Mice were anesthetized using a mixture of 2:1 ketamine:xylazine; recommended dosage is 10 μl/gm mouse b.w. s.c. Anesthetized mice were scanned directly before and after injection of labeled peptide with an iCor Odyssey Imager. Anesthetized mice were injected i.v. (tail vein) with 100 μl of IRDye™ 800 cw labeled p18/p28 at a concentration of 1.25 μg/μl-125 μg per mouse. Mice were scanned at least once every 24 hours until excess dye cleared their system (generally ~5 days). On the fifth day, mice were sacrificed and individual animals scanned a final time. Organs, including the kidneys, stomach, intestine, spleen, brain, heart, and lungs, and tumors were excised, split in half, and half were fixed for histological examination. The other half of the organs and tumors was covered with a small amount of PBS, and then scanned.

---

What is claimed is:

1. A method for treating a patient at risk for or diagnosed with cancer comprising:
    administering to a mammalian patient a pharmaceutical composition comprising one or more of a peptide selected from the group consisting of: SEQ ID NO: 36 and SEQ ID NO: 37 and a pharmaceutically acceptable carrier; and
    wherein the pharmaceutical composition is administered by a mode selected from the group consisting of intravenous injection, intramuscular injection, subcutaneous injection, inhalation, topical administration, transdermal patch, suppository, vitreous injection, and oral administration.

2. The method of claim 1, wherein the patient is human.

3. The method of claim 2, wherein the patient is at a higher risk to develop cancer than the general population.

4. The method of claim 3, wherein the cancer is selected from the group consisting of melanoma, breast, pancreas, glioblastoma, astrocytoma, lung, colorectal, neck and head, bladder, prostate, skin, and cervical cancer.

5. The method of claim 2, wherein the patient has at least one high risk feature.

6. The method of claim 2, wherein the patient has pre-malignant lesions.

7. The method of claim 1, wherein the mode of administration is by intravenous injection.

8. The method of claim 1, wherein the pharmaceutical composition further comprises a cargo compound.

* * * * *

SEQUENCE LISTING

```
<160> NUMBER OF SEQ ID NOS: 96

<210> SEQ ID NO 1
<211> LENGTH: 128
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
                100                 105                 110

Thr Phe Pro Gly His Ser Ala Leu Met Lys Gly Thr Leu Thr Leu Lys
            115                 120                 125

<210> SEQ ID NO 2
<211> LENGTH: 28
<212> TYPE: PRT
<213> ORGANISM: Pseudomonas aeruginosa

<400> SEQUENCE: 2

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 3
<211> LENGTH: 105
<212> TYPE: PRT
<213> ORGANISM: Phormidium laminosum
```

<400> SEQUENCE: 3

```
Glu Thr Phe Thr Val Lys Met Gly Ala Asp Ser Gly Leu Leu Gln Phe
1               5                   10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
        35                  40                  45

Pro Gly Ala Ser Lys Glu Leu Ala Asp Lys Leu Ser His Ser Gln Leu
    50                  55                  60

Met Phe Ser Pro Gly Glu Ser Tyr Glu Ile Thr Phe Ser Ser Asp Phe
65              70                  75                  80

Pro Ala Gly Thr Tyr Thr Tyr Tyr Cys Ala Pro His Arg Gly Ala Gly
                85                  90                  95

Met Val Gly Lys Ile Thr Val Glu Gly
                100                 105
```

<210> SEQ ID NO 4
<211> LENGTH: 155
<212> TYPE: PRT
<213> ORGANISM: Thiobacillus ferrooxidans

<400> SEQUENCE: 4

```
Gly Thr Leu Asp Thr Thr Trp Lys Glu Ala Thr Leu Pro Gln Val Lys
1               5                   10                  15

Ala Met Leu Glu Lys Asp Thr Gly Lys Val Ser Gly Asp Thr Val Thr
            20                  25                  30

Tyr Ser Gly Lys Thr Val His Val Val Ala Ala Val Leu Pro Gly
        35                  40                  45

Phe Pro Phe Pro Ser Phe Glu Val His Asp Lys Lys Asn Pro Thr Leu
    50                  55                  60

Glu Ile Pro Ala Gly Ala Thr Val Asp Val Thr Phe Ile Asn Thr Asn
65              70                  75                  80

Lys Gly Phe Gly His Ser Phe Asp Ile Thr Lys Lys Gly Pro Pro Tyr
                85                  90                  95

Ala Val Met Pro Val Ile Asp Pro Ile Val Ala Gly Thr Gly Phe Ser
                100                 105                 110

Pro Val Pro Lys Asp Gly Lys Phe Gly Tyr Thr Asp Phe Thr Trp His
            115                 120                 125

Pro Thr Ala Gly Thr Tyr Tyr Tyr Val Cys Gln Ile Pro Gly His Ala
        130                 135                 140

Ala Thr Gly Met Phe Gly Lys Ile Val Val Lys
145                 150                 155
```

<210> SEQ ID NO 5
<211> LENGTH: 124
<212> TYPE: PRT
<213> ORGANISM: Achromobacter cycloclastes

<400> SEQUENCE: 5

```
Ala Asp Phe Glu Val His Met Leu Asn Lys Gly Lys Asp Gly Ala Met
1               5                   10                  15

Val Phe Glu Pro Ala Ser Leu Lys Val Ala Pro Gly Asp Thr Val Thr
            20                  25                  30

Phe Ile Pro Thr Asp Lys Gly His Asn Val Glu Thr Ile Lys Gly Met
        35                  40                  45
```

```
Ile Pro Asp Gly Ala Glu Ala Phe Lys Ser Lys Ile Asn Glu Asn Tyr
    50                  55                  60

Lys Val Thr Phe Thr Ala Pro Gly Val Tyr Gly Val Lys Cys Thr Pro
 65                  70                  75                  80

His Tyr Gly Met Gly Met Val Gly Val Gln Val Gly Asp Ala Pro
                 85                  90                  95

Ala Asn Leu Glu Ala Val Lys Gly Ala Lys Asn Pro Lys Lys Ala Gln
            100                 105                 110

Glu Arg Leu Asp Ala Ala Leu Ala Ala Leu Gly Asn
            115                 120
```

<210> SEQ ID NO 6
<211> LENGTH: 128
<212> TYPE: PRT
<213> ORGANISM: Alcaligenes faecalis

<400> SEQUENCE: 6

```
Ala Cys Asp Val Ser Ile Glu Gly Asn Asp Ser Met Gln Phe Asn Thr
 1               5                  10                  15

Lys Ser Ile Val Val Asp Lys Thr Cys Lys Glu Phe Thr Ile Asn Leu
                20                  25                  30

Lys His Thr Gly Lys Leu Pro Lys Ala Ala Met Gly His Asn Val Val
            35                  40                  45

Val Ser Lys Lys Ser Asp Glu Ser Ala Val Ala Thr Asp Gly Met Lys
 50                  55                  60

Ala Gly Leu Asn Asn Asp Tyr Val Lys Ala Gly Asp Glu Arg Val Ile
 65                  70                  75                  80

Ala His Thr Ser Val Ile Gly Gly Gly Glu Thr Asp Ser Val Thr Phe
                 85                  90                  95

Asp Val Ser Lys Leu Lys Glu Gly Glu Asp Tyr Ala Phe Phe Cys Ser
            100                 105                 110

Phe Pro Gly His Trp Ser Ile Met Lys Gly Thr Ile Glu Leu Gly Ser
            115                 120                 125
```

<210> SEQ ID NO 7
<211> LENGTH: 129
<212> TYPE: PRT
<213> ORGANISM: Achromobacter xylosoxidans

<400> SEQUENCE: 7

```
Ala Gln Cys Glu Ala Thr Ile Glu Ser Asn Asp Ala Met Gln Tyr Asn
 1               5                  10                  15

Leu Lys Glu Met Val Val Asp Lys Ser Cys Lys Gln Phe Thr Val His
                20                  25                  30

Leu Lys His Val Gly Lys Met Ala Lys Val Ala Met Gly His Asn Trp
            35                  40                  45

Val Leu Thr Lys Glu Ala Asp Lys Gln Gly Val Ala Thr Asp Gly Met
 50                  55                  60

Asn Ala Gly Leu Ala Gln Asp Tyr Val Lys Ala Gly Asp Thr Arg Val
 65                  70                  75                  80

Ile Ala His Thr Lys Val Ile Gly Gly Gly Glu Ser Asp Ser Val Thr
                 85                  90                  95

Phe Asp Val Ser Lys Leu Thr Pro Gly Glu Ala Tyr Ala Tyr Phe Cys
            100                 105                 110

Ser Phe Pro Gly His Trp Ala Met Met Lys Gly Thr Leu Lys Leu Ser
            115                 120                 125
```

Asn

<210> SEQ ID NO 8
<211> LENGTH: 129
<212> TYPE: PRT
<213> ORGANISM: Bordetella bronchiseptica

<400> SEQUENCE: 8

```
Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
            20                  25                  30

Leu Lys His Thr Gly Lys Leu Pro Arg Asn Val Met Gly His Asn Trp
        35                  40                  45

Val Leu Thr Lys Thr Ala Asp Met Gln Ala Val Glu Lys Asp Gly Ile
    50                  55                  60

Ala Ala Gly Leu Asp Asn Gln Tyr Leu Lys Ala Gly Asp Thr Arg Val
65                  70                  75                  80

Leu Ala His Thr Lys Val Leu Gly Gly Glu Ser Asp Ser Val Thr
            85                  90                  95

Phe Asp Val Ala Lys Leu Ala Ala Gly Asp Asp Tyr Thr Phe Phe Cys
                100                 105                 110

Ser Phe Pro Gly His Gly Ala Leu Met Lys Gly Thr Leu Lys Leu Val
            115                 120                 125

Asp
```

<210> SEQ ID NO 9
<211> LENGTH: 129
<212> TYPE: PRT
<213> ORGANISM: Methylomonas sp.

<400> SEQUENCE: 9

```
Ala Ser Cys Glu Thr Thr Val Thr Ser Gly Asp Thr Met Thr Tyr Ser
1               5                   10                  15

Thr Arg Ser Ile Ser Val Pro Ala Ser Cys Ala Glu Phe Thr Val Asn
            20                  25                  30

Phe Glu His Lys Gly His Met Pro Lys Thr Gly Met Gly His Asn Trp
        35                  40                  45

Val Leu Ala Lys Ser Ala Asp Val Gly Asp Val Ala Lys Glu Gly Ala
    50                  55                  60

His Ala Gly Ala Asp Asn Asn Phe Val Thr Pro Gly Asp Lys Arg Val
65                  70                  75                  80

Ile Ala Phe Thr Pro Ile Ile Gly Gly Gly Glu Lys Thr Ser Val Lys
            85                  90                  95

Phe Lys Val Ser Ala Leu Ser Lys Asp Glu Ala Tyr Thr Tyr Phe Cys
                100                 105                 110

Ser Tyr Pro Gly His Phe Ser Met Met Arg Gly Thr Leu Lys Leu Glu
            115                 120                 125

Glu
```

<210> SEQ ID NO 10
<211> LENGTH: 166
<212> TYPE: PRT
<213> ORGANISM: Neisseria meningitidis

<400> SEQUENCE: 10

```
Cys Ser Gln Glu Pro Ala Ala Pro Ala Ala Gl

```
               1               5                  10                 15
   Glu Ala Pro Ala Ser Glu Ala Pro Ala Ala Glu Ala Ala Pro Ala Asp
                    20                 25                 30
   Ala Ala Glu Ala Pro Ala Ala Gly Asn Cys Ala Ala Thr Val Glu Ser
                    35                 40                 45
   Asn Asp Asn Met Gln Phe Asn Thr Lys Asp Ile Gln Val Ser Lys Ala
        50                     55                 60
   Cys Lys Glu Phe Thr Ile Thr Leu Lys His Thr Gly Thr Gln Pro Lys
   65                 70                 75                 80
   Thr Ser Met Gly His Asn Ile Val Ile Gly Lys Thr Glu Asp Met Asp
                        85                 90                 95
   Gly Ile Phe Lys Asp Gly Val Gly Ala Ala Asp Thr Asp Tyr Val Lys
                    100                105                110
   Pro Asp Asp Ala Arg Val Val Ala His Thr Lys Leu Ile Gly Gly Gly
                    115                120                125
   Glu Glu Ser Ser Leu Thr Leu Asp Pro Ala Lys Leu Ala Asp Gly Glu
                    130                135                140
   Tyr Lys Phe Ala Cys Thr Phe Pro Gly His Gly Ala Leu Met Asn Gly
   145                    150                155                160
   Lys Val Thr Leu Val Asp
                    165

<210> SEQ ID NO 11
<211> LENGTH: 128
<212> TYPE: PRT
<213> ORGANISM: Pseudomonas fluorescen

<400> SEQUENCE: 11

Ala Glu Cys Lys Thr Thr Ile Asp Ser Thr Asp Gln Met Ser Phe Asn
   1               5                  10                 15
   Thr Lys Ala Ile Glu Ile Asp Lys Ala Cys Lys Thr Phe Thr Val Glu
                    20                 25                 30
   Leu Thr His Ser Gly Ser Leu Pro Lys Asn Val Met Gly His Asn Leu
                    35                 40                 45
   Val Ile Ser Lys Gln Ala Asp Met Gln Pro Ile Ala Thr Asp Gly Leu
        50                     55                 60
   Ser Ala Gly Ile Asp Lys Asn Tyr Leu Lys Glu Gly Asp Thr Arg Val
   65                 70                 75                 80
   Ile Ala His Thr Lys Val Ile Gly Ala Gly Glu Lys Asp Ser Leu Thr
                        85                 90                 95
   Ile Asp Val Ser Lys Leu Asn Ala Ala Glu Lys Tyr Gly Phe Phe Cys
                    100                105                110
   Ser Phe Pro Gly His Ile Ser Met Met Lys Gly Thr Val Thr Leu Lys
                    115                120                125

<210> SEQ ID NO 12
<211> LENGTH: 128
<212> TYPE: PRT
<213> ORGANISM: Pseudomonas chlororaphis

<400> SEQUENCE: 12

Ala Glu Cys Lys Val Asp Val Asp Ser Thr Asp Gln Met Ser Phe Asn
   1               5                  10                 15
   Thr Lys Glu Ile Thr Ile Asp Lys Ser Cys Lys Thr Phe Thr Val Asn
                    20                 25                 30
   Leu Thr His Ser Gly Ser Leu Pro Lys Asn Val Met Gly His Asn Trp
```

```
        35                  40                  45

Val Leu Ser Lys Ser Ala Asp Met Ala Gly Ile Ala Thr Asp Gly Met
    50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Glu Phe Phe Cys
            100                 105                 110

Ser Phe Pro Gly His Asn Ser Met Met Lys Gly Ala Val Val Leu Lys
        115                 120                 125

<210> SEQ ID NO 13
<211> LENGTH: 129
<212> TYPE: PRT
<213> ORGANISM: Xylella fastidiosa

<400> SEQUENCE: 13

Lys Thr Cys Ala Val Thr Ile Ser Ala Asn Asp Gln Met Lys Phe Asp
1               5                   10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp
        35                  40                  45

Val Leu Thr Lys Thr Thr Asp Met Gln Ala Val Ala Leu Ala Gly Leu
    50                  55                  60

His Ala Thr Leu Ala Asp Asn Tyr Val Pro Lys Ala Asp Pro Arg Val
65                  70                  75                  80

Ile Ala His Thr Ala Ile Ile Gly Gly Gly Glu Arg Thr Ser Ile Thr
                85                  90                  95

Phe Pro Thr Asn Thr Leu Ser Lys Asn Val Ser Tyr Thr Phe Phe Cys
            100                 105                 110

Ser Phe Pro Gly His Trp Ala Leu Met Lys Gly Thr Leu Asn Phe Gly
        115                 120                 125

Gly

<210> SEQ ID NO 14
<211> LENGTH: 138
<212> TYPE: PRT
<213> ORGANISM: Cucumis sativus

<400> SEQUENCE: 14

Met Gln Ser Thr Val His Ile Val Gly Asp Asn Thr Gly Trp Ser Val
1               5                   10                  15

Pro Ser Ser Pro Asn Phe Tyr Ser Gln Trp Ala Ala Gly Lys Thr Phe
            20                  25                  30

Arg Val Gly Asp Ser Leu Gln Phe Asn Phe Pro Ala Asn Ala His Asn
        35                  40                  45

Val His Glu Met Glu Thr Lys Gln Ser Phe Asp Ala Cys Asn Phe Val
    50                  55                  60

Asn Ser Asp Asn Asp Val Glu Arg Thr Ser Pro Val Ile Glu Arg Leu
65                  70                  75                  80

Asp Glu Leu Gly Met His Tyr Phe Val Cys Thr Val Gly Thr His Cys
                85                  90                  95

Ser Asn Gly Gln Lys Leu Ser Ile Asn Val Val Ala Ala Asn Ala Thr
            100                 105                 110

```
Val Ser Met Pro Pro Ser Ser Pro Pro Ser Ser Val Met Pro
        115                 120                 125

Pro Pro Val Met Pro Pro Ser Pro Ser
        130                 135

<210> SEQ ID NO 15
<211> LENGTH: 162
<212> TYPE: PRT
<213> ORGANISM: Chloroflexus aurantiacus

<400> SEQUENCE: 15

Met Lys Ile Thr Leu Arg Met Met Val Leu Ala Val Leu Thr Ala Met
1               5                   10                  15

Ala Met Val Leu Ala Ala Cys Gly Gly Gly Ser Ser Gly Gly Ser
            20                  25                  30

Thr Gly Gly Gly Ser Gly Ser Gly Pro Val Thr Ile Glu Ile Gly Ser
        35                  40                  45

Lys Gly Glu Glu Leu Ala Phe Asp Lys Thr Glu Leu Thr Val Ser Ala
    50                  55                  60

Gly Gln Thr Val Thr Ile Arg Phe Lys Asn Asn Ser Ala Val Gln Gln
65                  70                  75                  80

His Asn Trp Ile Leu Val Lys Gly Gly Glu Ala Glu Ala Ala Asn Ile
                85                  90                  95

Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu
        115                 120                 125

Thr Val Glu Val Thr Phe Thr Ala Pro Ala Ala Gly Thr Tyr Leu Tyr
    130                 135                 140

Ile Cys Thr Val Pro Gly His Tyr Pro Leu Met Gln Gly Lys Leu Val
145                 150                 155                 160

Val Asn

<210> SEQ ID NO 16
<211> LENGTH: 140
<212> TYPE: PRT
<213> ORGANISM: Chloroflexus aurantiacus

<400> SEQUENCE: 16

Ala Ala Asn Ala Pro Gly Gly Ser Asn Val Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
        35                  40                  45

Asn Gln Asn Asn Leu Gly Val Gln His Asn Trp Val Leu Val Asn Gly
    50                  55                  60

Gly Asp Asp Val Ala Ala Val Asn Thr Ala Ala Gln Asn Asn Ala
65                  70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
            100                 105                 110

Pro Ala Pro Gly Thr Tyr Leu Tyr Ile Cys Thr Phe Pro Gly His Tyr
        115                 120                 125
```

```
Leu Ala Gly Met Lys Gly Thr Leu Thr Val Thr Pro
    130                 135                 140

<210> SEQ ID NO 17
<211> LENGTH: 96
<212> TYPE: PRT
<213> ORGANISM: Cucumis sativus

<400> SEQUENCE: 17

Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
            20                  25                  30

Asn Tyr Asn Pro Ser Met His Asn Val Val Val Asn Gln Gly Gly
        35                  40                  45

Phe Ser Thr Cys Asn Thr Pro Ala Gly Ala Lys Val Tyr Thr Ser Gly
    50                  55                  60

Arg Asp Gln Ile Lys Leu Pro Lys Gly Gln Ser Tyr Phe Ile Cys Asn
65                  70                  75                  80

Phe Pro Gly His Cys Gln Ser Gly Met Lys Ile Ala Val Asn Ala Leu
                85                  90                  95

<210> SEQ ID NO 18
<211> LENGTH: 166
<212> TYPE: PRT
<213> ORGANISM: Neisseria gonorrhoeae

<400> SEQUENCE: 18

Cys Ser Gln Glu Pro Ala Ala Pro Ala Ala Glu Ala Thr Pro Ala Gly
1               5                   10                  15

Glu Ala Pro Ala Ser Glu Ala Pro Ala Ala Glu Ala Ala Pro Ala Asp
            20                  25                  30

Ala Ala Glu Ala Pro Ala Ala Gly Asn Cys Ala Ala Thr Val Glu Ser
            35                  40                  45

Asn Asp Asn Met Gln Phe Asn Thr Lys Asp Ile Gln Val Ser Lys Ala
    50                  55                  60

Cys Lys Glu Phe Thr Ile Thr Leu Lys His Thr Gly Thr Gln Pro Lys
65                  70                  75                  80

Ala Ser Met Gly His Asn Leu Val Ile Ala Lys Ala Glu Asp Met Asp
                85                  90                  95

Gly Val Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
            115                 120                 125

Glu Glu Ser Ser Leu Thr Leu Asp Pro Ala Lys Leu Ala Asp Gly Asp
    130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 19
<211> LENGTH: 150
<212> TYPE: PRT
<213> ORGANISM: Vibrio parahaemolyticus

<400> SEQUENCE: 19

Met Ser Leu Arg Ile Leu Ala Ala Thr Leu Ala Leu Ala Gly Leu Ser
```

```
              1               5                  10                 15
            Phe Gly Ala Gln Ala Ser Ala Glu Cys Glu Val Ser Ile Asp Ala Asn
                            20                 25                 30

Asp Met Met Gln Phe Ser Thr Lys Thr Leu Ser Val Pro Ala Thr Cys
                        35                 40                 45

Lys Glu Val Thr Leu Thr Leu Asn His Thr Gly Lys Met Pro Ala Gln
                    50                 55                 60

Ser Met Gly His Asn Val Val Ile Ala Asp Thr Ala Asn Ile Gln Ala
            65                  70                 75                 80

Val Gly Thr Asp Gly Met Ser Ala Gly Ala Asp Asn Ser Tyr Val Lys
                            85                 90                 95

Pro Asp Asp Glu Arg Val Tyr Ala His Thr Lys Val Val Gly Gly Gly
                        100                105                110

Glu Ser Thr Ser Ile Thr Phe Ser Thr Glu Lys Met Thr Ala Gly Gly
                        115                120                125

Asp Tyr Ser Phe Phe Cys Ser Phe Pro Gly His Trp Ala Ile Met Gln
                    130                135                140

Gly Lys Phe Glu Phe Lys
            145                150

<210> SEQ ID NO 20
<211> LENGTH: 33
<212> TYPE: PRT
<213> ORGANISM: Chloroflexus aurantiacus

<400> SEQUENCE: 20

His Asn Trp Val Leu Val Asn Gly Gly Asp Val Ala Ala Val
1               5                  10                 15

Asn Thr Ala Ala Gln Asn Asn Ala Asp Ala Leu Phe Val Pro Pro
            20                 25                 30

Asp

<210> SEQ ID NO 21
<211> LENGTH: 27
<212> TYPE: PRT
<213> ORGANISM: Pseudomonas syringae

<400> SEQUENCE: 21

Ser Lys Lys Ala Asp Ala Ser Ala Ile Thr Thr Asp Gly Met Ser Val
1               5                  10                 15

Gly Ile Asp Lys Asp Tyr Val Lys Pro Asp Asp
            20                 25

<210> SEQ ID NO 22
<211> LENGTH: 27
<212> TYPE: PRT
<213> ORGANISM: Neisseria meningitidis

<400> SEQUENCE: 22

Ile Gly Lys Thr Glu Asp Met Asp Gly Ile Phe Lys Asp Gly Val Gly
1               5                  10                 15

Ala Ala Asp Thr Asp Tyr Val Lys Pro Asp Asp
            20                 25

<210> SEQ ID NO 23
<211> LENGTH: 27
<212> TYPE: PRT
<213> ORGANISM: Vibrio parahaemolyticus
```

-continued

```
<400> SEQUENCE: 23

Ala Asp Thr Ala Asn Ile Gln Ala Val Gly Thr Asp Gly Met Ser Ala
1               5                   10                  15

Gly Ala Asp Asn Ser Tyr Val Lys Pro Asp Asp
            20                  25

<210> SEQ ID NO 24
<211> LENGTH: 27
<212> TYPE: PRT
<213> ORGANISM: Bordetella bronchiseptica

<400> SEQUENCE: 24

Thr Lys Thr Ala Asp Met Gln Ala Val Glu Lys Asp Gly Ile Ala Ala
1               5                   10                  15

Gly Leu Asp Asn Gln Tyr Leu Lys Ala Gly Asp
            20                  25

<210> SEQ ID NO 25
<211> LENGTH: 18
<212> TYPE: PRT
<213> ORGANISM: Pseudomonas aeruginosa

<400> SEQUENCE: 25

Leu Ser Thr Ala Ala Asp Met Gln Gly Val Val Thr Asp Gly Met Ala
1               5                   10                  15

Ser Gly

<210> SEQ ID NO 26
<211> LENGTH: 53
<212> TYPE: PRT
<213> ORGANISM: Pseudomonas aeruginosa

<400> SEQUENCE: 26

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly
    50

<210> SEQ ID NO 27
<211> LENGTH: 42
<212> TYPE: PRT
<213> ORGANISM: Pseudomonas aeruginosa

<400> SEQUENCE: 27

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp
        35                  40

<210> SEQ ID NO 28
<211> LENGTH: 54
<212> TYPE: PRT
<213> ORGANISM: Pseudomonas aeruginosa

<400> SEQUENCE: 28
```

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly Ser
    50

<210> SEQ ID NO 29
<211> LENGTH: 93
<212> TYPE: PRT
<213> ORGANISM: Pseudomonas aeruginosa

<400> SEQUENCE: 29

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly Ser Gly Glu Lys Asp Ser Val Thr Phe Asp Val
    50                  55                  60

Ser Lys Leu Lys Glu Gly Glu Gln Tyr Met Phe Phe Cys Thr Phe Pro
65                  70                  75                  80

Gly His Ser Ala Leu Met Lys Gly Thr Leu Thr Leu Lys
                85                  90

<210> SEQ ID NO 30
<211> LENGTH: 18
<212> TYPE: PRT
<213> ORGANISM: Pseudomonas aeruginosa

<400> SEQUENCE: 30

Ala Ala Asp Met Gln Gly Val Val Thr Asp Gly Met Ala Ser Gly Leu
1               5                   10                  15

Asp Lys

<210> SEQ ID NO 31
<211> LENGTH: 12
<212> TYPE: PRT
<213> ORGANISM: Pseudomonas aeruginosa

<400> SEQUENCE: 31

Ala Ala Asp Met Gln Gly Val Val Thr Asp Gly Met
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid

```
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 32

Asp Gly Xaa Xaa Xaa Xaa Xaa Asp Xaa Xaa Tyr Xaa Lys Xaa Xaa Asp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid

<400> SEQUENCE: 33

Asp Gly Xaa Xaa Xaa Xaa Asp Xaa Xaa Tyr Xaa Lys Xaa Xaa Asp
1               5                   10                  15

<210> SEQ ID NO 34
<211> LENGTH: 18
<212> TYPE: PRT
<213> ORGANISM: Pseudomonas aeruginosa

<400> SEQUENCE: 34

Val Thr Asp Gly Met Ala Ser Gly Leu Asp Lys Asp Tyr Leu Lys Pro
1               5                   10                  15

Asp Asp

<210> SEQ ID NO 35
<211> LENGTH: 12
<212> TYPE: PRT
<213> ORGANISM: Pseudomonas aeruginosa

<400> SEQUENCE: 35

Ser Gly Leu Asp Lys Asp Tyr Leu Lys Pro Asp Asp
1               5                   10

<210> SEQ ID NO 36
<211> LENGTH: 10
<212> TYPE: PRT
<213> ORGANISM: Pseudomonas aeruginosa

<400> SEQUENCE: 36

Leu Asp Lys Asp Tyr Leu Lys Pro Asp Asp
1               5                   10
```

```
<210> SEQ ID NO 37
<211> LENGTH: 11
<212> TYPE: PRT
<213> ORGANISM: Pseudomonas aeruginosa

<400> SEQUENCE: 37

Gly Leu Asp Lys Asp Tyr Leu Lys Pro Asp Asp
1               5                   10

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Ser Thr Ala Ala Asp Met Gln Ala Val Val Thr Asp Thr Met Ala
1               5                   10                  15

Ser Gly Leu Asp Lys Asp Tyr Leu Lys Pro Asp Asp
            20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Ser Thr Ala Ala Asp Leu Gln Gly Val Val Thr Asp Gly Leu Ala
1               5                   10                  15

Ser Gly Leu Asp Lys Asp Tyr Leu Lys Pro Asp Asp
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Ser Thr Ala Ala Asp Val Gln Gly Val Val Thr Asp Gly Val Ala
1               5                   10                  15

Ser Gly Leu Asp Lys Asp Tyr Leu Lys Pro Asp Asp
            20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Asp Pro Lys Leu Tyr Asp Lys Asp Leu Gly Ser Ala Met Gly Asp
1               5                   10                  15

Thr Val Val Gly Gln Met Asp Ala Ala Thr Ser Leu
            20                  25
```

```
<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 42

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Ser Pro Pro Ala Arg
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Thr Pro Pro Ala Leu
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Ser Phe Phe Ala Phe
1               5

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Ser Thr Ala Ala Asp Met Gln Gly Val Val Thr Asp Gly Met Ala
1               5                   10                  15

Ser Gly Leu Asp Lys Asp Tyr Leu Thr Pro Gly Cys
            20                  25
```

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Ser Thr Ala Ala Asp Cys Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Ser Thr Ala Ala Cys Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Ser Thr Ala Cys Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Ser Thr Ala Ala Thr Met Gln Cys Val Val Thr Asp Gly Met Ala
1               5                   10                  15

Ser Gly Leu Asp Lys Asp Tyr Leu Lys Pro Asp Asp
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Leu Ser Thr Ala Ala Thr Met Gln Gly Cys Val Thr Asp Gly Met Ala
1               5                   10                  15

Ser Gly Leu Asp Lys Asp Tyr Leu Lys Pro Asp Asp
            20                  25
```

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Leu Ser Thr Ala Ala Asn Thr Gln Gly Cys Val Thr Asp Gly Met Ala
1               5                   10                  15

Ser Gly Leu Asp Lys Asp Tyr Leu Lys Pro Asp Asp
            20                  25
```

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Leu Ser Thr Ala Ala Asn Thr Gln Gly Val Cys Thr Asp Gly Met Ala
1               5                   10                  15

Ser Gly Leu Asp Lys Asp Tyr Leu Lys Pro Asp Asp
            20                  25
```

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Leu Ser Thr Ala Ala Asp Met Thr Ala Val Cys Thr Asp Gly Met Ala
1               5                   10                  15

Ser Gly Leu Asp Lys Asp Tyr Leu Lys Pro Asp Asp
            20                  25
```

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Leu Ser Thr Ala Ala Asp Met Thr Ala Val Val Cys Asp Gly Met Ala
1               5                   10                  15

Ser Gly Leu Asp Lys Asp Tyr Leu Lys Pro Asp Asp
            20                  25
```

<210> SEQ ID NO 56
<211> LENGTH: 28
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 56

Leu Ser Thr Ala Ala Asp Met Gln Thr Val Val Cys Asp Gly Met Ala
1               5                   10                  15

Ser Gly Leu Asp Lys Asp Tyr Leu Lys Pro Asp Asp
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Ser Thr Ala Ala Asp Met Gln Thr Val Val Thr Cys Gly Met Ala
1               5                   10                  15

Ser Gly Leu Asp Lys Asp Tyr Leu Lys Pro Asp Asp
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Ser Thr Ala Ala Asp Met Gln Ala Thr Val Thr Cys Gly Met Ala
1               5                   10                  15

Ser Gly Leu Asp Lys Asp Tyr Leu Lys Pro Asp Asp
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Ser Thr Ala Ala Asp Met Gln Ala Thr Val Thr Asp Cys Met Ala
1               5                   10                  15

Ser Gly Leu Asp Lys Asp Tyr Leu Lys Pro Asp Asp
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Ser Thr Ala Ala Asp Met Gln Gly Val Thr Ala Asp Cys Met Ala
1               5                   10                  15

Ser Gly Leu Asp Lys Asp Tyr Leu Lys Pro Asp Asp
```

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Leu Ser Thr Ala Ala Asp Met Gln Gly Val Thr Ala Asp Gly Cys Ala
1               5                   10                  15

Ser Gly Leu Asp Lys Asp Tyr Leu Lys Pro Asp Asp
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Leu Ser Thr Ala Ala Asp Met Gln Gly Val Val Thr Asn Gly Cys Ala
1               5                   10                  15

Ser Gly Leu Asp Lys Asp Tyr Leu Lys Pro Asp Asp
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Leu Ser Thr Ala Ala Asp Met Gln Gly Val Val Thr Ala Thr Met Gly
1               5                   10                  15

Ser Gly Leu Cys Lys Asp Tyr Leu Lys Pro Asp Asp
            20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Leu Ser Thr Ala Ala Asp Met Gln Gly Val Val Thr Asp Leu Thr Ala
1               5                   10                  15

Ser Gly Leu Cys Lys Asp Tyr Leu Lys Pro Asp Asp
            20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 65

Leu Ser Trp Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Ser Thr Ala Ala Asp Met Trp Gly Val Val Thr Asp Gly Met Ala
1               5                   10                  15

Ser Gly Leu Asp Lys Asp Tyr Leu Lys Pro Asp Asp
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Ser Thr Ala Ala Asp Met Gln Gly Val Val Trp Asp Gly Met Ala
1               5                   10                  15

Ser Gly Leu Asp Lys Asp Tyr Leu Lys Pro Asp Asp
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Ser Thr Ala Ala Asp Met Gln Gly Val Val Thr Asp Trp Met Ala
1               5                   10                  15

Ser Gly Leu Asp Lys Asp Tyr Leu Lys Pro Asp Asp
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ser Trp Ala Ala Asp Met Trp Gly Val Val Thr Asp Gly Met Ala
1               5                   10                  15

Ser Gly Leu Asp Lys Asp Tyr Leu Lys Pro Asp Asp
            20                  25

<210> SEQ ID NO 70
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Ser Trp Ala Ala Asp Met Gln Gly Val Val Trp Asp Gly Met Ala
1               5                   10                  15

Ser Gly Leu Asp Lys Asp Tyr Leu Lys Pro Asp Asp
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Ser Trp Ala Ala Asp Met Gln Gly Val Val Thr Asp Trp Met Ala
1               5                   10                  15

Ser Gly Leu Asp Lys Asp Tyr Leu Lys Pro Asp Asp
            20                  25

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Ser Thr Ala Ala Asp Met Trp Gly Val Val Trp Asp Gly Met Ala
1               5                   10                  15

Ser Gly Leu Asp Lys Asp Tyr Leu Lys Pro Asp Asp
            20                  25

<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Ser Thr Ala Ala Asp Met Trp Gly Val Val Thr Asp Trp Met Ala
1               5                   10                  15

Ser Gly Leu Asp Lys Asp Tyr Leu Lys Pro Asp Asp
            20                  25

<210> SEQ ID NO 74
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Ser Thr Ala Ala Asp Met Gln Gly Val Val Trp Asp Trp Met Ala
1               5                   10                  15
```

Ser Gly Leu Asp Lys Asp Tyr Leu Lys Pro Asp Asp
            20                  25

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Ser Trp Ala Ala Asp Met Trp Gly Val Val Trp Asp Trp Met Ala
1               5                   10                  15

Ser Gly Leu Asp Lys Asp Tyr Leu Lys Pro Asp Asp
            20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May or may not be N-term acetylated
<220> FEATURE:
<221> NAME/KEY: MOD_RES
<222> LOCATION: (3)..(3)
<223> OTHER INFORMATION: Thr or Trp
<220> FEATURE:
<221> NAME/KEY: MOD_RES
<222> LOCATION: (7)..(7)
<223> OTHER INFORMATION: Met, Leu or Val
<220> FEATURE:
<221> NAME/KEY: MOD_RES
<222> LOCATION: (8)..(8)
<223> OTHER INFORMATION: Gln or Trp
<220> FEATURE:
<221> NAME/KEY: MOD_RES
<222> LOCATION: (9)..(9)
<223> OTHER INFORMATION: Gly or Ala
<220> FEATURE:
<221> NAME/KEY: MOD_RES
<222> LOCATION: (12)..(12)
<223> OTHER INFORMATION: Thr or Trp
<220> FEATURE:
<221> NAME/KEY: MOD_RES
<222> LOCATION: (14)..(14)
<223> OTHER INFORMATION: Gly, Thr or Trp
<220> FEATURE:
<221> NAME/KEY: MOD_RES
<222> LOCATION: (15)..(15)
<223> OTHER INFORMATION: Met, Leu or Val
<220> FEATURE:
<223> OTHER INFORMATION: May or may not be C-term amidated

<400> SEQUENCE: 76

Leu Ser Xaa Ala Ala Asp Xaa Xaa Xaa Val Val Xaa Asp Xaa Xaa Ala
1               5                   10                  15

Ser Gly Leu Asp Lys Asp Tyr Leu Lys Pro Asp Asp
            20                  25

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May or may not be N-term acetylated

```
<220> FEATURE:
<221> NAME/KEY: MOD_RES
<222> LOCATION: (14)..(14)
<223> OTHER INFORMATION: Met, Leu or Val
<220> FEATURE:
<221> NAME/KEY: MOD_RES
<222> LOCATION: (15)..(15)
<223> OTHER INFORMATION: Gly, Thr or Trp
<220> FEATURE:
<221> NAME/KEY: MOD_RES
<222> LOCATION: (17)..(17)
<223> OTHER INFORMATION: Thr or Trp
<220> FEATURE:
<221> NAME/KEY: MOD_RES
<222> LOCATION: (20)..(20)
<223> OTHER INFORMATION: Gly or Ala
<220> FEATURE:
<221> NAME/KEY: MOD_RES
<222> LOCATION: (21)..(21)
<223> OTHER INFORMATION: Gln or Trp
<220> FEATURE:
<221> NAME/KEY: MOD_RES
<222> LOCATION: (22)..(22)
<223> OTHER INFORMATION: Met, Leu or Val
<220> FEATURE:
<221> NAME/KEY: MOD_RES
<222> LOCATION: (26)..(26)
<223> OTHER INFORMATION: Thr or Trp
<220> FEATURE:
<223> OTHER INFORMATION: May or may not be C-term amidated

<400> SEQUENCE: 77

Asp Asp Pro Lys Leu Tyr Asp Lys Asp Leu Gly Ser Ala Xaa Xaa Asp
1               5                   10                  15

Xaa Val Val Xaa Xaa Xaa Asp Ala Ala Xaa Ser Leu
            20                  25

<210> SEQ ID NO 78
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cgggatcccc ggcaacctgc cgaagaacgt catgggc                             37

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cggaattcgc atcacttcag ggtcaggg                                       28

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggccacaact gggtactgtg aaccgccgcc gacatgcag                           39
```

```
<210> SEQ ID NO 81
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgcatgtcg gcggcggttc acagtaccca gttgtggcc                          39

<210> SEQ ID NO 82
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctgaagccc gacgactgac gtgtcatcgc ccacacc                            37

<210> SEQ ID NO 83
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ggtgtgggcg atgacacgtc agtcgtcggg cttcagg                            37

<210> SEQ ID NO 84
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccaagctgat cggctcgtga gagaaggact cggtgacc                           38

<210> SEQ ID NO 85
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggtcaccgag tccttctctc acgagccgat cagcttgg                           38

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cgggatcctg agcaccgccg ccgacatgca ggg                                33

<210> SEQ ID NO 87
```

```
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cgggatcccc ggcctggaca aggattacct gaagcccg                              38

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cggaattcgc atcacttcag ggtcaggg                                         28

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gacggcatgg cttcctgact ggacaaggat tacc                                  34

<210> SEQ ID NO 90
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggtaatcctt gtccagtcag gaagccatgc cgtc                                  34

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cgggatcccc atggtgagca agggcg                                           26

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cggaattcct tgtacagctc gtccatgccg                                       30

<210> SEQ ID NO 93
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ccgctcgagc ctgagcaccg ccgccatgca ggg                                 33

<210> SEQ ID NO 94
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ttttcctttt gcggccgctc agtcgtcggg cttcaggtaa tcc                      43

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Arg Arg Arg Arg Arg Arg
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Gly Leu Asp Lys Asp
1               5
```